United States Patent
Long et al.

(10) Patent No.: US 12,054,727 B2
(45) Date of Patent: Aug. 6, 2024

(54) PLANTS WITH INCREASED WATER USE EFFICIENCY

(71) Applicants: The Board of Trustees of the University of Illinois, Urbana, IL (US); The Regents of the University of California, Oakland, CA (US)

(72) Inventors: Stephen P. Long, Urbana, IL (US); Katarzyna Glowacka, Lincoln, NE (US); Johannes Kromdijk, Cambridge (GB); Krishna K. Niyogi, Oakland, CA (US); Laurie Beth Leonelli, Oakland, CA (US)

(73) Assignees: The Regents of the University of California, Oakland, CA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/808,881

(22) Filed: Mar. 4, 2020

(65) Prior Publication Data

US 2020/0283788 A1 Sep. 10, 2020

Related U.S. Application Data

(60) Provisional application No. 62/814,005, filed on Mar. 5, 2019.

(51) Int. Cl.
*C12N 15/82* (2006.01)

(52) U.S. Cl.
CPC ................. *C12N 15/8273* (2013.01)

(58) Field of Classification Search
CPC ................................. C12N 15/8273
USPC ....................................... 800/278
See application file for complete search history.

(56) References Cited

U.S. PATENT DOCUMENTS

| | | | |
|---|---|---|---|
| 11,572,569 B2 | 2/2023 | Long et al. | |
| 2006/0150283 A1 | 7/2006 | Alexandrov et al. | |
| 2019/0161765 A1 | 5/2019 | Long et al. | |
| 2023/0183731 A1 | 6/2023 | Long et al. | |

FOREIGN PATENT DOCUMENTS

| | | |
|---|---|---|
| CA | 2300692 A1 | 8/2000 |
| CA | 2302828 A1 | 10/2000 |
| CN | 109207508 A | 1/2019 |
| EP | 1033405 A2 | 9/2000 |
| EP | 1059354 A2 | 12/2000 |
| WO | WO 1997/17447 A2 | 5/1997 |
| WO | WO-0040695 A2 | 7/2000 |
| WO | WO 2008/069496 A1 | 6/2008 |
| WO | WO-2016030885 A1 | 3/2016 |
| WO | WO 2017/205834 A1 | 11/2017 |

OTHER PUBLICATIONS

Anderson, J. et al., "Antagonistic Interaction Between Abscisic Acid and Jasmonate-ethylene Signaling Pathways Modulates Defense Gene Expression and Disease Resistance in *Arabidopsis*", The Plant cell, Dec. 2004, vol. 16, No. 12, pp. 3460-3479.
Arnoux, P. et al., "A Structural Basis for the pH-dependent Xanthophyll Cycle in *Arabidopsis thaliana*", The Plant cell, Jul. 2009, vol. 21, No. 7, pp. 2036-2044.
Audran, C. et al., "Localisation and expression of zeaxanthin epoxidase mRNA in *Arabidopsis* in response to drought stress and during seed development ", 2001, 28, pp. 1161-1173.
Barrero, J. et al., "A Mutational Analysis of the ABA1 Gene of *Arabidopsis thaliana* Highlights the Involvement of ABA in Vegetative Development", Journal of Experimental Botany, Aug. 2005, vol. 56, No. 418, pp. 2071-2083.
Barrero, J. M. et al., "The ABA1 Gene and Carotenoid Biosynthesis are Required for Late Skotomorphogenic Growth in *Arabidopsis thaliana*", Plant, Cell and Environment, Feb. 2008, vol. 31, No. 2, pp. 227-234.
Bugos, R. C. et al., "Xanthophyll Cycle Enzymes are Members of The Lipocalin Family, The First Identified from Plants", The Journal of Biological Chemistry, Jun. 19, 1998, vol. 273, No. 25, pp. 15321-15324.
Cheng, C. et al., "Araport11: A Complete Reannotation of the *Arabidopsis thaliana* Reference Genome", Feb. 2017, vol. 89, No. 4, pp. 789-804.
EP Office Action dated Nov. 19, 2021, in Application No. EP17729973.2.
Hall, M. et al., "Thioredoxin Targets of The Plant Chloroplast Lumen and their Implications for Plastid Function", Proteomics, Mar. 2010, vol. 10, No. 5, pp. 987-1001.
Havaux, M. et al., "Photodamage of The Photosynthetic Apparatus and its Dependence on the Leaf Developmental Stage in The npq1 *Arabidopsis* Mutant Deficient in the Xanthophyll Cycle Enzyme Violaxanthin De-epoxidase", Plant Physiology, Sep. 2000, vol. 124, No. 1, pp. 273-284.
Havaux, M. et al., "The Effect of Zeaxanthin as the Only Xanthophyll on the Structure and Function of the Photosynthetic Apparatus in *Arabidopsis thaliana*", The Journal of Biological Chemistry, Apr. 2, 2004, vol. 279, No. 14, pp. 13878-13888.
Hieber, A. D. et al., "Overexpression of Violaxanthin De-epoxidase: Properties of C-terminal Deletions on Activity and pH-dependent Lipid Binding", Planta, Jan. 2002, vol. 214, No. 3, pp. 476-483.
Jakab, G. et al., "Enhancing *Arabidopsis* Salt and Drought Stress Tolerance by Chemical Priming for its Abscisic Acid Responses", Plant Physiology, Sep. 2005, vol. 139, No. 1, pp. 267-274.

(Continued)

*Primary Examiner* — Li Zheng
(74) *Attorney, Agent, or Firm* — Christian S. Hans; Bozicevic, Field & Francis LLP

(57) ABSTRACT

Aspects of the present disclosure relate to methods of cultivating genetically altered plants with increased activity of the PsbS protein. These genetically altered plants have increased water use efficiency and substantially similar photosynthetic efficiency as compared to WT plants grown under the same conditions.

9 Claims, 32 Drawing Sheets
(31 of 32 Drawing Sheet(s) Filed in Color)
Specification includes a Sequence Listing.

(56) References Cited

OTHER PUBLICATIONS

JP Office Action dated Jun. 22, 2021 issued in JP 2018-561589.
Kalituho, L. et al., "The Transiently Generated Nonphotochemical Quenching of Excitation Energy in Arabidopsis Leaves Is Modulated by Zeaxanthin", Plant Physiology, Apr. 2007, vol. 143, pp. 1861-1870.
Kayoko, Y. et al., "Empirical Analysis of Transcriptional Activity in the Arabidopsis Genome", Science, Oct. 31, 2003, vol. 302, No. 5646, pp. 842-846.
Koornneef, M. et al., "In Vivo Inhibition of Seed Development and Reserve Protein Accumulation in Recombinants of Abscisic Acid Biosynthesis and Responsiveness Mutants in Arabidopsis thaliana", Plant Physiology, Jun. 1989, vol. 90, No. 2, pp. 463-469.
Lu, Y. et al., "Identification of Potential Targets for Thylakoid Oxidoreductase AtVKOR/LTO1 in Chloroplasts", Protein and Peptide Letters, 2015, vol. 22, No. 3, pp. 219-225.
Merlot, S. et al., "Use of Infrared Thermal Imaging to Isolate Arabidopsis Mutants Defective in Stomatal Regulation", The Plant Journal : for Cell and Molecular Biology, Jun. 2002, vol. 30, No. 4, pp. 601-609.
Müller-Moulé, P. et al., "Ascorbate Deficiency Can Limit Violaxanthin De-epoxidase Activity in Vivo", Plant Physiology, Mar. 2002, vol. 128, No. 3, pp. 970-977.
Morillon, R. et al., "The Role of ABA and the Transpiration Stream in the Regulation of the Osmotic Water Permeability of Leaf Cells", Proceedings of the National Academy of Sciences of the United States of America, Nov. 20, 20010, vol. 98, No. 24, pp. 14138-14143.
Niyogi, K. et al., "Arabidopsis Mutants Define A Central Role for The Xanthophyll Cycle in the Regulation of Photosynthetic Energy Conversion", The Plant Cell, Jul. 1998, vol. 10, No. 7, pp. 1121-1134.
Nowicka, B. et al., "New Transgenic Line of Arabidopsis thaliana with Partly Disabled Zeaxanthin Epoxidase Activity Displays Changed Carotenoid Composition, Xanthophyll Cycle Activity and Non-photochemical Quenching Kinetics", Journal of Plant Physiology, 2009, vol. 166, pp. 1045-1056.
Park, H.Y et al., "Overexpression Of Arabidopsis Zep Enhances Tolerance to Osmotic Stress", Biochemical and Biophysical Research Communications, Oct. 10, 2008, vol. 375, No. 1, pp. 80-85.
Raz, V. et al., "Sequential Steps for Developmental Arrest in Arabidopsis Seeds", Development (Cambridge, England), Jan. 2001, vol. 128, vol. 2, pp. 243-252.
Sato, S. et al., "Structural analysis of Arabidopsis thaliana chromosome 5. X. Sequence features of the regions of 3,076,755 bp covered by sixty P1 and TAC clones". DNA Research, Feb. 28, 2000, vol. 7, No. 1, pp. 31-63.
Schubert, M. et al., "Proteome Map of The Chloroplast Lumen Of Arabidopsis thaliana", The Journal of Biological Chemistry, Mar. 8, 2002, vol. 277, No. 10, pp. 8354-8365.
Takahashi, N. et al., "Hydrotropism in Abscisic Acid, Wavy, and Gravitropic Mutants of Arabidopsis thaliana", Planta, Dec. 2002, vol. 216, No. 2, pp. 203-211.
Theologis, A. et al., "Sequence and Analysis of Chromosome 1 of the Plant Arabidopsis thaliana", Nature, Dec. 2000, vol. 408, No. 6814, pp. 816-820.
Ton, J. et al., "Beta-amino-butyric Acid-induced Resistance Against Necrotrophic Pathogens is Based on ABA-dependent Priming for Callose", The Plant journal : for cell and molecular biology, Apr. 2004, vol. 38, No. 1, pp. 119-130.
Ton, J. et al., "Dissecting the Beta-aminobutyric Acid-induced Priming Phenomenon in Arabidopsis", Mar. 2005, vol. 17, No. 3, pp. 987-999.
U.S. Non-Final Office Action dated Dec. 21, 2021, in U.S. Appl. No. 16/304,633.
Willing, E. M. et al., "Genome Expansion of Arabis Alpina Linked with Retrotransposition and Reduced Symmetric DNA Methylation", Nature plants, Feb. 2, 2015, vol. 1, No. 14023, pp. 1-7.
Xiong, L. et al., "Regulation of Osmotic Stress-responsive Gene Expression by the LOS6/ABA1 Locus in Arabidopsis", The Journal of Biological Chemistry, Mar. 8, 2002, vol. 277, No. 10, pp. 8588-8596.
Yamamoto, H. Y. "Functional Roles of the Major Chloroplast Lipids in the Violaxanthin Cycle", Planta, Aug. 2006, vol. 224, No. 3, pp. 719-724.
Zhang, L. et al., "Global Analysis of Gene Expression Profiles in Physic Nut (Jatropha curcas L.) Seedlings Exposed to Salt Stress", PLoS One, May 16, 2014, vol. 9, No. 5, pp. 1-9.
PCT International Search Report and Written Opinion dated Jul. 26, 2017 issued in PCT/US2017/034840.
PCT International Preliminary Report on Patentability dated Nov. 27, 2018 issued in PCT/US2017/034840.
EP Office Action dated Jan. 15, 2020 issued in EP 17729973.2.
EP Office Action dated Oct. 29, 2020 issued in EP 17729973.2.
US Office Action [Restriction Requirement] dated Feb. 20, 2020 issued in U.S. Appl. No. 16/304,633.
US Office Action dated Sep. 9, 2020 issued in U.S. Appl. No. 16/304,633.
US Final Office Action dated Apr. 27, 2021 issued in U.S. Appl. No. 16/304,633.
Busch (2014) "Opinion: the red-light response of stomatal movement is sensed by the redox state of the photosynthetic electron transport chain," Photosynth. Res., 119:131-140 [11 pages], Epub Mar. 13, 2013, doi: 10.1007/s11120-013-9805-6.
Coesel et al. (2008) "Evolutionary Origins and Functions of the Carotenoid Biosynthetic Pathway in Marine Diatoms." PLOS One 3: 1-16.
Glowacka et al. (2018) "Photosystem II Subunit S overexpression increases the efficiency of water use in a field-grown crop," Nat. Commun., 9: 868 [9 pages], doi: 10.1038/s41467-018-03231-x.
Hieber et al. (2004) "Significance of the lipid phase in the dynamics and functions of the xanthophyll cycle as revealed by PsbS overexpression in tobacco and in-vitro de-epoxidation in monogalactosyldiacylglycerol micelles," Plant Cell Physiology, 45(1): 92-102.
Huang et al. (2019) "The Arabidopsis Transcriptome Responds Specifically and Dynamically to High Light Stress" Cell Reports, 29: 4186-99.
Iuchi et al. (2000) "A Stress-Inducible Gene for 9-cis-Epoxycarotenoid Dioxygenase Involved in Abscisic Acid Biosynthesis under Water Stress in Drought-Tolerant Cowpea." Plant Physiol., 123: 553-562.
Izumi et al. (2012) "RBCS1A and RBCS3B, two major members within the Arabidopsis RBCS multigene family, function to yield sufficient Rubisco content for leaf photosynthetic capacity." Journal of Experimental Botany, 63(5): 2159-2170.
Kromdijk et al. (2016) "Improving photosynthesis and crop productivity by accelerating recovery from photoprotection." Science, 354: 857-861.
Lambrev et al. (2012) "On the relationship between non-photochemical quenching and photoprotection of Photosystem II." Biochimica et Biophysica Acta, 1817: 760-769.
Liu et al. (2014) "Comparative analysis of carotenoid accumulation in two goji (Lycium barbarum L. and L. ruthenicum Murr.) fruits." Plant Biology 14:269 (14 pages).
Müller et al. (2001) "Non-photochemical quenching. A response to excess light energy." Plant Physiol., 125: 1558-1566, doi: 10.1104/pp.125.4.1558.
Murchie et al. (2011) "Manipulation of Photoprotection to Improve Plant Photosynthesis," Plant Physiology, 155(1): 86-92.
Pinnola et al. (2013) "Zeaxanthin Binds to Light-Harvesting Complex Stress-Related Protein to Enhance Nonphotochemical Quenching in Physcomitrella patens." The Plant Cell, 25: 3519-3534.
Ruban (2016) "Nonphotochemical chlorophyll fluorescence quenching: mechanism and effectiveness in protecting plants from photodamage." Plant Physiol. 170: 1903-1916, doi: 10.1104/p. 15.01935.
Vogl et al. (2015) "A Toolbox of Diverse Promoters Related to Methanol Utilization: Functionally Verified Parts for Heterologous Pathway Expression in Pichia pastoris." ACS Synth. Biol., 5: 172-186.

(56) References Cited

OTHER PUBLICATIONS

Zhang et al. (2015) "MsZEP, a novel zeaxanthin epoxidase gene from alfalfa (*Medicago saliva*), confers drought and salt tolerance in transgenic tobacco." *Plant Cell Rep* 35:439-453 (published online Nov. 2015).
Zhu et al. (2004) "The slow reversibility of photosystem II thermal energy dissipation on transfer from high to low light may cause large losses in carbon gain by crop canopies: A theoretical analysis," *Journal of Experimental Botany*, 55(400): 1167-1175.
Zia et al. (2011) "Acclimation- and mutation-induced enhancement of PsbS levels affects the kinetics of non-photochemical quenching in *Arabidopsis thaliana*," Planta, 233(6): 1253-1264.
Ali, S. B. et al., "Genetic and Epigenetic Characterization of the cry1Ab Coding Region and its 3' Flanking Genomic Region in MON810 Maize using Next-Generation Sequencing", European Food Research and Technology, 2018, vol. 244, pp. 1473-1485.
KR Office Action dated Apr. 1, 2022, in Application No. KR1020187037434 with English translation.
AU Office Action dated Oct. 11, 2022, in Application No. AU2017270579.
BR Office Action dated Sep. 19, 2022 in Application No. BR20181174094 with English translation.
CN Office Action dated Aug. 3, 2022 in Application No. CN201780045867 with English translation.
KR Office Action dated Aug. 30, 2022, in Application No. KR1020187037434 with English translation.
U.S. Notice of Allowance dated Sep. 23, 2022 in U.S. Appl. No. 16/304,633.
U.S. Appl. No. 18/057,190, Inventors Long et al., filed Nov. 18, 2022.
AU Office Action dated Jul. 3, 2023, in AU Application No. AU2017270579.
CN Office Action dated Jun. 25, 2023, in Application No. CN201780045867 with English translation.
EP Office Action dated Nov. 4, 2022, in Application No. EP17729973.2.
IN Office Action dated Nov. 15, 2022 in Application No. IN201817049254.

```
Os_BAA12337.1              RFYDD----ATGLERAVIPPGKGFRAALGLSGGGPLRFTRANLFVGRLARVGIAFSLIG  200  (SEQ ID NO:245)
Os_CAH68096.1              RFYDD----ATGLERAVIPPGKGFRAALGLSGGGPLRFTRANLFVGRLAQLGIAFSLIG  194  (SEQ ID NO:246)
Os_CAE01809.2              RFYDD----ATGLERAVIPPGKGFRAALGLSGGPLRFTKANLFVGRLAQLGIAFSLIG   194  (SEQ ID NO:247)
Os_XP_015633953.1          RFYDD----ATGLERAVIPPGKGFRAALGLSGGPLRFTKANLFVGRLAQLGIAFSLIG   200  (SEQ ID NO:248)
Os_XP_015621169.1          RFYDQ----PVTGLLRAVIPQGKGFRAALGLSGGPLRFTKANLFVGRLAQLGIAFSLIG  215  (SEQ ID NO:249)
Zm_ACG37564.1              RFYDD----EVTGLLRAVIPQGKGFRAALGLSGGPLRFTKNNLFVGRMAQLGVAFSLIG  218  (SEQ ID NO:250)
Zm_NP_001105228.2          RFYDE----EVTGLLRAVIPQGKGFRAALGLSGGPLRFTKSNLFVGRMAQLGVAFSLIG  219  (SEQ ID NO:251)
Zm_AAQ55066.1              RFYDD----EVTGLLRAVIPDGKGFRAALGLSGGPLRFTKSNLFVGRMAQLGVAFSLIG  212  (SEQ ID NO:252)
Nb_ABC59516.1              RFIDPTPTPGLLDKAVIPDGKGFRSALGLSGGPLRFTKANLFVGRLAQLGIAFSLIG   224  (SEQ ID NO:253)
Nt_NP_001312190.1          KFIDDPAPTPGLDKAVIPPGKGFKSALGLSGGPLRFTKANLFVGRLAQLGIAFSLIG   221  (SEQ ID NO:254)
Nt_XP_016484565.1          KFIDDRAPASLLGKAVIPPGKGFTRSALGLKSGGPLRFTKANLFVGRLAQLGIAFSLIG  221  (SEQ ID NO:255)
Nb_ABC59515.1              KFIDDPVFATGLDKAVIPPGKGFKSALGLSGGPLRFTKANLFVGRLAQLGIAFSLIG   221  (SEQ ID NO:256)
At_sp|Q9XF91|PSBS_ARATH    KFVDDP---PTGLEKAVIPGKHVRSALGLKNGPLRFTKANLFVGRLAQLGIAFSLIG   211  (SEQ ID NO:257)
Hb_XP_021647432.1          KFVDDP---PTGLLGAVIPPGKGFTSALGLGLG-SGPLRFTKANLFVGRLAQLGIAFSLIG  219  (SEQ ID NO:258)
Me_Cassava_V7_genomic_Chr18 KFVDDP---PTGLLGAVIPGKSRSALGLGLG-SGPLRFTKANLFVGRLAQLGIAFSLIG  218  (SEQ ID NO:259)
8840000to8855000_rev Vg_Vigun09g165900.1        KFVDDE---BP-MTGGVIPRGKGFTRALGLG-SGPLRFTKANLFVGRLAQLGFYFSLIG  215  (SEQ ID NO:260)
Gm_XP_003523444.1          KFVDDD---BP-TTGGVIPGKGFTRKALGLG-SGPLRFTKANLFVGRLAQLGFYFSLIG  219  (SEQ ID NO:261)
Gm_ACU23291.1              KFVDDD---BP-TTGGVIPGKGFTRKALGLG-SGPLRFTKANLFVGRLAQLGFYFSLIG  219  (SEQ ID NO:262)
Gm_KRH53237.1              KFVDDD---BP-TTGGVIPGKGFTRKALGLG-SGPLRFTKANLFVGRLAQLGFYFSLIG  219  (SEQ ID NO:263)
Gm_NP_001276237.1          KFVDDD---BP-TTGGVIPGKGFTRKALGLG-SGPLRFTKANLFVGRLAQLGFYFSLIG  219  (SEQ ID NO:264)

PLANTS WITH INCREASED WATER USE EFFICIENCY

CROSS-REFERENCE TO RELATED APPLICATION

This application claims the benefit of U.S. Provisional Application No. 62/814,005, filed Mar. 5, 2019, which is hereby incorporated by reference in its entirety.

INCORPORATION BY REFERENCE OF SEQUENCE LISTING PROVIDED AS A TEXT FILE

This application contains references to nucleic acid sequences that have been submitted concurrently herewith as the sequence listing text file "UCAL-P096US_ST25.txt", file size 504,176 bytes, created on May 16, 2021, which is incorporated by reference in its entirety pursuant to 37 C.F.R. § 1.52(e)(5).

TECHNICAL FIELD

The present disclosure relates to genetically altered plants. In particular, the present disclosure relates to genetically altered plants with increased water use efficiency.

BACKGROUND

Water use efficiency (WUE) in plants is becoming increasingly important and is especially important in arid and semiarid regions for environmentally sustainable food production. Food crop production in such regions requires significant supplies of water. Improving WUE in crops will be needed to ensure that these regions can transition to and maintain such environmentally sustainable food production. As time passes the need will only increase. Climate change predictions show increasing temperatures and even drought in these regions and more areas becoming semiarid. Thus, with time, food crops with improved WUE will become a necessity for meeting global food production demands in light of increasing populations and climate change. Equally, food crops with improved WUE will decrease the amount of water required in irrigated agriculture and improve the yield stability of rain fed crops in drier years.

One significant area for improving WUE in crops is through reducing transpiration. Plants lose upwards of 98-99% of the water they absorb via transpiration through their stomata. Stomatal opening and closing impacts both water vapor efflux and $CO_2$ influx in the leaf. If the stomata remain open to allow for maximal $CO_2$ capture, the plant will lose water. Conversely, if the stomata remain closed to reduce stomatal conductance and conserve water, $CO_2$ influx is reduced and the rate of photosynthesis will decline. Therefore, stomatal opening and closing is regulated by a variety of environmental cues, and these environmental cues are perceived and integrated within the plant in order to optimally balance water vapor efflux and $CO_2$ influx.

Progress has been made in unraveling the molecular mechanisms underlying stomatal response to the environmental cues of $CO_2$ concentration and blue light. However, the molecular mechanisms underlying stomatal response to red light remain elusive. Even though individual components relating to stomatal response have been identified, it is not yet clear how the diverse signals regulating stomatal response are integrated in the plant and translated into signals regulating stomata. Given the potential tradeoffs in reducing transpiration and the risk of adversely impacting yields through reduced photosynthesis, stomatal regulation of WUE remains a challenging problem.

A related area of research into improving crops involves a similarly complex issue affecting photosynthesis: dynamic and fluctuating light intensity, especially high light intensity or rapidly increasing light intensity. Over time, this can damage the photosynthetic apparatus, which can result in photoinhibition or persistent reduction of photosynthetic yield. In order to avoid this, plants have evolved photoprotective mechanisms, which are induced when excess light energy is present. One photoprotective mechanism, non-photochemical quenching of chlorophyll fluorescence (NPQ), harmlessly dissipates the excess light energy as heat. NPQ changes, while fast, still lag behind light intensity changes, i.e. changes in absorbed light energy. This lag increases with prolonged or repeated high light conditions, meaning that under these conditions, the plant is increasingly exposed to potential photodamage. While the NPQ quenching sites and mechanisms are still being elucidated, research has demonstrated that photosystem II subunits as well as multiple components of the carotenoid biosynthesis pathway are important for NPQ processes. Therefore, developing plants with reduced NPQ lag that can be used to engineer crops with improved photosynthetic efficiency and therefore higher yields requires multi-component engineering.

Photosystem II Subunit S (PsbS) is a primary component of the photosynthetic apparatus, which is conserved across all plants. When PsbS is overexpressed in conjunction with two other proteins important for NPQ processes, namely zeaxanthin epoxidase (ZEP) and violaxanthin de-epoxidase (VDE), improves the rate of NPQ changes. This multi-component engineering was found to accelerate recovery of NPQ on sun to shade transitions, in turn allowing faster recovery of photosynthetic efficiency and improved crop productivity (Kromdijk et al., Science 2016).

BRIEF SUMMARY

In order to test whether the improvement in photosynthetic efficiency and crop productivity observed when modifying three components of the NPQ pathway could be achieved through modification of a single component, PsbS overexpression was evaluated on its own. PsbS overexpression alone did not improve the photosynthetic efficiency. However, surprisingly, it was found that PsbS overexpression resulted in plants with reduced stomatal conductance and increased water use efficiency. This surprising new utility for PsbS identified by the inventors serves as the basis for many of the aspects and their various embodiments of the present disclosure.

An aspect of the disclosure includes a method of cultivating a genetically altered plant with increased water use efficiency, including the steps of: (a) providing the genetically altered plant, wherein the plant or a part thereof includes one or more genetic alterations; and (b) cultivating the genetically altered plant under conditions wherein the one or more genetic alterations increase activity of a Photosystem II Subunit S (PsbS) protein as compared to a wild type (WT) plant without the one or more genetic alterations, and wherein the increased activity of the PsbS protein increases water use efficiency as compared to the WT plant grown under the same conditions. An additional embodiment of this aspect includes the conditions being reduced irrigation conditions. A further embodiment of this aspect includes the conditions being rain fed conditions. Yet another embodiment of this aspect includes the conditions being high density growth conditions. Still another embodiment of this aspect includes the conditions being mild salinity. In an additional embodiment of this aspect, the conditions are fertilized or providing additional nutrients. In a further embodiment of this aspect, the conditions are humid conditions or conditions resulting in wet leaf surfaces. In another embodiment of this present aspect, which may be combined with any of the preceding embodiments, the increased activity of the PsbS protein provides the genetically altered plant with a higher yield, an increased biomass, an increased growth rate, an increased tolerance of salinity, an increased ability to withstand salinity, an increased flow of nutrients to the roots, an increased availability of nutrients over time, an increased utilization of fertilizer, an increased utilization of nutrients, a decreased susceptibility to a plant disease requiring humid conditions and/or wet leaf surfaces for infection, a decreased susceptibility to infection by the plant disease, a reduced incidence of the plant disease, or a reduced incidence of infection by the plant disease as compared to the WT plant without the increased activity grown under the same conditions where the activity of the PsbS protein is increased.

In yet another embodiment of this present aspect, which may be combined with any of the preceding embodiments, the genetically altered plant does not include increased activity of zeaxanthin epoxidase (ZEP) protein, violaxanthin de-epoxidase (VDE) protein, or both, as compared to a WT plant. In a further embodiment of this present aspect, which may be combined with any of the preceding embodiments, the genetically altered plant does not include reduced activity of $K^+$ efflux antiporter 3 (KEA3) as compared to a WT plant.

In still another embodiment of this aspect that can be combined with any of the relevant preceding embodiments, the genetically altered plant further includes increased activity of a ZEP protein and increased activity of a VDE protein, wherein the increased activity of the PsbS protein is greater than the increased activity of the PsbS protein required for increased photosynthetic efficiency when each of the ZEP protein, the PsbS protein, and the VDE protein are overexpressed together. An additional embodiment of this aspect includes increased activity of the PsbS protein being due to an increased amount of the PsbS protein. In yet another embodiment of this aspect, the increased amount of the PsbS protein is at least 10% greater, at least 20% greater, at least 30% greater, at least 40% greater, at least 50% greater, at least 75% greater, at least 100% greater, at least 150% greater, or at least 200% greater than the increased activity of the PsbS protein required for increased photosynthetic efficiency when each of the ZEP protein, the PsbS protein, and the VDE protein are overexpressed together. Still another embodiment of this aspect includes the increased amount of the PsbS protein being no greater than 500%, no greater than 400%, no greater than 300%, no greater than 200%, no greater than 150%, no greater than 100%, no greater than 75%, or no greater than 50%, of the increased activity of the PsbS protein required for increased photosynthetic efficiency when each of the ZEP protein, the PsbS protein, and the VDE protein are overexpressed together. Another embodiment of this aspect includes the increased amount of PsbS, the increased amount of ZEP, and the increased amount of VDE being increased relative to an amount of endogenous PsbS protein, an amount of endogenous ZEP protein, and an amount of endogenous VDE protein, and wherein the increased amount of PsbS is 10% or more, 12% or more, 14% or more, 16% or more, 18% or more, 20% or more, 22% or more, 24% or more, 30% or more, 40% or more, 50% or more, 100% or more, or 200% or more increased relative to the amount of endogenous PsbS protein, the increased amount of ZEP is 90% increased relative to the amount of endogenous ZEP protein, and the increased amount of VDE is 80% increased relative to the amount of endogenous VDE protein. In a further embodiment of this aspect, the increased amount of PsbS, the increased amount of ZEP, and the increased amount of VDE is increased relative to an amount of endogenous PsbS protein, an amount of endogenous ZEP protein, and an amount of endogenous VDE protein, and wherein the increased amount of PsbS is 12% increased relative to the amount of endogenous PsbS protein, the increased amount of ZEP is 90% increased relative to the amount of endogenous ZEP protein, and the increased amount of VDE is 80% increased relative to the amount of endogenous VDE protein. In yet another embodiment of this aspect, which may be combined with any of the preceding embodiments that has increased activity of a ZEP protein and increased activity of a VDE protein, the increased activity of the PsbS, VDE, and ZEP proteins provides the genetically altered plant with increased photosynthetic efficiency under non-steady state conditions as compared to the WT plant without the increased activity grown under the same conditions where the activity of the PsbS, VDE, and ZEP proteins is increased.

Still another embodiment of this present aspect, which may be combined with any of the preceding embodiments, includes the genetically altered plant being selected from the group of cowpea, soybean, cassava, wheat, barley, corn, sorghum, rice, cotton, sugarcane, eucalyptus, poplar, willow, orange, grapefruit, lemon, lime, avocado, cherry, peach, plum, apricot, nectarine, fig, olive, almond, pistachio, walnut, chestnut, hazelnut, pecan, tomato, eggplant, potato, or alfalfa. An additional embodiment of this aspect includes the genetically altered plant not being rice or *Arabidopsis*.

A further embodiment of this aspect that can be combined with any of the preceding embodiments includes the genetically altered plant being provided in step (a) by planting a genetically altered seedling, a genetically altered plantlet, a genetically altered cutting, a genetically altered tuber, a genetically altered root, or a genetically altered seed to produce the genetically altered plant, or by grafting the genetically altered seedling, the genetically altered plantlet, or the genetically altered cutting to a root stock or a second plant to produce the genetically altered plant. In still another embodiment of this aspect that can be combined with any of the preceding embodiments, the genetically altered plant is cultivated in step (b) to produce harvestable seed and fruits or vegetatively produced harvested items. An additional embodiment of this aspect includes the harvestable seed and fruits being selected from seed, fruit, pods, grain, kernels, beans, and peas; and wherein the vegetatively produced harvested items are selected from tubers, rhizomes, buds, roots, cuttings, and leaves. A further embodiment of this aspect that can be combined with any of the preceding embodiments that has harvestable seed and fruit or vegetatively produced harvestable items further includes harvesting the harvestable seed, harvestable leaves, harvestable roots, harvestable cuttings, harvestable fruit, harvestable kernels, harvestable tubers, harvestable pods, harvestable peas, harvestable beans, and/or harvestable grain.

Still another embodiment of this aspect that can be combined with any of the preceding embodiments includes the increased activity of the PsbS protein providing the genetically altered plant with decreased stomatal conductance as compared to the WT plant without the increased activity grown under the same conditions where the activity of the PsbS protein is increased. In yet another embodiment of this aspect, which may be combined with any of the preceding embodiments that does not have increased activity of a ZEP protein and increased activity of a VDE protein, the increased activity of the PsbS protein provides the genetically altered plant with substantially similar photosynthetic efficiency as compared to the WT plant grown under the same conditions where the activity of the PsbS protein is increased.

In a further embodiment of this aspect that can be combined with any of the preceding embodiments, increased activity is increased expression. An additional embodiment of this aspect includes the increased expression being due to expression of a heterologous PsbS protein. A further embodiment of this aspect includes the heterologous PsbS protein including at least 70% sequence identity to, at least 75% sequence identity to, at least 80% sequence identity to, at least 85% sequence identity to, at least 90% sequence identity to, at least 95% sequence identity to, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. Yet another embodiment of this aspect includes the heterologous PsbS protein being selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. A further embodiment of this aspect that can be combined with any of the preceding embodiments that has a heterologous PsbS protein includes the heterologous PsbS protein containing a glutamate at a position corresponding to amino acid 149 of reference sequence SEQ ID NO: 21 and a glutamate at a position corresponding to amino acid 255 of reference sequence SEQ ID NO: 21. Still another embodiment of this aspect that can be combined with any of the preceding embodiments that has a heterologous PsbS protein includes the heterologous PsbS protein being encoded by a first nucleic acid and the first nucleic acid being operably linked to a second nucleic acid including a promoter. An additional embodiment of this aspect includes the promoter being selected from the group of a CaMV35S promoter, a ubiquitin promoter, a Rbcs1A promoter, a GAPA-1 promoter, a FBA2 promoter, or any combination thereof. Still another embodiment of this aspect that can be combined with any of the preceding embodiments that has a nucleic acid sequence includes the first nucleic acid sequence and the second nucleic acid sequence being stably integrated into a nuclear genome of the plant or into a chloroplast genome of the plant. A further embodiment of this aspect includes the increased expression being due to overexpression of an endogenous PsbS protein. An additional embodiment of this aspect includes overexpression of the endogenous PsbS protein being achieved using a gene editing technique to introduce the one or more genetic alterations that increase the activity of the endogenous PsbS protein. Still another embodiment of this aspect includes the gene editing technique being selected from the group of transcription activator-like effector nuclease (TALEN) gene editing techniques, clustered Regularly Interspaced Short Palindromic Repeat (CRISPR/Cas) gene editing techniques, or zinc-finger nuclease (ZFN) gene editing techniques. Still another embodiment of this aspect that can be combined with any of the preceding embodiments that has a gene editing technique includes the one or more genetic alterations that increase the activity of the endogenous PsbS protein being selected from the group of inactivating a repressor element that represses expression of the endogenous PsbS protein, removing a repressor element that represses expression of the endogenous PsbS protein, modulating the methylation state of a repressor element that represses expression of the endogenous PsbS protein, activating an enhancer element that increases expression of the endogenous PsbS protein, adding an enhancer element that increases expression of the endogenous PsbS protein, modulating the methylation state of an enhancer element that increases expression of the endogenous PsbS protein, adding a transcriptional activator recruiting or binding element that activates expression of the endogenous PsbS protein, replacing the endogenous promoter with an overexpression promoter that directs expression of the endogenous PsbS protein, modulating the methylation state of the endogenous promoter; modulating the methylation state of the endogenous PsbS coding sequence; adding elements that stabilize an endogenous PsbS mRNA, removing elements that destabilize the endogenous PsbS mRNA, modifying a PsbS coding sequence to increase stability of the PsbS protein, or modifying a PsbS coding sequence to increase activity of the PsbS protein.

In still another embodiment of this aspect that can be combined with any of the preceding embodiments, the PsbS protein is localized to a thylakoid membrane of at least one chloroplast within a cell of the genetically altered plant. An additional embodiment of this aspect includes the cell being a chloroplast containing leaf cell. A further embodiment of this aspect includes the cell being a mesophyll cell or a guard cell. In yet another embodiment of this aspect that can be combined with any of the preceding embodiments that has localization of the PsbS protein, the PsbS protein is expressed in at least 70% of the cells.

Yet another embodiment of this aspect that can be combined with any of the relevant preceding embodiments with respect to a genetically altered plant includes a genetically altered plant produced from the method of any one of the preceding embodiments. An additional embodiment of this aspect includes a genetically altered plant part produced from the genetically altered plant, wherein the plant part is a leaf, a stem, a root, a flower, a seed, a kernel, a grain, a pod, a bean, a pea, a fruit, a chloroplast, a cell, or a portion thereof and the genetically altered plant part includes the one or more genetic alterations. A further embodiment of this aspect includes the plant part being a fruit, a kernel, a grain, a pod, a bean, or a pea. Still another embodiment of this aspect includes a genetically altered pollen grain or a genetically altered ovule of the genetically altered plant, wherein the genetically altered pollen grain or the genetically altered ovule includes the one or more genetic alterations. Yet another embodiment of this aspect includes a genetically altered protoplast produced from the genetically altered plant, wherein the genetically altered protoplast includes the one or more genetic alterations. A further embodiment of this aspect includes a genetically altered tissue culture produced from protoplasts or cells from the genetically altered plant wherein the cells or protoplasts are produced from a plant part selected from the group of leaf, leaf mesophyll cell, anther, pistil, stem, petiole, root, root tip, fruit, seed, kernel, grain, pod, bean, pea, flower, cotyledon, hypocotyl, embryo, or meristematic cell, wherein genetically altered tissue culture includes the one or more genetic alterations. An additional embodiment of this aspect includes a genetically altered plant regenerated from the genetically altered tissue culture that includes the one or more genetic alterations. In still another embodiment of this aspect, the genetically altered plant regenerated from the genetically altered tissue culture has all the physiological and morphological characteristics of the genetically altered plant produced from the method of any one of the preceding embodiments.

An additional aspect of the disclosure includes a genetically altered plant or part thereof including one or more genetic alterations that increase activity of a PsbS protein as compared to a WT plant without the one or more genetic alterations, wherein the genetically altered plant shows increased water use efficiency as compared to the WT plant grown under the same conditions. An additional embodiment of this aspect includes the conditions being selected from the group of reduced irrigation conditions, rain fed conditions, high density growth conditions, mild salinity, fertilized or providing additional nutrients, humid conditions, or conditions resulting in wet leaf surfaces. In yet another embodiment of this aspect, which may be combined with any of the preceding embodiments, the increased activity of the PsbS protein provides the genetically altered plant with a higher yield, an increased biomass, an increased growth rate, an increased tolerance of salinity, an increased ability to withstand salinity, an increased flow of nutrients to the roots, an increased availability of nutrients over time, an increased utilization of fertilizer, an increased utilization of nutrients, a decreased susceptibility to a plant disease requiring humid conditions and/or wet leaf surfaces for infection, a decreased susceptibility to infection by the plant disease, a reduced incidence of the plant disease, or a reduced incidence of infection by the plant disease as compared to the WT plant without the increased activity grown under the same conditions where the activity of the PsbS protein is increased. In still another embodiment of this aspect that can be combined with any of the preceding embodiments, the genetically altered plant does not include increased activity of proteins ZEP, VDE, or both, as compared to a WT plant. In an additional embodiment of this aspect that can be combined with any of the preceding embodiments, the genetically altered plant does not include reduced activity of KEA3 as compared to a WT plant.

In still another embodiment of this aspect that can be combined with any of the relevant preceding embodiments, the genetically altered plant further includes increased activity of a ZEP protein and increased activity of a VDE protein, wherein the increased activity of the PsbS protein is greater than the increased activity of the PsbS protein required for increased photosynthetic efficiency when each of the ZEP protein, the PsbS protein, and the VDE protein are overexpressed together. An additional embodiment of this aspect includes increased activity of the PsbS protein being due to an increased amount of the PsbS protein. In yet another embodiment of this aspect, the increased amount of PsbS protein is at least 10% greater, at least 20% greater, at least 30% greater, at least 40% greater, at least 50% greater, at least 75% greater, at least 100% greater, at least 150% greater, or at least 200% greater than the increased activity of the PsbS protein required for increased photosynthetic efficiency when each of the ZEP protein, the PsbS protein, and the VDE protein are overexpressed together. Still another embodiment of this aspect includes the increased amount of PsbS protein being no greater than 500%, no greater than 400%, no greater than 300%, no greater than 200%, no greater than 150%, no greater than 100%, no greater than 75%, or no greater than 50%, of the increased activity of the PsbS protein required for increased photosynthetic efficiency when each of the ZEP protein, the PsbS protein, and the VDE protein are overexpressed together. Another embodiment of this aspect includes the increased amount of PsbS, the increased amount of ZEP, and the increased amount of VDE being increased relative to an amount of endogenous PsbS protein, an amount of endogenous ZEP protein, and an amount of endogenous VDE protein, and wherein the increased amount of PsbS is 10% or more, 12% or more, 14% or more, 16% or more, 18% or more, 20% or more, 22% or more, 24% or more, 30% or more, 40% or more, 50% or more, 100% or more, or 200% or more increased relative to the amount of endogenous PsbS protein, the increased amount of ZEP is 90% increased relative to the amount of endogenous ZEP protein, and the increased amount of VDE is 80% increased relative to the amount of endogenous VDE protein. In a further embodiment of this aspect, the increased amount of PsbS, the increased amount of ZEP, and the increased amount of VDE is increased relative to an amount of endogenous PsbS protein, an amount of endogenous ZEP protein, and an amount of endogenous VDE protein, and wherein the increased amount of PsbS is 12% increased relative to the amount of endogenous PsbS protein, the increased amount of ZEP is 90% increased relative to the amount of endogenous ZEP protein, and the increased amount of VDE is 80% increased relative to the amount of endogenous VDE protein. In yet another embodiment of this aspect, which may be combined with any of the preceding embodiments that has increased activity of a ZEP protein and increased activity of a VDE protein, the increased activity of the PsbS, VDE, and ZEP proteins provides the genetically altered plant with increased photosynthetic efficiency under non-steady state conditions as compared to the WT plant without the increased activity grown under the same conditions where the activity of the PsbS, VDE, and ZEP proteins is increased.

Still another embodiment of this present aspect, which may be combined with any of the preceding embodiments, includes the genetically altered plant being selected from the group of cowpea, soybean, cassava, wheat, barley, corn, sorghum, rice, cotton, sugarcane, eucalyptus, poplar, willow, orange, grapefruit, lemon, lime, avocado, cherry, peach, plum, apricot, nectarine, fig, olive, almond, pistachio, walnut, chestnut, hazelnut, pecan, tomato, eggplant, potato, or alfalfa. An additional embodiment of this aspect includes the genetically altered plant not being rice or *Arabidopsis*.

Still another embodiment of this aspect that can be combined with any of the preceding embodiments includes the increased activity of the PsbS protein providing the genetically altered plant with decreased stomatal conductance as compared to the WT plant without the increased activity grown under the same conditions where the activity of the PsbS protein is increased. In yet another embodiment of this aspect, which may be combined with any of the preceding embodiments that does not have increased activity of a ZEP protein and increased activity of a VDE protein, the increased activity of the PsbS protein provides the genetically altered plant with substantially similar photosynthetic efficiency as compared to the WT plant grown under the same conditions where the activity of the PsbS protein is increased.

In a further embodiment of this aspect that can be combined with any of the preceding embodiments, increased activity is increased expression. An additional embodiment of this aspect includes the increased expression being due to expression of a heterologous PsbS protein. A further embodiment of this aspect includes the heterologous PsbS protein including an amino acid sequence with at least 70% sequence identity to, at least 75% sequence identity to, at least 80% sequence identity to, at least 85% sequence identity to, at least 90% sequence identity to, at least 95% sequence identity to, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO:

102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. Yet another embodiment of this aspect includes the heterologous PsbS protein being selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. A further embodiment of this aspect that can be combined with any of the preceding embodiments that has a heterologous PsbS protein includes the heterologous PsbS protein containing a glutamate at a position corresponding to amino acid 149 of reference sequence SEQ ID NO: 21 and a glutamate at a position corresponding to amino acid 255 of reference sequence SEQ ID NO: 21. Still another embodiment of this aspect that can be combined with any of the preceding embodiments that has a heterologous PsbS protein includes the heterologous PsbS protein being encoded by a first nucleic acid and the first nucleic acid being operably linked to a second nucleic acid including a promoter. An additional embodiment of this aspect includes the promoter being selected from the group of a CaMV35S promoter, a ubiquitin promoter, a Rbcs1A promoter, a GAPA-1 promoter, a FBA2 promoter, or any combination thereof. Still another embodiment of this aspect that has a nucleic acid sequence includes the first nucleic acid sequence and the second nucleic acid sequence being stably integrated into a nuclear genome of the plant or into a chloroplast genome of the plant. A further embodiment of this aspect includes the increased expression being due to overexpression of an endogenous PsbS protein. An additional embodiment of this aspect includes overexpression of the endogenous PsbS protein being achieved using a gene editing technique to introduce the one or more genetic alterations that increase the activity of the endogenous PsbS protein. Still another embodiment of this aspect includes the gene editing technique being selected from the group of transcription activator-like effector nuclease (TALEN) gene editing techniques, clustered Regularly Interspaced Short Palindromic Repeat (CRISPR/Cas) gene editing techniques, or zinc-finger nuclease (ZFN) gene editing techniques. Still another embodiment of this aspect that can be combined with any of the preceding embodiments that has a gene editing technique includes the one or more genetic alterations that increase the activity of the endogenous PsbS protein are selected from the group of inactivating a repressor element that represses expression of the endogenous PsbS protein, removing a repressor element that represses expression of the endogenous PsbS protein, modulating the methylation state of a repressor element that represses expression of the endogenous PsbS protein, activating an enhancer element that increases expression of the endogenous PsbS protein, adding an enhancer element that increases expression of the endogenous PsbS protein, modulating the methylation state of an enhancer element that increases expression of the endogenous PsbS protein, adding a transcriptional activator recruiting or binding element that activates expression of the endogenous PsbS protein, replacing the endogenous promoter with an overexpression promoter that directs expression of the endogenous PsbS protein, modulating the methylation state of the endogenous promoter; modulating the methylation state of the endogenous PsbS coding sequence; adding elements that stabilize an endogenous PsbS mRNA, removing elements that destabilize the endogenous PsbS mRNA, modifying a PsbS coding sequence to increase stability of the PsbS protein, or modifying a PsbS coding sequence to increase activity of the PsbS protein.

In still another embodiment of this aspect that can be combined with any of the preceding embodiments, the PsbS protein is localized to a thylakoid membrane of at least one chloroplast within a cell of the genetically altered plant. An additional embodiment of this aspect includes the cell being a chloroplast containing leaf cell. A further embodiment of this aspect includes the cell being a mesophyll cell or a guard cell. In yet another embodiment of this aspect that can be combined with any of the preceding embodiments that has localization of the PsbS protein, the PsbS protein is expressed in at least 70% of the cells.

Yet another embodiment of this aspect that can be combined with any of the preceding embodiments with respect to seed includes a genetically altered seed produced from the genetically altered plant of any one of the preceding embodiments. Still another embodiment of this aspect that can be combined with any of the preceding embodiments with respect to plant part includes the plant part being a leaf, a stem, a root, a flower, a seed, a kernel, a grain, a pod, a bean, a pea, a fruit, a chloroplast, a cell, or a portion thereof and the genetically altered plant part including the one or more genetic alterations. A further embodiment of this aspect includes the plant part being a fruit, a kernel, a grain, a pod, a bean, or a pea. Still another embodiment of this aspect that can be combined with any of the preceding embodiments with respect to pollen grain or ovules includes a genetically altered pollen grain or a genetically altered ovule of the plant of any one of the preceding embodiments, wherein the genetically altered pollen grain or the genetically altered ovule includes the one or more genetic alterations. A further embodiment of this aspect that can be combined with any of the preceding embodiments includes a genetically altered protoplast produced from the genetically altered plant of any of the preceding embodiments, wherein the genetically altered protoplast includes the one or more genetic alterations. An additional embodiment of this aspect that can be combined with any of the preceding embodiments includes a genetically altered tissue culture produced from protoplasts or cells from the genetically altered plant of any one of the preceding embodiments, wherein the cells or protoplasts are produced from a plant part selected from the group of leaf, leaf mesophyll cell, anther, pistil, stem, petiole, root, root tip, tuber, fruit, seed, kernel, grain, flower, cotyledon, hypocotyl, embryo, or meristematic cell, wherein the genetically altered tissue culture includes the one or more genetic alterations. An additional embodiment of this aspect includes a genetically altered plant regenerated from the genetically altered tissue culture that includes the one or more genetic alterations. In still another embodiment of this aspect, the genetically altered plant regenerated from the genetically altered tissue culture has all the physiological and morphological characteristics of the genetically altered plant produced from the method of any one of the preceding embodiments.

An additional aspect of the disclosure includes methods of cultivating the genetically altered plant of any of the preceding embodiments including the steps of (a) planting a genetically altered seedling, a genetically altered plantlet, a genetically altered cutting, a genetically altered tuber, a genetically altered root, or a genetically altered seed to produce the genetically altered plant, or by grafting the genetically altered seedling, the genetically altered plantlet, or the genetically altered cutting to a root stock or a second plant to produce the genetically altered plant; (b) cultivating the genetically altered plant to produce harvestable seed and fruits or vegetatively produced harvested items, wherein the harvestable seed and fruits is selected from seed, fruit, pods, grain, kernels, beans, and peas, and wherein the vegetatively produced harvested items are selected from tubers, rhizomes, buds, roots, cuttings, and leaves; and (c) harvesting the harvestable seed, harvestable leaves, harvestable roots, harvestable cuttings, harvestable fruit, harvestable kernels, harvestable tubers, harvestable pods, harvestable peas, harvestable beans, and/or harvestable grain.

An additional aspect of the disclosure includes methods of producing the genetically altered plant of any of the preceding embodiments including the steps of (a) transforming a plant cell, tissue, or other explant with a vector including a first nucleic acid sequence encoding a PsbS protein operably linked to a second nucleic acid sequence encoding a promoter; (b) selecting successful transformation events by means of a selection agent, marker-assisted selection, or selective media; (c) regenerating the transformed cell, tissue, or other explant into a genetically altered plantlet; and (d) growing the genetically altered plantlet into a genetically altered plant with increased activity of a PsbS protein as compared to an untransformed WT plant. An additional embodiment of this aspect further includes identifying successful introduction of the one or more genetic alterations by screening or selecting the plant cell, tissue, or other explant prior to step (b); screening or selecting plantlets between step (b) and (c); or screening or selecting plants after step (c). In yet another embodiment of this aspect, which may be combined with any of the preceding embodiments, transformation is done using a transformation method selected from the group of particle bombardment (i.e., biolistics, gene gun), *Agrobacterium*-mediated transformation, *Rhizobium*-mediated transformation, or protoplast transfection or transformation. In still another embodiment of this aspect, which may be combined with any of the preceding embodiments, the vector is pEG100. A further embodiment of this aspect includes the PsbS protein including an amino acid sequence with at least 70% sequence identity to, at least 75% sequence identity to, at least 80% sequence identity to, at least 85% sequence identity to, at least 90% sequence identity to, at least 95% sequence identity to, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. Yet another embodiment of this aspect includes the PsbS protein being selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. A further embodiment of this aspect that can be combined with any of the preceding embodiments includes the PsbS protein containing a glutamate at a position corresponding to amino acid 149 of reference sequence SEQ ID NO: 21 and a glutamate at a position corresponding to amino acid 255 of reference sequence SEQ ID NO: 21. Still another embodiment of this aspect that can be combined with any of the preceding embodiments includes the heterologous PsbS protein being encoded by a first nucleic acid and the first nucleic acid being operably linked to a second nucleic acid including a promoter. An additional embodiment of this aspect includes the promoter being selected from the group of a CaMV35S promoter, a ubiquitin promoter, a Rbcs1A promoter, a GAPA-1 promoter, a FBA2 promoter, or any combination thereof. Still another embodiment of this aspect that can be combined with any of the preceding embodiments that has a nucleic acid sequence includes the first nucleic acid sequence and the second nucleic acid sequence being stably integrated into a nuclear genome of the plant or into a chloroplast genome of the plant.

A further aspect of the disclosure includes methods of producing the genetically altered plant of any of the preceding embodiments, including the steps of (a) transforming a plant cell, tissue, or other explant with one or more gene editing components that target a nuclear genome sequence operably linked to an endogenous PsbS protein; (b) selecting successful transformation events by means of a screening technology, an enriching technology, a selection agent, marker-assisted selection, or selective media; (c) regenerating the transformed cell, tissue, or other explant into a genetically altered plantlet; and (d) growing the genetically altered plantlet into a genetically altered plant with increased activity of a PsbS protein as compared to an untransformed WT plant. An additional embodiment of this aspect includes the one or more gene editing components including a ribonucleoprotein complex that targets the nuclear genome sequence; a vector including a TALEN protein encoding sequence, wherein the TALEN protein targets the nuclear genome sequence; a vector including a ZFN protein encoding sequence, wherein the ZFN protein targets the nuclear genome sequence; an oligonucleotide donor (OND), wherein the OND targets the nuclear genome sequence; or a vector CRISPR/Cas enzyme encoding sequence and a targeting sequence, wherein the targeting sequence targets the nuclear genome sequence.

Still another aspect of the disclosure includes methods of identifying genetic markers associated with increased PsbS protein activity in a plant, including the steps of (a) screening a population of plants from the same species or closely related species for PsbS protein activity; (b) identifying a subset of plants from the population with higher levels of PsbS activity as compared to the other plants in the population; and (c) identifying genetic markers associated with increased PsbS activity in the subset of plants. An additional embodiment of this aspect includes the increased PsbS protein activity being due to increased expression of a PsbS mRNA and the screening in step (a) being assaying levels of the PsbS mRNA, optionally using a method selected from the group of RNA-Seq, microarray, Northern blot, or qRT-PCR. A further embodiment of this aspect includes the increased PsbS protein activity being due to increased amount of the PsbS protein and the screening in step (a) being assaying levels of the PsbS protein, optionally using a method selected from the group of Western blot, ELISA, immunoprecipitation, HPLC, or LC/MS.

Yet another aspect of the disclosure includes methods of producing a plant with increased WUE activity and a second desired trait, including the steps of (a) providing a first plant including a genetic marker associated with increased PsbS activity and a second plant including the second desired trait; (b) crossing the first plant with the second plant to create a population of progeny plants; and (c) selecting the plant with increased WUE activity and the second desired trait using the genetic marker associated with increased PsbS activity. An additional embodiment of this aspect includes the second desired trait being increased PsbS activity unlinked to the genetic marker associated with increased PsbS activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows NPQ as a function of incident light intensity in WT and mutant *N. tabacum* lines grown under controlled conditions. Open circles represent partially silenced PsbS mutant line psbs-4, gray circles represent WT, red triangles represent PsbS overexpression line PSBS-28, and red circles represent PsbS overexpression line PSBS-43. (Asterisks/lines show significant differences from WT (P<0.0001), black for silencing, red for overexpressing lines; Dunnett's two-way test; α=0.05; error bars indicate standard error of the mean (s.e.m.); n=6 to 10 biological replicates). FIG. 1B shows NPQ levels in leaf discs of WT and mutant *N. tabacum* lines grown under field-test conditions.

FIG. 2A shows relative PsbS mRNA expression normalized to actin and tubulin for WT and mutant *N. tabacum* lines grown under controlled conditions. The white column represents partially silenced PsbS mutant line psbs-4, the gray column represents WT, and the red columns represent PsbS overexpression lines PSBS-28 and PSBS-43. (Asterisks show significant differences from WT (P<0.0001); Dunnett's two-way test; α=0.05; error bars indicate s.e.m.; n=6 to 10 biological replicates). FIG. 2B shows a developmental time-course of relative PsbS mRNA expression normalized to actin and tubulin, which were used as internal standards, in WT and mutant *N. tabacum* lines grown under field-test conditions. The white column represents partially silenced PsbS mutant line psbs-4, the gray column represents WT, and the red columns represent PsbS overexpression lines PSBS-28, PSBS-34, PSBS-43, and PSBS-46. (All genotypes significantly different from WT; Dunnett's two-way test; p≤0.008; error bars indicate s.e.m; n=4 biological replicates).

FIG. 3A shows PsbS protein expression normalized to PsbO expression, which was used as an internal control, as determined from immunoblot densitometry readings for WT and mutant *N. tabacum* lines grown under controlled conditions. The white column represents partially silenced PsbS mutant line psbs-4, the gray column represents WT, and the red columns represent PsbS overexpression lines PSBS-28 and PSBS-43. (Asterisks show significant differences from WT (P<0.0001); Dunnett's two-way test; α=0.05; error bars indicate s.e.m.; n=6 to 10 biological replicates). FIG. 3B shows a representative immunoblot for PsbS and PsbO protein expression in WT and mutant *N. tabacum* plant lines grown under control conditions. FIG. 3C shows a developmental time-course of PsbS protein expression normalized to PsbO expression, which was used as an internal control, in WT and mutant *N. tabacum* lines grown under field-test conditions. The white column represents partially silenced PsbS mutant line psbs-4, the gray column represents WT, and the red columns represent PsbS overexpression lines PSBS-28, PSBS-34, PSBS-43, and PSBS-46. (All genotypes significantly different from WT; Dunnett's two-way test; p≤0.001; error bars indicate s.e.m; n=4 biological replicates).

FIG. 4A shows net $CO_2$ assimilation ($A_n$) as a function of incident light intensity in WT and mutant *N. tabacum* lines grown under controlled conditions (P=0.60). FIG. 4B shows stomatal conductance as a function of incident light intensity in WT and mutant *N. tabacum* lines grown under controlled conditions (P=0.73). FIG. 4C shows a strong positive correlation between water use efficiency (net $CO_2$ assimilation ($A_n$)/stomatal conductance ($g_s$)) and PsbS expression ($R^2$=0.92; P=0.03). Thus, plants with increased PsbS expression have improved WUE. FIG. 4D shows redox state of plastoquinone ($Q_A$) as a function of incident light intensity in WT and mutant *N. tabacum* lines grown under controlled conditions (P=0.0001). FIG. 4E shows a highly significant positive correlation and linear relationship between $Q_A$ redox state and stomatal conductance ($g_s$) in WT and mutant *N. tabacum* lines grown under controlled conditions ($R^2$=0.98; P<0.0001). (Broken lines indicate measurements at highest light intensity). For all figures, open circles represent partially silenced PsbS mutant line psbs-4, gray circles represent WT, red triangles represent PsbS overexpression line PSBS-28, and red circles represent PsbS overexpression line PSBS-43. (Asterisks/lines show significant differences from WT, black for silencing, red for overexpressing lines; Dunnett's two-way test; α=0.05; error bars indicate s.e.m.; n=6 to 10 biological replicates).

FIG. 5A shows stomatal density (abaxial leaf side P=0.006; adaxial leaf side P=0.02), FIG. 5B shows stomatal complex width (abaxial leaf side P=0.62; adaxial leaf side P=0.41), FIG. 5C shows stomatal complex length (abaxial leaf side P=0.96; adaxial leaf side P=0.69), and FIG. 5D shows stomatal complex width×length (abaxial leaf side P=0.92; adaxial leaf side P=0.53) in WT and mutant N. tabacum lines grown under controlled conditions. The white column represents partially silenced PsbS mutant line psbs-4, the gray column represents WT, the red column represents PsbS overexpression line PSBS-28, and the red lined column represent PsbS overexpression line PSBS-43. (Asterisks show significant differences from WT; Dunnett's two-way test; α=0.05; error bars indicate s.e.m.; n=4 biological replicates).

FIG. 6A shows net $CO_2$ assimilation ($A_n$) as a function of incident light intensity in WT and mutant N. tabacum lines grown under field-test conditions. FIG. 6B shows net $CO_2$ assimilation ($A_n$) in mutant N. tabacum lines relative to WT grown under field-test conditions (P=0.96). FIG. 6C shows stomatal conductance ($g_s$) as a function of incident light intensity in WT and mutant N. tabacum lines grown under field-test conditions. The effect on $g_s$ is much larger than the effect on $CO_2$ assimilation ($A_n$) shown in FIG. 6A. FIG. 6D shows stomatal conductance ($g_s$) in mutant N. tabacum lines relative to WT grown under field-test conditions (P=0.0001). FIG. 6E shows water use efficiency ($A_n/g_s$) in mutant N. tabacum lines relative to WT grown under field-test conditions (P=0.007). FIG. 6F shows a strong positive correlation between water use efficiency ($A_n/g_s$) and relative PsbS expression ($R^2$=0.94; P=0.004). For FIGS. 6A, 6C, and 6F, open circles represent partially silenced PsbS mutant line psbs-4, gray circles represent WT, red triangles represent PsbS overexpression line PSBS-28, red diamonds represent PsbS overexpression line PSBS-34, and red circles represent PsbS overexpression line PSBS-43. For FIGS. 6B, 6D, and 6E, the white column represents partially silenced PsbS mutant line psbs-4 and the red columns represent PsbS overexpression lines PSBS-28, PSBS-34, and PSBS-43. (Error bars indicate s.e.m.; n=4 biological replicates).

FIG. 7A shows $CO_2$ fixation rate as a function of chloroplastic $CO_2$ concentration in WT and mutant N. tabacum lines grown under controlled conditions. FIG. 7B shows electron transport rate as a function of incident light intensity in WT and mutant N. tabacum lines grown under controlled conditions. FIG. 7C shows maximum ribulose bisphosphate carboxylation capacity (P=0.29), FIG. 7D shows maximum rate linear electron transport (P=0.07), FIG. 7E shows Rubisco content (P=0.90), FIG. 7F Rubisco activation state (P=0.06), and FIG. 7G shows stomatal limitation in the youngest fully expanded leaves of WT and mutant N. tabacum lines grown under controlled conditions (P=0.006). For FIGS. 7A and 7B, open circles represent partially silenced PsbS mutant line psbs-4, gray circles represent WT, red triangles represent PsbS overexpression line PSBS-28, and red circles represent PsbS overexpression line PSBS-43. For FIGS. 7C-7G, the white column represents partially silenced PsbS mutant line psbs-4, the gray column represents WT, and the red columns represent PsbS overexpression lines PSBS-28 and PSBS-43. (Error bars indicate s.e.m.; n=6-10 biological replicates for FIGS. 7A-7D and 7G; n=3 biological replicates for FIG. 7E; n=4 biological replicates for FIG. 7F).

FIG. 8A shows total dry weight (P=0.0001), FIG. 8B shows root dry weight (P=0.001), FIG. 8C shows stem dry weight (P=0.0006), FIG. 8D shows leaf dry weight (P=0.0005), FIG. 8E shows leaf area (P=0.008), and FIG. 8F shows plant height in mutant N. tabacum lines relative to WT grown under field-test conditions (P<0.0001). The white columns represent partially silenced PsbS mutant lines psbs-4 and psbs-50 and the red columns represent PsbS overexpression lines PSBS-28, PSBS-34, PSBS-43, and PSBS-46. (Asterisks indicate significant differences between transgenic and WT; Dunnett's two-way test; α=0.05; error bars indicate s.e.m.; n=6 blocks for transgenics and n=12 blocks for WT).

FIGS. 10A-10E show the alignment of PsbS polypeptide sequences from Arabidopsis thaliana (At; SEQ ID NO: 1), Oryza sativa (Os; SEQ ID NO: 2, SEQ ID NO: 3, SEQ ID NO: 4, SEQ ID NO: 5, SEQ ID NO: 6), Vigna unguiculata (Vg; SEQ ID NO: 7), Glycine max (Gm; SEQ ID NO: 8, SEQ ID NO: 9, SEQ ID NO: 10, SEQ ID NO: 11), Zea mays (Zm; SEQ ID NO: 12, SEQ ID NO: 13, SEQ ID NO: 14), Nicotiana tabacum (Nt; SEQ ID NO: 15, SEQ ID NO: 16), Nicotiana benthamiana (Nb; SEQ ID NO: 17, SEQ ID NO: 18), Hevea brasiliensis (Hb; SEQ ID NO: 19), and Manihot esculenta (Me; SEQ ID NO: 20). FIG. 10A shows the alignment of the N terminal portion of the PsbS protein (Os_BAA12337.1, Os_CAH68096.1, Os_CAE01809.2, Os_XP_015633953.1, Os_XP_015621169.1, Zm_ACG37564.1, Zm_NP_001105228.2, Zm_AAQ55066.1, Nb_ABC59516.1, Nt_NP_001312190.1, Nt_XP_016484565.1, Nb_ABC59515.1, At_sp|Q9XF91|PSBS_ARATH, Hb_XP_021647432.1, Me_Cassava_V7_genomic_Chr18_8840000to8855000_rev, Vg_Vigun09g165900.1, Gm_XP_003523444.1, Gm_ACU23291.1, Gm_KRH53237.1, and Gm_NP_001276237.1, SEQ ID NOs:185-204, respectively). FIG. 10B shows the alignment of the central portion of the PsbS protein (Os_BAA12337.1, Os_CAH68096.1, Os_CAE01809.2, Os_XP_015633953.1, Os_XP_015621169.1, Zm_ACG37564.1, Zm_NP_001105228.2, Zm_AAQ55066.1, Nb_ABC59516.1, Nt_NP_001312190.1, Nt_XP_016484565.1, Nb_ABC59515.1, At_sp|Q9XF91|PSBS_ARATH, Hb_XP_021647432.1, Me_Cassava_V7_genomic_Chr18_8840000to8855000_rev, Vg_Vigun09g165900.1, Gm_XP_003523444.1, Gm_ACU23291.1, Gm_KRH53237.1, and Gm_NP_001276237.1, SEQ ID NOs:205-224, respectively). FIG. 10C continues the alignment of the central portion of the PsbS protein (Os_BAA12337.1, Os_CAH68096.1, Os_CAE01809.2, Os_XP_015633953.1, Os_XP_015621169.1, Zm_ACG37564.1, Zm_NP_001105228.2, Zm_AAQ55066.1, Nb_ABC59516.1, Nt_NP_001312190.1, Nt_XP_016484565.1, Nb_ABC59515.1, At_sp|9XF91|PSBS_ARATH, Hb_XP_021647432.1, Me_Cassava_V7_genomic_Chr18_8840000to8855000_rev, Vg_Vigun09g165900.1, Gm_XP_003523444.1, Gm_ACU23291.1, Gm_KRH53237.1, and Gm_NP_001276237.1, SEQ ID NOs:225-244, respectively). FIG. 10D continues the alignment of the central portion of the PsbS protein (Os_BAA12337.1, Os_CAH68096.1, Os_CAE01809.2, Os_XP_015633953.1, Os_XP_015621169.1, Zm_ACG37564.1, Zm_NP_001105228.2, Zm_AAQ55066.1, Nb_ABC59516.1, Nt_NP_001312190.1, Nt_XP_016484565.1, Nb_ABC59515.1, At_sp|Q9XF91|PSBS_ARATH, Hb_XP_021647432.1, Me_Cassava_V7_genomic_Chr18_8840000to8855000_rev, Vg_Vigun09g165900.1, Gm_XP_003523444.1, Gm_ACU23291.1, Gm_KRH53237.1, Gm_NP_001276237.1 (SEQ ID NOs:245-264, respectively). FIG. 10E shows the alignment of the C terminal portion of the PsbS protein (Os_BAA12337.1, Os_CAH68096.1, Os_CAE01809.2, Os_XP_015633953.1, Os_XP_015621169.1, Zm_ACG37564.1, Zm_NP_001105228.2, Zm_AAQ55066.1, Nb_ABC59516.1, Nt_NP_001312190.1, Nt_XP_016484565.1, Nb_ABC59515.1, At_sp|Q9XF91|PSBS_ARATH, Hb_XP_021647432.1, Me_Cassava_V7_genomic_Chr18_8840000to8855000_rev, Vg_Vigun09g165900.1, Gm_XP_003523444.1, Gm_ACU23291.1, Gm_KRH53237.1, and Gm_NP_001276237.1, SEQ ID NOs:265-284, respectively). In FIGS. 10A-10E, the amino acids are color coded by identity. In FIG. 10C and FIG. 10E, a green box indicates the location of a glutamate (E) within a short loop sequence that is located in the chloroplast lumen when the PsbS protein is expressed.

DETAILED DESCRIPTION

Figure 1A:
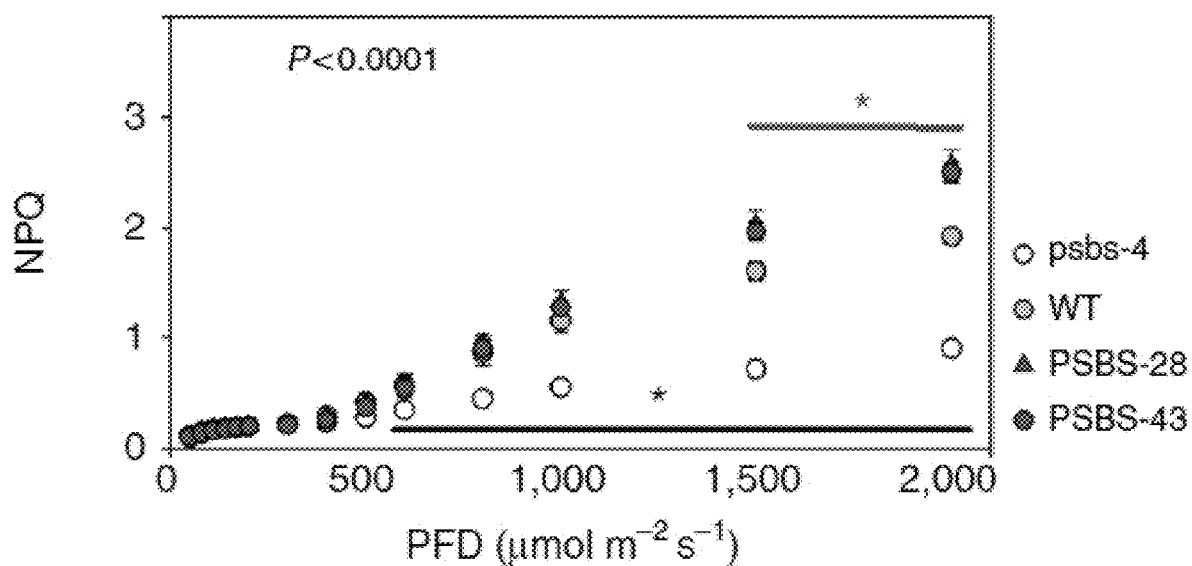
FIGS. 1A-1B show NPQ levels under different conditions.

This disclosure is based, in part, upon the inventors' identification of a surprising new utility for increased PsbS activity that results in plants with reduced stomatal conductance and increased water use efficiency. This surprising new utility for PsbS identified by the inventors serves as the basis for many of the aspects and their various embodiments of the present disclosure. Stomatal opening and closing is regulated by a variety of environmental cues in order to balance water vapor efflux and $CO_2$ influx. Some of these environmental cues include $CO_2$ concentration and light intensity, particularly of blue and red light. Although progress has been made in unraveling the molecular mechanisms underlying stomatal response to $CO_2$ concentration and blue light, the molecular mechanisms underlying stomatal response to red light remain elusive.

One possible molecule involved in the stomatal response to red light is chloroplastic plastoquinone ($Q_A$). A correlation between the redox state of $Q_A$ and stomatal conductance has been shown, suggesting that the $Q_A$ redox state may serve as a photosynthetic signal that controls stomatal opening in response to red light. However, no causative link between $Q_A$ redox state and stomatal conductance had been established.

Without wanting to be limited by theory, increasing PsbS activity may exert its effect by regulating $Q_A$ redox state. Moreover, PsbS acts on light harvesting and energy dissipation, which impacts $Q_A$ redox state, and thereby may indirectly link regulation of photosynthetic light harvesting to stomatal regulation.

Growth Conditions

Reductions in the inherent water use (i.e., increased WUE) per unit of growth and/or harvest of any crop can increase yield, and reduce cost and risk, especially under conditions without other rate-limiting factors. Under irrigation, crops that require less water per unit of yield will require less irrigation, saving water cost, and reducing the risk of loss from short, local water stress conditions between rain and irrigation cycles. Under rain-fed conditions where choice of planting density, variety maturity group and other management choices are optimized to the expected total seasonal water availability, crops that require less water can be managed more intensively for greater yield per acre—primarily by increasing plant density, but under certain conditions also choosing longer season varieties or more cost-effective fertilizer regimes, both of which can be influenced by seasonal water availability parameters. Even the effective growing range of a valuable crop can be extended into more marginal areas by reducing the seasonal water needs of the crop.

A particular feature of many crops such as corn, soybean and others is a heightened sensitivity to water stress at particular times during their growth cycle, where a short period of water stress can disproportionately reduce yield compared to a similar short period of water stress during other parts of the growing season. Conserving soil water, which can be achieved by growing plants of the current invention, would help to bridge these most damaging short periods of water stress between rainfall variations. Further, a study done on corn yields showed that increased yields were associated with increased sensitivity to drought stress (Lobell et al. (2014) Greater Sensitivity to Drought Accompanies Maize Yield Increase in the US Midwest. Science, 344, 516-519). Plants of the current invention, which have increased WUE, could reduce drought sensitivity of yields at the field scale.

One of skill in the art would know that the choice of planting density and fertilizer rate are affected by the chosen water regime. A study done in cowpea (*Vigna unguiculata* L. Walp.) showed that water limitation decreased yield, and further showed that the interaction between moisture and planting density was significant for measures such as total biomass (Lemma et al., Journal of Agronomy, 2008). This study indicates the importance of employing agricultural practices, such as planting density, to optimally utilize available moisture. This is particularly true under rain fed conditions, which require knowledge of the expected seasonal rainfall and the water available in the soil at the beginning of the planting season (i.e., the soil water bank). One of skill in the art would utilize available tools to quantify when water availability is limiting plant yield or growth (e.g., Friedman, Soil Science of America, 2016). One of skill in the art would further understand that the plants of the present invention keep more water in the soil water bank. Therefore, the plants of the current invention allow planting at a higher density with more fertilizer. In addition, this means that there are less local stress conditions within the field. The reduction of local stress conditions results in a higher yield at the end of the season.

Further, one of skill in the art would know that decisions regarding water regime application are dependent on the crop species. For example, a crop producing smaller plants will require less water than a crop producing larger plants, as leaf area, and therefore transpiration, will also be smaller. Similarly, a crop growing for a full season will require more water than a crop growing for part of a season. One of skill in the art would also know that water requirements are also dependent on the developmental stage of a crop. Early growth stages often do not require irrigation, but can be rain fed and use the soil water bank. Vegetative growth stages may need to be irrigated, but are able to survive if water stress should occur. Generally, reproductive growth stages require the most water, and the water available during this stage directly affects yield. One of skill in the art would know that reproductive growth stages are sensitive to water availability, and that in particular the early reproductive growth stages are the critical time when water is required.

The environment during the growing season will also affect water requirements. Factors such as heat, sun, humidity, and wind can all affect availability of water. One of skill in the art would be aware that a hot, sunny day with high winds and low humidity will result in more soil water evaporation than a cool, overcast day with high humidity and no wind.

Finally, the characteristics of the soil also contribute to crop water requirements. One of skill in the art would know that soils with a fine texture are able to hold more water than soils with a coarse texture. As described above, one of skill in the art would also be aware of the importance of the soil water bank for plant water availability. In addition, one of skill in the art would know that soil water evaporation can be reduced by agricultural practices such as conservation tillage and increased surface crop residue. Tillage is known to expose soil surface area, increase runoff, increase evaporation, remove remnants of previous crops that could have caught precipitation, and to compact some areas of soil, thereby potentially reducing the amount of water able to enter the soil. Therefore, conservation tillage can reduce these effects. Similarly, residue on the soil surface can increase water infiltration by preventing surface sealing due to water droplets. Residue on the soil surface also catches water and prevents it from running off, giving the water more time to enter the soil profile.

Methods of Cultivating Genetically Altered Plants

An aspect of the disclosure includes methods of cultivating genetically altered plants with increased water use efficiency, including the steps of: (a) providing the genetically altered plant, wherein the plant or a part thereof includes one or more genetic alterations; and (b) cultivating the genetically altered plant under conditions wherein the one or more genetic alterations increase activity of a Photosystem II Subunit S (PsbS) protein as compared to a wild type (WT) plant without the one or more genetic alterations, and wherein the increased activity of the PsbS protein increases water use efficiency as compared to the WT plant grown under the same conditions. An additional embodiment of this aspect includes the conditions being reduced irrigation conditions. A further embodiment of this aspect includes the conditions being rain fed conditions. Yet another embodiment of this aspect includes the conditions being high density growth conditions. Still another embodiment of this aspect includes the conditions being mild salinity. In an additional embodiment of this aspect, the conditions are fertilized or providing additional nutrients. In a further embodiment of this aspect, the conditions are humid conditions or conditions resulting in wet leaf surfaces. In another embodiment of this present aspect, which may be combined with any of the preceding embodiments, the increased activity of the PsbS protein provides the genetically altered plant with a higher yield, an increased biomass, an increased growth rate, an increased tolerance of salinity, an increased ability to withstand salinity, an increased flow of nutrients to the roots, an increased availability of nutrients over time, an increased utilization of fertilizer, an increased utilization of nutrients, a decreased susceptibility to a plant disease requiring humid conditions and/or wet leaf surfaces for infection, a decreased susceptibility to infection by the plant disease, a reduced incidence of the plant disease, or a reduced incidence of infection by the plant disease as compared to the WT plant without the increased activity grown under the same conditions where the activity of the PsbS protein is increased.

A further embodiment of this aspect that can be combined with any of the preceding embodiments includes the genetically altered plant being provided in step (a) by planting a genetically altered seedling, a genetically altered plantlet, a genetically altered cutting, a genetically altered tuber, a genetically altered root, or a genetically altered seed to produce the genetically altered plant, or by grafting the genetically altered seedling, the genetically altered plantlet, or the genetically altered cutting to a root stock or a second plant to produce the genetically altered plant. In still another embodiment of this aspect that can be combined with any of the preceding embodiments, the genetically altered plant is cultivated in step (b) to produce harvestable seed and fruits or vegetatively produced harvested items. An additional embodiment of this aspect includes the harvestable seed and fruits being selected from seed, fruit, pods, grain, kernels, beans, and peas; and wherein the vegetatively produced harvested items are selected from tubers, rhizomes, buds, roots, cuttings, and leaves. A further embodiment of this aspect that can be combined with any of the preceding embodiments that has harvestable seed and fruit or vegetatively produced harvestable items further includes harvesting the harvestable seed, harvestable leaves, harvestable roots, harvestable cuttings, harvestable fruit, harvestable kernels, harvestable tubers, harvestable pods, harvestable peas, harvestable beans, and/or harvestable grain.

Still another embodiment of this aspect that can be combined with any of the preceding embodiments includes the increased activity of the PsbS protein providing the genetically altered plant with decreased stomatal conductance as compared to the WT plant without the increased activity grown under the same conditions where the activity of the PsbS protein is increased. In yet another embodiment of this aspect, the increased activity of the PsbS protein provides the genetically altered plant with substantially similar photosynthetic efficiency as compared to the WT plant grown under the same conditions where the activity of the PsbS protein is increased.

Genetically Altered Plants

An additional aspect of the disclosure includes a genetically altered plant or part thereof including one or more genetic alterations that increase activity of a PsbS protein as compared to a WT plant without the one or more genetic alterations, wherein the genetically altered plant shows increased water use efficiency as compared to the WT plant grown under the same conditions. An additional embodiment of this aspect includes the conditions being selected from the group of reduced irrigation conditions, rain fed conditions, high density growth conditions, mild salinity, fertilized or providing additional nutrients, humid conditions, and conditions resulting in wet leaf surfaces. In yet another embodiment of this aspect, which may be combined with any of the preceding embodiments, the increased activity of the PsbS protein provides the genetically altered plant with a higher yield, an increased biomass, an increased growth rate, an increased tolerance of salinity, an increased ability to withstand salinity, an increased flow of nutrients to the roots, an increased availability of nutrients over time, an increased utilization of fertilizer, an increased utilization of nutrients, a decreased susceptibility to a plant disease requiring humid conditions and/or wet leaf surfaces for infection, a decreased susceptibility to infection by the plant disease, a reduced incidence of the plant disease, or a reduced incidence of infection by the plant disease as compared to the WT plant without the increased activity grown under the same conditions where the activity of the PsbS protein is increased. In still another embodiment of this present aspect, which may be combined with any of the preceding embodiments, the genetically altered plant does not include increased activity of zeaxanthin epoxidase (ZEP) protein, violaxanthin de-epoxidase (VDE) protein, or both, as compared to a WT plant. In a further embodiment of this present aspect, which may be combined with any of the preceding embodiments, the genetically altered plant does not include reduced activity of K+ efflux antiporter 3 (KEA3) as compared to a WT plant. In yet another embodiment of this aspect that can be combined with any of the preceding embodiments, the genetically altered plant does not include reduced activity of K+/H+ antiporters or K+ efflux antiporters localized to the chloroplast thylakoid membrane (e.g., KEA3).

In still another embodiment of this aspect that can be combined with any of the relevant preceding embodiments, the genetically altered plant further includes increased activity of a ZEP protein and increased activity of a VDE protein, wherein the increased activity of the PsbS protein is greater than the increased activity of the PsbS protein required for increased photosynthetic efficiency when each of the ZEP protein, the PsbS protein, and the VDE protein are overexpressed together. An additional embodiment of this aspect includes increased activity of the PsbS protein being due to an increased amount of the PsbS protein. In yet another embodiment of this aspect, the increased amount of the PsbS protein is at least 10% greater, at least 11% greater, at least 12% greater, at least 13% greater, at least 14% greater, at least 15% greater, at least 16% greater, at least 17% greater, at least 18% greater, at least 19% greater, at least 20% greater, at least 21% greater, at least 22% greater, at least 23% greater, at least 24% greater, at least 25% greater, at least 26% greater, at least 27% greater, at least 28% greater, at least 29% greater, at least 30% greater, at least 31% greater, at least 32% greater, at least 33% greater, at least 34% greater, at least 35% greater, at least 36% greater, at least 37% greater, at least 38% greater, at least 39% greater, at least 40% greater, at least 41% greater, at least 42% greater, at least 43% greater, at least 44% greater, at least 45% greater, at least 46% greater, at least 47% greater, at least 48% greater, at least 49% greater, at least 50% greater, at least 55% greater, at least 60% greater, at least 65% greater, at least 70% greater, at least 75% greater, at least 80% greater, at least 85% greater, at least 90% greater, at least 95% greater, at least 100% greater, at least 110% greater, at least 120% greater, at least 130% greater, at least 140% greater, at least 150% greater, at least 160% greater, at least 170% greater, at least 180% greater, at least 190% greater, or at least 200% greater than the increased activity of the PsbS protein required for increased photosynthetic efficiency when each of the ZEP protein, the PsbS protein, and the VDE protein are overexpressed together. Still another embodiment of this aspect includes the increased amount of PsbS protein being no greater than 500%, no greater than 450%, no greater than 400%, no greater than 350%, no greater than 300%, no greater than 250%, no greater than 200%, no greater than 190%, no greater than 180%, no greater than 170%, no greater than 160%, no greater than 150%, no greater than 140%, no greater than 130%, no greater than 120%, no greater than 110%, no greater than 100%, no greater than 95%, no greater than 90%, no greater than 85%, no greater than 80%, no greater than 75%, no greater than 70%, no greater than 65%, no greater than 60%, no greater than 55%, or no greater than 50% of the increased activity of the PsbS protein required for increased photosynthetic efficiency when each of the ZEP protein, the PsbS protein, and the VDE protein are overexpressed together. Another embodiment of this aspect includes the increased amount of PsbS, the increased amount of ZEP, and the increased amount of VDE being increased relative to an amount of endogenous PsbS protein, an amount of endogenous ZEP protein, and an amount of endogenous VDE protein, and wherein the increased amount of PsbS is 10% or more, 11% or more, 12% or more, 13% or more, 14% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more, 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 46% or more, 47% or more, 48% or more, 49% or more, 50% or more, 55% or more, 60% or more, 65% or more, 70% or more, 75% or more, 80% or more, 85% or more, 90% or more, 95% or more, 100% or more, 110% or more, 120% or more, 130% or more, 140% or more, 150% or more, 160% or more, 170% or more, 180% or more, 190% or more, or 200% or more increased relative to the amount of endogenous PsbS protein, the increased amount of ZEP is 90% increased relative to the amount of endogenous ZEP protein, and the increased amount of VDE is 80% increased relative to the amount of endogenous VDE protein. In a further embodiment of this aspect, the increased amount of PsbS, the increased amount of ZEP, and the increased amount of VDE is increased relative to an amount of endogenous PsbS protein, an amount of endogenous ZEP protein, and an amount of endogenous VDE protein, and wherein the increased amount of PsbS is 12% increased relative to the amount of endogenous PsbS protein, the increased amount of ZEP is 90% increased relative to the amount of endogenous ZEP protein, and the increased amount of VDE is 80% increased relative to the amount of endogenous VDE protein. In still another embodiment of this aspect, the increased amount of PsbS, the increased amount of ZEP, and the increased amount of VDE is increased relative to an amount of endogenous PsbS protein, an amount of endogenous ZEP protein, and an amount of endogenous VDE protein, and wherein the increased amount of PsbS is 24% increased relative to the amount of endogenous PsbS protein, the increased amount of ZEP is 90% increased relative to the amount of endogenous ZEP protein, and the increased amount of VDE is 80% increased relative to the amount of endogenous VDE protein. In yet another embodiment of this aspect, which may be combined with any of the preceding embodiments that has increased activity of a ZEP protein and increased activity of a VDE protein, the increased activity of the PsbS, VDE, and ZEP proteins provides the genetically altered plant with increased photosynthetic efficiency under non-steady state conditions as compared to the WT plant without the increased activity grown under the same conditions where the activity of the PsbS, VDE, and ZEP proteins is increased.

Still another embodiment of this present aspect, which may be combined with any of the preceding embodiments, includes the genetically altered plant being selected from the group of cowpea (e.g., black-eyed pea, catjang, yardlong bean, *Vigna unguiculata*), soybean (e.g., *Glycine max, Glycine soja*), cassava (e.g., manioc, yucca, *Manihot esculenta*), wheat (e.g., common wheat, spelt, durum, einkorn, emmer, kamut, *Triticum aestivum, Triticum spelta, Triticum durum, Triticum urartu, Triticum monococcum, Triticum turanicum, Triticum* spp.), barley (e.g., *Hordeum vulgare*), corn (e.g., maize, *Zea mays*), sorghum (e.g., *Sorghum bicolor*), rice (e.g., indica rice, japonica rice, aromatic rice, glutinous rice, *Oryza sativa, Oryza glaberrima*), cotton (e.g., *Gossypium* hirsutum, Gossypium barbadense, Gossypium arboretum, Gossypium herbaceum), rubber (e.g., Hevea brasiliensis), sugarcane (e.g., Saccharum officinarum, Saccharum spp.), eucalyptus (e.g., Eucalyptus spp.), willow (e.g., Salix spp.), birch (e.g., Betula spp.), beech (e.g., Fagus spp.), poplar (e.g., hybrid poplar, Populus trichocarpa, Populus tremula, Populus alba, Populus spp.), chestnut (e.g., Castanea spp.), citrus (e.g., lemon, lime, orange, grapefruit, pomelo, citron, trifoliate orange, bergamot orange, bitter orange, blood orange, satsuma, clementine, mandarin, yuzu, finger lime, kaffir lime, kumquat, Citrus clementina, Citrus sinensis, Citrus trifoliata, Citrus japonica, Citrus maxima, Citrus australasica, Citrus reticulata, Citrus aurantifolia, Citrus hystrix, Citrus x paradisi, Citrus x clementina, Citrus spp.), avocado (e.g., Persea americana), apple (e.g., Malus pumila, Malus x domestica, Pyrus malus), pear (e.g., Pyrus communis, Pyrus x bretschneideri, Pyrus pyrifolia, Pyrus sinkiangensis, Pyrus pashia, Pyrus spp.), cherry (e.g., Prunus avium Prunus cerasus), peach (e.g., Prunus persica), plum (e.g., Mirabelle, greengage, damson, Prunus domestica, Prunus salicina, Prunus mume), apricot (e.g., Prunus armeniaca, Prunus brigantine, Prunus mandshurica), fig (e.g., Ficus carica), olive (e.g., Olea europaea), almond (e.g., Prunus dulcis, Prunus amygdalus), pistachio (e.g., Pistacia vera), walnut (e.g., Persian walnut, English walnut, black walnut, Juglans regia, Juglans nigra, Juglans cinerea, Juglans californica), hazelnut (e.g., Corylus avellana, Corylus spp.), pecan (e.g., Carya illinoinensis), tomato (e.g., Solanum lycopersicum), eggplant (e.g., Solanum melongena), potato (e.g., russet potatoes, yellow potatoes, red potatoes, Solanum tuberosum), or alfalfa (e.g., Lucerne, Medicago sativa). An additional embodiment of this aspect includes the genetically altered plant not being rice or Arabidopsis (e.g., Arabidopsis thaliana).

Still another embodiment of this aspect that can be combined with any of the preceding embodiments includes the increased activity of the PsbS protein providing the genetically altered plant with decreased stomatal conductance as compared to the WT plant without the increased activity grown under the same conditions where the activity of the PsbS protein is increased. In yet another embodiment of this aspect, which may be combined with any of the preceding embodiments that does not have increased activity of a ZEP protein and increased activity of a VDE protein, the increased activity of the PsbS protein provides the genetically altered plant with substantially similar photosynthetic efficiency as compared to the WT plant grown under the same conditions where the activity of the PsbS protein is increased.

In a further embodiment of this aspect that can be combined with any of the preceding embodiments, increased activity is increased expression. An additional embodiment of this aspect includes the increased expression being due to expression of a heterologous PsbS protein. A further embodiment of this aspect includes the heterologous PsbS protein including at least 70% sequence identity to, at least 75% sequence identity to, at least 80% sequence identity to, at least 85% sequence identity to, at least 90% sequence identity to, at least 95% sequence identity to, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. Yet another embodiment of this aspect includes the heterologous PsbS protein being selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. A further embodiment of this aspect that can be combined with any of the preceding embodiments that has a heterologous PsbS protein includes the heterologous PsbS protein containing a glutamate at a position corresponding to amino acid 149 of reference sequence SEQ ID NO: 21 and a glutamate at a position corresponding to amino acid 255 of reference sequence SEQ ID NO: 21. When the PsbS protein is expressed, it localizes to the chloroplast thylakoid membrane, and these two glutamates are located in short loop sequences that connect transmembrane domains. Both of these short loop sequences are located on the chloroplast lumen. The two glutamates are thought to act as pH sensors; by sensing the acidification of the chloroplast lumen, the glutamates allow PsbS to function as an excess light sensor (Li et al., J. Biol. Chem., (2004), 279 (22), 22866-22874). FIGS. 10A-10E show an alignment of exemplary PsbS protein sequences, and SEQ ID NO: 21 is a consensus protein sequence generated from the alignment. Still another embodiment of this aspect that can be combined with any of the preceding embodiments that has a heterologous PsbS protein includes the heterologous PsbS protein being encoded by a first nucleic acid and the first nucleic acid being operably linked to a second nucleic acid including a promoter. An additional embodiment of this aspect includes the promoter being selected from the group of a CaMV35S promoter, a ubiquitin promoter, a Rbcs1A promoter, a GAPA-1 promoter, a FBA2 promoter, and any combination thereof. Still another embodiment of this aspect that can be combined with any of the preceding embodiments that has a nucleic acid sequence includes the first nucleic acid sequence and the second nucleic acid sequence being stably integrated into a nuclear genome of the plant or into a chloroplast genome of the plant. A further embodiment of this aspect includes the increased expression being due to overexpression of an endogenous PsbS protein. An additional embodiment of this aspect includes overexpression of the endogenous PsbS protein being achieved using a gene editing technique to introduce the one or more genetic alterations that increase the activity of the endogenous PsbS protein. Still another embodiment of this aspect includes the gene editing technique being selected from the group of transcription activator-like effector nuclease (TALEN) gene editing techniques, clustered Regularly Interspaced Short Palindromic Repeat (CRISPR/Cas) gene editing techniques, or zinc-finger nuclease (ZFN) gene editing techniques. Still another embodiment of this aspect that can be combined with any of the preceding embodiments that has a gene editing technique includes the one or more genetic alterations that increase the activity of the endogenous PsbS protein are selected from the group of inactivating a repressor element that represses expression of the endogenous PsbS protein, removing a repressor element that represses expression of the endogenous PsbS protein, modulating the methylation state of a repressor element that represses expression of the endogenous PsbS protein, activating an enhancer element that increases expression of the endogenous PsbS protein, adding an enhancer element that increases expression of the endogenous PsbS protein, modulating the methylation state of an enhancer element that increases expression of the endogenous PsbS protein, adding a transcriptional activator recruiting or binding element that activates expression of the endogenous PsbS protein, replacing the endogenous promoter with an overexpression promoter that directs expression of the endogenous PsbS protein, modulating the methylation state of the endogenous promoter; modulating the methylation state of the endogenous PsbS coding sequence; adding elements that stabilize an endogenous PsbS mRNA, removing elements that destabilize the endogenous PsbS mRNA, modifying a PsbS coding sequence to increase stability of the PsbS protein, or modifying a PsbS coding sequence to increase activity of the PsbS protein. A further embodiment of this aspect that can be combined with any of the preceding embodiments that has a gene editing technique includes the one or more genetic alterations being epigenetic modifications.

In still another embodiment of this aspect that can be combined with any of the preceding embodiments, the PsbS protein is localized to a thylakoid membrane of at least one chloroplast within a cell of the genetically altered plant. An additional embodiment of this aspect includes the cell being a chloroplast containing leaf cell. A further embodiment of this aspect includes the cell being a mesophyll cell or a guard cell. In yet another embodiment of this aspect that can be combined with any of the preceding embodiments that has localization of the PsbS protein, the PsbS protein is expressed in at least 70% of the cells.

Yet another embodiment of this aspect that can be combined with any of the preceding embodiments with respect to seeds includes a genetically altered seed produced from the genetically altered plant of any one of the preceding embodiments. Still another embodiment of this aspect that can be combined with any of the preceding embodiments with respect to plant part includes the plant part being a leaf, a stem, a root, a flower, a seed, a kernel, a grain, a pod, a bean, a pea, a fruit, a chloroplast, a cell, or a portion thereof and the genetically altered plant part including the one or more genetic alterations. A further embodiment of this aspect includes the plant part being a fruit, a kernel, a grain, a pod, a bean, or a pea. Still another embodiment of this aspect that can be combined with any of the preceding embodiments with respect to pollen grain or ovules includes a genetically altered pollen grain or a genetically altered ovule of the plant of any one of the preceding embodiments, wherein the genetically altered pollen grain or the genetically altered ovule includes the one or more genetic alterations. A further embodiment of this aspect that can be combined with any of the preceding embodiments includes a genetically altered protoplast produced from the genetically altered plant of any of the preceding embodiments, wherein the genetically altered protoplast includes the one or more genetic alterations. An additional embodiment of this aspect that can be combined with any of the preceding embodiments includes a genetically altered tissue culture produced from protoplasts or cells from the genetically altered plant of any one of the preceding embodiments, wherein the cells or protoplasts are produced from a plant part selected from the group of leaf, leaf mesophyll cell, anther, pistil, stem, petiole, root, root tip, tuber, fruit, seed, kernel, grain, flower, cotyledon, hypocotyl, embryo, or meristematic cell, wherein the genetically altered tissue culture includes the one or more genetic alterations. An additional embodiment of this aspect includes a genetically altered plant regenerated from the genetically altered tissue culture that includes the one or more genetic alterations. In still another embodiment of this aspect, the genetically altered plant regenerated from the genetically altered tissue culture has all the physiological and morphological characteristics of the genetically altered plant produced from the method of any one of the preceding embodiments.

Methods of Cultivating and Producing Genetically Altered Plants

An additional aspect of the disclosure includes methods of cultivating the genetically altered plant of any of the preceding embodiments including the steps of (a) planting a genetically altered seedling, a genetically altered plantlet, a genetically altered cutting, a genetically altered tuber, a genetically altered root, or a genetically altered seed to produce the genetically altered plant, or by grafting the genetically altered seedling, the genetically altered plantlet, or the genetically altered cutting to a root stock or a second plant to produce the genetically altered plant; (b) cultivating the genetically altered plant to produce harvestable seed and fruits or vegetatively produced harvested items, wherein the harvestable seed and fruits is selected from seed, fruit, pods, grain, kernels, beans, and peas, and wherein the vegetatively produced harvested items are selected from tubers, rhizomes, buds, roots, cuttings, and leaves; and (c) harvesting the harvestable seed, harvestable leaves, harvestable roots, harvestable cuttings, harvestable fruit, harvestable kernels, harvestable tubers, harvestable pods, harvestable peas, harvestable beans, and/or harvestable grain.

An additional aspect of the disclosure includes methods of producing the genetically altered plant of any of the preceding embodiments including the steps of (a) transforming a plant cell, tissue, or other explant with a vector including a first nucleic acid sequence encoding a PsbS protein operably linked to a second nucleic acid sequence encoding a promoter; (b) selecting successful transformation events by means of a selection agent, marker-assisted selection, or selective media; (c) regenerating the transformed cell, tissue, or other explant into a genetically altered plantlet; and (d) growing the genetically altered plantlet into a genetically altered plant with increased activity of a PsbS protein as compared to an untransformed WT plant. An additional embodiment of this aspect further includes identifying successful introduction of the one or more genetic alterations by screening or selecting the plant cell, tissue, or other explant prior to step (b); screening or selecting plantlets between step (b) and (c); or screening or selecting plants after step (c). In yet another embodiment of this aspect, which may be combined with any of the preceding embodiments, transformation is done using a transformation method selected from the group of particle bombardment (i.e., biolistics, gene gun), *Agrobacterium*-mediated transformation, *Rhizobium*-mediated transformation, or protoplast transfection or transformation. In still another embodiment of this aspect, which may be combined with any of the preceding embodiments, the vector is pEG100. A further embodiment of this aspect includes the PsbS protein including at least 70% sequence identity to, at least 75% sequence identity to, at least 80% sequence identity to, at least 85% sequence identity to, at least 90% sequence identity to, at least 95% sequence identity to, or at least 99% sequence identity to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. Yet another embodiment of this aspect includes the PsbS protein being selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, or SEQ ID NO: 184. A further embodiment of this aspect that can be combined with any of the preceding embodiments includes the PsbS protein containing a glutamate at a position corresponding to amino acid 149 of reference sequence SEQ ID NO: 21 and a glutamate at a position corresponding to amino acid 255 of reference sequence SEQ ID NO: 21. Still another embodiment of this aspect that can be combined with any of the preceding embodiments includes the heterologous PsbS protein being encoded by a first nucleic acid and the first nucleic acid being operably linked to a second nucleic acid including a promoter. An additional embodiment of this aspect includes the promoter being selected from the group of a CaMV35S promoter, a ubiquitin promoter, a Rbcs1A promoter, a GAPA-1 promoter, a FBA2 promoter, and any combination thereof. Still another embodiment of this aspect that can be combined with any of the preceding embodiments that has a nucleic acid sequence includes the first nucleic acid sequence and the second nucleic acid sequence being stably integrated into a nuclear genome of the plant or into a chloroplast genome of the plant.

A further aspect of the disclosure includes methods of producing the genetically altered plant of any of the preceding embodiments, including the steps of (a) transforming a plant cell, tissue, or other explant with one or more gene editing components that target a nuclear genome sequence operably linked to an endogenous PsbS protein; (b) selecting successful transformation events by means of a screening technology, an enriching technology, a selection agent, marker-assisted selection, or selective media; (c) regenerating the transformed cell, tissue, or other explant into a genetically altered plantlet; and (d) growing the genetically altered plantlet into a genetically altered plant with increased activity of a PsbS protein as compared to an untransformed WT plant. An additional embodiment of this aspect includes the one or more gene editing components including a ribonucleoprotein complex that targets the nuclear genome sequence; a vector including a TALEN protein encoding sequence, wherein the TALEN protein targets the nuclear genome sequence; a vector including a ZFN protein encoding sequence, wherein the ZFN protein targets the nuclear genome sequence; an oligonucleotide donor (OND), wherein the OND targets the nuclear genome sequence; or a vector CRISPR/Cas enzyme encoding sequence and a targeting sequence, wherein the targeting sequence targets the nuclear genome sequence.

Molecular Biological Methods to Produce Genetically Altered Plants and Plant Cells One embodiment of the present invention provides a genetically altered plant or plant cell containing one or more genetic alterations, which increase activity of a PsbS protein as compared to a WT plant without the one or more genetic alterations, and the increased activity increases water use efficiency as compared to the WT plant grown under the same conditions. For example, the present disclosure provides plants with increased activity of a PsbS protein due to expression of a heterologous PsbS protein. In addition, the present disclosure provides plants with increased activity of a PsbS protein due to overexpression of an endogenous PsbS protein.

Transformation and generation of genetically altered monocotyledonous and dicotyledonous plant cells is well known in the art. See, e.g., Weising, et al., Ann. Rev. Genet. 22:421-477 (1988); U.S. Pat. No. 5,679,558; *Agrobacterium Protocols*, ed: Gartland, Humana Press Inc. (1995); and Wang, et al. Acta Hort. 461:401-408 (1998). The choice of method varies with the type of plant to be transformed, the particular application and/or the desired result. The appropriate transformation technique is readily chosen by the skilled practitioner.

Any methodology known in the art to delete, insert or otherwise modify the cellular DNA (e.g., genomic DNA and organelle DNA) can be used in practicing the inventions disclosed herein. For example, a disarmed Ti plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., Bio/Technology (1990) 8, 833-839); Gordon-Kamm et al., The Plant Cell, (1990) 2, 603-618) and rice (Shimamoto et al., Nature, (1989) 338, 274-276; Datta et al., Bio/Technology, (1990) 8, 736-740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

Genetically altered plants of the present invention can be used in a conventional plant breeding scheme to produce more genetically altered plants with the same characteristics, or to introduce the genetic alteration(s) in other varieties of the same or related plant species. Seeds, which are obtained from the altered plants, preferably contain the genetic alteration(s) as a stable insert in nuclear DNA or as modifications to an endogenous gene or promoter. Plants including the genetic alteration(s) in accordance with the invention include plants including, or derived from, root stocks of plants including the genetic alteration(s) of the invention, e.g., fruit trees or ornamental plants. Hence, any non-transgenic grafted plant parts inserted on a transformed plant or plant part are included in the invention.

Introduced genetic elements, whether in an expression vector or expression cassette, which result in the expression of an introduced gene, will typically utilize a plant-expressible promoter. A 'plant-expressible promoter' as used herein refers to a promoter that ensures expression of the genetic alteration(s) of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871-2887), CabbB S (Franck et al., Cell (1980) 21, 285-294; Kay et al., Science, (1987) 236, 4805) and CabbB JI (Hull and Howell, Virology, (1987) 86, 482-493); promoters from the ubiquitin family (e.g., the maize ubiquitin promoter of Christensen et al., Plant Mol Biol, (1992) 18, 675-689, or the *Arabidopsis* UBQ10 promoter of Norris et al. Plant Mol. Biol. (1993) 21, 895-906), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T DNA (Velten et al., EMBO J, (1984) 3, 2723 2730).

Alternatively, a plant-expressible promoter can be a tissue-specific promoter, i.e., a promoter directing a higher level of expression in some cells or tissues of the plant, e.g., in leaf mesophyll cells. In preferred embodiments, leaf mesophyll specific promoters or leaf guard cell specific promoters are used. Non-limiting examples include the leaf specific Rbcs1A promoter (*A. thaliana* RuBisCO small subunit 315 1A (AT1G67090) promoter), GAPA-1 promoter (*A. thaliana* Glyceraldehyde 3-phosphate dehydrogenase 316 A subunit 1 (AT3G26650) promoter), and FBA2 promoter (*A. thaliana* Fructose-bisphosphate aldolase 2 317 (AT4G38970) promoter) (Kromdijk et al., Science, 2016). Further non-limiting examples include the leaf mesophyll specific FBPase promoter (Peleget al., Plant J, 2007), the maize or rice rbcS promoter (Nomura et al., Plant Mol Biol, 2000), the leaf guard cell specific *Arabidopsis* KAT1 promoter (Nakamura et al., Plant Phys, 1995), the *Arabidopsis* Myrosinase-Thioglucoside glucohydrolase 1 (TGG1) promoter (Husebye et al., Plant Phys, 2002), the *Arabidopsis* rha1 promoter (Terryn et al., Plant Cell, 1993), the *Arabidopsis* AtCHX20 promoter (Padmanaban et al., Plant Phys, 2007), the *Arabidopsis* HIC (High carbon dioxide) promoter (Gray et al., Nature, 2000), the *Arabidopsis* CYTOCHROME P450 86A2 (CYP86A2) mono-oxygenase promoter (pCYP) (Francia et al., Plant Signal & Behav, 2008; Galbiati et al., The Plant Journal, 2008), the potato ADP-glucose pyrophosphorylase (AGPase) promoter (Muller-Rober et al., The Plant Cell 1994), the grape R2R3 MYB60 transcription factor promoter (Galbiati et al., BMC Plant Bio, 2011), the *Arabidopsis* AtMYB60 promoter (Cominelli et al., Current Bio, 2005; Cominelli et al., BMC Plant Bio, 2011), the *Arabidopsis* At1g22690-promoter (pGC1) (Yang et al., Plant Methods, 2008), and the *Arabidopsis* AtMYB 61 promoter (Liang et al., Curr Biol, 2005). These plant promoters can be combined with enhancer elements, they can be combined with minimal promoter elements, or can include repeated elements to ensure the expression profile desired.

In some embodiments, genetic elements to increase expression in plant cells can be utilized. For example, an intron at the 5' end or 3' end of an introduced gene, or in the coding sequence of the introduced gene, e.g., the hsp70 intron. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

An introduced gene of the present invention can be inserted in host cell DNA so that the inserted gene part is upstream (i.e., 5') of suitable 3' end transcription regulation signals (e.g., transcript formation and polyadenylation signals). This is preferably accomplished by inserting the gene in the plant cell genome (nuclear or chloroplast). Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835 845), the SCSV or the Malic enzyme terminators (Schunmann et al., Plant Funct Biol, (2003) 30:453-460), and the T DNA gene 7 (Velten and Schell, Nucleic Acids Res, (1985) 13, 6981 6998), which act as 3' untranslated DNA sequences in transformed plant cells. In some embodiments, one or more of the introduced genes are stably integrated into the nuclear genome. Stable integration is present when the nucleic acid sequence remains integrated into the nuclear genome and continues to be expressed (e.g., detectable mRNA transcript or protein is produced) throughout subsequent plant generations. Stable integration into and/or editing of the nuclear genome can be accomplished by any known method in the art (e.g., microparticle bombardment, *Agrobacterium*-mediated transformation, CRISPR/Cas9, electroporation of protoplasts, microinjection, etc.).

Further, any epigenetic methodology known in the art to alter expression of the cellular DNA (e.g., genomic DNA and organelle DNA) can be used in practicing the inventions disclosed herein (e.g., genetic alterations include epigenetic modifications). One type of epigenetic modification well known in the art is DNA methylation (and hydroxymethylation). For example, the methylation state of a gene promoter can affect the expression of a gene (as described, for example, in Ikeda et al., Plant Cell Physiol., (2007), 48(2), 205-220). The methylation state of the promoter can be changed using CRISPR-Cas SunTag systems (as described, for example, in Huang et al., Genome Biol., (2017) 18(1), 176 and Papikian et al., Nat. Commun., (2019) 10(1), 729) or demethylase zinc finger fusion systems (as described, for example, in Gallego-Bartolomé et al., PNAS, (2018) 115(9), E2125-E2134). Using these methods, the methylation of the endogenous PsbS promoter can be changed, and this changed methylation state can result in altered (e.g., increased) PsbS expression. Other types of epigenetic modifications well known in the art are histone modifications (e.g., acetylation, methylation, sumoylation, ubiquitination), which result in chromatin remodeling. Chromatin remodeling can increase gene expression, for example via regulation of transcription elongation efficiency (Nonogaki, Front. Plant. Sci., (2014) 5, 233), and can also result in gene silencing (Xu and Shen, Curr. Biol., (2008) 18(24), 1966-1971). Trithorax and Polycomb group proteins (Kleinmanns and Schubert, Biological Chemistry, (2014) 395(11), 1291-1300) as well as SWI/SNF proteins (Ojolo et al., Front. Plant. Sci., (2018) 9, 1232) have been identified as important components in histone methylation processes in plants. Epigenetic modifications, in particular DNA methylomes, in plants have been shown to be heritable over multiple generations, and are therefore well-suited for developing plant lines. One caveat is that the heritability of methylomes requires sexual reproduction: a study done to determine why oil palm trees had decreased yield revealed that the clonal reproduction of these trees had hindered the re-establishment of DNA methylation marks (Ong-Abdullah et al., Nature, (2015) 525, 533-537).

The term recombinant or modified nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As used herein, the terms "overexpression" and "upregulation" refer to increased expression (e.g., of mRNA, polypeptides, etc.) relative to expression in a wild type organism (e.g., plant) as a result of genetic modification. In some embodiments, the increase in expression is a slight increase of about 10% more than expression in wild type. In some embodiments, the increase in expression is an increase of 50% or more (e.g., 60%, 70%, 80%, 100%, etc.) relative to expression in wild type. In some embodiments, an endogenous gene is overexpressed. In some embodiments, an exogenous gene is overexpressed by virtue of being expressed. Overexpression of a gene in plants can be achieved through any known method in the art, including but not limited to, the use of constitutive promoters, inducible promoters, high expression promoters, enhancers, transcriptional and/or translational regulatory sequences, codon optimization, modified transcription factors, and/or mutant or modified genes that control expression of the gene to be overexpressed.

Where a recombinant nucleic acid is intended for expression, cloning, or replication of a particular sequence, DNA constructs prepared for introduction into a host cell will typically include a replication system (e.g. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., plasma membrane localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology (e.g., sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the BLASTN, BLASTP, and BLASTX, programs of Altschul et al. (1990) J. Mol. Biol. 215:402-410. BLAST nucleotide searches are performed with the BLASTN program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (BLASTN and BLASTX) are used. See www.ncbi.nih.gov. One of skill in the art can readily determine in a sequence of interest where a position corresponding to amino acid or nucleic acid in a reference sequence occurs by aligning the sequence of interest with the reference sequence using the suitable BLAST program with the default settings (e.g., for BLASTP: Gap opening penalty: 11, Gap extension penalty: 1, Expectation value: 10, Word size: 3, Max scores: 25, Max alignments: 15, and Matrix: blosum62; and for BLASTN: Gap opening penalty: 5, Gap extension penalty: 2, Nucleic match: 1, Nucleic mismatch—3, Expectation value: 10, Word size: 11, Max scores: 25, and Max alignments: 15).

Preferred host cells are plant cells. Recombinant host cells, in the present context, are those which have been genetically modified to contain an isolated nucleic molecule, contain one or more deleted or otherwise non-functional genes normally present and functional in the host cell, or contain one or more genes to produce at least one recombinant protein. The nucleic acid(s) encoding the protein(s) of the present invention can be introduced by any means known to the art which is appropriate for the particular type of cell, including without limitation, transformation, lipofection, electroporation or any other methodology known by those skilled in the art.

Marker-Assisted Breeding of Plants with Increased WUE Activity

Still another aspect of the disclosure includes methods of identifying genetic markers associated with increased PsbS protein activity in a plant, including the steps of (a) screening a population of plants from the same species or closely related species for PsbS protein activity; (b) identifying a subset of plants from the population with higher levels of PsbS activity as compared to the other plants in the population; and (c) identifying genetic markers associated with increased PsbS activity in the subset of plants. An additional embodiment of this aspect includes the increased PsbS protein activity being due to increased expression of a PsbS mRNA and the screening in step (a) being assaying levels of the PsbS mRNA, optionally using a method selected from the group of RNA-Seq, microarray, Northern blot, or qRT-PCR. A further embodiment of this aspect includes the increased PsbS protein activity being due to increased amount of the PsbS protein and the screening in step (a) being assaying levels of the PsbS protein, optionally using a method selected from the group of Western blot, ELISA, immunoprecipitation, HPLC, or LC/MS.

Yet another aspect of the disclosure includes methods of producing a plant with increased WUE activity and a second desired trait, including the steps of (a) providing a first plant including a genetic marker associated with increased PsbS activity and a second plant including the second desired trait; (b) crossing the first plant with the second plant to create a population of progeny plants; and (c) selecting the plant with increased WUE activity and the second desired trait using the genetic marker associated with increased PsbS activity. An additional embodiment of this aspect includes the second desired trait being increased PsbS activity unlinked to the genetic marker associated with increased PsbS activity. An additional embodiment that can be combined with any of the preceding embodiments includes the plant being selected from the group of cowpea, soybean, cassava, wheat, barley, corn, sorghum, rice, cotton, sugarcane, eucalyptus, poplar, willow, orange, grapefruit, lemon, lime, avocado, cherry, peach, plum, apricot, nectarine, fig, olive, almond, pistachio, walnut, chestnut, hazelnut, pecan, tomato, eggplant, potato, and alfalfa.

Plant Breeding Methods

Plant breeding begins with the analysis of the current germplasm, the definition of problems and weaknesses of the current germplasm, the establishment of program goals, and the definition of specific breeding objectives. The next step is the selection of germplasm that possess the traits to meet the program goals. The selected germplasm is crossed in order to recombine the desired traits and through selection, varieties or parent lines are developed. The goal is to combine in a single variety or hybrid an improved combination of desirable traits from the parental germplasm. These important traits may include higher yield, field performance, improved fruit and agronomic quality, resistance to biological stresses, such as diseases and pests, and tolerance to environmental stresses, such as drought and heat.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.). Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection. These processes, which lead to the final step of marketing and distribution, usually take five to ten years from the time the first cross or selection is made.

The choice of breeding or selection methods depends on the mode of plant reproduction, the heritability of the trait(s) being improved, and the type of cultivar used commercially (e.g., $F_1$ hybrid cultivar, inbred cultivar, etc.). For highly heritable traits, a choice of superior individual plants evaluated at a single location will be effective, whereas for traits with low heritability, selection should be based on mean values obtained from replicated evaluations of families of related plants. The complexity of inheritance also influences the choice of the breeding method. Backcross breeding is used to transfer one or a few genes for a highly heritable trait into a desirable cultivar (e.g., for breeding disease-resistant cultivars), while recurrent selection techniques are used for quantitatively inherited traits controlled by numerous genes, various recurrent selection techniques are used. Commonly used selection methods include pedigree selection, modified pedigree selection, mass selection, and recurrent selection.

Pedigree selection is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding (i.e., recurrent selection) may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Molecular markers, or "markers", can also be used during the breeding process for the selection of qualitative traits. For example, markers closely linked to alleles or markers containing sequences within the actual alleles of interest can be used to select plants that contain the alleles of interest. The use of markers in the selection process is often called genetic marker enhanced selection or marker-assisted selection. Methods of performing marker analysis are generally known to those of skill in the art.

Mutation breeding may also be used to introduce new traits into plant varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development: Theory and Technique*, Walter Fehr (1991), *Agronomy Books,* 1 (lib.dr.iastate.edu/agron_books/1).

The production of double haploids can also be used for the development of homozygous lines in a breeding program. Double haploids are produced by the doubling of a set of chromosomes from a heterozygous plant to produce a completely homozygous individual. For example, see Wan, et al., *Theor. Appl. Genet.,* 77:889-892, 1989.

Additional non-limiting examples of breeding methods that may be used include, without limitation, those found in *Principles of Plant Breeding*, John Wiley and Son, pp. 115-161 (1960); *Principles of Cultivar Development: Theory and Technique*, Walter Fehr (1991), *Agronomy Books*, 1 (lib.dr.iastate.edu/agron_books/1), which are herewith incorporated by reference.

Having generally described this invention, the same will be better understood by reference to certain specific examples, which are included herein to further illustrate the invention and are not intended to limit the scope of the invention as defined by the claims.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

Example 1

Manipulation of PsbS Expression in *Nicotiana Tabacum* Plants Under Controlled and Field-Grown Conditions The following example describes the development and validation of *Nicotiana tabacum* (*N. tabacum*) lines with altered PsbS expression grown under controlled and field-grown conditions. *N. tabacum* lines with increased or decreased PsbS expression were generated.

Materials and Methods

Developing *N. Tabacum* Lines with Altered PsbS Expression

Figure 1B:
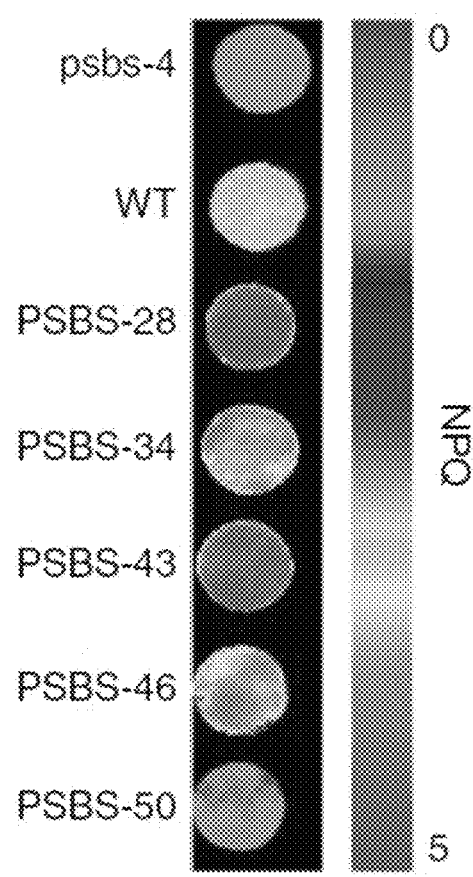
Figure 9:
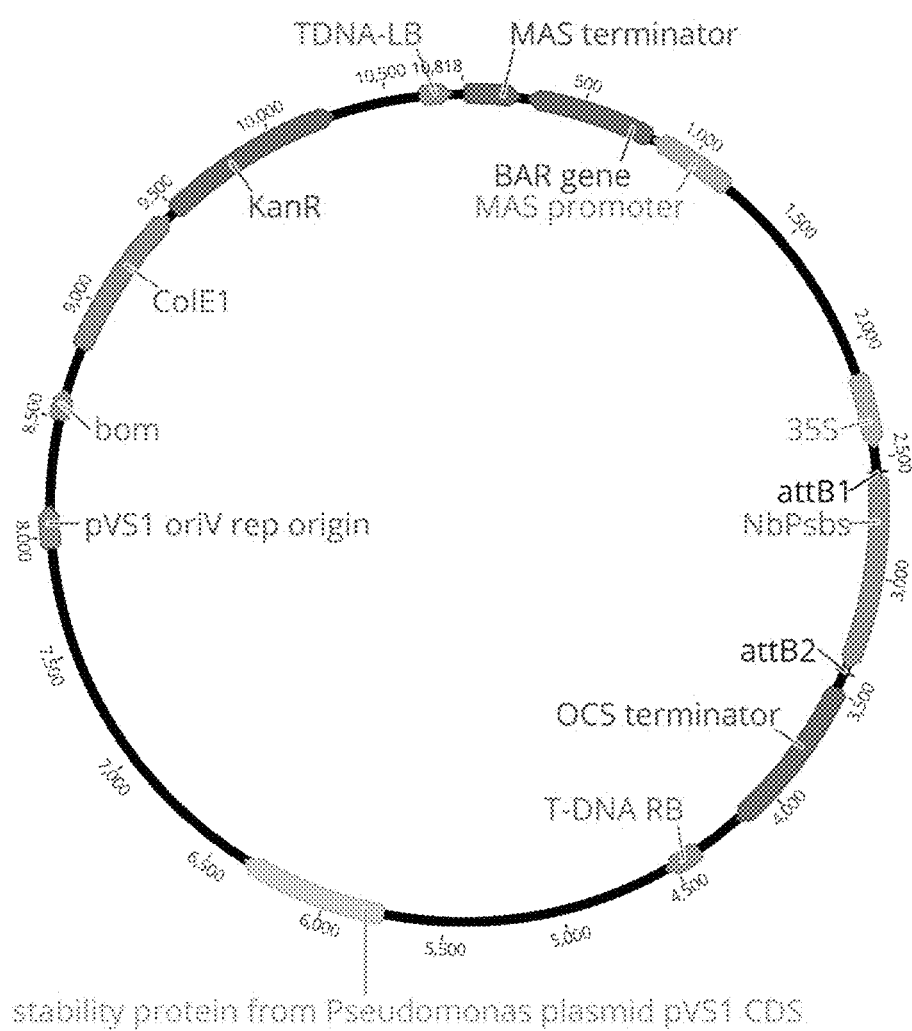
FIG. 9 shows the plasmid map for pEG100-NbPsbS used to transform N. tabacum.

The *N. benthamiana* PsbS gene coding sequence (Uniprot—Q2LAH0_NICBE; e.g., encoding the protein of SEQ ID NO: 17 or SEQ ID NO: 18) was cloned between the cauliflower mosaic virus 35S and octopine synthase terminator in the pEARLYGATE 100 binary vector (pEG100-NbPsbS) (FIG. 9). *N. tabacum* cv. "Petite Havana" was transformed with pEG100-NbPsbS using the *Agrobacterium tumefaciens*-mediated protocol. Four independent, single-copy transformation events with increased NPQ amplitude (PSBS-28, PSBS-34, PSBS-43, and PSBS-46) were selected and selfed to obtain progeny homozygous for the transgene (FIGS. 1A and 1B). Copy number and homozygosity were assessed using digital droplet PCR (dd-PCR) as in Glowacka et al. (2016) Plant Cell Env 39, 908. In addition, two events exhibiting spontaneous partial silencing of PsbS expression (psbs-4 and PSBS-50) were selected. Spontaneous partial silencing through RNAi inhibition is a common occurrence when using genes from the same or a closely related species. Here, an *N. benthamiana* gene was used in *N. tabacum*.

Seedling Propagation for Controlled Conditions

Seedlings were germinated on growing medium (LC1 Sunshine mix, Sun Gro Horticulture) in a controlled-environment cabinet (Environmental Growth Chambers) with photoperiod set to 12 h and temperature controlled at 23/18° C. (day/night). Five days after germination, seedlings were transplanted to 3.8-L pots and randomly positioned in a controlled-environment chamber (PGC20, Conviron) with photoperiod set to 16 h and air temperature controlled at 20/25° C. (day/night). Light intensity at leaf-level was controlled at 500 $\mu$mol m$^{-2}$ s$^{-1}$. Plants were watered and repositioned at random every 2 days until the fifth leaf was fully expanded.

Seedling Propagation for Field-Grown Conditions

Homozygous seeds were sown in a greenhouse. Five days after germination, seedlings were propagated hydroponically for 2 weeks in floating trays (Transplant Tray GP009 6×12 cells, Speedling Inc.) filled with hydroponics growing medium (Pro-mix PGX, Premier Tech). The concentration of total dissolved solids in the solution was measured every 2 days with a handheld TDS meter (COM-100, HM Digital Inc.) and adjusted to 100 ppm by the addition of 20-10-20 water-soluble fertilizer (Jack's Professional, JR Peters Inc.). Five days after the transplant to trays, Etridiazole fungicide (Terramaster 4EC to a final concentration of 78 $\mu$L L$^-$, Crompton Manufacturing Company Inc.) was added to the solution to protect the plants against root fungus disease in the field. Two applications of Mancozeb (Dithane Rainshield Fungicide at 1 g L$^{-1}$, Dow AgroSciences) were applied 6 and 9 days after transplant to prevent foliar fungus disease. On the same days, seedlings were sprayed with fermentation solids and solubles from *Bacillus thuringiensis*, (strain AM65-52, Gnatrol WDG Biological larvicide at 1 mL L$^{-1}$, Valent Biosciences Corp.) to reduce the greenhouse population of fungus gnats.

Field-Grown Conditions

Seedlings were transplanted to an experimental field site. The field was prepared 2 weeks prior to transplant by rototilling, cultivation, and harrowing. At this time, chlorpyrifos (1.5 g m$^{-2}$ Lorsban 15 G Insecticide, Dow AgroSciences) was worked into the soil to suppress cutworm damage, sulfentrazone (29 $\mu$L m$^{-2}$ Spartan 4 F pre-emergence herbicide, FMC Agricultural Solutions) was applied to reduce the emergence of weeds and slow-release fertilizer (30.8 g m$^{-2}$ ESN Smart Nitrogen, Agrium US Inc.) was put down. After transplant, all seedlings were sprayed with thiamethoxam (7 mg/plant Platinum 75 SG insecticide, Syngenta Crop Protection) to prevent damage from insect herbivory, and 12 days after the field transplant, all plants were sprayed with fermentation solids, spores, and insecticidal toxins from *Bacillus thuringiensis*, (strain ABTS-351, DiPel Pro dry flowable biological insecticide, Valent Biosciences Corp.) to suppress tobacco hornworm. The field experiment was set up as an incomplete randomized block design with 12 blocks of 6x6 plants spaced 30 cm apart. Each block contained four rows of four plants per genotype in north-south (N-S) orientation, surrounded by one border row of WT. WT was present in all blocks (n=12), whereas the PsbS mutant lines were randomly assigned to six blocks (n=6). The blocks were positioned in 3 (N-S)×4 (E-W) rectangles with 75 cm spacing between blocks. The entire experiment was surrounded by two border rows of WT plants.

Light intensity (LI-190R quantum sensor, LI-COR) and air temperature (Model 109 temperature probe, Campbell Scientific) were measured nearby on the same field site and half-hourly averages were logged using a datalogger (CR1000, Campbell Scientific). Precipitation was measured at two locations close to the field using precipitation gauges (NOAH IV Precipitation Gauge, ETI Instrument Systems Inc.). Watering to restore field capacity was provided daily when needed through parallel drip irrigation lines with emitters every 30 cm (17 mm PC Drip Line #DL077, The Drip Store).

mRNA Expression Analysis

Five leaf discs (total 2.9 cm$^2$) from the youngest fully expanded leaf were collected for mRNA extraction. For plants grown under field-grown conditions, leaf discs were collected at 34, 37, 41, and 45 days after emergence. Leaf discs were isolated 2 hours (h) after the start of the photoperiod. mRNA was harvested using the NucleoSpin RNA/Protein kit (Macherey-Nagel GmbH & Co., REF740933). Then, the extracted mRNA was treated with DNase (Turbo DNA-free kit; Thermo Fisher Scientific, AM1907). Next, the mRNA was transcribed into cDNA using Superscript III First-Strand Synthesis System for RT-PCR (Thermo Fisher Scientific, 18089-051). Quantitative reverse transcription PCR (qRT-PCR) was used to quantify the amount of PsbS transcript expression relative to NtActin and NtTubulin.

Protein Expression Analysis

Five leaf discs (total area of 2.9 cm$^2$) from the youngest fully expanded leaf of five plants per genotype (when grown under controlled conditions) or four plants per genotype (when grown under field-grown conditions) were collected for protein extraction. Samples were isolated 2 h after the start of the photoperiod. Protein was harvested using the NucleoSpin RNA/Protein kit (Macherey-Nagel GmbH & Co., REF740933). Total protein concentration was quantified using a protein quantification assay (Macherey-Nagel GmbH & Co., REF740967.50). Samples containing 1 μg total protein were separated by sodium dodecyl sulfate-polyacrylamide gel electrophoresis (SDS-PAGE) electrophoresis (Immobilon-P, Millipore, IPVH00010). Following separation, the samples were blotted to a membrane using semi-dry blotting (Trans-Blot SD, Bio-Rad). Then, the samples were labeled with primary antibodies raised against AtPsbS (AS09533, Agrisera) at a dilution of 1:2,000 and AtPsbO (AS06142-33, Agrisera) at a dilution of 1:20,000. Following primary antibody labeling, the samples were labeled with secondary antibody (W401B, Promega) at a dilution of 1:2,500. Last, the total protein in each labeled band was quantified using densitometry (ImageQuant LAS-4010, GE Healthcare Life Sciences) with ImageQuant TL software (Version 7.0 GE Healthcare Life Sciences). PsbS expression was normalized based on PsbO bands.

NPQ Measurements in Plants Grown Under Controlled Conditions

NPQ measurements were performed using an open gas exchange system equipped with a 2-cm$^2$ leaf chamber and integrated modulated fluorometer (LI-COR, LI6400XT).

NPQ of chlorophyll fluorescence was determined assuming a Stern-Volmer quenching model according to the following equation: $NPQ=F_m/F_m'-1$. Block temperature was controlled at 25° C., $CO_2$ inside the cuvette was maintained at 380 μmol mol$^{-1}$, and leaf-to-air water VPD was controlled to 1.1-1.4 kPa. Leaves were clamped in the leaf cuvette and dark-adapted for 1 h, after which minimal ($F_0$) and maximal fluorescence ($F_m$) were measured to determine maximal efficiency of whole-chain electron transport. Subsequently, light intensity (100% red LEDs, $\lambda_{peak}$ 630 nm) was slowly increased from 0 to 50, 80, 110, 140, 170, 200, 300, 400, 500, 600, 800, 1,000, 1,500, and 2,000 μmol m$^{-2}$ s$^{-1}$. When steady state was reached, maximal fluorescence without dark adaptation ($F_m'$) was measured.

NPQ Measurements in Plants Grown Under Field-Grown Conditions

Leaf discs were sampled pre-dawn from field-grown plants and stored in darkness in glass vials for up to 4 h until measurement. Humidity in the vials was maintained fully saturated by placing a piece of wet filter paper in each vial. Dark-adapted leaf discs were positioned on a piece of wet filter paper in a chlorophyll fluorescence imager to determine maximal fluorescence ($F_m$) (CFimager, Technologica). Subsequently, leaf discs were exposed to 15 min of 1000 μmol m$^{-2}$ s$^{-1}$, after which maximal fluorescence without dark adaptation was determined ($F_m'$). NPQ was then determined according to the following equation: $NPQ=F_m/F_m'-1$.

Results

Figure 2A:
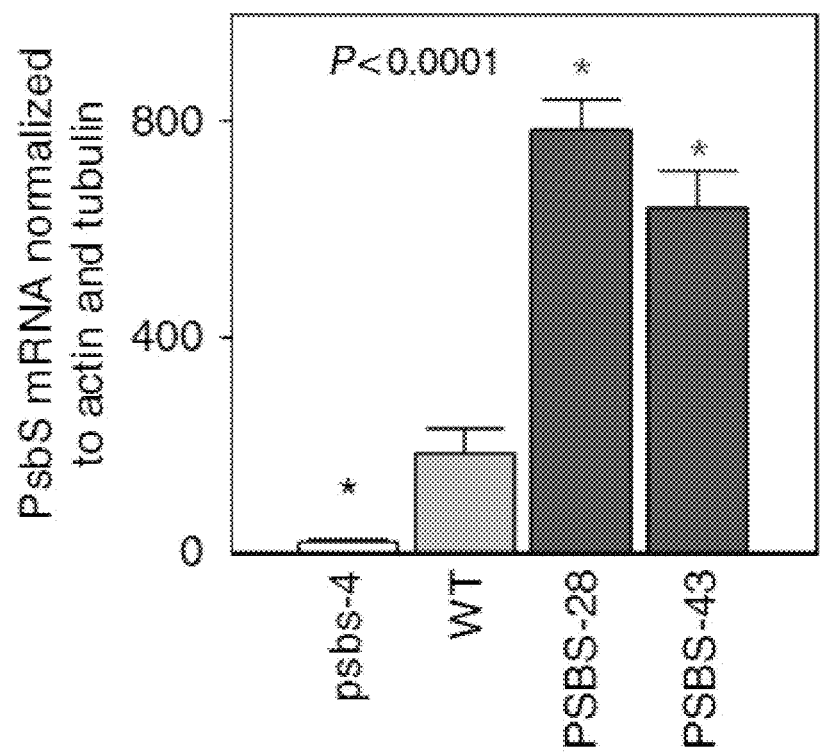
FIGS. 2A-2B show PsbS mRNA expression.

FIG. 2A shows PsbS mRNA expression in WT and *N. tabacum* plants with altered PsbS expression grown under controlled conditions. In particular, FIG. 2A shows PsbS expression increased 4.2-fold and 3.5-fold in the overexpression lines PSBS-28 and PSBS-43 respectively relative to WT plants grown under the same conditions. In contrast, PsbS expression decreased 10-fold in the partially silenced line psbs-4 relative to the WT samples (FIG. 2A).

Figure 2B:
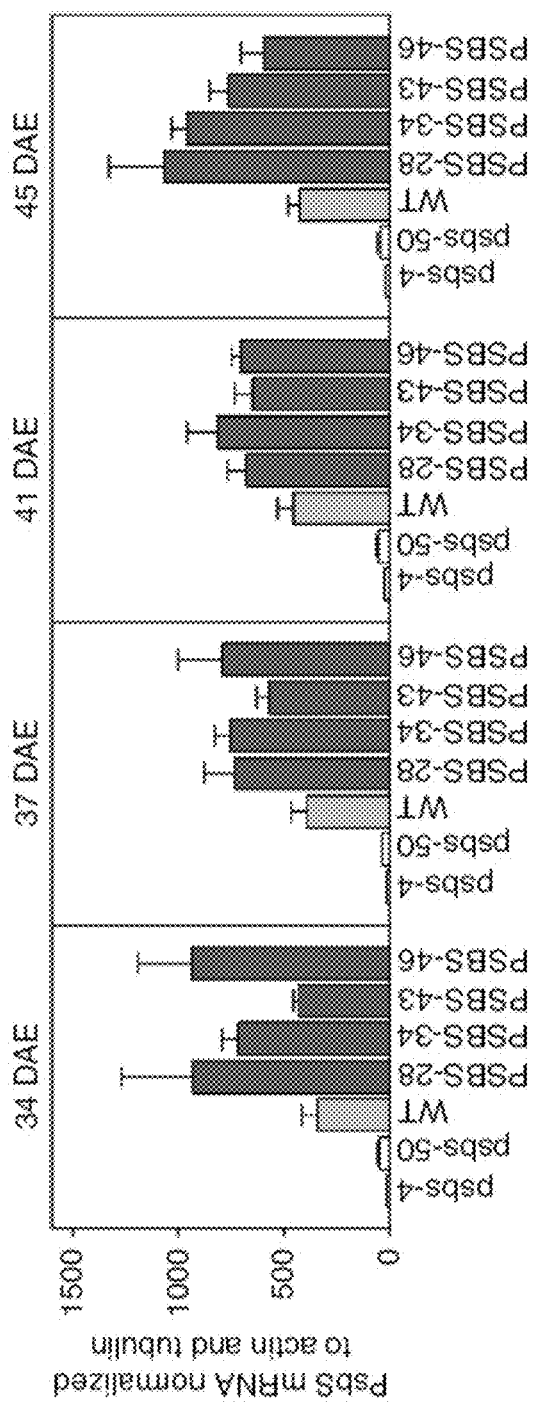

FIG. 2B shows PsbS mRNA expression in WT and *N. tabacum* plants with altered PsbS expression under field-grown conditions. The overexpression lines PSBS-28, PSBS-34, PSBS-43, and PSBS-46 had elevated PsbS expression under field-grown conditions relative to WT, while the partially silenced lines psbs-4 and psbs-50 had decreased PsbS expression relative to WT (FIG. 2B).

Figure 3A:
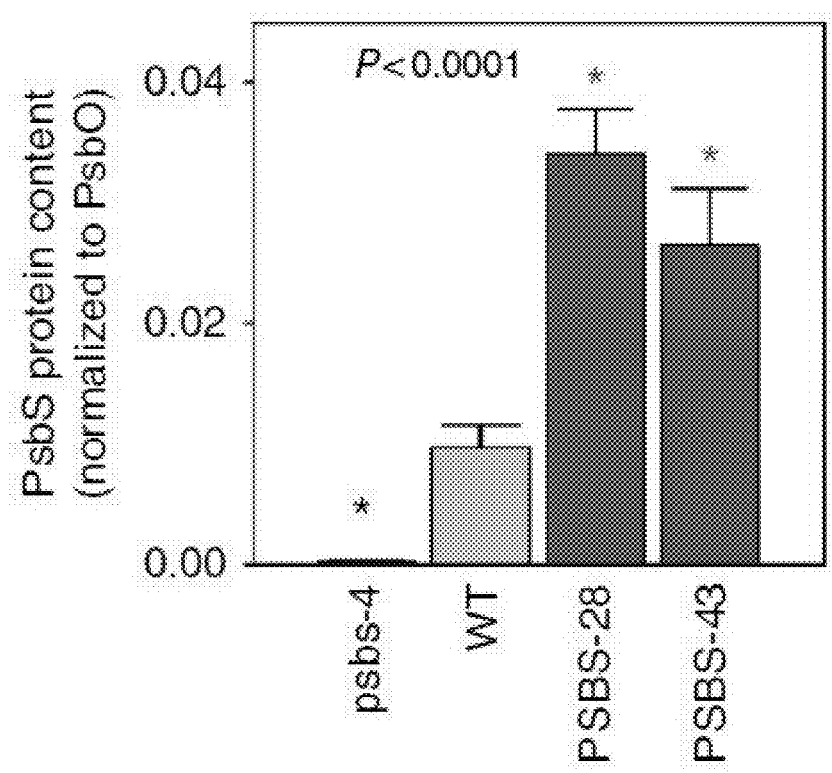
FIGS. 3A-3C show PsbS protein expression.
Figure 3B:
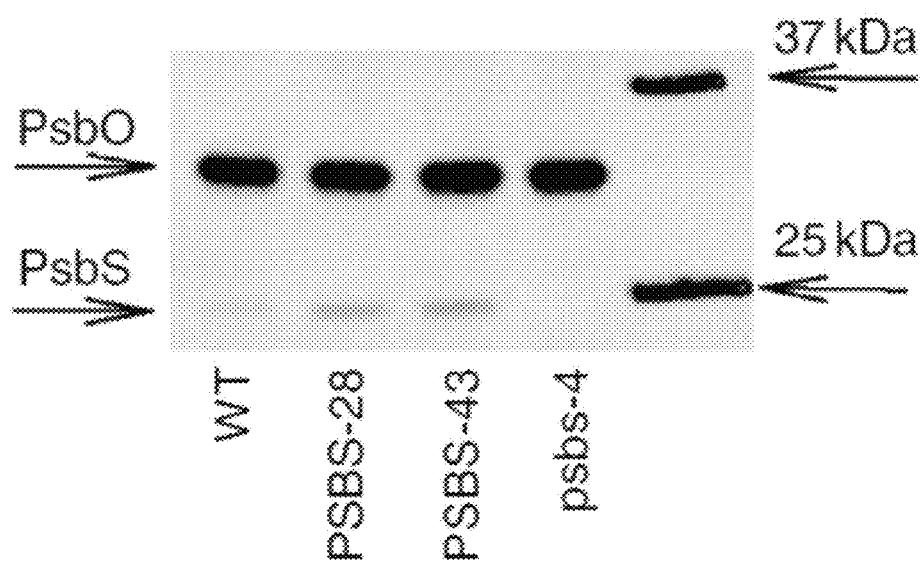

FIGS. 3A and 3B show PsbS protein expression normalized to PsbO protein expression in WT and mutant *N. tabacum* lines grown under controlled conditions. Specifically, PsbS protein expression was 2.7-fold and 3.5-fold higher in the overexpression lines PSBS-43 and PSBS-28 relative to WT (FIGS. 3A and 3B). PsbS protein was virtually absent in the partially silenced line psbs-4 (FIGS. 3A and 3B).

Figure 3C:
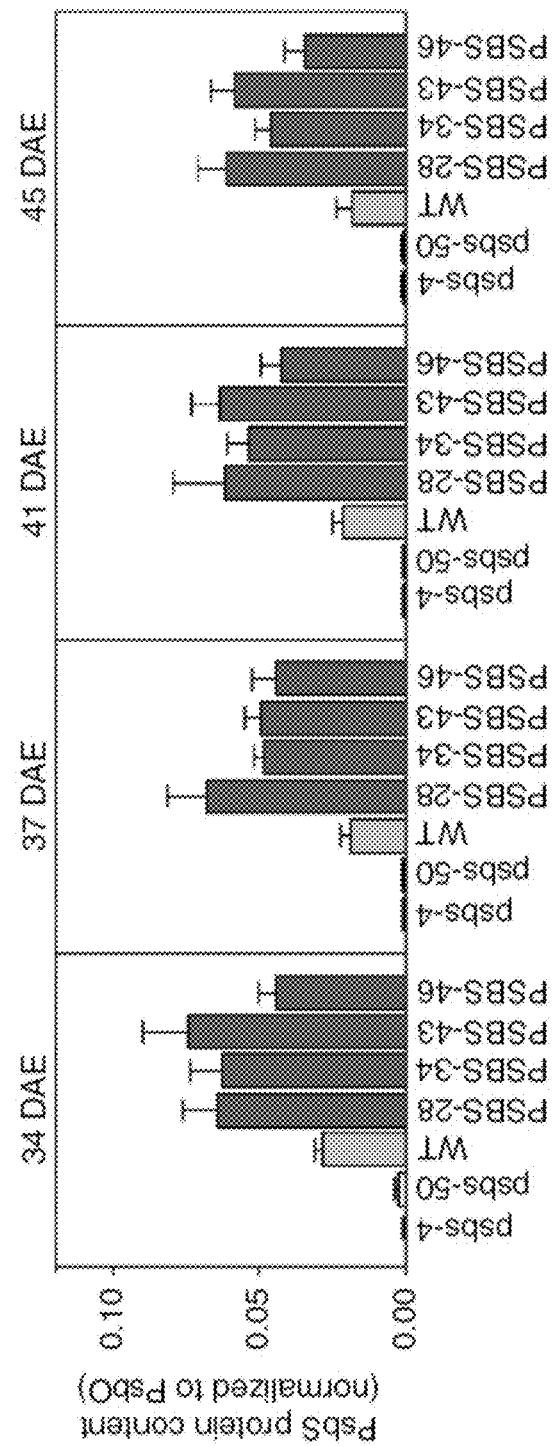

FIG. 3C shows PsbS protein expression normalized to PsbO protein expression in WT and mutant *N. tabacum* lines under field-grown conditions. FIG. 3C demonstrates that the overexpression lines PSBS-28, PSBS-34, PSBS-43, and PSBS-46 had elevated PsbS protein expression under field-grown conditions relative to WT (FIG. 3C). The partially silenced lines psbs-4 and psbs-50 had decreased PsbS expression relative to WT.

The results presented in FIGS. 2A-2B and FIGS. 3A-3C demonstrate that in the overexpression lines (PSBS-28, PSBS-34, PSBS-43, and PSBS-46), both mRNA and protein levels were increased relative to WT plants, while in the partially silenced lines (psbs-4 and psbs-50), both mRNA and protein levels were decreased relative to WT plants. These effects were seen regardless of growth conditions (i.e., both under controlled conditions and field-grown conditions).

Example 2

PsbS Expression Affects Water Use Efficiency in Plants Grown Under Controlled and Field-Grown Conditions Example 1 detailed the development of *N. tabacum* lines with altered PsbS mRNA/protein expression. The following example describes the effect of altered PsbS expression levels in these lines on leaf-level instantaneous water use efficiency (iWUE) in plants grown under controlled and field-grown conditions.

Materials and Methods

Photosynthetic Gas Exchange Measurements in Plants Grown Under Controlled Conditions Gas exchange measurements were performed using an open gas exchange system equipped with a 2-cm$^2$ leaf chamber and integrated modulated fluorometer (LI6400XT, LI-COR). All chlorophyll fluorescence measurements were performed using the multiphase flash routine.

To determine the light response of net $CO_2$ assimilation rate ($A_n$) and whole-chain photosynthetic electron transport, gas exchange and pulse amplitude-modulated chlorophyll fluorescence were measured at a range of light intensities. Block temperature was controlled at 25° C., $CO_2$ inside the cuvette was maintained at 380 µmol mol$^{-1}$, and leaf-to-air water vapor pressure deficit (VPD) was controlled to 1.1-1.4 kPa. Leaves were clamped in the leaf cuvette and dark-adapted for 1 h, after which minimal ($F_0$) and maximal fluorescence ($F_m$) were measured to determine maximal efficiency of whole-chain electron transport (Equation: $F_v/F_m=(F_m-F_0)/F_m$).

Subsequently, light intensity (100% red LEDs, $\lambda_{peak}$ 630 nm) was slowly increased from 0 to 50, 80, 110, 140, 170, 200, 300, 400, 500, 600, 800, 1,000, 1,500, and 2,000 µmol m$^{-2}$ s$^{-1}$. When steady state was reached, net $CO_2$ fixation rate ($A_n$), stomatal conductance ($g_s$), and $CO_2$ in the intercellular airspaces within the leaf ($C_i$), were logged. Instantaneous water use efficiency (iWUE) was determined by dividing net $CO_2$ assimilation by stomatal conductance ($A_n/g_s$). Further, F' and $F_m$' were measured to estimate the operating efficiency of whole-chain electron transport ($F_q'/F_m'=(F_m'-F')/F_m'$). Given that stomatal movements can include very long-term diurnal components, the routine was aimed at measuring only relatively short-term stomatal responses to changes in light intensity, and steady-state waiting times were kept between 10 and 20 minutes per step.

To evaluate the $CO_2$ response of $A_n$, leaves were allowed to reach steady state at a light intensity of 2,000 µmol m$^{-2}$ s$^{-1}$ (100% red LEDs, $\lambda_{peak}$ 630 nm), with block temperature controlled to 25° C. and $CO_2$ in the airstream set to 400 µmol mol$^{-1}$. Subsequently, $CO_2$ was varied from 400 to 300, 200, 100, 75, 400, 400, 500, 600, 700, 800, 1,000, 1,200, and 1,500 µmol mol$^{-1}$. When steady state was attained, $A_n$, $g_s$, and $C_i$ were logged. $V_{cmax}$ was determined from the response of $A_n$ to chloroplastic $CO_2$ concentration ($C_c$) by fitting a biochemical model with temperature corrections to measurements. $J_{max}$ was determined by fitting a non-rectangular hyperbola to light response curves of linear electron transport estimated from chlorophyll fluorescence. Stomatal limitation of $A_n$ was computed using measurements at ambient $CO_2$ (Ca=380 µmol mol$^{-1}$) and saturating light intensity, and predicted values of $A_n$ when stomata are not limiting.

Photosynthetic Gas Exchange Measurements in Plants Grown Under Field-Grown Conditions The response of photosynthetic gas exchange to light intensity was measured on the youngest fully expanded leaf of plants. Measurements were performed in four complete sets to account for random effects of North to South positioning of plants, and time of day. Leaves were clamped in the cuvette of an open gas exchange system (LI6400XT, LI-COR) and allowed to reach steady-state gas exchange at saturating light intensity of 2000 µmol m$^{-2}$ s$^{-1}$, with block temperature set to 30° C. and $CO_2$ in the airstream controlled to 400 µmol mol$^{-1}$ and VPD between air and leaf kept below 1.5 kPa. Subsequently, light intensity was varied from 2,000 to 1,500, 1,000, 800, 600, 400, 300, 200, 170, 140, 110, 80, and 50 µmol m$^{-2}$ s$^{-1}$. Due to the limited window suitable for measuring gas exchange in field-grown trials, waiting time for steady state was kept between 5 and 10 min for these measurements. When steady state was reached, net assimilation rate ($A_n$), stomatal conductance ($g_s$), and intercellular $CO_2$ ($C_i$) were logged.

Stomatal Density and Stomatal Complex Dimensions

Fresh leaf samples were taken from the youngest fully expanded leaf and mounted onto a microscope slide. Topographies of the adaxial and abaxial surfaces were measured using a µsurf explorer optical topometer (Nanofocus, Oberhausen). The 20×/0.60 objective lens was used for stomatal density quantification (Image J 1.51K, NIH). The 50×/0.80 objective lens was used for measurements of stomatal complex dimensions.

Results

Figure 4A:
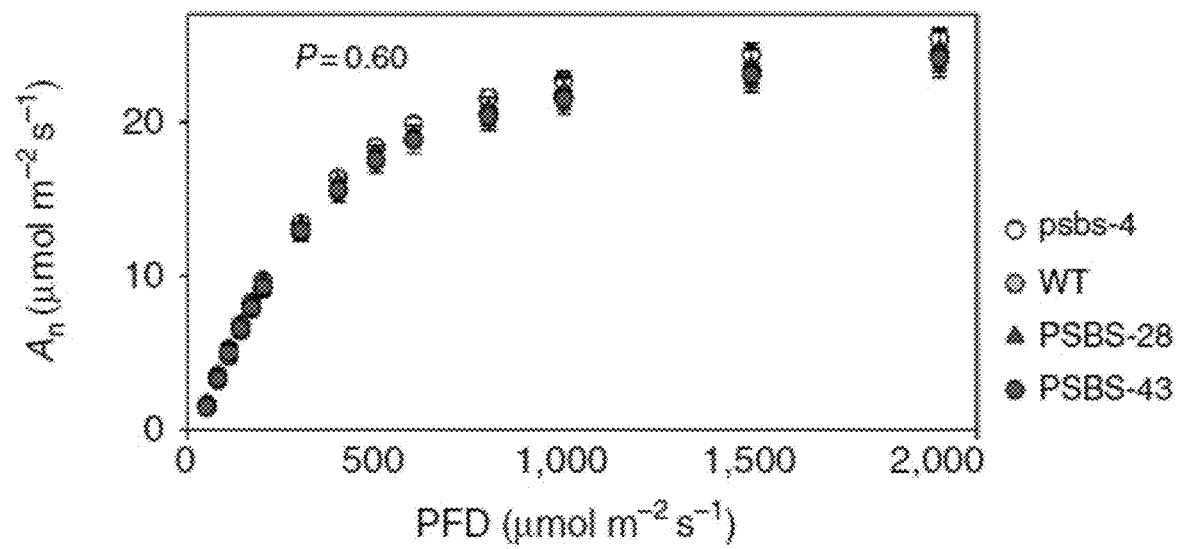
FIGS. 4A-4E show measurements of photosynthesis and stomatal conductance in PsbS suppressed lines, PsbS overexpression lines, and WT under controlled conditions.
Figure 4B:
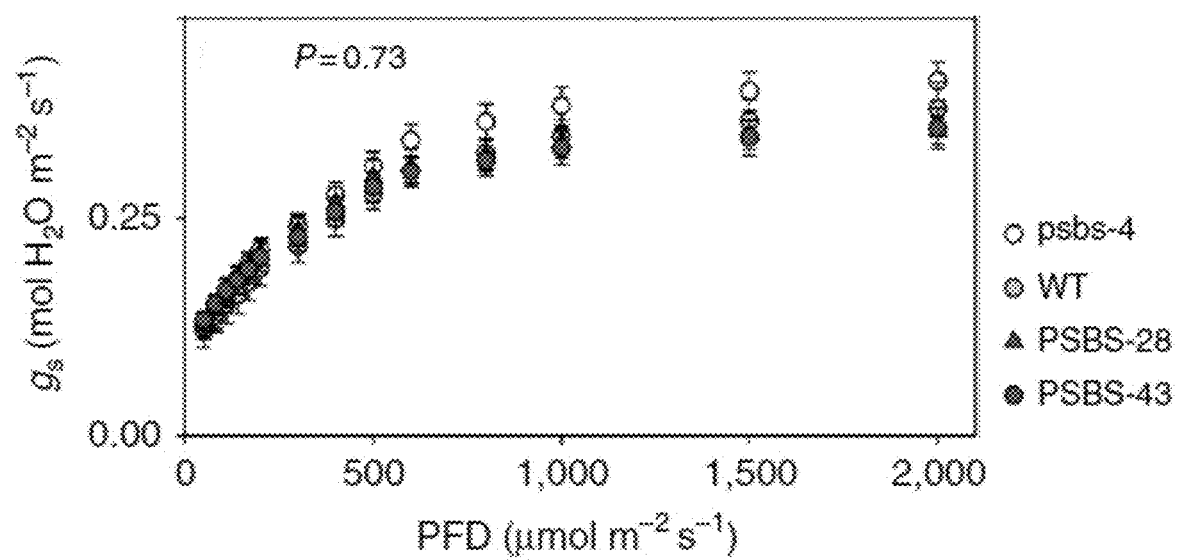

FIGS. 4A-4E show the impact of PsbS expression on photosynthesis and iWUE on plants grown under controlled conditions. In particular, FIG. 4A shows that there was no difference in net $CO_2$ assimilation ($A_n$) in plants with increased or decreased PsbS expression relative to WT plants. FIG. 4B shows that stomatal conductance levels were lower in plants with elevated PsbS expression relative to WT. Further, stomatal conductance levels were higher in plants with decreased PsbS expression relative to WT (FIG. 4B). Notably, the impact on stomatal conductance was larger than the impact on $CO_2$ assimilation ($A_n$), which was minimally affected.

Figure 4C:
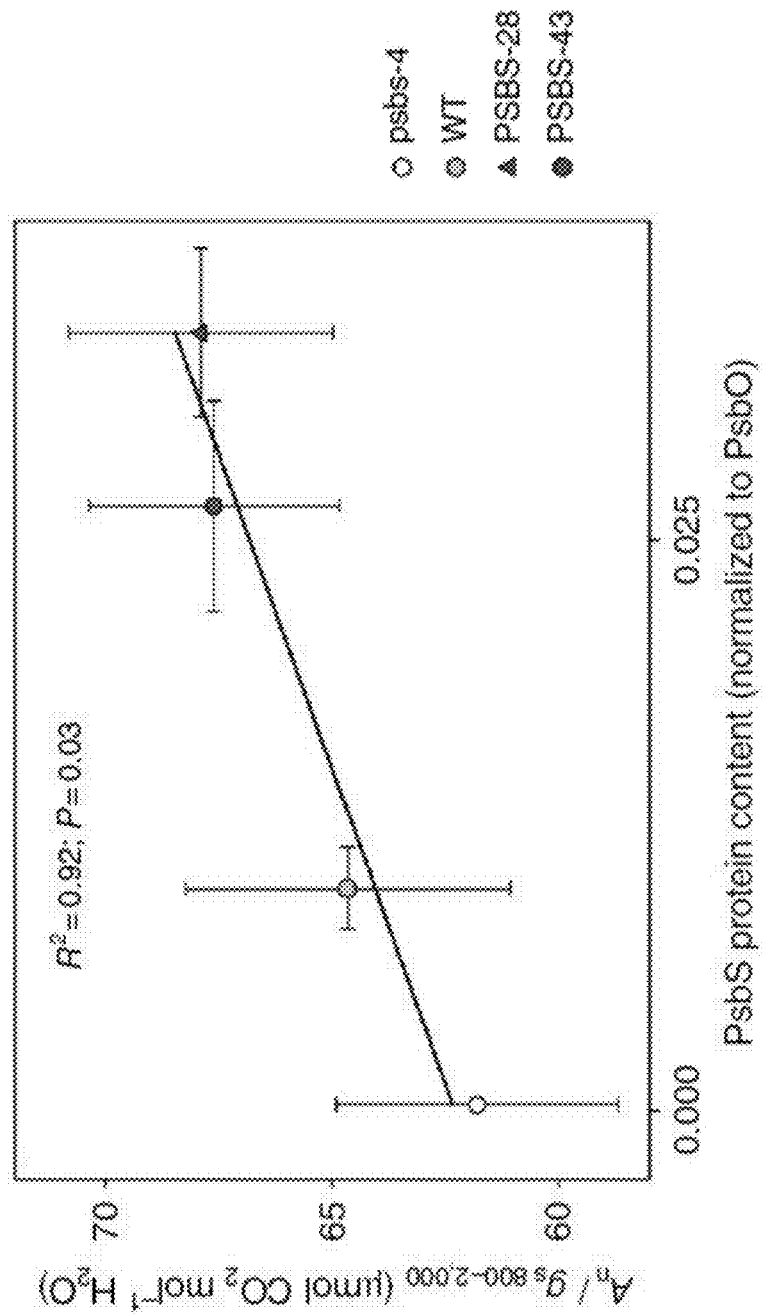
Figure 4D:
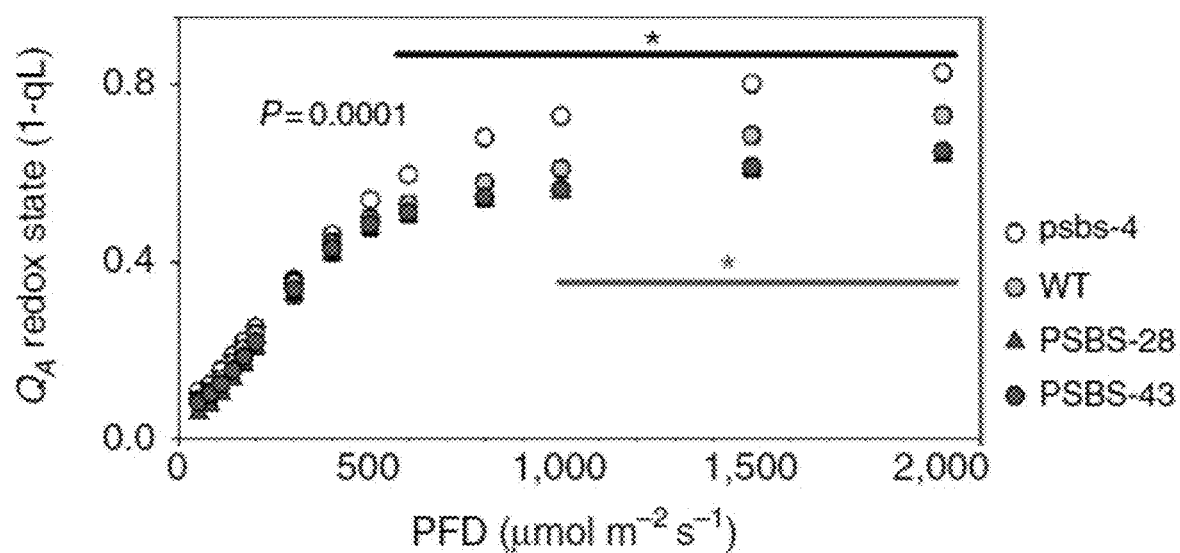
Figure 4E:
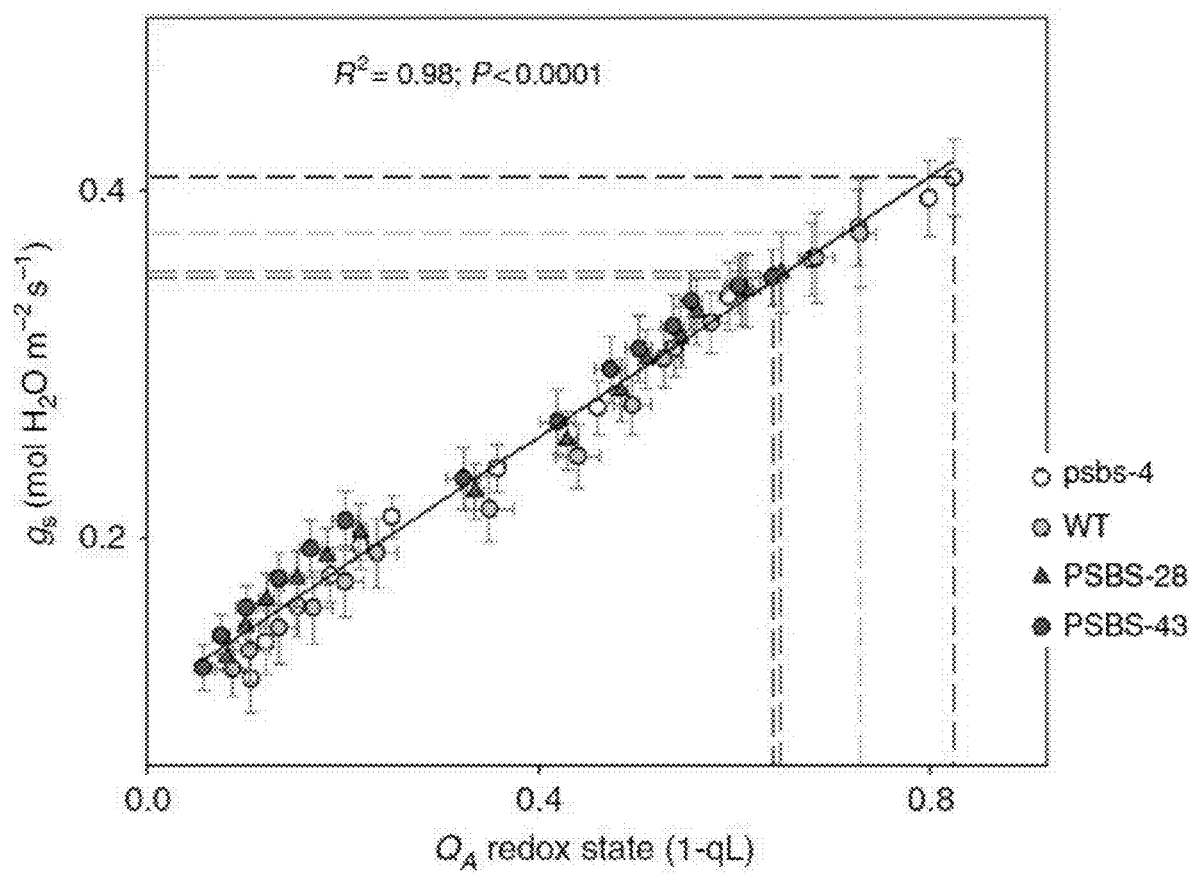

FIG. 4C demonstrates that there was a strong positive correlation between iWUE and PsbS expression ($R^2$=0.92, P=0.03, ANOVA). Thus, the data demonstrate that manipulation of PsbS expression significantly impacts iWUE. In particular, the data show that increased PsbS expression improves iWUE. FIG. 4D shows that the redox state of $Q_A$ was significantly more oxidized in lines overexpressing PsbS compared to WT ($R^2$=0.98, P<0.0001, ANOVA). FIG. 4E shows that there was a significant positive correlation between $Q_A$ redox state and stomatal conductance ($g_s$) in all tested plant lines. The results presented in FIGS. 4A-4E demonstrate that plants with elevated PsbS expression had improved iWUE when grown under controlled conditions. Further, the results presented in FIGS. 4A-4E show that there was a link between $Q_A$ redox state and stomatal conductance.

Figure 5A:
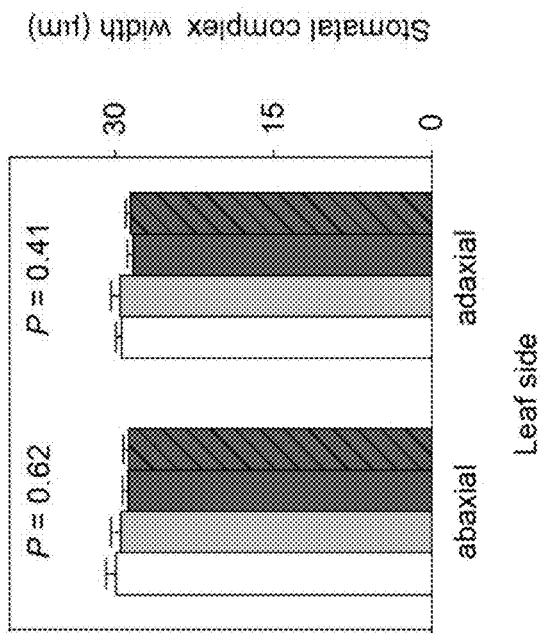
FIGS. 5A-5D show measurements of stomatal characteristics in PsbS mutant lines, PsbS overexpressing lines, and WT.
Figure 5B:
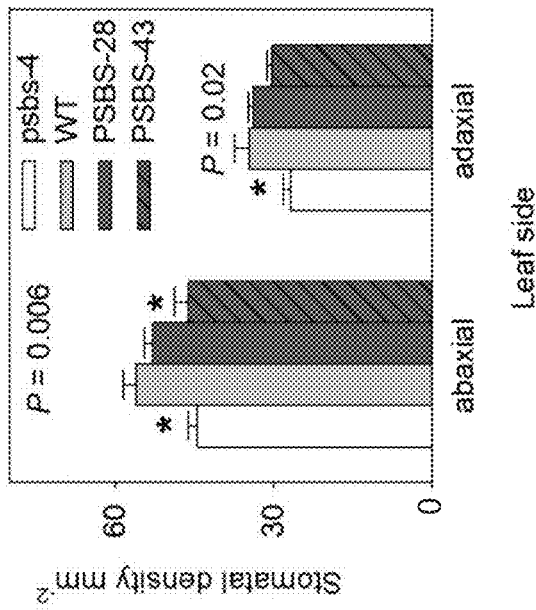
Figure 5D:
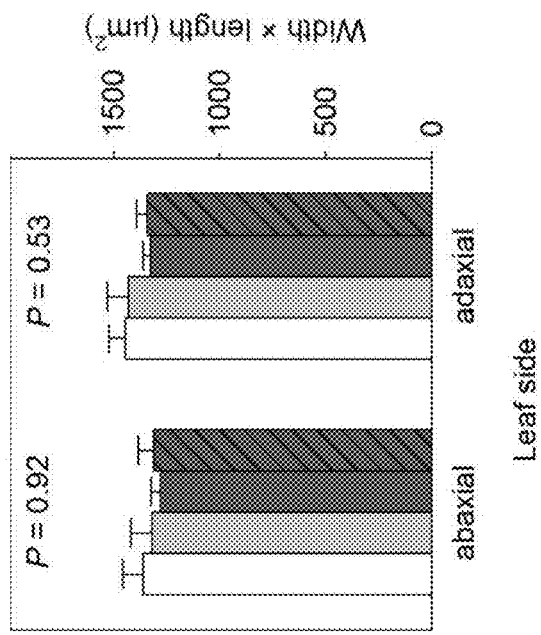
Figure 5C:
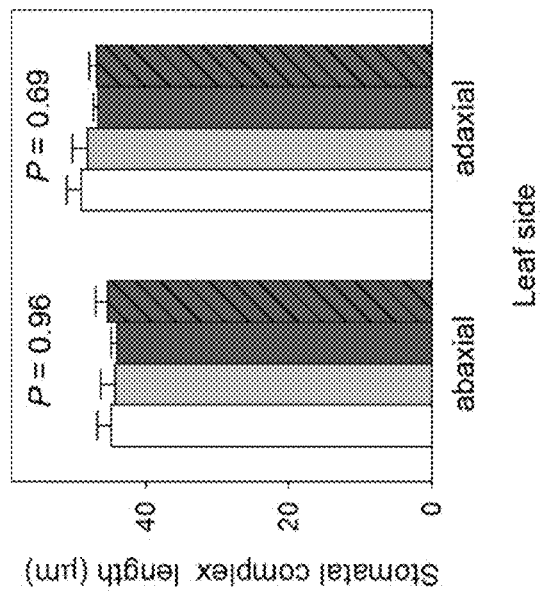

FIG. 5A shows that plants with elevated PsbS did not have increased stomatal density compared to WT plants. FIG. 5B shows that there was no difference in stomatal complex width in plants with altered PsbS expression compared to WT plants. FIG. 5C shows that there was no difference in stomatal complex length in plants with altered PsbS expression compared to WT plants. FIG. 5D shows that there was no difference in stomatal complex width×length (µM$^2$) in plants with altered PsbS expression compared to WT plants. The results presented in FIGS. 5A-5D show that the change in stomatal conductance observed in plants with elevated PsbS expression was not due to any change in stomatal pore dimensions or stomatal density. Therefore, the combined data in FIGS. 4A-4E and 5A-5D demonstrate that the change in stomatal conductance linked to altered PsbS expression was due to regulation of stomatal opening.

Figure 6A:
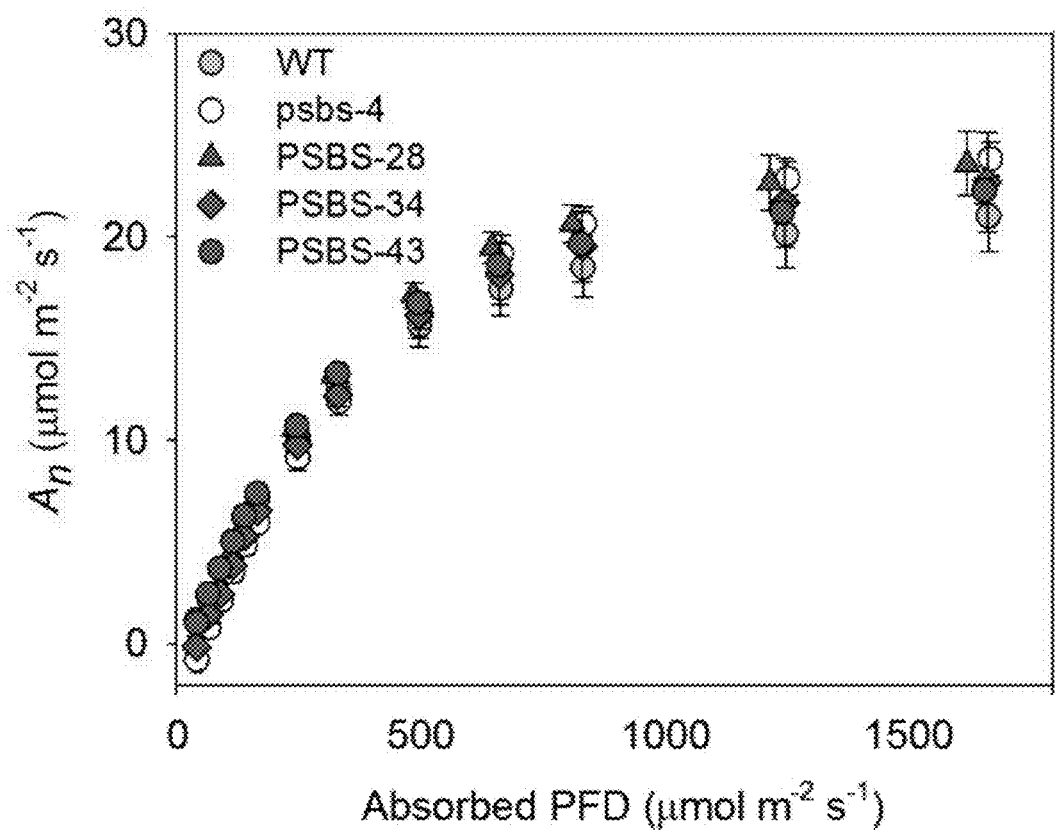
FIGS. 6A-6F show measurements of photosynthesis and stomatal conductance in PsbS suppressed lines, PsbS overexpression lines, and WT under field-test conditions.
Figure 6B:
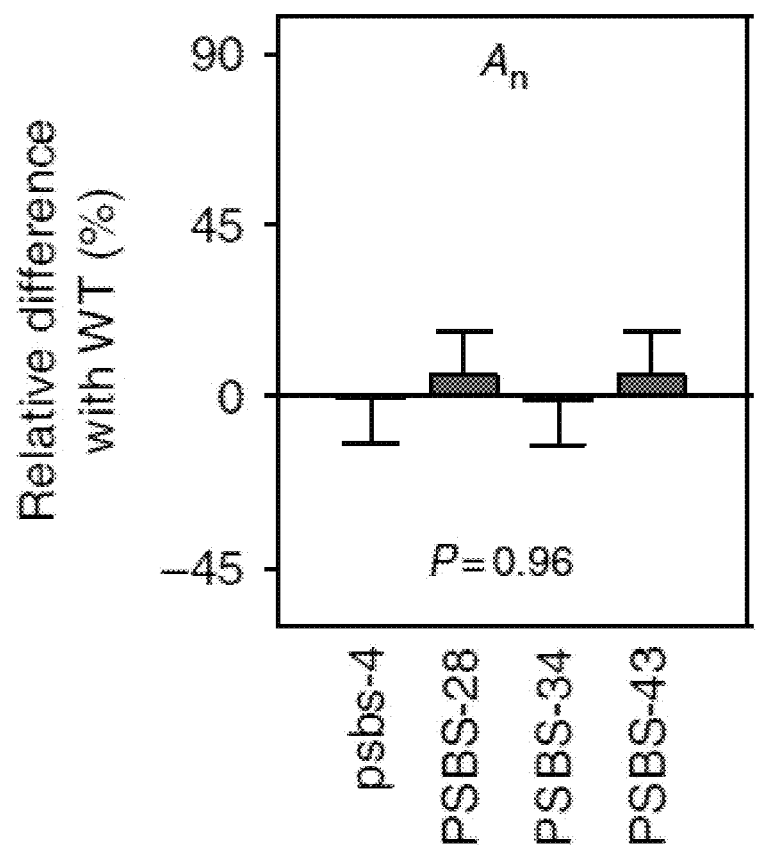
Figure 6C:
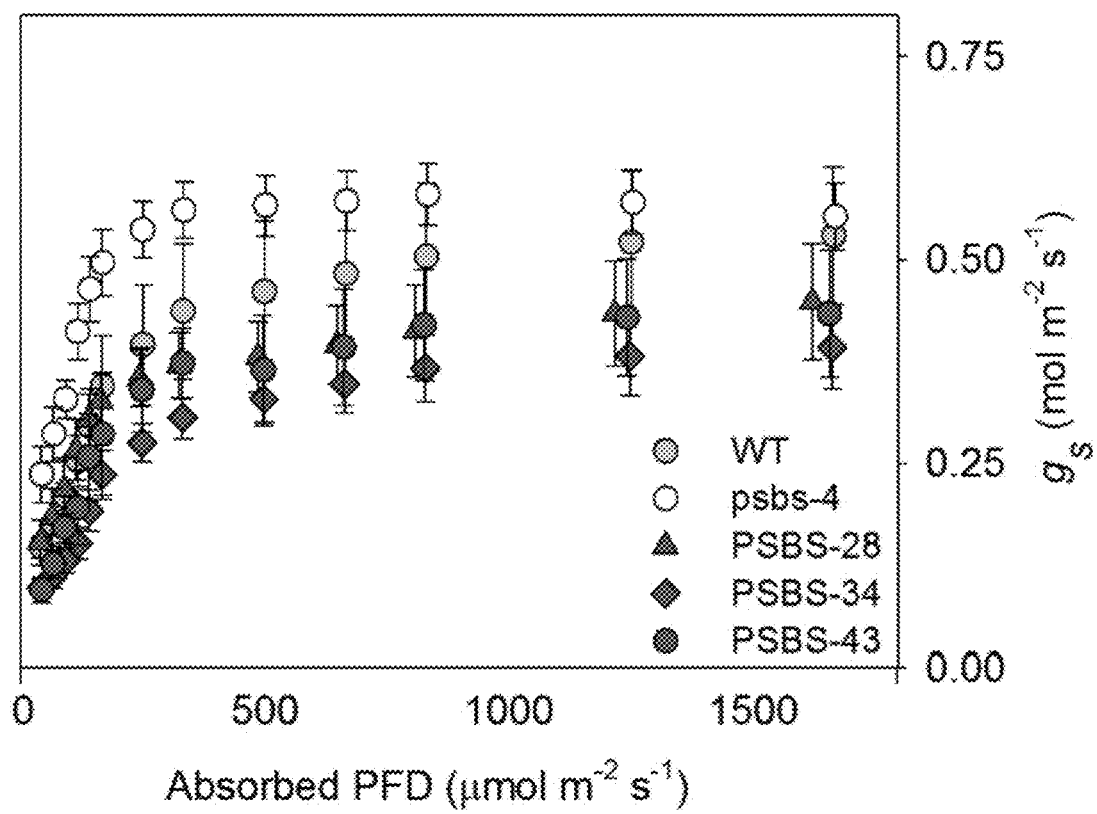
Figure 6E:
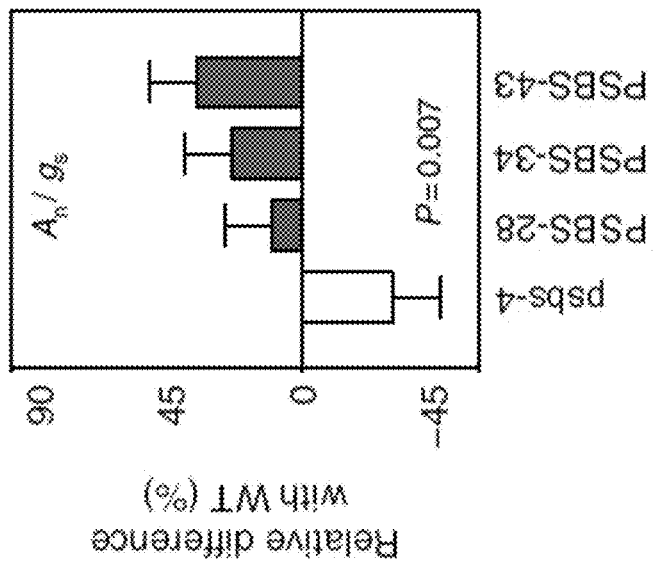
Figure 6D:
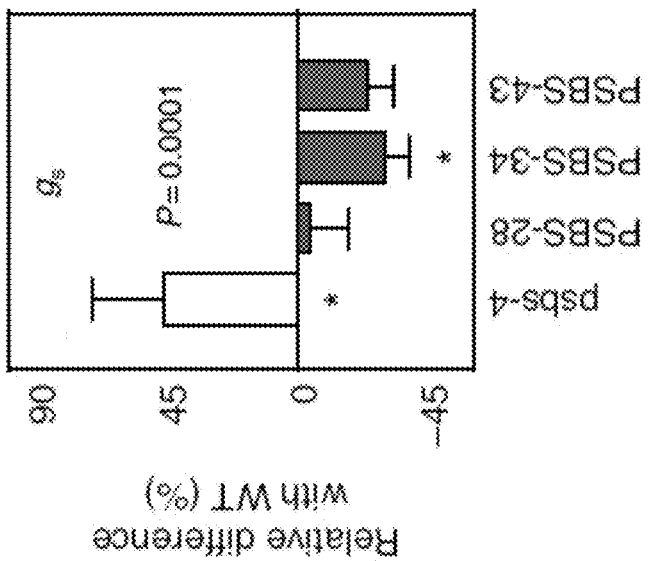
Figure 6F:
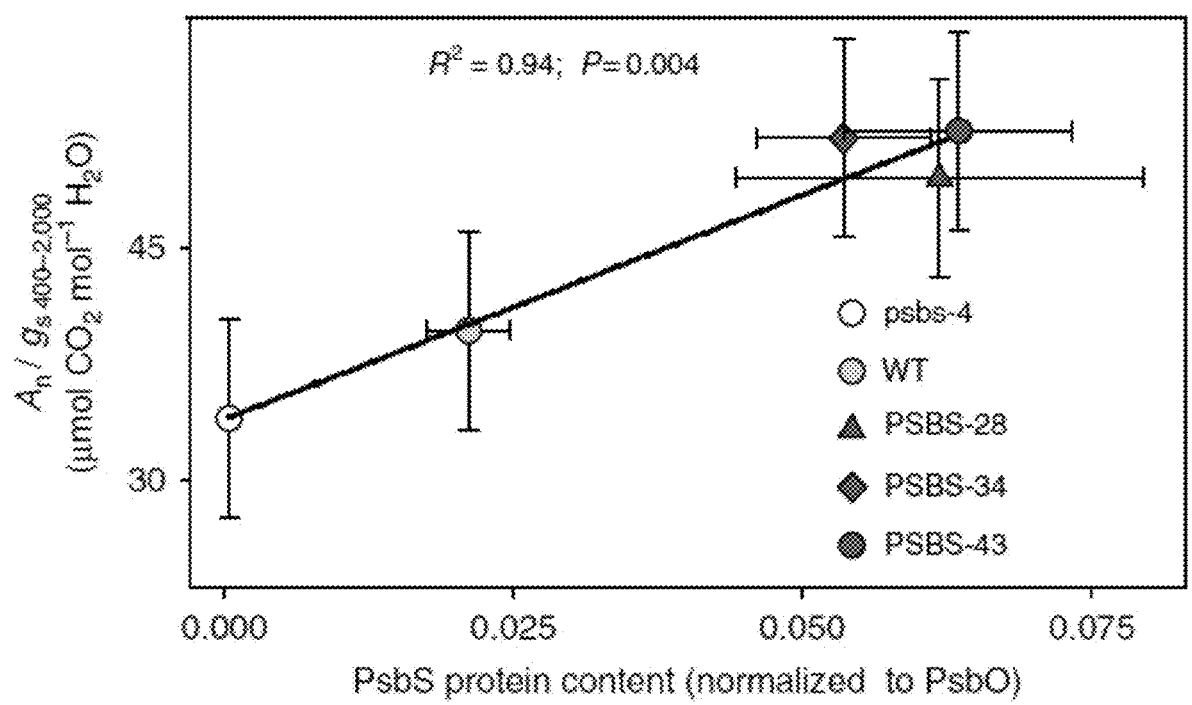

FIGS. 6A-6F show the impact of PsbS expression on photosynthesis and iWUE in plants under field-grown conditions. In particular, FIGS. 6A and 6B show that there was little difference in net $CO_2$ assimilation ($A_n$) in plants with increased or decreased PsbS expression. FIGS. 6C and 6D show that by contrast to $A_n$, stomatal conductance decreased in plants with elevated PsbS expression relative to WT. Further, plants with decreased PsbS expression had increased stomatal conductance relative to WT, and these effects were seen across all light levels, suggesting that increased iWUE occurred under all lighting conditions. (FIGS. 6C and 6D). FIG. 6E shows improved iWUE in *N. tabacum* plants with elevated PsbS expression relative to WT. However, the iWUE of *N. tabacum* plants with decreased PsbS expression dropped relative to WT (FIG. 6E). FIG. 6F demonstrates that there was a strong positive correlation and linear relationship between iWUE and PsbS expression ($R^2=0.94$, $P=0.004$, ANOVA). The results presented in FIGS. 6A-6F demonstrate that plants with elevated PsbS expression had improved iWUE under field-grown conditions.

The results in this example demonstrate that plants with elevated PsbS expression had improved iWUE when grown in both controlled and field-grown conditions. The results further demonstrate that the change in stomatal conductance linked to altered PsbS expression was due to regulation of stomatal opening rather than changes in stomatal pore dimensions or stomatal density.

Example 3

PsbS Expression Does Not Affect Biochemical Photosynthetic Processes in Plants Grown Under Controlled Conditions The following example describes the effect of altered PsbS expression on biochemical photosynthetic processes in plants grown under controlled conditions. These experiments were conducted to determine if potential alterations in biochemical photosynthetic processes following manipulation of PsbS expression (i.e., pleiotropic effects) could explain the change in iWUE.

Materials and Methods

Photosynthetic Gas Exchange Measurements

All photosynthetic gas exchange measurements were conducted as in Example 2.

Rubisco Activation State and Content

The youngest fully expanded leaves were clamped in the cuvette of an open gas exchange system (LI6400XT with 2×3 LED Light Source, LI-COR) with light intensity set to 1,800 µmol m$^{-2}$ s$^{-1}$, $CO_2$ set to 400 µmol mol$^{-1}$, and block temperature set to 25° C. After steady-state gas exchange was reached, leaves were rapidly removed and a disc of 0.55 cm$^2$ from the center of the portion of the leaf that had been enclosed in the cuvette was snap frozen in liquid nitrogen. Rubisco activity was determined by the incorporation of $^{14}CO_2$ into acid-stable products at 25° C. Samples were ground in tenbroek glass homogenizers with ~2 mL cm$^{-2}$ $CO_2$-free extraction buffer containing 100 mM Hepes-KOH (pH 7.5), 2 mM Na$_2$EDTA, 20 mM MgCl$_2$, 5 mM dithiothreitol (DTT), 5 mg mL$^{-1}$ polyvinyl pyrrolidine, 15 mM amino-n-caproic acid and 3.5 mM benzamidine, and 5% v/v protease inhibitor cocktail (Unless indicated otherwise all reagents from Sigma). Within 30 s of extraction, samples were assayed for initial Rubisco activity in a buffer containing 100 mM Bicine-NaOH (pH 8.2), 1 mM Na$_2$EDTA, 20 mM MgCl$_2$, 5 mM dithiothreitol (DTT), 1 mM ATP, 0.5 mM ribulose-1,5-bisphosphate, and 12.8 mM NaH$^{14}CO_3$ (NaH$^{14}CO_3$ purchased from Vitrax). Assays were run for 30 s and terminated with the addition of 300 µL 5 N formic acid. The radioactivity of acid-stable products was determined by liquid scintillation counting (Packard Tri-Carb 1900 TR, Canberra Packard Instruments Co.). After determining initial activity, the extract was incubated with 10 mM NaHCO$_3$ and 20 mM MgCl$_2$ for 20 min at room temperature, and the total activity of the extract was assayed as above. The activation state of Rubisco was determined by the ratio of initial activity to total activity.

Results

Figure 7A:
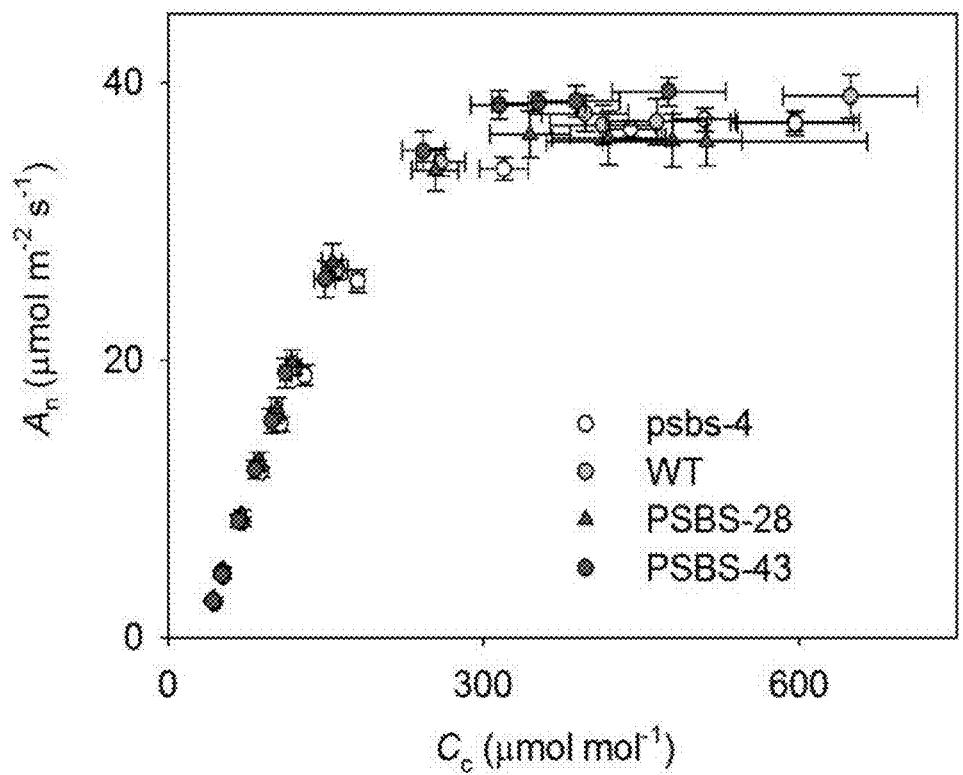
FIGS. 7A-7G show comparative measurements of a PsbS mutant line, two PsbS overexpression lines, and the WT plant for various photosynthetic components and their biochemical characteristics.
Figure 7B:
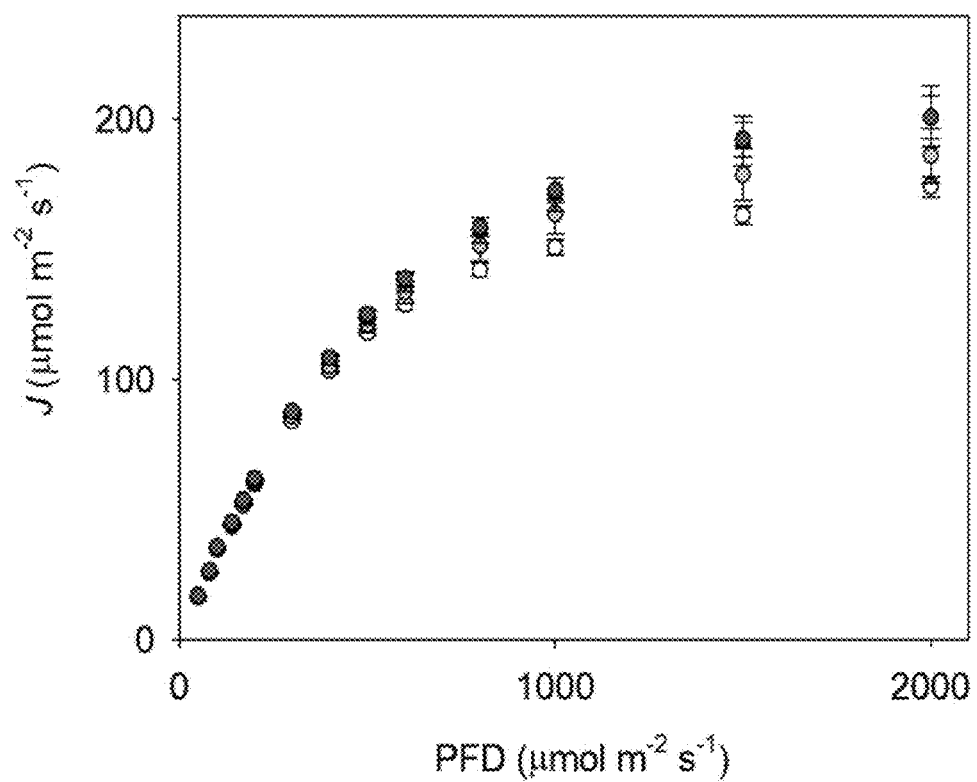
Figure 7C:
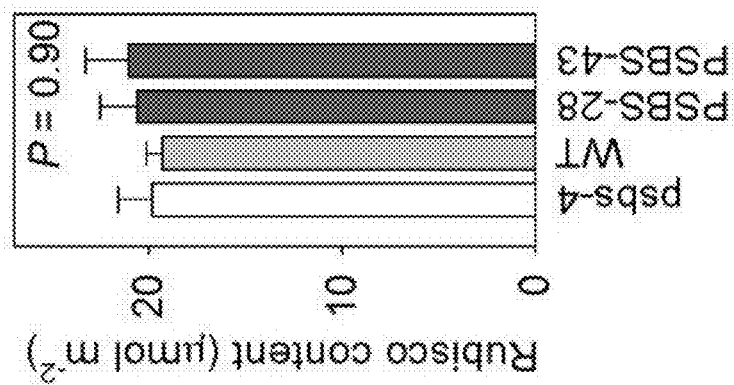
Figure 7D:
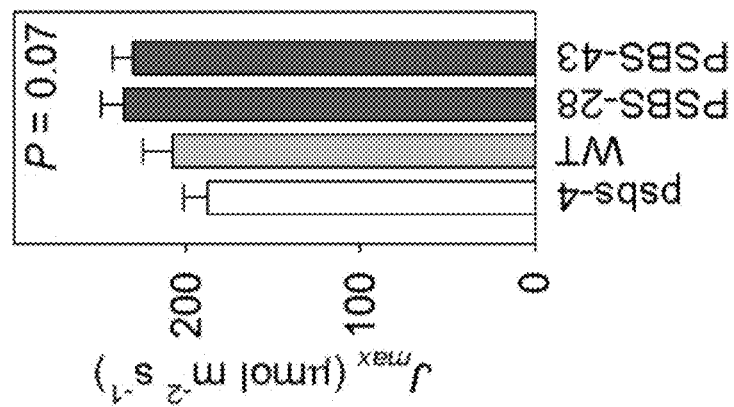
Figure 7E:
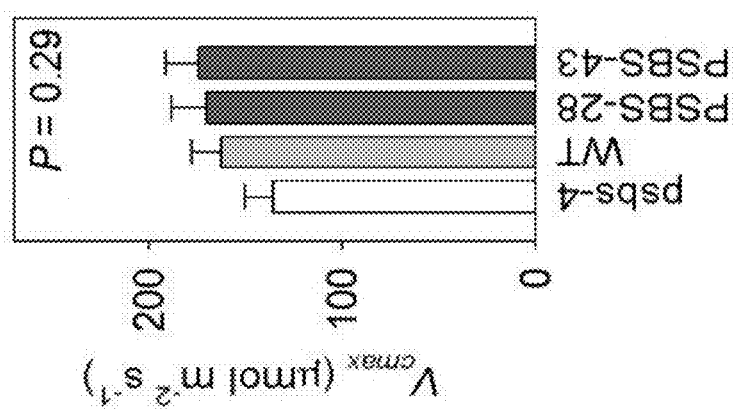
Figure 7F:
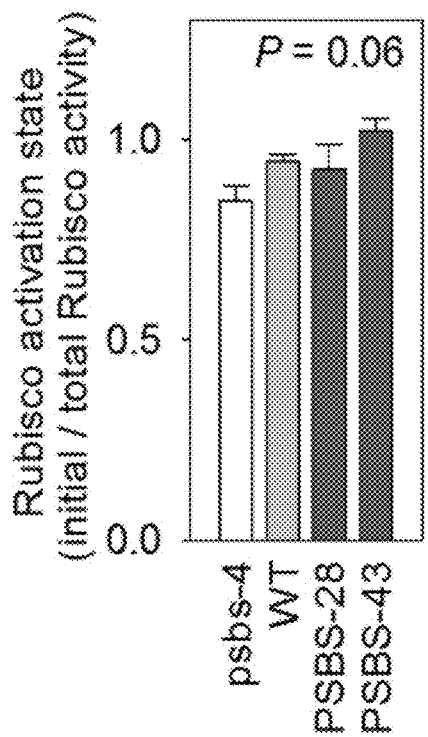
Figure 7G:
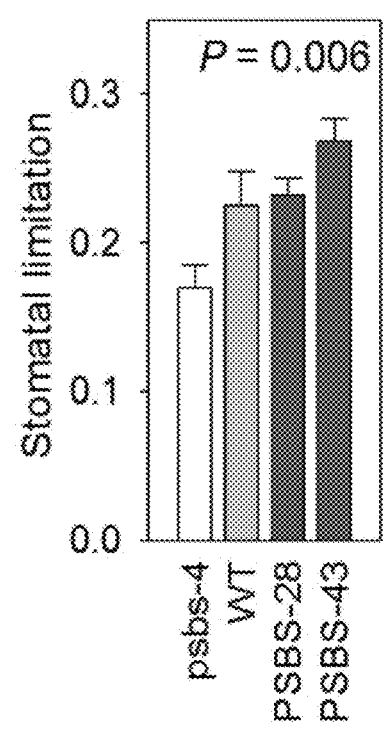

FIGS. 7A-7G show that the weak effects on photosynthetic capacity of PsbS overexpression lines balance the slight reduction in $CO_2$ availability due to greater stomatal limitation. In particular, PsbS overexpression lines had higher $J_{max}$ (i.e., capacity of electron transport; FIG. 7D) and Rubisco activity (i.e., activation status of Rubisco; FIG. 7F). While these were both weak trends, they bordered on significance ($J_{max}$ $P=0.07$ and Rubisco activation state $P=0.06$). FIG. 7E demonstrates that Rubisco content was similar between PsbS mutant lines and WT, indicating that the increased Rubisco activity was not merely due to increased Rubisco amount. Additional parameters were also used to measure photosynthetic activity. FIG. 7A shows that $CO_2$ fixation rate, as a function of chloroplastic $CO_2$ concentration, was slightly increased for PsbS overexpressing plants relative to WT. FIG. 7B demonstrates that electron transport rate, as a function of incident light, was slightly elevated for PsbS overexpressing plants relative to WT. FIG. 7C shows that maximum ribulose bisphosphate carboxylation capacity was slightly elevated in PsbS overexpressing plants relative to WT, whereas the maximum ribulose bisphosphate carboxylation capacity for plants with reduced PsbS expression was slightly reduced relative to WT. Finally, FIG. 7G shows that stomatal limitation rose with increased PsbS expression (i.e., there was a reduction in $CO_2$ availability), and fell with decreased PsbS expression (i.e., there was an increase in $CO_2$ availability). This effect was significant ($P=0.006$). These results, particularly those shown in FIG. 7D, FIG. 7F, and FIG. 7G, indicate that the weak effects on photosynthetic capacity (i.e., slight improvement of photosynthetic capacity) were able to balance the reduced $CO_2$ availability stemming from greater stomatal limitation (FIG. 7G) in the PsbS overexpression lines.

The results presented in Example 3 demonstrate that the PsbS overexpression lines were able to maintain photosynthetic rates while having lower stomatal conductance. Taken together, the results in Examples 2 and 3 show that the increase in iWUE observed following PsbS overexpression can be attributed to a decrease in stomatal conductance at all light levels, sufficient to decrease transpiration with minimal effect on $CO_2$ uptake. Thus, the decrease in stomatal conductance achieved through PsbS overexpression does not compromise photosynthesis.

Example 4

PsbS Expression Affects Biomass Productivity Traits in Plants Under Field-Grown Conditions The following example describes the effect of altered PsbS expression on biomass productivity traits in plants under fully irrigated field-grown conditions.

Materials and Methods

Seedling Propagation for Field-Grown Conditions

Plants were grown as described above in Example 1.

Biomass Productivity Trait Measurement

At final harvest, stem length and the number of leaves were determined, and leaf area was measured with a conveyor-belt scanner (LI-3100C Area meter, LI-COR). Leaf, stem, and root fractions were dried to constant weight at 60° C. after which the dry weights were determined.

Results

Figure 8A:
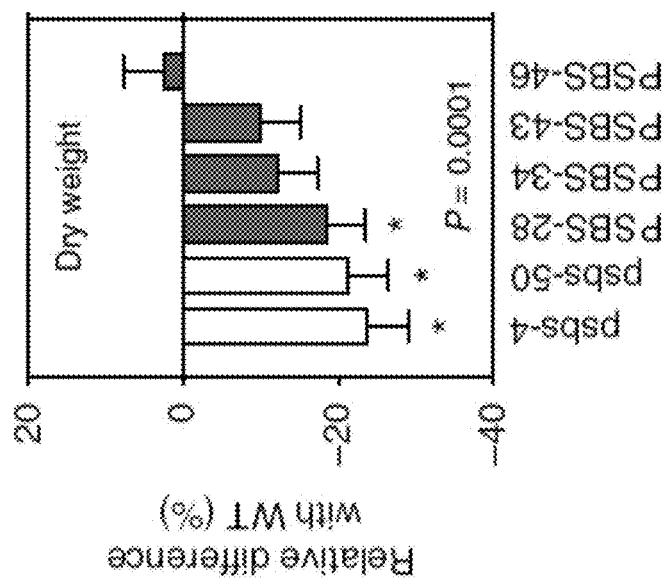
FIGS. 8A-8F show plant biomass measurements in PsbS suppressed lines, PsbS overexpression lines, and WT grown under fully irrigated conditions.
Figure 8B:
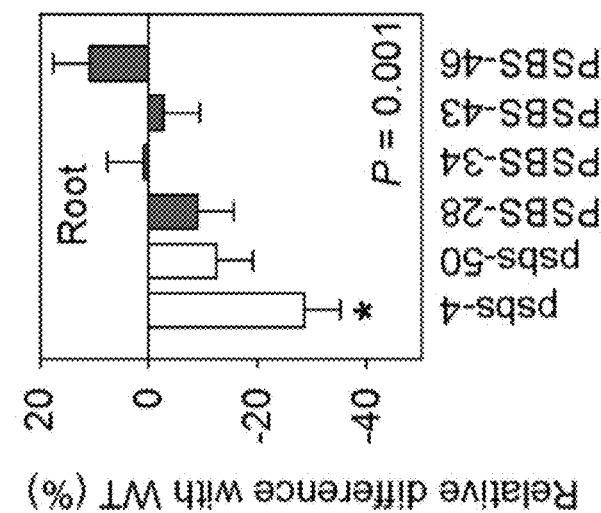
Figure 8D:
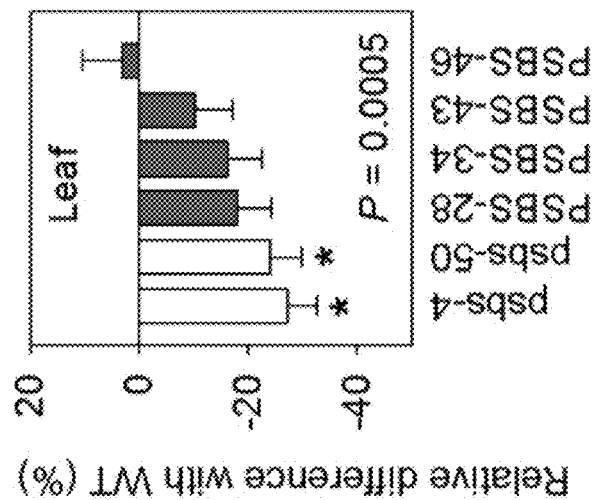
Figure 8C:
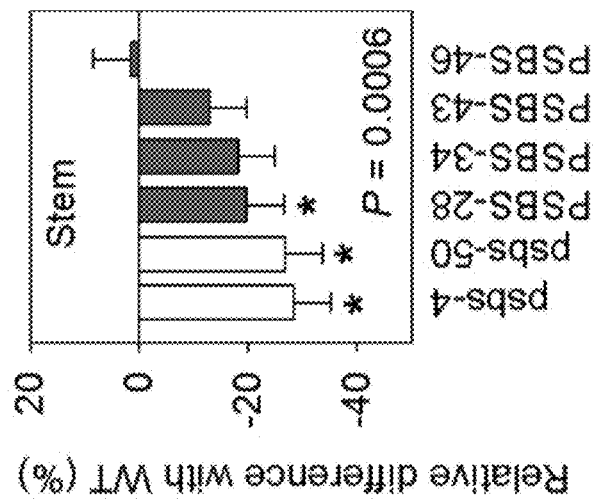
Figure 8F:
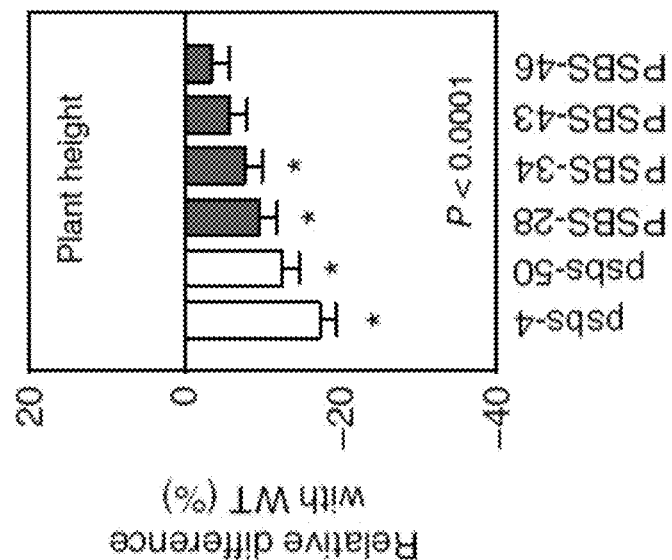
Figure 8E:
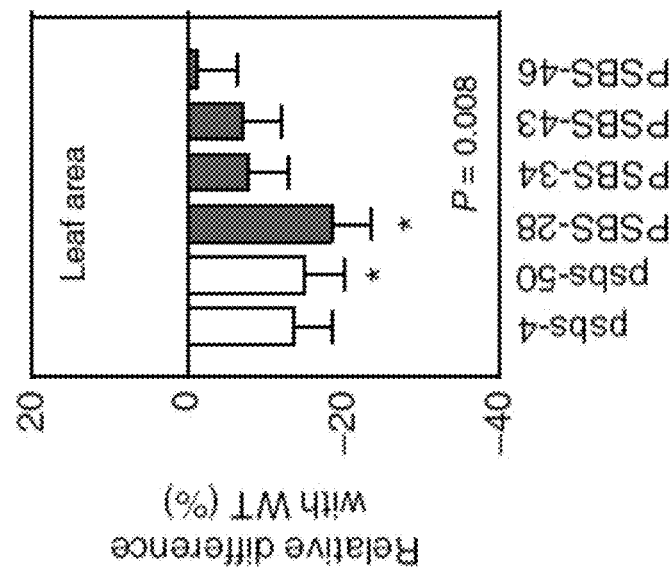

FIGS. 8A-8F show the impact of PsbS expression on biomass productivity for plants under field-grown conditions. FIGS. 8A-8D show total dry weight, root dry weight, stem dry weight, and leaf dry weight were significantly decreased in plants with reduced PsbS expression relative to WT. However, the data show that biomass productivity measures in plants with increased PsbS did not show a consistent response (FIGS. 8A-8F). It should be noted that growing the plants under fully-irrigated conditions (i.e., with sufficient water), was expected to offset the impact of improved iWUE on productivity, regardless of efficiency. Therefore, the inconsistent biomass productivity responses observed were maybe the result of the conditions under which these plants were grown. In addition, FIGS. 8E-8F show that leaf areas and plant height were significantly decreased in plants with reduced PsbS expression relative to WT. Plants with increased PsbS expression relative to WT also had decreased leaf area and plant height relative to WT. The results presented in FIGS. 8A-8F demonstrate that PsbS expression can alter biomass productivity traits in tobacco plants under field-grown conditions.

The results described in Examples 1-4 demonstrate that PsbS overexpression affected both iWUE and biomass productivity. Taken together, these results strongly indicate that manipulation of PsbS in crops may offer farmers an approach to improve iWUE and increase biomass productivity in water limited regions.

Example 5

PsbS Expression Affects Yield and/or Biomass Productivity Traits in Plants Under High Density Field-Grown Conditions Field-Grown Conditions The following example describes experiments to investigate the effect of altered PsbS expression, using PsbS mutant lines psbs-4, psbs-50, PSBS-28, PSBS-34, PSBS-43, and PSBS-46, on biomass productivity under high density field-grown conditions.

Materials and Methods

Seedling Propagation for High Density Field-Grown Conditions

PsbS mutant lines psbs-4, psbs-50, PSBS-28, PSBS-34, PSBS-43, and PSBS-46 will be prepared and transferred as described in Example 1.

High Density Field-Grown Conditions

Following initial propagation, seedlings will be transplanted to an experimental field site. As in Example 1, the field will be prepared 2 weeks prior to transplant by rototilling, cultivation, and harrowing. At this time, chlorpyrifos (1.5 g m$^{-2}$ Lorsban 15 G Insecticide, Dow AgroSciences) will be worked into the soil to suppress cutworm damage, sulfentrazone (29 μL m$^{-2}$ Spartan 4 F pre-emergence herbicide, FMC Agricultural Solutions) will be applied to reduce the emergence of weeds and slow-release fertilizer (30.8 g m$^{-2}$ ESN Smart Nitrogen, Agrium US Inc.) will be put down. After transplant, all seedlings will be sprayed with thiamethoxam (7 mg/plant Platinum 75 SG insecticide, Syngenta Crop Protection) to prevent damage from insect herbivory, and 12 days after the field transplant, all plants will be sprayed with fermentation solids, spores, and insecticidal toxins from Bacillus thuringiensis, (strain ABTS-351, DiPel Pro dry flowable biological insecticide, Valent Biosciences Corp.) to suppress tobacco hornworm. The field experiment will be set up as an incomplete randomized block design with 8 replicated plots of each of the 6 PsbS mutant lines and a WT control. 4 plots will consist of 6×6 plants spaced 30 cm apart. Further, 4 plots will consist of 12×12 plants spaced 15 cm apart. Each block will contain four rows of flour plants per genotype in north-south (N-S) orientation, surrounded by one border row of WT. The blocks will be positioned in 3 (N-S)×4 (E-W) rectangles with 75 cm spacing between blocks. The entire experiment will be surrounded by two border rows of WT plants. Standard irrigation will be applied during initial establishment, then withdrawn from all plots.

Photosynthetic Gas Exchange Measurements

Photosynthetic gas exchange measurements will be conducted as described in Example 2.

Rubisco Activation State and Content

Rubisco activation state and content measurements will be conducted as described in Example 3.

Biomass Productivity Trait Measurement

Biomass productivity trait measurements will be conducted as described in Example 4.

Soil Moisture

The vertical distribution of soil moisture (v/v) in each of the experimental plots (as described above in "High Density Field-Grown Conditions") will be measured by lowering a capacitance sensor through an access tube in the middle of each plot (Diviner-2000, Sentek Technologies, Adelaide, Australia). Measurements will be made at 2 day intervals and coupled with precipitation measurement will provide a measure of water use in each plot (Gray et al. 2016, Nature Plants 16132). Raw data obtained from the capacitance probe will be calibrated against gravimetric data as described by previously (Paltineanu et al. 1997 Soil Sci. Soc. Am. J. 61, 1576).

Plant Water Potential

To measure the leaf water potential, samples will be collected from three plants from each plot at two day intervals. Samples will be collected at midday from the field, corresponding to midday gas exchange measurements. Five leaf discs of approximately 1.2 cm in diameter will be collected from each plant and immediately sealed in psychrometer chambers (C-30; Wescor Environmental Products, Logan, Utah). As previously described, samples will be equilibrated at 25° C., and an integrated dew-point microvoltometer (HR-33T; Wescor) will be used to measure water potential in each psychrometer chamber (Leakey et al. 2006, Plant Cell Environ. 29, 1794).
Results Final yield is measured, and shows that those lines overexpressing PsbS have higher yields, especially at the higher planting density. Yet, the water use of lines overexpressing PsbS is no greater, showing that the plants overexpressing PsbS yield more for the same amount, or a lesser amount, of water than the controls. Further, at mid-day, leaf water potential of the plants overexpressing PsbS equals, or is higher, than that of the controls, showing that these plants are no more, or less, stressed than the controls despite higher productivity.

Example 6

PsbS Overexpression in *Glycine Max* (Soybean) Plants Under Controlled and Field-Grown Conditions The following example describes the development of *Glycine max* (*G. max*) lines with altered PsbS expression, and the assessment of these lines under controlled and field-grown conditions.
Materials and Methods Developing *G. Max* Lines with Altered PsbS Expression The pEG100-NbPsbS (FIG. 9) construct described in Example 1 will be codon-optimized for soybean, and used to develop *G. max* lines with altered PsbS expression. Soybean-optimized pEG100-NbPsbS will be transformed into an elite *G. max* cultivar using the *Agrobacterium tumefaciens*-mediated protocol (Olhoft, P. M. et al., *Soybean (Glycine max) Transformation Using Mature Cotyledonary Node Explants*, and Ko, T.-S. et al., *Soybean (Glycine max) Transformation Using Immature Cotyledon Explants*, in *Agrobacterium Protocols*, K. Wang, Editor. 2006, Humana Press Inc: Totowa, NJ. p. 385-406) with the aim of obtaining single copy transformants of the elite *G. max* cultivar. Then, copy number and homozygosity will be assessed using digital droplet PCR (Glowacka, K., et al., *An evaluation of new and established methods to determine T-DNA copy number and homozygosity in transgenic plants*. Plant Cell and Environment, 2016. 39: p. 908-917).

A second construct will also be made, in which the dicot rbcS promoter is used in place of the 35S promoter. This construct will be used to develop *G. max* lines with altered PsbS expression as described above.

Sixty independent transformants will be produced for each construct. Modulated chlorophyll fluorescence imaging will be used to detect the transformants showing the largest increase in the amplitude of NPQ as a means to identifying 10 lines expressing PsbS most strongly. NPQ measurements to identify lines showing the largest increase in the amplitude of NPQ will be performed as described in Example 1. These 10 lines will then be screened for expression of the transgene mRNA and recombinant protein, and copy number. mRNA expression analysis and protein expression analysis will be performed as described in Example 1.

Soybean is a seed-planted crop, and so single copy transformants will be selected to obtain seed homozygous for the transgene. Seedling propagation for controlled condition experiments will be performed as described in Example 1. These will then be screened for improvement of instantaneous water use efficiency (iWUE) under controlled conditions. Screening for improved iWUE will be performed as described in Example 2. The lines showing the highest iWUE will be screened for increased whole plant water use efficiency (WUE) under greenhouse or artificial controlled environment conditions using load cells to simultaneously track plant mass accumulation and mass loss of water (Negin, B. and M. Moshelion, *The advantages of functional phenotyping in pre-field screening for drought-tolerant crops*. Functional Plant Biology, 2017. 44(1): p. 107-118).

The three independent transformants showing high WUE without compromise to production will then be multiplied up for field trials. Soybean will be planted following established agronomic recommendations for maximizing the yield of soybean. Field-grown conditions will be conducted as in Example 1 at a sites climatically suited to *G. max* (e.g., Illinois). 8 plots of 4 rows of each independent transformant will be planted. 4 plots will be irrigated to field capacity and 4 plots rainfed only. An access tube for time domain reflectometry (TDR) will be inserted in the center of each plot prior to planting, following procedures previously used for soybean field trials (Gray, S. B., et al., *Intensifying drought eliminates the expected benefits of elevated carbon dioxide for soybean*. Nature Plants, 2016. 2(9)). An onsite meteorological station, along with TDR, will be used to determine daily plot water use. Growth will be monitored over the course of the season and final productivity will be determined by harvest at crop dry down as in Example 4.

Trials will then be undertaken at up to 5 locations within the typical growing region(s) of the given crop (e.g., Illinois), to establish the efficacy of the trait in a wider range of environments.

Example 7

PsbS Overexpression in *Zea Mays* (Maize) Plants Under Controlled and Field-Grown Conditions The following example describes the development of *Zea mays* (*Z. mays*) lines with altered PsbS expression, and the assessment of these lines under controlled and field-grown conditions.
Materials and Methods The constructs used to develop *Z. mays* lines with altered PsbS expression will contain the *Sorghum bicolor* SbPsbs gene coding sequence (e.g., encoding the protein of SEQ ID NO: 154) cloned between the mesophyll plastid specific C4-Pepc promoter and octopine synthase terminator in a plasmid vector. The vector will be transformed into *Z. mays* inbred line B73 using the *Agrobacterium tumefaciens*-mediated protocol. The further development of *Z. mays* lines with altered PsbS expression will proceed as described in Example 6, with the exception that the transformed inbred line will be crossed with a second productive inbred line to provide hybrid seed, because in maize the commercial seed is hybrid. The lines will be planted following established agronomic recommendations for maximizing the yield of maize, and tested at a site climatically suited to maize (e.g., Illinois). Otherwise, all experimental protocols and analyses will be performed as in Example 6.

Example 8

PsbS Overexpression in *Triticum Aestivum* (Wheat) or *Oryza Sativa* (Rice) Plants Under Controlled and Field-Grown Conditions The following example describes the development of *Triticum aestivum* (*T. aestivum*) or *Oryza sativa* (*O. sativa*) lines with altered PsbS expression, and the assessment of these lines under controlled and field-grown conditions.

Materials and Methods

The constructs used to develop *T. aestivum* or *O. sativa* lines with altered PsbS expression will contain the *Brachypodium distachyon* BdPsbs gene coding sequence (e.g., encoding the protein of SEQ ID NO: 160) cloned between either the 35S promoter or the rbcs promoter and the octopine synthase terminator in a plasmid vector. The further development of *T. aestivum* or *O. sativa* lines with altered PsbS expression will proceed as described in Example 6, and all experimental protocols and analyses will be performed as in Example 6.

Example 9

PsbS Overexpression in *Vigna Unguiculata* (Cowpea), *Lycopersicon Esculentum* (Tomato), *Solanum Melogena* (Eggplant), *Solanum Tuberosum* (Potato), *Manihot Esculenta* (Cassava), or *Gossypium Hirsutum* (Cotton) Plants Under Controlled and Field-Grown Conditions The following example describes the development and validation of *Vigna unguiculata* (*V. unguiculata*), *Lycopersicon esculentum* (*L. esculentum*), *Solanum melogena* (*S. melogena*), *Solanum tuberosum* (*S. tuberosum*), *Manihot esculenta* (*M. esculenta*), or *Gossypium hirsutum* (*G. hirsutum*) lines with altered PsbS expression grown under controlled and field-grown conditions.

Materials and Methods

The constructs used to develop *V. unguiculata*, *L. esculentum*, *S. melogena*, *S. tuberosum*, *M. esculenta*, or *G. hirsutum* lines with altered PsbS expression will be codon-optimized for each crop. Each crop will be planted following established agronomic recommendations for maximizing the yield of the given crop, and tested at a site climatically suited to the crop (e.g., Puerto Rico for cowpea and cassava). All experimental protocols and analyses will be performed as in Example 6.

---

SEQUENCE LISTING

```
<160> NUMBER OF SEQ ID NOS: 284

<210> SEQ ID NO 1
<211> LENGTH: 265
<212> TYPE: PRT
<213> ORGANISM: Arabidopsis thaliana

<400> SEQUENCE: 1

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
    50                  55                  60

Val Glu Lys Pro Lys Ser Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
```

```
              195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 2
<211> LENGTH: 268
<212> TYPE: PRT
<213> ORGANISM: Oryza sativa

<400> SEQUENCE: 2

Met Ala Gln Ser Met Leu Val Ser Gly Ala Asn Gly Thr Val Ala Ala
1               5                   10                  15

Ala Ser Thr Ser Arg Leu Gln Pro Val Arg Pro Thr Pro Phe Ser Arg
                20                  25                  30

Leu Val Leu Ser Gln Pro Ser Ser Ser Leu Gly Arg Ala Val Ser Val
            35                  40                  45

Lys Thr Val Ala Leu Phe Gly Arg Ser Lys Thr Lys Ala Ala Pro Ala
    50                  55                  60

Arg Lys Ala Glu Pro Lys Pro Lys Phe Lys Thr Glu Asp Gly Ile Phe
65                  70                  75                  80

Gly Thr Ser Gly Gly Ile Gly Phe Thr Lys Glu Asn Glu Leu Phe Val
                85                  90                  95

Gly Arg Val Ala Met Leu Gly Phe Ala Ala Ser Ile Leu Gly Glu Ala
            100                 105                 110

Ile Thr Gly Lys Gly Ile Leu Ala Gln Leu Asn Leu Glu Thr Gly Ile
    115                 120                 125

Pro Ile Tyr Glu Ala Glu Pro Leu Leu Leu Phe Phe Ile Leu Phe Thr
130                 135                 140

Leu Leu Gly Ala Ile Gly Ala Leu Gly Asp Arg Gly Ser Phe Val Asp
145                 150                 155                 160

Asp Gln Pro Val Thr Gly Leu Asp Lys Ala Val Ile Ala Pro Gly Lys
                165                 170                 175

Gly Phe Arg Ser Ala Leu Gly Leu Ser Glu Gly Pro Leu Phe Gly
            180                 185                 190

Phe Thr Lys Ala Asn Glu Leu Phe Val Gly Arg Leu Ala Gln Leu Gly
    195                 200                 205

Ile Ala Phe Ser Ile Ile Gly Glu Ile Ile Thr Gly Lys Gly Ala Leu
    210                 215                 220

Ala Gln Leu Asn Ile Glu Thr Gly Val Pro Ile Asn Glu Ile Glu Pro
225                 230                 235                 240

Leu Val Leu Phe Asn Val Val Phe Phe Ile Ala Ala Ile Asn Pro
                245                 250                 255

Gly Thr Gly Lys Phe Val Ser Asp Asp Asp Glu Glu
            260                 265

<210> SEQ ID NO 3
<211> LENGTH: 248
<212> TYPE: PRT
<213> ORGANISM: Oryza sativa
```

<400> SEQUENCE: 3

```
Met Ala Met Pro Met Met Val Val Ser Gly Leu Gly Thr Ala Pro Arg
1               5                   10                  15

Ser Ser Pro Met Val Gln Leu Gln Arg Met Lys Lys His Leu Val Val
            20                  25                  30

Val Ala Ala Phe Lys Ser Arg Thr Lys Ala Ser Pro Lys Val Asp Lys
        35                  40                  45

Ser Asn Lys Asn Lys Ser Ile Val Glu Asp Gly Ile Phe Gly Thr Ser
    50                  55                  60

Gly Gly Ile Gly Phe Thr Lys Glu Asn Glu Leu Phe Val Gly Arg Val
65                  70                  75                  80

Ala Met Leu Gly Phe Ala Ala Ser Leu Leu Gly Glu Ala Val Thr Gly
                85                  90                  95

Lys Gly Ile Leu Ala Gln Leu Asn Leu Glu Thr Gly Ile Pro Ile Tyr
            100                 105                 110

Glu Ala Glu Pro Leu Leu Leu Phe Phe Ile Leu Phe Thr Leu Leu Gly
        115                 120                 125

Ala Ile Gly Ala Leu Gly Asp Arg Gly Arg Phe Val Asp Asp Ala Thr
    130                 135                 140

Gly Leu Glu Arg Ala Val Ile Pro Pro Gly Lys Gly Phe Arg Ala Ala
145                 150                 155                 160

Leu Gly Leu Ser Glu Gly Gly Pro Leu Phe Gly Phe Thr Lys Ala Asn
                165                 170                 175

Glu Leu Phe Val Gly Arg Leu Ala Gln Leu Gly Ile Ala Phe Ser Leu
            180                 185                 190

Ile Gly Glu Ile Ile Thr Gly Lys Gly Ala Leu Ala Gln Leu Asn Ile
        195                 200                 205

Glu Thr Gly Val Pro Ile Asn Glu Ile Glu Pro Leu Leu Leu Phe Asn
    210                 215                 220

Ile Leu Phe Phe Phe Phe Ala Ala Ile Asn Pro Gly Thr Gly Lys Phe
225                 230                 235                 240

Val Thr Asp Asp Asn Asp Asp Gln
                245
```

<210> SEQ ID NO 4
<211> LENGTH: 248
<212> TYPE: PRT
<213> ORGANISM: Oryza sativa

<400> SEQUENCE: 4

```
Met Ala Met Pro Met Met Val Val Ser Asp Leu Gly Thr Ala Pro Arg
1               5                   10                  15

Ser Ser Pro Met Val Gln Leu Gln Arg Met Lys Lys His Leu Val Val
            20                  25                  30

Val Ala Ala Phe Lys Ser Arg Thr Lys Ala Ser Pro Lys Val Asp Lys
        35                  40                  45

Ser Asn Lys Asn Lys Ser Ile Val Glu Asp Gly Ile Phe Gly Thr Ser
    50                  55                  60

Gly Gly Ile Gly Phe Thr Lys Glu Asn Glu Leu Phe Val Gly Arg Val
65                  70                  75                  80

Ala Met Leu Gly Phe Ala Ala Ser Leu Leu Gly Glu Ala Val Thr Gly
                85                  90                  95

Lys Gly Ile Leu Ala Gln Leu Asn Leu Glu Thr Gly Ile Pro Ile Tyr
            100                 105                 110
```

```
Glu Ala Glu Pro Leu Leu Leu Phe Ile Leu Phe Thr Leu Leu Gly
            115                 120                 125

Ala Ile Gly Ala Leu Gly Asp Arg Gly Arg Phe Val Asp Asp Ala Thr
130                 135                 140

Gly Leu Glu Arg Ala Val Ile Pro Pro Gly Lys Gly Phe Arg Ala Ala
145                 150                 155                 160

Leu Gly Leu Ser Glu Gly Pro Leu Phe Gly Phe Thr Lys Ala Asn
            165                 170                 175

Glu Leu Phe Val Gly Arg Leu Ala Gln Leu Gly Ile Ala Phe Ser Leu
                180                 185                 190

Ile Gly Glu Ile Ile Thr Gly Lys Gly Ala Leu Ala Gln Leu Asn Ile
            195                 200                 205

Glu Thr Gly Val Pro Ile Asn Glu Ile Glu Pro Leu Leu Leu Phe Asn
            210                 215                 220

Ile Leu Phe Phe Phe Ala Ala Ile Asn Pro Gly Thr Gly Lys Phe
225                 230                 235                 240

Val Thr Asp Asp Asn Asp Asp Gln
                245
```

```
<210> SEQ ID NO 5
<211> LENGTH: 254
<212> TYPE: PRT
<213> ORGANISM: Oryza sativa

<400> SEQUENCE: 5
```

```
Met Ala Leu Gln Gln Ser Met Ala Met Pro Met Met Val Val Ser Asp
1               5                   10                  15

Leu Gly Thr Ala Pro Arg Ser Ser Pro Met Val Gln Leu Gln Arg Met
                20                  25                  30

Lys Lys His Leu Val Val Val Ala Ala Phe Lys Ser Arg Thr Lys Ala
            35                  40                  45

Ser Pro Lys Val Asp Lys Ser Asn Lys Asn Lys Ser Ile Val Glu Asp
        50                  55                  60

Gly Ile Phe Gly Thr Ser Gly Ile Gly Phe Thr Lys Glu Asn Glu
65                  70                  75                  80

Leu Phe Val Gly Arg Val Ala Met Leu Gly Phe Ala Ala Ser Leu Leu
                85                  90                  95

Gly Glu Ala Val Thr Gly Lys Gly Ile Leu Ala Gln Leu Asn Leu Glu
            100                 105                 110

Thr Gly Ile Pro Ile Tyr Glu Ala Glu Pro Leu Leu Leu Phe Phe Ile
        115                 120                 125

Leu Phe Thr Leu Leu Gly Ala Ile Gly Ala Leu Gly Asp Arg Gly Arg
130                 135                 140

Phe Val Asp Asp Ala Thr Gly Leu Glu Arg Ala Val Ile Pro Pro Gly
145                 150                 155                 160

Lys Gly Phe Arg Ala Ala Leu Gly Leu Ser Glu Gly Pro Leu Phe
                165                 170                 175

Gly Phe Thr Lys Ala Asn Glu Leu Phe Val Gly Arg Leu Ala His Val
            180                 185                 190

Gly Ile Ala Phe Ser Leu Ile Gly Glu Ile Ile Thr Gly Lys Gly Ala
        195                 200                 205

Leu Ala Gln Leu Asn Ile Glu Thr Gly Val Pro Ile Asn Glu Ile Glu
210                 215                 220

Pro Leu Leu Leu Phe Asn Ile Leu Phe Phe Phe Ala Ala Ile Asn
225                 230                 235                 240
```

```
Pro Gly Thr Gly Lys Phe Val Thr Asp Asp Asn Asp Asp Gln
                245                 250
```

```
<210> SEQ ID NO 6
<211> LENGTH: 254
<212> TYPE: PRT
<213> ORGANISM: Oryza sativa

<400> SEQUENCE: 6
```

```
Met Ala Leu Gln Gln Ser Met Ala Met Pro Met Met Val Val Ser Asp
1               5                   10                  15

Leu Gly Thr Ala Pro Arg Ser Ser Pro Met Val Gln Leu Gln Arg Met
            20                  25                  30

Lys Lys His Leu Val Val Val Ala Ala Phe Lys Ser Arg Thr Lys Ala
        35                  40                  45

Ser Pro Lys Val Asp Lys Ser Asn Lys Asn Lys Ser Ile Val Glu Asp
    50                  55                  60

Gly Ile Phe Gly Thr Ser Gly Gly Ile Gly Phe Thr Lys Glu Asn Glu
65                  70                  75                  80

Leu Phe Val Gly Arg Val Ala Met Leu Gly Phe Ala Ala Ser Leu Leu
                85                  90                  95

Gly Glu Ala Val Thr Gly Lys Gly Ile Leu Ala Gln Leu Asn Leu Glu
            100                 105                 110

Thr Gly Ile Pro Ile Tyr Glu Ala Glu Pro Leu Leu Leu Phe Phe Ile
        115                 120                 125

Leu Phe Thr Leu Leu Gly Ala Ile Gly Ala Leu Gly Asp Arg Gly Arg
    130                 135                 140

Phe Val Asp Asp Ala Thr Gly Leu Glu Arg Ala Val Ile Pro Pro Gly
145                 150                 155                 160

Lys Gly Phe Arg Ala Ala Leu Gly Leu Ser Glu Gly Pro Leu Phe
                165                 170                 175

Gly Phe Thr Lys Ala Asn Glu Leu Phe Val Gly Arg Leu Ala Gln Leu
            180                 185                 190

Gly Ile Ala Phe Ser Leu Ile Gly Glu Ile Thr Gly Lys Gly Ala
        195                 200                 205

Leu Ala Gln Leu Asn Ile Glu Thr Gly Val Pro Ile Asn Glu Ile Glu
    210                 215                 220

Pro Leu Leu Leu Phe Asn Ile Leu Phe Phe Phe Ala Ala Ile Asn
225                 230                 235                 240

Pro Gly Thr Gly Lys Phe Val Thr Asp Asp Asn Asp Asp Gln
                245                 250
```

```
<210> SEQ ID NO 7
<211> LENGTH: 269
<212> TYPE: PRT
<213> ORGANISM: Vigna unguiculata

<400> SEQUENCE: 7
```

```
Met Ala Gln Thr Met Leu Leu Met Ser Ser Val Ser Ser Ser His Ser
1               5                   10                  15

Leu Gly Leu Lys Lys Asp Leu Phe Leu Gln Leu Arg Pro Lys Phe Ser
            20                  25                  30

Gln Leu Ser Phe Asn Pro Leu Pro Ser Thr Pro Phe Pro Ser Ser
        35                  40                  45

Pro Arg Thr Phe Thr Thr Leu Ala Leu Phe Lys Ser Lys Thr Lys Ala
    50                  55                  60
```

```
Pro Pro Ala Lys Thr Lys Val Val Lys Pro Lys Gln Lys Val Glu Asp
 65                  70                  75                  80

Gly Ile Phe Gly Thr Ser Gly Gly Phe Gly Phe Thr Lys Gln Asn Glu
                 85                  90                  95

Leu Phe Val Gly Arg Val Ala Met Leu Gly Phe Ala Ala Ser Leu Leu
            100                 105                 110

Gly Glu Gly Val Thr Gly Lys Gly Ile Leu Ala Gln Leu Asn Leu Glu
        115                 120                 125

Thr Gly Ile Pro Ile Tyr Glu Ala Glu Pro Leu Leu Leu Phe Phe Ile
130                 135                 140

Leu Phe Thr Leu Leu Gly Ala Ile Gly Gly Leu Gly Asp Arg Gly Lys
145                 150                 155                 160

Phe Val Asp Asp Glu Glu Pro Asn Thr Gly Gly Val Ile Pro Gly Gly
                165                 170                 175

Lys Gly Phe Arg Glu Ala Leu Gly Leu Gly Ser Gly Pro Leu Phe Gly
            180                 185                 190

Phe Thr Lys Ala Asn Glu Leu Phe Val Gly Arg Leu Ala Gln Leu Gly
        195                 200                 205

Phe Val Phe Ser Leu Ile Gly Glu Ile Val Thr Gly Lys Gly Ala Leu
210                 215                 220

Ala Gln Leu Asn Ile Glu Thr Gly Val Pro Ile Asn Glu Ile Glu Pro
225                 230                 235                 240

Leu Val Leu Phe Asn Val Leu Phe Phe Val Ala Ala Leu Asn Pro
                245                 250                 255

Gly Thr Gly Lys Phe Val Thr Asp Glu Gly Asp Asp Glu
            260                 265

<210> SEQ ID NO 8
<211> LENGTH: 273
<212> TYPE: PRT
<213> ORGANISM: Glycine max

<400> SEQUENCE: 8

Met Ala Gln Thr Met Leu Leu Met Ser Ser Val Ser Ser Ser Tyr Ser
 1                   5                  10                  15

Val Asp Leu Lys Lys Asp Leu Phe Leu Gln Leu Gln Ser Gln Ser Leu
                 20                  25                  30

Arg Pro Lys Phe Ser Gln Leu Ser Phe Asn Pro Leu Pro Pro Ser Thr
             35                  40                  45

Ser Ser Phe Ser Ser Pro Arg Thr Phe Thr Thr Leu Ala Leu Phe Lys
 50                  55                  60

Ser Lys Thr Lys Ala Ala Pro Ala Lys Thr Lys Val Thr Lys Pro Lys
 65                  70                  75                  80

Gln Lys Val Glu Asp Gly Ile Phe Gly Thr Ser Gly Gly Phe Gly Phe
                 85                  90                  95

Thr Lys Gln Asn Glu Leu Phe Val Gly Arg Val Ala Met Leu Gly Phe
            100                 105                 110

Ala Ala Ser Leu Leu Gly Glu Gly Ile Thr Gly Lys Gly Ile Leu Ala
        115                 120                 125

Gln Leu Asn Leu Glu Thr Gly Ile Pro Ile Tyr Glu Ala Glu Pro Leu
130                 135                 140

Leu Leu Phe Phe Ile Leu Phe Thr Leu Leu Gly Ala Ile Gly Gly Leu
145                 150                 155                 160

Gly Asp Arg Gly Lys Phe Val Asp Asp Glu Pro Thr Thr Gly Gly Val
```

```
            165                 170                 175
Ile Pro Ser Gly Lys Gly Phe Arg Glu Ala Leu Gly Leu Gly Ser Gly
            180                 185                 190

Pro Leu Phe Gly Phe Thr Lys Ala Asn Glu Leu Phe Val Gly Arg Leu
            195                 200                 205

Ala Gln Leu Gly Phe Val Phe Ser Leu Ile Gly Glu Ile Ile Thr Gly
            210                 215                 220

Lys Gly Ala Leu Ala Gln Leu Asn Ile Glu Thr Gly Val Pro Ile Asn
225                 230                 235                 240

Glu Ile Glu Pro Leu Val Leu Phe Asn Val Leu Phe Phe Ile Ala
            245                 250                 255

Ala Leu Asn Pro Gly Thr Gly Lys Phe Val Thr Asp Asp Gly Glu Asp
            260                 265                 270

Asp

<210> SEQ ID NO 9
<211> LENGTH: 273
<212> TYPE: PRT
<213> ORGANISM: Glycine max

<400> SEQUENCE: 9

Met Ala Gln Thr Met Leu Leu Met Ser Ser Val Ser Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Ser Ser Thr
            35                  40                  45

Ser Ser Phe Ser Ser Pro Arg Thr Phe Thr Thr Leu Ala Leu Phe Lys
        50                  55                  60

Ser Lys Thr Lys Ala Ala Pro Ala Lys Thr Lys Val Thr Lys Pro Lys
65                  70                  75                  80

Gln Lys Val Glu Asp Gly Ile Phe Gly Thr Ser Gly Gly Phe Gly Phe
                85                  90                  95

Thr Lys Gln Asn Glu Leu Phe Val Gly Arg Val Ala Met Leu Gly Phe
            100                 105                 110

Ala Ala Ser Leu Leu Gly Glu Gly Ile Thr Gly Lys Gly Ile Leu Ala
            115                 120                 125

Gln Leu Asn Leu Glu Thr Gly Ile Pro Leu Tyr Glu Ala Glu Pro Leu
            130                 135                 140

Leu Leu Phe Phe Ile Leu Phe Thr Leu Leu Gly Ala Ile Gly Gly Leu
145                 150                 155                 160

Gly Asp Arg Gly Lys Phe Val Asp Asp Glu Pro Thr Thr Gly Gly Val
                165                 170                 175

Ile Pro Pro Gly Lys Gly Phe Arg Glu Ala Leu Gly Leu Gly Ser Gly
            180                 185                 190

Pro Leu Phe Gly Phe Thr Lys Ala Asn Glu Leu Phe Val Gly Arg Leu
            195                 200                 205

Ala Gln Leu Gly Phe Val Phe Ser Leu Ile Gly Glu Ile Ile Thr Gly
            210                 215                 220

Lys Gly Ala Leu Ala Gln Leu Asn Ile Glu Thr Gly Val Pro Ile Asn
225                 230                 235                 240

Glu Ile Glu Pro Leu Val Leu Phe Asn Val Leu Phe Phe Ile Ala
            245                 250                 255

Ala Leu Asn Pro Gly Thr Gly Lys Phe Val Thr Asp Glu Gly Glu Asp
```

260                 265                 270
Asp

<210> SEQ ID NO 10
<211> LENGTH: 273
<212> TYPE: PRT
<213> ORGANISM: Glycine max

<400> SEQUENCE: 10

Met Ala Gln Thr Met Leu Leu Met Ser Ser Val Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Pro Ser Thr
        35                  40                  45

Ser Ser Phe Ser Ser Pro Arg Thr Phe Thr Thr Leu Ala Leu Phe Lys
    50                  55                  60

Ser Lys Thr Lys Ala Ala Pro Ala Lys Thr Lys Val Thr Lys Pro Lys
65                  70                  75                  80

Gln Lys Val Glu Asp Gly Ile Phe Gly Thr Ser Gly Gly Phe Gly Phe
                85                  90                  95

Thr Lys Gln Asn Glu Leu Phe Val Gly Arg Val Ala Met Leu Gly Phe
            100                 105                 110

Ala Ala Ser Leu Leu Gly Glu Gly Ile Thr Gly Lys Gly Ile Leu Ala
        115                 120                 125

Gln Leu Asn Leu Glu Thr Gly Ile Pro Ile Tyr Glu Ala Glu Pro Leu
    130                 135                 140

Leu Leu Phe Phe Ile Leu Phe Thr Leu Leu Gly Ala Ile Gly Gly Leu
145                 150                 155                 160

Gly Asp Arg Gly Lys Phe Val Asp Asp Glu Pro Thr Thr Gly Gly Val
                165                 170                 175

Ile Pro Ser Gly Lys Gly Phe Arg Glu Ala Leu Gly Leu Gly Ser Gly
            180                 185                 190

Pro Leu Phe Gly Phe Thr Lys Ala Asn Glu Leu Phe Val Gly Arg Leu
        195                 200                 205

Ala Gln Leu Gly Phe Val Ser Ser Leu Ile Gly Glu Ile Ile Thr Gly
    210                 215                 220

Lys Gly Ala Leu Ala Gln Leu Asn Ile Glu Thr Gly Val Pro Ile Asn
225                 230                 235                 240

Glu Ile Glu Pro Leu Val Leu Phe Asn Val Leu Phe Phe Phe Ile Ala
                245                 250                 255

Ala Leu Asn Pro Gly Thr Gly Lys Phe Val Thr Gly Asp Gly Glu Asp
            260                 265                 270

Asp

<210> SEQ ID NO 11
<211> LENGTH: 273
<212> TYPE: PRT
<213> ORGANISM: Glycine max

<400> SEQUENCE: 11

Met Ala Gln Thr Met Leu Leu Met Ser Ser Val Ser Ser Tyr Ser
1               5                   10                  15

Val Asp Leu Lys Lys Asp Leu Phe Leu Gln Leu Gln Ser Gln Ser Leu
            20                  25                  30

-continued

```
Arg Pro Lys Phe Ser Gln Leu Ser Phe Asn Pro Leu Pro Ser Ser Thr
         35                  40                  45

Ser Ser Phe Ser Ser Pro Arg Thr Phe Thr Thr Leu Ala Leu Phe Lys
 50                  55                  60

Ser Lys Thr Lys Ala Ala Pro Ala Lys Thr Lys Val Thr Lys Pro Lys
 65                  70                  75                  80

Gln Lys Val Glu Asp Gly Ile Phe Gly Thr Ser Gly Gly Phe Gly Phe
                 85                  90                  95

Thr Lys Gln Asn Glu Leu Phe Val Gly Arg Val Ala Met Leu Gly Phe
            100                 105                 110

Ala Ala Ser Leu Leu Gly Glu Gly Ile Thr Gly Lys Gly Ile Leu Ala
        115                 120                 125

Gln Leu Asn Leu Glu Thr Gly Ile Pro Leu Tyr Glu Ala Glu Pro Leu
130                 135                 140

Leu Leu Phe Phe Ile Leu Phe Thr Leu Leu Gly Ala Ile Gly Gly Leu
145                 150                 155                 160

Gly Asp Arg Gly Lys Phe Val Asp Asp Glu Pro Thr Thr Gly Gly Val
                165                 170                 175

Ile Pro Pro Gly Lys Gly Phe Arg Glu Ala Leu Gly Leu Gly Ser Gly
            180                 185                 190

Pro Leu Phe Gly Phe Thr Lys Ala Asn Glu Pro Phe Val Gly Arg Leu
        195                 200                 205

Ala Gln Leu Gly Phe Val Phe Ser Leu Ile Gly Glu Ile Ile Thr Gly
    210                 215                 220

Lys Gly Ala Leu Ala Gln Leu Asn Ile Glu Thr Gly Val Pro Ile Asn
225                 230                 235                 240

Glu Ile Glu Pro Leu Val Leu Phe Asn Val Leu Phe Phe Phe Ile Ala
                245                 250                 255

Ala Leu Asn Pro Gly Thr Gly Lys Phe Val Thr Asp Glu Gly Glu Asp
            260                 265                 270

Asp
```

<210> SEQ ID NO 12
<211> LENGTH: 272
<212> TYPE: PRT
<213> ORGANISM: Zea mays

<400> SEQUENCE: 12

```
Met Ala Ala Gln Ser Met Leu Met Ser Thr Ser Val Asn Gly Gly Arg
 1               5                  10                  15

Ala Leu Pro Ser Leu Gln Ala Val Arg Pro Ala Pro Tyr Pro Arg Leu
             20                  25                  30

Pro Leu Pro Ser Ser Ser Ser Ser Ala Gly Tyr Arg His Ser Lys
         35                  40                  45

Ser Val Ser Val Lys Thr Leu Ala Leu Phe Gly Lys Ser Lys Val Lys
 50                  55                  60

Thr Ala Pro Ala Lys Lys Ala Ala Pro Lys Pro Lys Pro Lys Val
 65                  70                  75                  80

Glu Asp Gly Ile Phe Gly Thr Ser Gly Gly Ile Gly Phe Thr Lys Glu
                 85                  90                  95

Asn Glu Leu Phe Val Gly Arg Val Ala Met Leu Gly Phe Ala Ala Ser
            100                 105                 110

Leu Leu Gly Glu Ala Ile Thr Gly Lys Gly Ile Leu Ala Gln Leu Asn
        115                 120                 125
```

```
Leu Glu Thr Gly Ile Pro Ile Tyr Glu Ala Glu Pro Leu Leu Leu Phe
130                 135                 140

Phe Ile Leu Phe Thr Leu Leu Gly Ala Ile Gly Ala Leu Gly Asp Arg
145                 150                 155                 160

Gly Arg Phe Val Asp Glu Glu Val Thr Gly Leu Asp Lys Ala Val Ile
                165                 170                 175

Gln Pro Gly Lys Gly Phe Arg Gly Ala Leu Gly Leu Ser Glu Gly Gly
                180                 185                 190

Pro Leu Phe Gly Phe Thr Lys Ser Asn Glu Leu Phe Val Gly Arg Met
                195                 200                 205

Ala Gln Leu Gly Val Ala Phe Ser Ile Ile Gly Glu Ile Ile Thr Gly
            210                 215                 220

Lys Gly Ala Leu Ala Gln Leu Asn Ile Glu Thr Gly Val Pro Ile Asn
225                 230                 235                 240

Glu Ile Glu Pro Leu Val Ile Phe Asn Val Leu Phe Phe Phe Ile Ala
                245                 250                 255

Ala Ile Asn Pro Gly Asn Gly Arg Phe Ile Ile Gly Glu Glu Glu
                260                 265                 270
```

<210> SEQ ID NO 13
<211> LENGTH: 271
<212> TYPE: PRT
<213> ORGANISM: Zea mays

<400> SEQUENCE: 13

```
Met Ala Ala Gln Ser Met Leu Met Ser Thr Ser Val Asn Gly Gly Arg
1               5                   10                  15

Ala Leu Pro Ser Leu Gln Ala Val Arg Pro Ala Pro Tyr Pro Arg Leu
                20                  25                  30

Pro Leu Pro Ser Ser Ser Ser Ser Gly Tyr Arg His Ser Lys Ser
                35                  40                  45

Val Ser Val Lys Thr Leu Ala Leu Phe Gly Lys Ser Lys Val Lys Thr
50                  55                  60

Ala Pro Ala Lys Lys Ala Ala Pro Lys Pro Lys Pro Lys Val Glu
65                  70                  75                  80

Asp Gly Ile Phe Gly Thr Ser Gly Gly Ile Gly Phe Thr Lys Glu Asn
                85                  90                  95

Glu Leu Phe Val Gly Arg Val Ala Met Leu Gly Phe Ala Ala Ser Leu
                100                 105                 110

Leu Gly Glu Ala Ile Thr Gly Lys Gly Ile Leu Ala Gln Leu Asn Leu
                115                 120                 125

Glu Thr Gly Ile Pro Ile Tyr Glu Ala Glu Pro Leu Leu Leu Phe Phe
130                 135                 140

Ile Leu Phe Thr Leu Leu Gly Ala Ile Gly Ala Leu Gly Asp Arg Gly
145                 150                 155                 160

Arg Phe Val Asp Glu Glu Val Thr Gly Leu Asp Lys Ala Val Ile Gln
                165                 170                 175

Pro Gly Lys Gly Phe Arg Gly Ala Leu Gly Leu Ser Glu Gly Gly Pro
                180                 185                 190

Leu Phe Gly Phe Thr Lys Ser Asn Glu Leu Phe Val Gly Arg Met Ala
                195                 200                 205

Gln Leu Gly Val Ala Phe Ser Ile Ile Gly Glu Ile Ile Thr Gly Lys
            210                 215                 220

Gly Ala Leu Ala Gln Leu Asn Ile Glu Thr Gly Val Pro Ile Asn Glu
225                 230                 235                 240
```

```
Ile Glu Pro Leu Val Ile Phe Asn Val Leu Phe Phe Phe Ile Ala Ala
                245                 250                 255

Ile Asn Pro Gly Asn Gly Arg Phe Ile Ile Gly Glu Glu Glu
            260                 265                 270
```

<210> SEQ ID NO 14
<211> LENGTH: 265
<212> TYPE: PRT
<213> ORGANISM: Zea mays

<400> SEQUENCE: 14

```
Met Ser Thr Ser Val Asn Gly Gly Arg Ala Leu Pro Ser Leu Gln Ala
1               5                   10                  15

Val Arg Pro Ala Pro Tyr Pro Arg Leu Pro Leu Pro Ser Ser Ser Ser
                20                  25                  30

Ser Ser Ala Gly Tyr Arg His Ser Lys Ser Val Ser Val Lys Thr Leu
            35                  40                  45

Ala Leu Phe Gly Lys Ser Lys Val Lys Thr Ala Pro Ala Lys Lys Ala
        50                  55                  60

Ala Ala Pro Lys Pro Lys Pro Lys Val Glu Asp Gly Ile Phe Gly Thr
65                  70                  75                  80

Ser Gly Gly Ile Gly Phe Thr Lys Glu Asn Glu Leu Phe Val Gly Arg
                85                  90                  95

Val Ala Met Leu Gly Phe Ala Ala Ser Leu Leu Gly Glu Ala Ile Thr
                100                 105                 110

Gly Lys Gly Ile Leu Ala Gln Leu Asn Leu Glu Thr Gly Ile Pro Ile
            115                 120                 125

Tyr Glu Ala Glu Pro Leu Leu Leu Phe Phe Ile Leu Phe Thr Leu Leu
        130                 135                 140

Gly Ala Ile Gly Ala Leu Gly Asp Arg Gly Arg Phe Val Asp Glu Glu
145                 150                 155                 160

Val Thr Gly Leu Asp Lys Ala Val Ile Gln Pro Gly Lys Gly Phe Arg
                165                 170                 175

Gly Ala Leu Gly Leu Ser Glu Gly Gly Pro Leu Phe Gly Phe Thr Lys
                180                 185                 190

Ser Asn Glu Leu Phe Val Gly Arg Met Ala Gln Leu Gly Val Ala Phe
            195                 200                 205

Ser Ile Ile Gly Glu Ile Ile Thr Gly Lys Gly Ala Leu Ala Gln Leu
        210                 215                 220

Asn Ile Glu Thr Gly Val Pro Ile Asn Glu Ile Glu Pro Leu Val Ile
225                 230                 235                 240

Phe Asn Val Leu Phe Phe Phe Ile Ala Ala Ile Asn Pro Gly Asn Gly
                245                 250                 255

Arg Phe Ile Ile Gly Glu Glu Glu Glu
                260                 265
```

<210> SEQ ID NO 15
<211> LENGTH: 274
<212> TYPE: PRT
<213> ORGANISM: Nicotiana tabacum

<400> SEQUENCE: 15

```
Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
                20                  25                  30
```

```
Phe Phe Leu Pro Ser Leu Pro Leu Lys Tyr Pro Ser Ala Ser Ser Ser
            35                  40                  45

Ser Ser Ser His Phe Ala Ser Thr Thr Val Ala Leu Phe Lys Ser Lys
        50                  55                  60

Ala Lys Ala Pro Ala Lys Lys Val Val Pro Lys Pro Lys Glu Lys Val
 65                 70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Ala Val Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Asn Leu Leu Gly Ala Ile Gly Ala Leu Gly Asp Arg
145                 150                 155                 160

Gly Lys Phe Ile Asp Asp Pro Ala Pro Ala Thr Gly Leu Asp Lys Ala
                165                 170                 175

Val Ile Pro Pro Gly Lys Gly Phe Lys Ala Ala Leu Gly Leu Arg Glu
            180                 185                 190

Gly Gly Pro Leu Phe Gly Phe Thr Lys Ala Asn Glu Leu Phe Val Gly
        195                 200                 205

Arg Leu Ala Gln Leu Gly Ile Ala Phe Ser Ile Ile Gly Glu Ile Ile
    210                 215                 220

Thr Gly Lys Gly Ala Leu Ala Gln Leu Asn Phe Glu Thr Gly Val Pro
225                 230                 235                 240

Ile Asn Glu Ile Glu Pro Leu Leu Leu Phe Asn Ile Val Phe Phe Phe
                245                 250                 255

Ile Ala Ala Ile Asn Pro Gly Thr Gly Lys Phe Val Thr Asp Glu Glu
                260                 265                 270

Glu Glu

<210> SEQ ID NO 16
<211> LENGTH: 274
<212> TYPE: PRT
<213> ORGANISM: Nicotiana tabacum

<400> SEQUENCE: 16

Met Ala Gln Thr Met Leu Leu Thr Ala Asn Ala Lys Val Asp Leu Arg
 1               5                  10                  15

Ser Lys Glu Ser Leu Val Glu Arg Leu Lys Pro Lys Pro Leu Ser Ser
            20                  25                  30

Phe Phe Leu Pro Ser Leu Pro Leu Lys Tyr Pro Ser Ala Ser Ala Ser
            35                  40                  45

Ala Ser Ser His Phe Thr Ser Thr Thr Val Ala Leu Phe Lys Ser Lys
        50                  55                  60

Ala Lys Ala Pro Ala Lys Lys Val Val Pro Lys Pro Lys Glu Lys Val
 65                 70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Ala Ile Thr Gly Lys Gly Ile Leu Ala Gln Leu Asn
        115                 120                 125
```

Leu Glu Thr Gly Ile Pro Ile Tyr Glu Ala Glu Pro Leu Leu Phe
            130                 135                 140

Phe Ile Leu Phe Asn Leu Leu Gly Ala Ile Gly Ala Leu Glu Asp Arg
145                 150                 155                 160

Gly Lys Phe Ile Asp Asp Pro Ala Pro Pro Thr Gly Leu Asp Lys Ala
                165                 170                 175

Val Ile Pro Pro Gly Lys Gly Phe Lys Ser Ala Leu Gly Leu Ser Glu
            180                 185                 190

Gly Gly Pro Leu Phe Glu Phe Thr Lys Ala Asn Glu Leu Phe Val Gly
        195                 200                 205

Arg Leu Ala Gln Leu Gly Ile Ala Phe Ser Ile Ile Gly Glu Ile Ile
210                 215                 220

Thr Gly Lys Gly Ala Leu Ala Gln Leu Asn Phe Glu Thr Gly Val Pro
225                 230                 235                 240

Ile Asn Glu Ile Glu Pro Leu Leu Phe Asn Ile Val Phe Phe Phe
                245                 250                 255

Val Ala Ala Ile Asn Pro Gly Thr Gly Lys Phe Val Thr Asp Glu Glu
            260                 265                 270

Glu Glu

<210> SEQ ID NO 17
<211> LENGTH: 274
<212> TYPE: PRT
<213> ORGANISM: Nicotiana benthamiana
<400> SEQUENCE: 17

Met Ala Gln Thr Met Leu Leu Thr Ala Asn Ala Lys Val Asp Leu Arg
1               5                   10                  15

Asn Lys Glu Pro Leu Val Glu Arg Leu Lys Pro Lys Pro Leu Ser Ser
            20                  25                  30

Phe Phe Leu Pro Ser Leu Pro Leu Lys Tyr Pro Ser Ala Ser Ser Ser
        35                  40                  45

Ser Ser Ser His Phe Thr Ser Thr Thr Val Ala Leu Phe Lys Ser Lys
    50                  55                  60

Ala Lys Ala Pro Ala Lys Lys Val Val Pro Lys Pro Lys Glu Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Ala Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Asn Leu Leu Gly Ala Ile Gly Ala Leu Gly Asp Arg
145                 150                 155                 160

Gly Lys Phe Ile Asp Asp Pro Val Pro Ala Thr Gly Leu Asp Lys Ala
                165                 170                 175

Val Ile Pro Pro Gly Lys Gly Phe Lys Ser Ala Leu Gly Leu Ser Glu
            180                 185                 190

Gly Gly Pro Leu Phe Gly Phe Thr Lys Ala Asn Glu Leu Phe Val Gly
        195                 200                 205

Arg Leu Ala Gln Leu Gly Ile Ala Phe Ser Ile Ile Gly Glu Ile Ile
210                 215                 220

```
Thr Gly Lys Gly Ala Leu Ala Gln Leu Asn Phe Glu Thr Gly Val Pro
225                 230                 235                 240

Ile Asn Glu Ile Glu Pro Leu Leu Leu Phe Asn Ile Val Phe Phe Phe
                245                 250                 255

Val Ala Ala Ile Asn Pro Gly Thr Gly Lys Phe Val Thr Asp Glu Glu
                260                 265                 270

Glu Glu
```

<210> SEQ ID NO 18
<211> LENGTH: 277
<212> TYPE: PRT
<213> ORGANISM: Nicotiana benthamiana

<400> SEQUENCE: 18

```
Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
                20                  25                  30

Phe Phe Leu Pro Ser Leu Ser Leu Lys Tyr Pro Ser Ala Ser Ser Ser
                35                  40                  45

Ser Ser Ser Ser Ser Ser His Phe Thr Ser Thr Thr Val Ala Leu Phe
        50                  55                  60

Lys Ser Lys Ala Lys Ala Pro Ala Lys Lys Val Val Pro Lys Pro Lys
65                  70                  75                  80

Glu Lys Val Glu Asp Gly Ile Phe Gly Thr Ser Gly Gly Ile Gly Phe
                85                  90                  95

Thr Lys Gln Asn Glu Leu Phe Val Gly Arg Val Ala Met Ile Gly Phe
                100                 105                 110

Ala Ala Ser Leu Leu Gly Glu Ala Ile Thr Gly Lys Gly Ile Leu Ala
                115                 120                 125

Gln Leu Asn Leu Glu Thr Gly Ile Pro Ile Tyr Glu Ala Glu Pro Leu
            130                 135                 140

Leu Leu Phe Phe Ile Leu Phe Asn Leu Leu Gly Ala Ile Gly Ala Leu
145                 150                 155                 160

Gly Asp Arg Gly Lys Phe Ile Asp Asp Pro Thr Pro Thr Gly Leu
                165                 170                 175

Asp Lys Ala Val Ile Pro Pro Gly Lys Gly Phe Lys Ser Ala Leu Gly
                180                 185                 190

Leu Ser Glu Gly Gly Pro Leu Phe Gly Phe Thr Lys Ala Asn Glu Leu
                195                 200                 205

Phe Val Gly Arg Leu Ala Gln Leu Gly Ile Ala Phe Ser Ile Ile Gly
            210                 215                 220

Glu Ile Ile Thr Gly Lys Gly Ala Leu Ala Gln Leu Asn Phe Glu Thr
225                 230                 235                 240

Gly Val Pro Ile Asn Glu Ile Glu Pro Leu Leu Leu Phe Asn Ile Val
                245                 250                 255

Phe Phe Phe Val Ala Ala Ile Asn Pro Gly Thr Gly Lys Phe Val Thr
                260                 265                 270

Asp Glu Glu Glu Glu
            275
```

<210> SEQ ID NO 19
<211> LENGTH: 273
<212> TYPE: PRT
<213> ORGANISM: Hevea brasiliensis

<400> SEQUENCE: 19

```
Met Ala Gln Thr Ile Leu Phe Met Ser Gly Val Ser Thr Lys His Val
1               5                   10                  15

Val Asn Leu Lys Arg Asp Pro Leu Leu Gln Phe Gln Val Glu Arg Leu
            20                  25                  30

Arg Pro Lys Pro Phe Ser Arg Leu Phe Phe Asn Pro Leu Pro Ser Asn
        35                  40                  45

Ser Ser Phe Ser Ser Lys Thr Phe Thr Thr Leu Ala Leu Phe Lys Ser
50                  55                  60

Lys Thr Lys Ala Pro Leu Lys Lys Ala Ala Glu Pro Lys Pro Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Leu Gly Phe Ala Ala Ser
            100                 105                 110

Leu Leu Gly Glu Ala Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
130                 135                 140

Phe Ile Leu Phe Thr Leu Leu Gly Ala Ile Gly Ala Leu Gly Asp Arg
145                 150                 155                 160

Gly Lys Phe Val Asp Asp Pro Pro Thr Gly Ile Glu Gly Ala Val Ile
                165                 170                 175

Pro Pro Gly Lys Gly Phe Arg Ser Ala Leu Gly Leu Lys Glu Gly Gly
            180                 185                 190

Pro Leu Phe Gly Phe Thr Lys Ala Asn Glu Leu Phe Val Gly Arg Leu
        195                 200                 205

Ala Gln Leu Gly Ile Ala Phe Ser Leu Ile Gly Glu Ile Ile Thr Gly
210                 215                 220

Lys Gly Ala Leu Ala Gln Leu Asn Ile Glu Thr Gly Ile Pro Val Asn
225                 230                 235                 240

Glu Ile Glu Pro Leu Val Leu Phe Asn Val Ile Phe Phe Ile Ala
                245                 250                 255

Ala Leu Asn Pro Gly Thr Gly Lys Phe Val Thr Asp Glu Asp Glu Asp
            260                 265                 270

Glu
```

<210> SEQ ID NO 20
<211> LENGTH: 272
<212> TYPE: PRT
<213> ORGANISM: Manihot esculenta

<400> SEQUENCE: 20

```
Met Ala Gln Thr Thr Met Phe Met Ser Gly Val Ser Thr Lys His Val
1               5                   10                  15

Val Asn Leu Lys Arg Asp Pro Leu Leu Gln Phe Gln Val Glu Arg Leu
            20                  25                  30

Arg Pro Lys Pro Leu Ser Pro Ile Phe Tyr Asn Pro Leu Pro Ser Cys
        35                  40                  45

Ser Ala Ser Ser Ser Lys Thr Phe Thr Thr Val Ala Leu Phe Arg Ser
50                  55                  60

Lys Thr Lys Ala Pro Val Lys Lys Val Ala Glu Pro Lys Pro Lys Val
65                  70                  75                  80
```

-continued

```
Glu Asp Gly Ile Phe Gly Thr Ser Gly Gly Ile Gly Phe Thr Lys Gln
                    85                  90                  95

Asn Glu Leu Phe Val Gly Arg Val Ala Met Leu Gly Phe Ala Ser Leu
                100                 105                 110

Leu Gly Glu Ala Ile Thr Gly Lys Gly Ile Leu Ser Gln Leu Asn Leu
            115                 120                 125

Glu Thr Gly Ile Pro Ile Tyr Glu Ala Glu Pro Leu Leu Phe Phe
        130                 135                 140

Ile Leu Phe Thr Leu Leu Gly Ala Ile Gly Ala Leu Gly Asp Arg Gly
145                 150                 155                 160

Lys Phe Val Asp Asp Pro Pro Thr Gly Leu Glu Gly Ala Val Ile Pro
                165                 170                 175

Pro Gly Lys Ser Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Ile Ala Phe Ser Leu Ile Gly Glu Ile Ile Thr Gly Lys
    210                 215                 220

Gly Ala Leu Ala Gln Leu Asn Ile Glu Thr Gly Ile Pro Val Ser Glu
225                 230                 235                 240

Ile Glu Pro Leu Val Leu Phe Asn Val Leu Phe Phe Val Ala Ala
                245                 250                 255

Leu Asn Pro Gly Thr Gly Lys Phe Val Thr Asp Glu Asp Glu Asp Glu
            260                 265                 270
```

<210> SEQ ID NO 21
<211> LENGTH: 294
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: Xaa = M or none
<220> FEATURE:
<221> NAME/KEY: VARIANT
<222> LOCATION: (2)..(2)
<223> OTHER INFORMATION: Xaa = A, M, or none
<220> FEATURE:
<221> NAME/KEY: VARIANT
<222> LOCATION: (3)..(3)
<223> OTHER INFORMATION: Xaa = L, M, A, or none
<220> FEATURE:
<221> NAME/KEY: VARIANT
<222> LOCATION: (4)..(4)
<223> OTHER INFORMATION: Xaa = Q, A, or none
<220> FEATURE:
<221> NAME/KEY: VARIANT
<222> LOCATION: (5)..(5)
<223> OTHER INFORMATION: Xaa = Q or none
<220> FEATURE:
<221> NAME/KEY: VARIANT
<222> LOCATION: (6)..(6)
<223> OTHER INFORMATION: Xaa = S, T, or none
<220> FEATURE:
<221> NAME/KEY: VARIANT
<222> LOCATION: (7)..(7)
<223> OTHER INFORMATION: Xaa = M, I, T, or none
<220> FEATURE:
<221> NAME/KEY: VARIANT
<222> LOCATION: (8)..(8)
<223> OTHER INFORMATION: Xaa = A or none
<220> FEATURE:
<221> NAME/KEY: VARIANT
<222> LOCATION: (9)..(9)
<223> OTHER INFORMATION: Xaa = M or none

```
<220> FEATURE:
<221> NAME/KEY: VARIANT
<222> LOCATION: (10)..(10)
<223> OTHER INFORMATION: Xaa = P or none
<220> FEATURE:
<221> NAME/KEY: VARIANT
<222> LOCATION: (11)..(11)
<223> OTHER INFORMATION: Xaa = M or none
<220> FEATURE:
<221> NAME/KEY: VARIANT
<222> LOCATION: (12)..(12)
<223> OTHER INFORMATION: Xaa = M, L, or none
<220> FEATURE:
<221> NAME/KEY: VARIANT
<222> LOCATION: (13)..(13)
<223> OTHER INFORMATION: Xaa = V, M, L, F
<220> FEATURE:
<221> NAME/KEY: VARIANT
<222> LOCATION: (14)..(14)
<223> OTHER INFORMATION: Xaa = V, S, T, M
<220> FEATURE:
<221> NAME/KEY: VARIANT
<222> LOCATION: (15)..(15)
<223> OTHER INFORMATION: Xaa = S, G, T, A
<220> FEATURE:
<221> NAME/KEY: VARIANT
<222> LOCATION: (16)..(16)
<223> OTHER INFORMATION: Xaa = D, G, A, S, N
<220> FEATURE:
<221> NAME/KEY: VARIANT
<222> LOCATION: (17)..(17)
<223> OTHER INFORMATION: Xaa = L, N, V, A
<220> FEATURE:
<221> NAME/KEY: VARIANT
<222> LOCATION: (18)..(18)
<223> OTHER INFORMATION: Xaa = G, K, T, S, or none
<220> FEATURE:
<221> NAME/KEY: VARIANT
<222> LOCATION: (19)..(19)
<223> OTHER INFORMATION: Xaa = T, V, A, S, or none
<220> FEATURE:
<221> NAME/KEY: VARIANT
<222> LOCATION: (20)..(20)
<223> OTHER INFORMATION: Xaa = A, V, N, D, G, K, S
<220> FEATURE:
<221> NAME/KEY: VARIANT
<222> LOCATION: (21)..(21)
<223> OTHER INFORMATION: Xaa = H, Y, or none
<220> FEATURE:
<221> NAME/KEY: VARIANT
<222> LOCATION: (22)..(22)
<223> OTHER INFORMATION: Xaa = F, V, S, or none
<220> FEATURE:
<221> NAME/KEY: VARIANT
<222> LOCATION: (23)..(23)
<223> OTHER INFORMATION: Xaa = L, V, or none
<220> FEATURE:
<221> NAME/KEY: VARIANT
<222> LOCATION: (24)..(24)
<223> OTHER INFORMATION: Xaa = R, N, G, D, or none
<220> FEATURE:
<221> NAME/KEY: VARIANT
<222> LOCATION: (25)..(25)
<223> OTHER INFORMATION: Xaa = L, N, or none
<220> FEATURE:
<221> NAME/KEY: VARIANT
<222> LOCATION: (26)..(26)
<223> OTHER INFORMATION: Xaa = R, K, or none
<220> FEATURE:
<221> NAME/KEY: VARIANT
<222> LOCATION: (27)..(27)
<223> OTHER INFORMATION: Xaa = S, N, R, K, or none
<220> FEATURE:
<221> NAME/KEY: VARIANT
<222> LOCATION: (28)..(28)
<223> OTHER INFORMATION: Xaa = A, G, P, D, or none
<220> FEATURE:
<221> NAME/KEY: VARIANT
<222> LOCATION: (29)..(29)
```

```
<223> OTHER INFORMATION: Xaa = P, A, G, L, or none
<220> FEATURE:
<221> NAME/KEY: VARIANT
<222> LOCATION: (30)..(30)
<223> OTHER INFORMATION: Xaa = R, A, L, F, or none
<220> FEATURE:
<221> NAME/KEY: VARIANT
<222> LOCATION: (31)..(31)
<223> OTHER INFORMATION: Xaa = S, A, K, L
<220> FEATURE:
<221> NAME/KEY: VARIANT
<222> LOCATION: (32)..(32)
<223> OTHER INFORMATION: Xaa = T, L, E, Q, or none
<220> FEATURE:
<221> NAME/KEY: VARIANT
<222> LOCATION: (33)..(33)
<223> OTHER INFORMATION: Xaa = S, P, F, L, or none
<220> FEATURE:
<221> NAME/KEY: VARIANT
<222> LOCATION: (34)..(34)
<223> OTHER INFORMATION: Xaa = R, S, L, Q, or none
<220> FEATURE:
<221> NAME/KEY: VARIANT
<222> LOCATION: (35)..(35)
<223> OTHER INFORMATION: Xaa = L, V, S, or none
<220> FEATURE:
<221> NAME/KEY: VARIANT
<222> LOCATION: (36)..(36)
<223> OTHER INFORMATION: Xaa = Q, E, or none
<220> FEATURE:
<221> NAME/KEY: VARIANT
<222> LOCATION: (37)..(37)
<223> OTHER INFORMATION: Xaa = P, A, R, S, or none
<220> FEATURE:
<221> NAME/KEY: VARIANT
<222> LOCATION: (38)..(38)
<223> OTHER INFORMATION: Xaa = V, L, or none
<220> FEATURE:
<221> NAME/KEY: VARIANT
<222> LOCATION: (39)..(39)
<223> OTHER INFORMATION: Xaa = R, K, or none
<220> FEATURE:
<221> NAME/KEY: VARIANT
<222> LOCATION: (40)..(40)
<223> OTHER INFORMATION: Xaa = P or none
<220> FEATURE:
<221> NAME/KEY: VARIANT
<222> LOCATION: (41)..(41)
<223> OTHER INFORMATION: Xaa = S, T, A, K
<220> FEATURE:
<221> NAME/KEY: VARIANT
<222> LOCATION: (42)..(42)
<223> OTHER INFORMATION: Xaa = P, V, or none
<220> FEATURE:
<221> NAME/KEY: VARIANT
<222> LOCATION: (43)..(43)
<223> OTHER INFORMATION: Xaa = M, F, Y, L, or none
<220> FEATURE:
<221> NAME/KEY: VARIANT
<222> LOCATION: (44)..(44)
<223> OTHER INFORMATION: Xaa = V, S, P, H
<220> FEATURE:
<221> NAME/KEY: VARIANT
<222> LOCATION: (45)..(45)
<223> OTHER INFORMATION: Xaa = Q, R, S, H, P
<220> FEATURE:
<221> NAME/KEY: VARIANT
<222> LOCATION: (46)..(46)
<223> OTHER INFORMATION: Xaa = L, F, I
<220> FEATURE:
<221> NAME/KEY: VARIANT
<222> LOCATION: (47)..(47)
<223> OTHER INFORMATION: Xaa = V, P, F, S, or none
<220> FEATURE:
<221> NAME/KEY: VARIANT
<222> LOCATION: (48)..(48)
<223> OTHER INFORMATION: Xaa = L, F, Y, or none
<220> FEATURE:
<221> NAME/KEY: VARIANT
```

```
<222> LOCATION: (49)..(49)
<223> OTHER INFORMATION: Xaa = S, P, L, N, or none
<220> FEATURE:
<221> NAME/KEY: VARIANT
<222> LOCATION: (50)..(50)
<223> OTHER INFORMATION: Xaa = Q, S, P, or none
<220> FEATURE:
<221> NAME/KEY: VARIANT
<222> LOCATION: (51)..(51)
<223> OTHER INFORMATION: Xaa = P, S, L, G, or none
<220> FEATURE:
<221> NAME/KEY: VARIANT
<222> LOCATION: (52)..(52)
<223> OTHER INFORMATION: Xaa = S, P, or none
<220> FEATURE:
<221> NAME/KEY: VARIANT
<222> LOCATION: (53)..(53)
<223> OTHER INFORMATION: Xaa = L or none
<220> FEATURE:
<221> NAME/KEY: VARIANT
<222> LOCATION: (54)..(54)
<223> OTHER INFORMATION: Xaa = K or none
<220> FEATURE:
<221> NAME/KEY: VARIANT
<222> LOCATION: (55)..(55)
<223> OTHER INFORMATION: Xaa = Y or none
<220> FEATURE:
<221> NAME/KEY: VARIANT
<222> LOCATION: (56)..(56)
<223> OTHER INFORMATION: Xaa = P or none
<220> FEATURE:
<221> NAME/KEY: VARIANT
<222> LOCATION: (57)..(57)
<223> OTHER INFORMATION: Xaa = S or none
<220> FEATURE:
<221> NAME/KEY: VARIANT
<222> LOCATION: (58)..(58)
<223> OTHER INFORMATION: Xaa = S, A, or none
<220> FEATURE:
<221> NAME/KEY: VARIANT
<222> LOCATION: (59)..(59)
<223> OTHER INFORMATION: Xaa = S, N, P, or none
<220> FEATURE:
<221> NAME/KEY: VARIANT
<222> LOCATION: (60)..(60)
<223> OTHER INFORMATION: Xaa = S, A, P, or none
<220> FEATURE:
<221> NAME/KEY: VARIANT
<222> LOCATION: (61)..(61)
<223> OTHER INFORMATION: Xaa = S, A, P, N, C, or none
<220> FEATURE:
<221> NAME/KEY: VARIANT
<222> LOCATION: (62)..(62)
<223> OTHER INFORMATION: Xaa = G, S, V, T, or none
<220> FEATURE:
<221> NAME/KEY: VARIANT
<222> LOCATION: (63)..(63)
<223> OTHER INFORMATION: Xaa = Q, Y, S, A, P, or none
<220> FEATURE:
<221> NAME/KEY: VARIANT
<222> LOCATION: (64)..(64)
<223> OTHER INFORMATION: Xaa = R, S, L, F, or none
<220> FEATURE:
<221> NAME/KEY: VARIANT
<222> LOCATION: (65)..(65)
<223> OTHER INFORMATION: Xaa = M, L, H, S, A, P, F, or none
<220> FEATURE:
<221> NAME/KEY: VARIANT
<222> LOCATION: (66)..(66)
<223> OTHER INFORMATION: Xaa = K, G, S, or none
<220> FEATURE:
<221> NAME/KEY: VARIANT
<222> LOCATION: (67)..(67)
<223> OTHER INFORMATION: Xaa = K, R, S
<220> FEATURE:
<221> NAME/KEY: VARIANT
<222> LOCATION: (68)..(68)
<223> OTHER INFORMATION: Xaa = H, A, S, R, P
<220> FEATURE:
```

-continued

```
<221> NAME/KEY: VARIANT
<222> LOCATION: (69)..(69)
<223> OTHER INFORMATION: Xaa = V, F, Q, K, R, or none
<220> FEATURE:
<221> NAME/KEY: VARIANT
<222> LOCATION: (70)..(70)
<223> OTHER INFORMATION: Xaa = S, T, A, or none
<220> FEATURE:
<221> NAME/KEY: VARIANT
<222> LOCATION: (71)..(71)
<223> OTHER INFORMATION: Xaa = L, V, S, F
<220> FEATURE:
<221> NAME/KEY: VARIANT
<222> LOCATION: (72)..(72)
<223> OTHER INFORMATION: Xaa = V, K, T
<220> FEATURE:
<221> NAME/KEY: VARIANT
<222> LOCATION: (73)..(73)
<223> OTHER INFORMATION: Xaa = V, T, P
<220> FEATURE:
<221> NAME/KEY: VARIANT
<222> LOCATION: (74)..(74)
<223> OTHER INFORMATION: Xaa = V, L
<220> FEATURE:
<221> NAME/KEY: VARIANT
<222> LOCATION: (76)..(76)
<223> OTHER INFORMATION: Xaa = A, L
<220> FEATURE:
<221> NAME/KEY: VARIANT
<222> LOCATION: (78)..(78)
<223> OTHER INFORMATION: Xaa = G or none
<220> FEATURE:
<221> NAME/KEY: VARIANT
<222> LOCATION: (79)..(79)
<223> OTHER INFORMATION: Xaa = K, R
<220> FEATURE:
<221> NAME/KEY: VARIANT
<222> LOCATION: (80)..(80)
<223> OTHER INFORMATION: Xaa = S, P
<220> FEATURE:
<221> NAME/KEY: VARIANT
<222> LOCATION: (81)..(81)
<223> OTHER INFORMATION: Xaa = R, K
<220> FEATURE:
<221> NAME/KEY: VARIANT
<222> LOCATION: (82)..(82)
<223> OTHER INFORMATION: Xaa = T, V, A
<220> FEATURE:
<221> NAME/KEY: VARIANT
<222> LOCATION: (84)..(84)
<223> OTHER INFORMATION: Xaa = A, T
<220> FEATURE:
<221> NAME/KEY: VARIANT
<222> LOCATION: (85)..(85)
<223> OTHER INFORMATION: Xaa = S, A, P
<220> FEATURE:
<221> NAME/KEY: VARIANT
<222> LOCATION: (86)..(86)
<223> OTHER INFORMATION: Xaa = P, A, L, V
<220> FEATURE:
<221> NAME/KEY: VARIANT
<222> LOCATION: (87)..(87)
<223> OTHER INFORMATION: Xaa = A or none
<220> FEATURE:
<221> NAME/KEY: VARIANT
<222> LOCATION: (88)..(88)
<223> OTHER INFORMATION: Xaa = K, R, A
<220> FEATURE:
<221> NAME/KEY: VARIANT
<222> LOCATION: (89)..(89)
<223> OTHER INFORMATION: Xaa = V, K, or none
<220> FEATURE:
<221> NAME/KEY: VARIANT
<222> LOCATION: (90)..(90)
<223> OTHER INFORMATION: Xaa = D, A, K, T, or none
<220> FEATURE:
<221> NAME/KEY: VARIANT
<222> LOCATION: (91)..(91)
<223> OTHER INFORMATION: Xaa = K, A, V, or none
```

-continued

```
<220> FEATURE:
<221> NAME/KEY: VARIANT
<222> LOCATION: (92)..(92)
<223> OTHER INFORMATION: Xaa = S, E, A, V
<220> FEATURE:
<221> NAME/KEY: VARIANT
<222> LOCATION: (93)..(93)
<223> OTHER INFORMATION: Xaa = N, P, E, A, V, T
<220> FEATURE:
<221> NAME/KEY: VARIANT
<222> LOCATION: (94)..(94)
<223> OTHER INFORMATION: Xaa = K, E
<220> FEATURE:
<221> NAME/KEY: VARIANT
<222> LOCATION: (95)..(95)
<223> OTHER INFORMATION: Xaa = N, P
<220> FEATURE:
<221> NAME/KEY: VARIANT
<222> LOCATION: (97)..(97)
<223> OTHER INFORMATION: Xaa = S, F, P, E, Q
<220> FEATURE:
<221> NAME/KEY: VARIANT
<222> LOCATION: (98)..(98)
<223> OTHER INFORMATION: Xaa = I, K
<220> FEATURE:
<221> NAME/KEY: VARIANT
<222> LOCATION: (99)..(99)
<223> OTHER INFORMATION: Xaa = V, T
<220> FEATURE:
<221> NAME/KEY: VARIANT
<222> LOCATION: (110)..(110)
<223> OTHER INFORMATION: Xaa = I, F
<220> FEATURE:
<221> NAME/KEY: VARIANT
<222> LOCATION: (115)..(115)
<223> OTHER INFORMATION: Xaa = E, Q, A
<220> FEATURE:
<221> NAME/KEY: VARIANT
<222> LOCATION: (126)..(126)
<223> OTHER INFORMATION: Xaa = L, I
<220> FEATURE:
<221> NAME/KEY: VARIANT
<222> LOCATION: (130)..(130)
<223> OTHER INFORMATION: Xaa = A or none
<220> FEATURE:
<221> NAME/KEY: VARIANT
<222> LOCATION: (132)..(132)
<223> OTHER INFORMATION: Xaa = L, I
<220> FEATURE:
<221> NAME/KEY: VARIANT
<222> LOCATION: (136)..(136)
<223> OTHER INFORMATION: Xaa = A, G
<220> FEATURE:
<221> NAME/KEY: VARIANT
<222> LOCATION: (137)..(137)
<223> OTHER INFORMATION: Xaa = V, I, L
<220> FEATURE:
<221> NAME/KEY: VARIANT
<222> LOCATION: (144)..(144)
<223> OTHER INFORMATION: Xaa = A, S
<220> FEATURE:
<221> NAME/KEY: VARIANT
<222> LOCATION: (149)..(255)
<223> OTHER INFORMATION: Xaa = Glutamate
<220> FEATURE:
<221> NAME/KEY: VARIANT
<222> LOCATION: (154)..(154)
<223> OTHER INFORMATION: Xaa = I, L
<220> FEATURE:
<221> NAME/KEY: VARIANT
<222> LOCATION: (168)..(168)
<223> OTHER INFORMATION: Xaa = T, N
<220> FEATURE:
<221> NAME/KEY: VARIANT
<222> LOCATION: (175)..(175)
<223> OTHER INFORMATION: Xaa = A, G
<220> FEATURE:
<221> NAME/KEY: VARIANT
<222> LOCATION: (177)..(177)
```

```
<223> OTHER INFORMATION: Xaa = G, E
<220> FEATURE:
<221> NAME/KEY: VARIANT
<222> LOCATION: (181)..(181)
<223> OTHER INFORMATION: Xaa = R, S, K
<220> FEATURE:
<221> NAME/KEY: VARIANT
<222> LOCATION: (183)..(183)
<223> OTHER INFORMATION: Xaa = V, I
<220> FEATURE:
<221> NAME/KEY: VARIANT
<222> LOCATION: (185)..(185)
<223> OTHER INFORMATION: Xaa = D, E
<220> FEATURE:
<221> NAME/KEY: VARIANT
<222> LOCATION: (186)..(186)
<223> OTHER INFORMATION: Xaa = Q, P, E, or none
<220> FEATURE:
<221> NAME/KEY: VARIANT
<222> LOCATION: (187)..(187)
<223> OTHER INFORMATION: Xaa = T, A, V, or none
<220> FEATURE:
<221> NAME/KEY: VARIANT
<222> LOCATION: (188)..(188)
<223> OTHER INFORMATION: Xaa = P, E, or none
<220> FEATURE:
<221> NAME/KEY: VARIANT
<222> LOCATION: (189)..(189)
<223> OTHER INFORMATION: Xaa = A, V, P, E
<220> FEATURE:
<221> NAME/KEY: VARIANT
<222> LOCATION: (190)..(190)
<223> OTHER INFORMATION: Xaa = T, P
<220> FEATURE:
<221> NAME/KEY: VARIANT
<222> LOCATION: (191)..(191)
<223> OTHER INFORMATION: Xaa = G or none
<220> FEATURE:
<221> NAME/KEY: VARIANT
<222> LOCATION: (192)..(192)
<223> OTHER INFORMATION: Xaa = L, I, N, T
<220> FEATURE:
<221> NAME/KEY: VARIANT
<222> LOCATION: (193)..(193)
<223> OTHER INFORMATION: Xaa = E, D, T
<220> FEATURE:
<221> NAME/KEY: VARIANT
<222> LOCATION: (194)..(194)
<223> OTHER INFORMATION: Xaa = R, K, G
<220> FEATURE:
<221> NAME/KEY: VARIANT
<222> LOCATION: (195)..(195)
<223> OTHER INFORMATION: Xaa = A, G
<220> FEATURE:
<221> NAME/KEY: VARIANT
<222> LOCATION: (198)..(198)
<223> OTHER INFORMATION: Xaa = P, A, Q
<220> FEATURE:
<221> NAME/KEY: VARIANT
<222> LOCATION: (199)..(199)
<223> OTHER INFORMATION: Xaa = P, G, S
<220> FEATURE:
<221> NAME/KEY: VARIANT
<222> LOCATION: (202)..(202)
<223> OTHER INFORMATION: Xaa = G, N, S
<220> FEATURE:
<221> NAME/KEY: VARIANT
<222> LOCATION: (203)..(203)
<223> OTHER INFORMATION: Xaa = F, V
<220> FEATURE:
<221> NAME/KEY: VARIANT
<222> LOCATION: (204)..(204)
<223> OTHER INFORMATION: Xaa = R, K
<220> FEATURE:
<221> NAME/KEY: VARIANT
<222> LOCATION: (205)..(205)
<223> OTHER INFORMATION: Xaa = A, S, G, E
<220> FEATURE:
<221> NAME/KEY: VARIANT
```

```
<222> LOCATION: (210)..(210)
<223> OTHER INFORMATION: Xaa = S, R, K, G
<220> FEATURE:
<221> NAME/KEY: VARIANT
<222> LOCATION: (211)..(211)
<223> OTHER INFORMATION: Xaa = E or none
<220> FEATURE:
<221> NAME/KEY: VARIANT
<222> LOCATION: (212)..(212)
<223> OTHER INFORMATION: Xaa = G, Q, S
<220> FEATURE:
<221> NAME/KEY: VARIANT
<222> LOCATION: (217)..(217)
<223> OTHER INFORMATION: Xaa = G, E
<220> FEATURE:
<221> NAME/KEY: VARIANT
<222> LOCATION: (221)..(221)
<223> OTHER INFORMATION: Xaa = A, S
<220> FEATURE:
<221> NAME/KEY: VARIANT
<222> LOCATION: (224)..(224)
<223> OTHER INFORMATION: Xaa = L, P
<220> FEATURE:
<221> NAME/KEY: VARIANT
<222> LOCATION: (229)..(229)
<223> OTHER INFORMATION: Xaa = L, M
<220> FEATURE:
<221> NAME/KEY: VARIANT
<222> LOCATION: (231)..(231)
<223> OTHER INFORMATION: Xaa = H, Q
<220> FEATURE:
<221> NAME/KEY: VARIANT
<222> LOCATION: (232)..(232)
<223> OTHER INFORMATION: Xaa = V, L
<220> FEATURE:
<221> NAME/KEY: VARIANT
<222> LOCATION: (234)..(234)
<223> OTHER INFORMATION: Xaa = I, V, F
<220> FEATURE:
<221> NAME/KEY: VARIANT
<222> LOCATION: (235)..(235)
<223> OTHER INFORMATION: Xaa = A, V
<220> FEATURE:
<221> NAME/KEY: VARIANT
<222> LOCATION: (236)..(236)
<223> OTHER INFORMATION: Xaa = F, S
<220> FEATURE:
<221> NAME/KEY: VARIANT
<222> LOCATION: (238)..(238)
<223> OTHER INFORMATION: Xaa = L, I
<220> FEATURE:
<221> NAME/KEY: VARIANT
<222> LOCATION: (243)..(243)
<223> OTHER INFORMATION: Xaa = I, V
<220> FEATURE:
<221> NAME/KEY: VARIANT
<222> LOCATION: (254)..(254)
<223> OTHER INFORMATION: Xaa = I, F
<220> FEATURE:
<221> NAME/KEY: VARIANT
<222> LOCATION: (258)..(258)
<223> OTHER INFORMATION: Xaa = V, I
<220> FEATURE:
<221> NAME/KEY: VARIANT
<222> LOCATION: (260)..(260)
<223> OTHER INFORMATION: Xaa = I, V
<220> FEATURE:
<221> NAME/KEY: VARIANT
<222> LOCATION: (261)..(261)
<223> OTHER INFORMATION: Xaa = N, Q, S
<220> FEATURE:
<221> NAME/KEY: VARIANT
<222> LOCATION: (262)..(262)
<223> OTHER INFORMATION: Xaa = E, D
<220> FEATURE:
<221> NAME/KEY: VARIANT
<222> LOCATION: (267)..(267)
<223> OTHER INFORMATION: Xaa = L, V
<220> FEATURE:
```

-continued

```
<221> NAME/KEY: VARIANT
<222> LOCATION: (268)..(268)
<223> OTHER INFORMATION: Xaa = L, I
<220> FEATURE:
<221> NAME/KEY: VARIANT
<222> LOCATION: (269)..(269)
<223> OTHER INFORMATION: Xaa = F, L
<220> FEATURE:
<221> NAME/KEY: VARIANT
<222> LOCATION: (271)..(271)
<223> OTHER INFORMATION: Xaa = I, V
<220> FEATURE:
<221> NAME/KEY: VARIANT
<222> LOCATION: (272)..(272)
<223> OTHER INFORMATION: Xaa = L, V, A, I
<220> FEATURE:
<221> NAME/KEY: VARIANT
<222> LOCATION: (276)..(276)
<223> OTHER INFORMATION: Xaa = F, I, V
<220> FEATURE:
<221> NAME/KEY: VARIANT
<222> LOCATION: (279)..(279)
<223> OTHER INFORMATION: Xaa = I, L
<220> FEATURE:
<221> NAME/KEY: VARIANT
<222> LOCATION: (283)..(283)
<223> OTHER INFORMATION: Xaa = T, N
<220> FEATURE:
<221> NAME/KEY: VARIANT
<222> LOCATION: (285)..(285)
<223> OTHER INFORMATION: Xaa = K, R
<220> FEATURE:
<221> NAME/KEY: VARIANT
<222> LOCATION: (287)..(287)
<223> OTHER INFORMATION: Xaa = V, I
<220> FEATURE:
<221> NAME/KEY: VARIANT
<222> LOCATION: (288)..(288)
<223> OTHER INFORMATION: Xaa = T, S, I
<220> FEATURE:
<221> NAME/KEY: VARIANT
<222> LOCATION: (289)..(289)
<223> OTHER INFORMATION: Xaa = D, G
<220> FEATURE:
<221> NAME/KEY: VARIANT
<222> LOCATION: (290)..(290)
<223> OTHER INFORMATION: Xaa = D, E
<220> FEATURE:
<221> NAME/KEY: VARIANT
<222> LOCATION: (291)..(291)
<223> OTHER INFORMATION: Xaa = N, D, E, G
<220> FEATURE:
<221> NAME/KEY: VARIANT
<222> LOCATION: (292)..(292)
<223> OTHER INFORMATION: Xaa = D, E
<220> FEATURE:
<221> NAME/KEY: VARIANT
<222> LOCATION: (293)..(293)
<223> OTHER INFORMATION: Xaa = D, E
<220> FEATURE:
<221> NAME/KEY: VARIANT
<222> LOCATION: (294)..(294)
<223> OTHER INFORMATION: Xaa = Q, S, E, D, or none

<400> SEQUENCE: 21

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Ala Xaa Phe Xaa Xaa Xaa
```

```
                65                  70                  75                  80
Xaa Xaa Lys Xaa Xaa Xaa Xaa Xaa Xaa Xaa Xaa Xaa Xaa Xaa Lys
                    85                  90                  95

Xaa Xaa Xaa Glu Asp Gly Ile Phe Gly Thr Ser Gly Gly Xaa Gly Phe
                100                 105                 110

Thr Lys Xaa Asn Glu Leu Phe Val Gly Arg Val Ala Met Xaa Gly Phe
                115                 120                 125

Ala Xaa Ser Xaa Leu Gly Glu Xaa Xaa Thr Gly Lys Gly Ile Leu Xaa
            130                 135                 140

Gln Leu Asn Leu Xaa Thr Gly Ile Pro Xaa Tyr Glu Ala Glu Pro Leu
145                 150                 155                 160

Leu Leu Phe Phe Ile Leu Phe Xaa Leu Gly Ala Ile Gly Xaa Leu
                    165                 170                 175

Xaa Asp Arg Gly Xaa Phe Xaa Asp Xaa Xaa Xaa Xaa Xaa Xaa Xaa
            180                 185                 190

Xaa Xaa Xaa Val Ile Xaa Xaa Gly Lys Xaa Xaa Xaa Xaa Ala Leu Gly
                195                 200                 205

Leu Xaa Xaa Xaa Gly Pro Leu Phe Xaa Phe Thr Lys Xaa Asn Glu Xaa
    210                 215                 220

Phe Val Gly Arg Xaa Ala Xaa Xaa Gly Xaa Xaa Xaa Ser Xaa Ile Gly
225                 230                 235                 240

Glu Ile Xaa Thr Gly Lys Gly Ala Leu Ala Gln Leu Asn Xaa Xaa Thr
                245                 250                 255

Gly Xaa Pro Xaa Xaa Xaa Ile Glu Pro Leu Xaa Xaa Xaa Asn Xaa Xaa
            260                 265                 270

Phe Phe Phe Xaa Ala Ala Xaa Asn Pro Gly Xaa Gly Xaa Phe Xaa Xaa
                275                 280                 285

Xaa Xaa Xaa Xaa Xaa Xaa
            290

<210> SEQ ID NO 22
<211> LENGTH: 267
<212> TYPE: PRT
<213> ORGANISM: Eutrema salsugineum

<400> SEQUENCE: 22

Met Ala Gln Thr Met Met Leu Thr Ser Gly Val Ser Ala Asn Gln Phe
1               5                   10                  15

Leu Arg Asn Lys Asn Pro Leu Ala Gln Pro Lys Val His His Leu Phe
                20                  25                  30

Leu Ser Gly Asn Ser Pro Val Val Ile Pro Ser Arg Arg Gln Ser Leu
            35                  40                  45

Val Pro Leu Ala Leu Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Val Thr Gly
                100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
        130                 135                 140
```

```
Ala Ile Gly Ala Leu Gly Asp Arg Gly Lys Phe Val Asp Asp Pro Pro
145                 150                 155                 160

Thr Pro Thr Gly Leu Glu Lys Ala Val Ile Ala Pro Gly Lys Asn Val
            165                 170                 175

Arg Ser Ala Leu Gly Leu Lys Glu Gln Gly Pro Leu Phe Gly Phe Thr
            180                 185                 190

Lys Ala Asn Glu Leu Phe Val Gly Arg Leu Ala Gln Leu Gly Ile Ala
        195                 200                 205

Phe Ser Leu Ile Gly Glu Ile Ile Thr Gly Lys Gly Ala Leu Ala Gln
        210                 215                 220

Leu Asn Ile Glu Thr Gly Ile Pro Ile Gln Asp Ile Glu Pro Leu Val
225                 230                 235                 240

Leu Leu Asn Val Ala Phe Phe Phe Ala Ala Ile Asn Pro Gly Asn
                245                 250                 255

Gly Lys Phe Ile Thr Asp Asp Gly Glu Asp Met
                260                 265
```

<210> SEQ ID NO 23
<211> LENGTH: 265
<212> TYPE: PRT
<213> ORGANISM: Raphanus sativus

<400> SEQUENCE: 23

```
Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
            20                  25                  30

Leu Ser Gly Asn Ser Pro Val Thr Leu Pro Ser Arg Arg Pro Ser Leu
        35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
        130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
            165                 170                 175

Ala Leu Gly Leu Lys Glu Gln Gly Pro Leu Phe Gly Phe Thr Lys Ala
        180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
        210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255
```

```
Phe Ile Thr Asp Asp Gly Glu Glu Ser
            260                 265
```

<210> SEQ ID NO 24
<211> LENGTH: 265
<212> TYPE: PRT
<213> ORGANISM: Brassica rapa

<400> SEQUENCE: 24

```
Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
                20                  25                  30

Leu Ser Gly Asn Ser Pro Val Thr Leu Pro Ser Arg Arg Pro Ser Leu
            35                  40                  45

Val Pro Leu Ala Ile Phe Lys Pro Lys Thr Lys Ala Ala Pro Lys Lys
50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Ala Ala Ala Ile Asn Pro Gly Asn Gly Lys
                245                 250                 255

Phe Ile Thr Asp Asp Gly Glu Glu Ser
            260                 265
```

<210> SEQ ID NO 25
<211> LENGTH: 265
<212> TYPE: PRT
<213> ORGANISM: Brassica oleracea

<400> SEQUENCE: 25

```
Met Asp Gln Thr Met Leu Leu Ser Gly Ile Ser Ala Asn His Phe
1               5                   10                  15

Leu Arg Asn Lys Asn Pro Leu Ala Gln Pro Lys Val His His Leu Phe
                20                  25                  30

Leu Ser Gly Asn Ser Pro Val Thr Leu Pro Ser Arg Ile Pro Ser Leu
            35                  40                  45
```

```
Val Pro Leu Ala Ile Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                    85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
                115                 120                 125

Glu Ala Glu Pro Leu Leu Leu Phe Phe Ile Leu Phe Thr Leu Leu Gly
                130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
                180                 185                 190

Asn Glu Leu Phe Val Gly Arg Leu Ala Gln Leu Gly Ile Ala Phe Ser
                195                 200                 205

Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Ala Ala Ala Ile Asn Pro Gly Asn Gly Lys
                    245                 250                 255

Phe Ile Thr Asp Asp Gly Glu Glu Ser
                260                 265

<210> SEQ ID NO 26
<211> LENGTH: 265
<212> TYPE: PRT
<213> ORGANISM: Brassica napus

<400> SEQUENCE: 26

Met Ala Gln Thr Met Leu Leu Thr Ser Gly Ile Ser Ala Asn His Phe
1               5                   10                  15

Leu Arg Asn Lys Asn Pro Leu Ala Gln Pro Lys Val His His Leu Phe
                20                  25                  30

Leu Ser Gly Asn Ser Pro Val Thr Leu Pro Ser Arg Ile Pro Ser Leu
            35                  40                  45

Val Pro Leu Ala Ile Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                    85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
                115                 120                 125

Glu Ala Glu Pro Leu Leu Leu Phe Phe Ile Leu Phe Thr Leu Leu Gly
                130                 135                 140

Ala Ile Gly Ala Leu Gly Asp Arg Gly Lys Phe Val Asp Asp Pro Pro
```

```
                145                 150                 155                 160
Thr Gly Leu Glu Lys Ala Val Ile Pro Pro Gly Lys Gly Val Arg Ser
                    165                 170                 175

Ala Leu Gly Leu Lys Glu Gln Gly Pro Leu Phe Gly Phe Thr Lys Ala
                    180                 185                 190

Asn Glu Leu Phe Val Gly Arg Leu Ala Gln Leu Gly Ile Ala Phe Ser
                    195                 200                 205

Leu Ile Gly Glu Ile Ile Thr Gly Lys Gly Ala Leu Ala Gln Leu Asn
                    210                 215                 220

Ile Glu Thr Gly Ile Pro Ile Gln Asp Ile Glu Pro Leu Val Leu Leu
225                 230                 235                 240

Asn Val Ala Phe Phe Ala Ala Ile Asn Pro Gly Asn Gly Lys
                    245                 250                 255

Phe Ile Thr Asp Asp Gly Glu Glu Ser
                    260                 265
```

<210> SEQ ID NO 27
<211> LENGTH: 265
<212> TYPE: PRT
<213> ORGANISM: Raphanus sativus

<400> SEQUENCE: 27

```
Met Ala Gln Thr Met Leu Leu Thr Ser Gly Val Ser Ala Asn Thr Phe
1               5                   10                  15

Leu Arg Asn Lys Asn Pro Leu Ala Gln Pro Lys Val His His Leu Phe
                20                  25                  30

Leu Ser Gly Asn Ser His Val Ile Leu Pro Ser Arg Pro Ser Leu
                35                  40                  45

Val Pro Leu Ala Ile Phe Lys Pro Lys Thr Lys Ala Ala Pro Lys Lys
                50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
                    100                 105                 110

Lys Gly Ile Leu Ala Gln Leu Asn Leu Glu Thr Gly Ile Pro Ile Tyr
                    115                 120                 125

Glu Ala Glu Pro Leu Leu Leu Phe Phe Ile Leu Phe Thr Leu Leu Gly
                    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                    165                 170                 175

Ala Leu Gly Leu Lys Glu Gln Gly Pro Leu Phe Gly Phe Thr Lys Ala
                    180                 185                 190

Asn Glu Leu Phe Val Gly Arg Leu Ala Gln Leu Gly Ile Ala Phe Ser
                    195                 200                 205

Leu Ile Gly Glu Ile Ile Thr Gly Lys Gly Ala Leu Ala Gln Leu Asn
                    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ile Asn Pro Gly Asn Gly Lys
                    245                 250                 255
```

```
Phe Ile Thr Asp Asp Gly Glu Glu Ser
            260                 265

<210> SEQ ID NO 28
<211> LENGTH: 265
<212> TYPE: PRT
<213> ORGANISM: Brassica oleracea

<400> SEQUENCE: 28

Met Ala Gln Thr Met Leu Leu Thr Ser Gly Val Ser Ala Asn Gln Phe
1               5                   10                  15

Leu Arg Asn Lys Asn Pro Leu Ala Gln Pro Lys Val His His Phe Phe
            20                  25                  30

Leu Ser Gly Asn Ser His Val Val Leu Pro Cys Arg Arg Pro Ser Leu
        35                  40                  45

Val Pro Leu Ala Ile Phe Lys Pro Lys Thr Lys Ala Ala Pro Lys Lys
    50                  55                  60

Val Glu Lys Val Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
            260                 265

<210> SEQ ID NO 29
<211> LENGTH: 265
<212> TYPE: PRT
<213> ORGANISM: Brassica rapa

<400> SEQUENCE: 29

Met Ala Gln Thr Met Leu Leu Thr Ser Gly Val Ser Ala Asn Gln Phe
1               5                   10                  15

Leu Arg Asn Lys Asn Pro Leu Ala Gln Pro Lys Val His His Phe Phe
            20                  25                  30

Leu Ser Gly Asn Ser His Val Val Leu Pro Ser Arg Arg Pro Ser Leu
        35                  40                  45
```

Val Pro Leu Ala Ile Phe Lys Pro Lys Thr Lys Ala Ala Pro Lys Lys
 50                  55                  60

Val Glu Lys Val Lys Pro Lys Val Glu Asp Gly Ile Phe Gly Thr Ser
 65                  70                  75                  80

Gly Gly Ile Gly Phe Thr Lys Gln Asn Glu Leu Phe Val Gly Arg Val
                 85                  90                  95

Ala Met Ile Gly Phe Ala Ala Ser Leu Leu Gly Glu Ala Leu Thr Gly
                 100                 105                 110

Lys Gly Ile Leu Ala Gln Leu Asn Leu Glu Thr Gly Ile Pro Ile Tyr
                 115                 120                 125

Glu Ala Glu Pro Leu Leu Leu Phe Phe Ile Leu Phe Thr Leu Leu Gly
 130                 135                 140

Ala Ile Gly Ala Leu Gly Asp Arg Gly Lys Phe Val Asp Asp Pro Pro
 145                 150                 155                 160

Thr Gly Leu Glu Lys Ala Val Ile Pro Gly Lys Gly Val Arg Ser
                 165                 170                 175

Ala Leu Gly Leu Lys Glu Gln Gly Pro Leu Phe Gly Phe Thr Lys Ala
                 180                 185                 190

Asn Glu Leu Phe Val Gly Arg Leu Ala Gln Leu Gly Ile Ala Phe Ser
                 195                 200                 205

Leu Ile Gly Glu Ile Ile Thr Gly Lys Gly Ala Leu Ala Gln Leu Asn
 210                 215                 220

Ile Glu Thr Gly Ile Pro Ile Gln Asp Ile Glu Pro Leu Val Leu Leu
 225                 230                 235                 240

Asn Val Ala Phe Phe Phe Ala Ala Ile Asn Pro Gly Asn Gly Lys
                 245                 250                 255

Phe Ile Thr Asp Asp Gly Glu Glu Arg
                 260                 265

<210> SEQ ID NO 30
<211> LENGTH: 265
<212> TYPE: PRT
<213> ORGANISM: Brassica oleracea

<400> SEQUENCE: 30

Met Ala Gln Thr Met Leu Leu Thr Ser Gly Val Ser Ala Asn Gln Phe
 1               5                   10                  15

Leu Arg Asn Lys Asn Pro Leu Ala Gln Pro Lys Val His His Phe Phe
                 20                  25                  30

Leu Ser Gly Asn Ser His Val Val Leu Pro Ser Arg Arg Pro Ser Leu
                 35                  40                  45

Val Pro Leu Ala Ile Phe Lys Pro Lys Thr Lys Ala Ala Pro Lys Lys
 50                  55                  60

Val Glu Lys Val Lys Pro Lys Val Glu Asp Gly Ile Phe Gly Thr Ser
 65                  70                  75                  80

Gly Gly Ile Gly Phe Thr Lys Gln Asn Glu Leu Phe Val Gly Arg Val
                 85                  90                  95

Ala Met Ile Gly Phe Ala Ala Ser Leu Leu Gly Glu Ala Leu Thr Gly
                 100                 105                 110

Lys Gly Ile Leu Ala Gln Leu Asn Leu Glu Thr Gly Ile Pro Ile Tyr
                 115                 120                 125

Glu Ala Glu Pro Leu Leu Leu Phe Phe Ile Leu Phe Thr Leu Leu Gly
 130                 135                 140

Ala Ile Gly Ala Leu Gly Asp Arg Gly Lys Phe Val Asp Asp Pro Pro
 145                 150                 155                 160

```
Thr Gly Leu Glu Lys Ala Val Ile Pro Pro Gly Lys Val Arg Ser
            165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 31
<211> LENGTH: 265
<212> TYPE: PRT
<213> ORGANISM: Arabidopsis thaliana

<400> SEQUENCE: 31

Met Ala Gln Thr Met Leu Leu Thr Ser Gly Val Ser Ala Gly Gln Phe
1               5                   10                  15

Leu Arg Asn Lys Ser Pro Leu Ala Gln Pro Lys Val His His Leu Phe
            20                  25                  30

Leu Ser Gly Asn Ser Pro Val Val Leu Pro Ser Arg Arg Gln Ser Phe
            35                  40                  45

Val Pro Leu Ala Leu Phe Lys Pro Lys Thr Lys Ala Ala Pro Lys Lys
        50                  55                  60

Val Glu Lys Pro Lys Lys Lys Val Glu Asp Gly Ile Phe Gly Thr Ser
65                  70                  75                  80

Gly Gly Ile Gly Phe Thr Lys Ala Asn Glu Leu Phe Val Gly Arg Val
            85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
            130                 135                 140

Ala Ile Gly Ala Leu Gly Asp Arg Gly Gln Phe Val Asp Asp Pro Pro
145                 150                 155                 160

Thr Gly Leu Glu Lys Ala Val Ile Pro Pro Gly Lys Asn Val Arg Ser
            165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
```

<210> SEQ ID NO 32
<211> LENGTH: 265
<212> TYPE: PRT
<213> ORGANISM: Arabidopsis thaliana

<400> SEQUENCE: 32

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
50                  55                  60

Val Glu Lys Pro Lys Ser Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
            260                 265

<210> SEQ ID NO 33
<211> LENGTH: 265
<212> TYPE: PRT
<213> ORGANISM: Arabidopsis thaliana

<400> SEQUENCE: 33

Met Ala Gln Thr Phe Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys

```
    50                  55                  60
Val Glu Lys Pro Lys Ser Lys Val Glu Asp Gly Ile Phe Gly Thr Ser
 65                  70                  75                  80

Gly Gly Ile Gly Phe Thr Lys Ala Asn Glu Leu Phe Val Gly Arg Val
                 85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
        130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Asn Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 34
<211> LENGTH: 265
<212> TYPE: PRT
<213> ORGANISM: Capsella rubella

<400> SEQUENCE: 34

Met Ala Gln Thr Met Leu Leu Thr Ser Gly Val Ser Ala Gly Gln Phe
  1               5                  10                  15

Leu Arg Asn Lys Asn Pro Leu Ala Gln Pro Lys Val His Gln Leu Phe
             20                  25                  30

Leu Ser Gly Thr Ser Pro Val Ala Leu Pro Ser Arg Arg Gln Ser Phe
         35                  40                  45

Val Pro Leu Ala Leu Phe Lys Pro Lys Thr Lys Ala Ala Pro Lys Lys
     50                  55                  60

Val Glu Lys Val Lys Pro Lys Val Glu Asp Gly Ile Phe Gly Thr Ser
 65                  70                  75                  80

Gly Gly Ile Gly Phe Thr Lys Ala Asn Glu Leu Phe Val Gly Arg Val
                 85                  90                  95

Ala Met Ile Gly Phe Ala Ala Ser Leu Leu Gly Glu Gly Ile Thr Gly
                100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
        130                 135                 140

Ala Ile Gly Ala Leu Gly Asp Arg Gly Lys Phe Val Asp Asp Pro Pro
145                 150                 155                 160
```

```
Thr Gly Leu Glu Lys Ala Val Ile Pro Pro Gly Lys Gly Val Arg Ser
            165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265

<210> SEQ ID NO 35
<211> LENGTH: 265
<212> TYPE: PRT
<213> ORGANISM: Camelina sativa

<400> SEQUENCE: 35

Met Ala Gln Thr Met Leu Leu Thr Ser Gly Val Ser Ala Gly Gln Phe
1               5                   10                  15

Leu Arg Asn Lys Asn Pro Leu Ala Gln Pro Lys Val His His Leu Phe
            20                  25                  30

Leu Ser Gly Thr Ser Pro Val Ala Leu Pro Ser Arg Arg Gln Leu Phe
            35                  40                  45

Val Pro Leu Ala Leu Phe Lys Pro Lys Thr Lys Ala Ala Pro Lys Lys
50                  55                  60

Val Val Lys Pro Lys Glu Lys Val Glu Asp Gly Ile Phe Gly Thr Ser
65                  70                  75                  80

Gly Gly Ile Gly Phe Thr Lys Ala Asn Glu Leu Phe Val Gly Arg Val
            85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
            130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
            165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
            245                 250                 255

Phe Ile Thr Asp Asp Gly Glu Glu Ser
            260                 265
```

<210> SEQ ID NO 36
<211> LENGTH: 265
<212> TYPE: PRT
<213> ORGANISM: Camelina sativa

<400> SEQUENCE: 36

Met Ala Gln Thr Met Leu Leu Thr Ser Gly Val Ser Ala Gly Gln Phe
1               5                   10                  15

Leu Arg Asn Lys Asn Pro Leu Ala Gln Pro Lys Val His His Leu Phe
            20                  25                  30

Leu Ser Gly Thr Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
50                  55                  60

Val Val Lys Pro Lys Asp Lys Val Glu Asp Gly Ile Phe Gly Thr Ser
65                  70                  75                  80

Gly Gly Ile Gly Phe Thr Lys Ala Asn Glu Leu Phe Val Gly Arg Val
                85                  90                  95

Ala Met Ile Gly Phe Ala Ala Ser Leu Leu Gly Glu Ala Leu Thr Gly
            100                 105                 110

Lys Gly Ile Leu Ala Gln Leu Asn Leu Glu Thr Gly Ile Pro Ile Tyr
        115                 120                 125

Glu Ala Glu Pro Leu Leu Leu Phe Phe Ile Leu Phe Thr Leu Leu Gly
    130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Leu Ile Gly Glu Ile Ile Thr Gly Lys Gly Ala Leu Ala Gln Leu Asn
    210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
            260                 265

<210> SEQ ID NO 37
<211> LENGTH: 265
<212> TYPE: PRT
<213> ORGANISM: Camelina sativa

<400> SEQUENCE: 37

Met Ala Gln Thr Met Leu Leu Thr Ser Gly Val Ser Ala Gly Gln Phe
1               5                   10                  15

Leu Arg Asn Lys Asn Pro Leu Ala Gln Pro Lys Val His His Leu Phe
            20                  25                  30

Leu Ser Gly Thr Ser Pro Val Ala Leu Pro Ser Arg Arg Gln Ser Phe
        35                  40                  45

Val Pro Leu Ala Leu Phe Lys Pro Lys Thr Lys Ala Ala Pro Lys Lys
50                  55                  60

```
Val Val Lys Pro Lys Glu Lys Val Glu Asp Gly Ile Phe Gly Thr Ser
 65                  70                  75                  80

Gly Gly Ile Gly Phe Thr Lys Ala Asn Glu Leu Phe Val Gly Arg Val
                 85                  90                  95

Ala Met Ile Gly Phe Ala Ala Ser Leu Leu Gly Glu Ala Leu Thr Gly
                100                 105                 110

Lys Gly Ile Leu Ala Gln Leu Asn Leu Glu Thr Gly Ile Pro Ile Tyr
                115                 120                 125

Glu Ala Glu Pro Leu Leu Phe Ile Leu Phe Thr Leu Leu Gly
130                 135                 140

Ala Ile Gly Ala Leu Gly Asp Arg Gly Lys Phe Val Asp Asp Pro Pro
145                 150                 155                 160

Thr Gly Leu Glu Lys Ala Val Ile Pro Pro Gly Lys Gly Val Arg Ser
                165                 170                 175

Ala Leu Gly Leu Lys Glu Gln Gly Pro Leu Phe Gly Phe Thr Lys Ala
                180                 185                 190

Asn Glu Leu Phe Val Gly Arg Leu Ala Gln Leu Gly Ile Ala Phe Ser
                195                 200                 205

Leu Ile Gly Glu Ile Ile Thr Gly Lys Gly Ala Leu Ala Gln Leu Asn
210                 215                 220

Ile Glu Thr Gly Ile Pro Ile Gln Asp Ile Glu Pro Leu Val Leu Leu
225                 230                 235                 240

Asn Val Ala Phe Phe Phe Ala Ala Ile Asn Pro Gly Asn Gly Lys
                245                 250                 255

Phe Ile Thr Asp Asp Gly Glu Glu Ser
                260                 265

<210> SEQ ID NO 38
<211> LENGTH: 270
<212> TYPE: PRT
<213> ORGANISM: Cucurbita pepo

<400> SEQUENCE: 38

Met Ala Ala Gln Thr Met Leu Leu Thr Ser Gly Ala Cys Ala Gly His
 1               5                  10                  15

Lys Lys Glu Phe Ala Ser Ile Phe Thr Arg Thr Leu Arg Pro Asn Thr
                20                  25                  30

Gln Phe Thr His Leu Leu Phe Asn Pro Ser Pro Ser His Ser Val Ser
                35                  40                  45

Leu Pro Ala Arg Gly Phe Thr Thr Leu Ala Val Phe Lys Ser Arg Thr
 50                  55                  60

Lys Val Pro Pro Lys Lys Val Ala Lys Pro Lys Val Glu Asp Gly Ile
 65                  70                  75                  80

Phe Gly Thr Ser Gly Gly Ile Gly Phe Thr Lys Gln Asn Glu Leu Phe
                 85                  90                  95

Val Gly Arg Val Ala Met Ile Gly Phe Ala Ala Ser Leu Leu Gly Glu
                100                 105                 110

Gly Ile Thr Gly Lys Gly Ile Leu Ala Gln Leu Asn Leu Glu Thr Gly
                115                 120                 125

Val Pro Ile Tyr Glu Ala Glu Pro Leu Leu Leu Phe Ile Leu Phe
130                 135                 140

Thr Leu Leu Gly Ala Ile Gly Ala Leu Gly Asp Arg Gly Lys Phe Ile
145                 150                 155                 160

Asp Asp Pro Glu Thr Ala Gly Leu Glu Arg Ala Val Ile Pro Pro Gly
```

```
                        165                 170                 175
Lys Gly Phe Arg Ser Ala Leu Gly Leu Lys Glu Gly Pro Leu Phe
                180                 185                 190

Gly Phe Thr Lys Ala Asn Glu Leu Phe Val Gly Arg Leu Ala Gln Leu
                195                 200                 205

Gly Phe Ala Phe Ser Leu Ile Gly Glu Ile Ile Thr Gly Lys Gly Ala
                210                 215                 220

Leu Ala Gln Leu Asn Ile Glu Thr Gly Val Pro Ile Asn Glu Ile Glu
225                 230                 235                 240

Pro Leu Val Leu Leu Asn Val Val Phe Phe Ile Ala Ala Leu Asn
                245                 250                 255

Pro Gly Thr Gly Lys Phe Val Thr Asp Glu Glu Asp Asp Asp
                260                 265                 270

<210> SEQ ID NO 39
<211> LENGTH: 270
<212> TYPE: PRT
<213> ORGANISM: Cucurbita moschata

<400> SEQUENCE: 39

Met Ala Ala Gln Thr Met Leu Leu Thr Ser Gly Ala Cys Ala Gly His
1               5                   10                  15

Lys Ile Asp Phe Ala Ser Ile Phe Thr Pro Thr Leu Arg Pro Asn Ala
                20                  25                  30

Gln Val Thr Arg Leu Leu Phe Asn Pro Ser Pro His Ser Val Ser
                35                  40                  45

Leu Pro Ala Arg Gly Phe Thr Thr Leu Ala Ala Phe Lys Ser Arg Thr
50                  55                  60

Lys Val Pro Pro Lys Lys Val Ser Lys Pro Lys Val Glu Asp Gly Ile
65                  70                  75                  80

Phe Gly Thr Ser Gly Gly Ile Gly Phe Thr Lys Gln Asn Glu Leu Phe
                85                  90                  95

Val Gly Arg Val Ala Met Ile Gly Phe Ala Ala Ser Leu Leu Gly Glu
                100                 105                 110

Gly Ile Thr Gly Lys Gly Ile Leu Ala Gln Leu Asn Leu Glu Thr Gly
                115                 120                 125

Val Pro Ile Tyr Glu Ala Glu Pro Leu Leu Leu Phe Phe Ile Leu Phe
                130                 135                 140

Thr Leu Leu Gly Ala Ile Gly Ala Leu Gly Asp Arg Gly Lys Phe Ile
145                 150                 155                 160

Asp Asp Pro Glu Thr Ala Gly Leu Glu Arg Ala Val Ile Pro Pro Gly
                165                 170                 175

Lys Ser Phe Arg Ser Ala Leu Gly Leu Lys Glu Gly Gly Pro Leu Phe
                180                 185                 190

Gly Phe Thr Lys Ala Asn Glu Leu Phe Val Gly Arg Leu Ala Gln Leu
                195                 200                 205

Gly Phe Ala Phe Ser Leu Ile Gly Glu Ile Ile Thr Gly Lys Gly Ala
                210                 215                 220

Leu Ala Gln Leu Asn Ile Glu Thr Gly Val Pro Ile Asn Glu Ile Glu
225                 230                 235                 240

Pro Leu Val Leu Leu Asn Val Val Phe Phe Ile Ala Ala Leu Asn
                245                 250                 255

Pro Gly Thr Gly Lys Phe Val Thr Asp Glu Glu Asp Asp Asp
                260                 265                 270
```

<210> SEQ ID NO 40
<211> LENGTH: 270
<212> TYPE: PRT
<213> ORGANISM: Cucurbita maxima

<400> SEQUENCE: 40

```
Met Ala Ala Gln Thr Met Leu Leu Thr Ser Gly Ala Cys Ala Gly His
1               5                   10                  15

Lys Arg Glu Phe Ala Ser Ile Phe Thr Gln Thr Leu Arg Pro Asn Ala
            20                  25                  30

Gln Val Thr Arg Leu Leu Phe Asn Pro Ser Pro Ser His Ser Val Thr
        35                  40                  45

Leu Pro Ala Arg Gly Phe Thr Thr Leu Ala Ala Phe Lys Ser Arg Thr
    50                  55                  60

Lys Val Pro Pro Lys Lys Val Ser Lys Pro Lys Val Glu Asp Gly Ile
65                  70                  75                  80

Phe Gly Thr Ser Gly Gly Ile Gly Phe Thr Lys Gln Asn Glu Leu Phe
                85                  90                  95

Val Gly Arg Val Ala Met Ile Gly Phe Ala Ala Ser Leu Leu Gly Glu
            100                 105                 110

Gly Ile Thr Gly Lys Gly Ile Leu Ala Gln Leu Asn Leu Glu Thr Gly
        115                 120                 125

Val Pro Ile Tyr Glu Ala Glu Pro Leu Leu Leu Phe Phe Ile Leu Phe
    130                 135                 140

Thr Leu Leu Gly Ala Ile Gly Ala Leu Gly Asp Arg Gly Lys Phe Ile
145                 150                 155                 160

Asp Asp Pro Glu Thr Ala Gly Leu Glu Arg Ala Val Ile Pro Pro Gly
                165                 170                 175

Lys Ser Phe Arg Ser Ala Leu Gly Leu Lys Glu Gly Gly Pro Leu Phe
            180                 185                 190

Gly Phe Thr Lys Ala Asn Glu Leu Phe Val Gly Arg Leu Ala Gln Leu
        195                 200                 205

Gly Phe Ala Phe Ser Leu Ile Gly Glu Ile Ile Thr Gly Lys Gly Ala
    210                 215                 220

Leu Ala Gln Leu Asn Ile Glu Thr Gly Val Pro Ile Asn Glu Ile Glu
225                 230                 235                 240

Pro Leu Val Leu Leu Asn Val Val Phe Phe Ile Ala Ala Leu Asn
                245                 250                 255

Pro Gly Thr Gly Lys Phe Val Thr Asp Glu Glu Asp Asp Asp
            260                 265                 270
```

<210> SEQ ID NO 41
<211> LENGTH: 273
<212> TYPE: PRT
<213> ORGANISM: Momordica charantia

<400> SEQUENCE: 41

```
Met Ala Ala Gln Thr Met Leu Leu Thr Ser Gly Val Cys Ala Ser His
1               5                   10                  15

Gly Val Gly Ala Lys Arg Glu Ala Ala Ala Leu Ala Gln Arg Leu Arg
            20                  25                  30

Pro Asn Ala Pro Leu Ala Arg Leu Phe Phe Asp Pro Ser Pro Leu Pro
        35                  40                  45

Cys Ser Pro Ala Arg Gly Leu Thr Thr Leu Ala Val Phe Lys Ser Arg
    50                  55                  60
```

```
Thr Lys Ala Thr Pro Lys Val Val Lys Pro Lys Gln Lys Val Glu
 65                  70                  75                  80

Asp Gly Ile Phe Gly Thr Ser Gly Gly Ile Gly Phe Thr Lys Gln Asn
                 85                  90                  95

Glu Leu Phe Val Gly Arg Val Ala Met Ile Gly Phe Ala Ala Ser Leu
                100                 105                 110

Leu Gly Glu Gly Ile Thr Gly Lys Gly Ile Leu Ala Gln Leu Asn Leu
            115                 120                 125

Glu Thr Gly Val Pro Ile Tyr Glu Ala Glu Pro Leu Leu Phe Phe
130                 135                 140

Ile Leu Phe Thr Leu Leu Gly Ala Ile Gly Ala Leu Gly Asp Arg Gly
145                 150                 155                 160

Lys Phe Ile Asp Asp Pro Glu Thr Ala Gly Leu Glu Arg Ala Val Ile
                165                 170                 175

Pro Pro Gly Lys Gly Phe Arg Ser Ala Leu Gly Leu Lys Glu Gly Gly
                180                 185                 190

Pro Leu Phe Gly Phe Thr Lys Ala Asn Glu Leu Phe Val Gly Arg Leu
            195                 200                 205

Ala Gln Leu Gly Phe Ala Phe Ser Leu Ile Gly Glu Ile Ile Thr Gly
            210                 215                 220

Lys Gly Ala Leu Ala Gln Leu Asn Ile Glu Thr Gly Val Pro Ile Asn
225                 230                 235                 240

Glu Ile Glu Pro Leu Val Leu Leu Asn Val Val Phe Phe Phe Ile Ala
                245                 250                 255

Ala Leu Asn Pro Gly Thr Gly Lys Phe Val Thr Asp Glu Glu Glu Asp
            260                 265                 270

Glu

<210> SEQ ID NO 42
<211> LENGTH: 272
<212> TYPE: PRT
<213> ORGANISM: Cucumis sativus

<400> SEQUENCE: 42

Met Ala Ala Gln Thr Met Leu Leu Thr Ser Gly Val Cys Val Gly His
  1               5                  10                  15

Gly Val Cys Leu Lys Arg Glu Leu Ser Leu Arg Pro Asn Tyr Thr Gln
                 20                  25                  30

Phe Thr Arg Leu Phe Phe Asn Pro Leu Pro Ser His Ser Val Ser Leu
                 35                  40                  45

Pro Pro Arg Gly Phe Thr Thr Leu Ala Val Phe Lys Ser Arg Thr Lys
 50                  55                  60

Ala Pro Pro Lys Lys Val Glu Lys Pro Lys Gln Lys Val Glu Asp Gly
 65                  70                  75                  80

Ile Phe Gly Thr Ser Gly Gly Ile Gly Phe Thr Lys Gln Asn Glu Leu
                 85                  90                  95

Phe Val Gly Arg Val Ala Met Ile Gly Phe Ala Ala Ser Ile Leu Gly
                100                 105                 110

Glu Ala Ile Thr Gly Lys Gly Ile Leu Ala Gln Leu Asn Leu Glu Thr
            115                 120                 125

Gly Ile Pro Ile Tyr Glu Ala Glu Pro Leu Leu Leu Phe Ile Leu
            130                 135                 140

Phe Thr Leu Leu Gly Ala Ile Gly Ala Leu Gly Asp Arg Gly Lys Phe
145                 150                 155                 160
```

```
Ile Asp Asp Pro Glu Pro Ala Thr Gly Leu Glu Arg Ala Val Ile Pro
                165                 170                 175

Pro Gly Lys Ser Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Phe Ala Phe Ser Leu Ile Gly Glu Ile Ile Thr Gly Lys
    210                 215                 220

Gly Ala Leu Ala Gln Leu Asn Ile Glu Thr Gly Val Pro Ile Asn Glu
225                 230                 235                 240

Ile Glu Pro Leu Val Leu Leu Asn Val Val Phe Phe Ile Ala Ala
                245                 250                 255

Val Asn Pro Gly Thr Gly Lys Phe Val Thr Asp Glu Glu Asp Asp Glu
            260                 265                 270
```

<210> SEQ ID NO 43
<211> LENGTH: 272
<212> TYPE: PRT
<213> ORGANISM: Cucumis melo

<400> SEQUENCE: 43

```
Met Ala Ala Gln Thr Met Leu Leu Thr Ser Gly Val Cys Val Gly His
1               5                   10                  15

Gly Val Cys Leu Lys Arg Glu Leu Ser Leu Arg Pro Asn Asn Asn Gln
            20                  25                  30

Phe Thr Arg Leu Phe Phe Asn Pro Leu Pro Asn His Ser Val Ser Leu
        35                  40                  45

Pro Ala Arg Gly Phe Thr Pro Leu Ala Val Phe Lys Ser Arg Thr Lys
    50                  55                  60

Ala Pro Pro Lys Lys Val Glu Lys Pro Lys Gln Lys Val Glu Asp Gly
65                  70                  75                  80

Ile Phe Gly Thr Ser Gly Gly Ile Gly Phe Thr Lys Gln Asn Glu Leu
                85                  90                  95

Phe Val Gly Arg Val Ala Met Ile Gly Phe Ala Ala Ser Leu Leu Gly
            100                 105                 110

Glu Ala Ile Thr Gly Lys Gly Ile Leu Ala Gln Leu Asn Leu Glu Thr
        115                 120                 125

Gly Ile Pro Ile Tyr Glu Ala Glu Pro Leu Leu Leu Phe Phe Ile Leu
    130                 135                 140

Phe Thr Leu Leu Gly Ala Ile Gly Ala Leu Gly Asp Arg Gly Lys Phe
145                 150                 155                 160

Ile Asp Asp Pro Glu Pro Ala Thr Gly Leu Glu Arg Ala Val Ile Pro
                165                 170                 175

Pro Gly Lys Ser Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Phe Ala Phe Ser Leu Ile Gly Glu Ile Ile Thr Gly Lys
    210                 215                 220

Gly Ala Leu Ala Gln Leu Asn Ile Glu Thr Gly Val Pro Ile Asn Glu
225                 230                 235                 240

Ile Glu Pro Leu Val Leu Leu Asn Val Val Phe Phe Ile Ala Ala
                245                 250                 255

Val Asn Pro Gly Thr Gly Lys Phe Val Thr Asp Glu Glu Asp Asp Glu
            260                 265                 270
```

<210> SEQ ID NO 44
<211> LENGTH: 275
<212> TYPE: PRT
<213> ORGANISM: Cucurbita moschata

<400> SEQUENCE: 44

```
Met Ala Ala Gln Thr Met Val Leu Ser Ser Gly Val Cys Ala Ser His
1               5                   10                  15

Gly Val Ala Leu Lys Arg Glu Ile Ala Ser Leu Thr Gln Arg Leu Arg
            20                  25                  30

Pro Asn Ala Gln Phe Ser Arg Leu Phe Phe Asn Pro Leu Pro Ser Ser
        35                  40                  45

Ser Val Ser Leu Pro Ala Arg Gly Phe Arg Thr Leu Ala Ile Phe Lys
    50                  55                  60

Ser Lys Ala Lys Val Pro Ala Lys Lys Val Val Lys Pro Lys Glu Lys
65                  70                  75                  80

Val Glu Asp Gly Ile Phe Gly Thr Ser Gly Ile Gly Phe Thr Lys
                85                  90                  95

Gln Asn Glu Leu Phe Val Gly Arg Val Ala Met Ile Gly Phe Ala Ala
            100                 105                 110

Ser Leu Leu Gly Glu Gly Ile Thr Gly Lys Gly Ile Leu Ala Gln Leu
        115                 120                 125

Asn Leu Glu Thr Gly Val Pro Ile Tyr Glu Ala Glu Pro Leu Leu Leu
    130                 135                 140

Phe Phe Ile Leu Phe Thr Leu Leu Gly Ala Ile Gly Ala Leu Gly Asp
145                 150                 155                 160

Arg Gly Lys Phe Ile Asp Asp Pro Glu Pro Ala Thr Gly Leu Glu Arg
                165                 170                 175

Ala Val Ile Pro Pro Gly Lys Gly Leu Arg Ser Ala Leu Gly Leu Lys
            180                 185                 190

Glu Gly Gly Pro Leu Phe Gly Phe Thr Lys Ala Asn Glu Leu Phe Val
        195                 200                 205

Gly Arg Leu Ala Gln Leu Gly Phe Ala Phe Ser Leu Ile Gly Glu Ile
    210                 215                 220

Ile Thr Gly Lys Gly Ala Leu Ala Gln Leu Asn Ile Glu Thr Gly Val
225                 230                 235                 240

Pro Ile Asn Glu Ile Glu Pro Leu Val Leu Leu Asn Val Leu Phe Phe
                245                 250                 255

Phe Ile Ala Ala Val Asn Pro Gly Thr Gly Lys Phe Val Thr Asp Glu
            260                 265                 270

Glu Glu Asp
        275
```

<210> SEQ ID NO 45
<211> LENGTH: 275
<212> TYPE: PRT
<213> ORGANISM: Cucurbita maxima

<400> SEQUENCE: 45

```
Met Ala Ala Gln Thr Met Val Leu Ser Ser Gly Val Cys Ala Ser His
1               5                   10                  15

Gly Val Ala Leu Lys Arg Glu Ile Ala Ser Leu Thr Arg Arg Leu Arg
            20                  25                  30

Pro Asn Ala Gln Ser Ser Arg Leu Phe Phe Asn Pro Leu Pro Ser Ser
        35                  40                  45
```

```
Ser Val Ser Leu Pro Ala Arg Gly Phe Arg Thr Leu Ala Ile Phe Lys
    50                  55                  60

Ser Lys Ala Lys Val Pro Ala Lys Lys Val Val Lys Pro Lys Glu Lys
65                  70                  75                  80

Val Glu Asp Gly Ile Phe Gly Thr Ser Gly Ile Gly Phe Thr Lys
                    85                  90                  95

Gln Asn Glu Leu Phe Val Gly Arg Val Ala Met Ile Gly Phe Ala Ala
                100                 105                 110

Ser Leu Leu Gly Glu Gly Ile Thr Gly Lys Gly Ile Leu Ala Gln Leu
            115                 120                 125

Asn Leu Glu Thr Gly Val Pro Ile Tyr Glu Ala Glu Pro Leu Leu Leu
        130                 135                 140

Phe Phe Ile Leu Phe Thr Leu Leu Gly Ala Ile Gly Ala Leu Gly Asp
145                 150                 155                 160

Arg Gly Lys Phe Ile Asp Asp Pro Glu Pro Ala Thr Gly Leu Glu Arg
                    165                 170                 175

Ala Val Ile Pro Pro Gly Lys Gly Leu Arg Ser Ala Leu Gly Leu Lys
                180                 185                 190

Glu Gly Gly Pro Leu Phe Gly Phe Thr Lys Ala Asn Glu Leu Phe Val
            195                 200                 205

Gly Arg Leu Ala Gln Leu Gly Phe Ala Phe Ser Leu Ile Gly Glu Ile
        210                 215                 220

Ile Thr Gly Lys Gly Ala Leu Ala Gln Leu Asn Ile Glu Thr Gly Val
225                 230                 235                 240

Pro Ile Asn Glu Ile Glu Pro Leu Val Leu Asn Val Leu Phe Phe
                    245                 250                 255

Phe Ile Ala Ala Val Asn Pro Gly Thr Gly Lys Phe Val Thr Asp Glu
                260                 265                 270

Glu Glu Asp
        275

<210> SEQ ID NO 46
<211> LENGTH: 277
<212> TYPE: PRT
<213> ORGANISM: Abrus precatorius

<400> SEQUENCE: 46

Met Ala Gln Thr Met Val Leu Met Ser Ser Val Pro Ala Ser Asn Ser
1               5                   10                  15

Met Asp Leu Lys Gly Asn Ser Leu Leu Gln Leu Arg Ser Gln Arg Leu
            20                  25                  30

Arg Pro Lys Phe Ser Arg His Phe Phe Asn Pro Leu Pro Ser Thr Phe
        35                  40                  45

Ser Phe Pro Ser Ser Ser Ser Thr Phe Thr Thr Ile Ala Ile Tyr Lys
    50                  55                  60

Thr Lys Thr Lys Ala Ser Pro Thr Ser Lys Val Val Lys Ser Lys Pro
65                  70                  75                  80

Lys Ser Lys Val Glu Asp Gly Ile Phe Gly Thr Ser Gly Gly Phe Gly
                    85                  90                  95

Phe Thr Lys Gln Asn Glu Leu Phe Val Gly Arg Val Ala Met Leu Gly
                100                 105                 110

Phe Ala Ala Ser Leu Leu Gly Glu Ala Ile Thr Gly Lys Gly Ile Leu
            115                 120                 125

Ala Gln Leu Asn Leu Glu Thr Gly Ile Pro Ile Tyr Glu Ala Glu Pro
```

```
                130                 135                 140
Leu Leu Leu Phe Phe Ile Ile Phe Thr Leu Leu Gly Ala Ile Gly Ala
145                 150                 155                 160

Leu Gly Asp Arg Gly Gln Phe Val Asp Asp Pro Thr Pro Leu Asp
                165                 170                 175

Lys Pro Phe Ile Pro Pro Gly Lys Gly Phe Arg Ala Ala Leu Gly Leu
                180                 185                 190

Arg Glu Gly Gly Pro Leu Phe Gly Phe Thr Lys Ala Asn Glu Leu Phe
                195                 200                 205

Val Gly Arg Leu Ala Gln Met Gly Phe Ala Phe Ser Leu Ile Gly Glu
                210                 215                 220

Ile Ile Thr Gly Lys Gly Ala Leu Ala Gln Leu Asn Ile Glu Thr Gly
225                 230                 235                 240

Val Pro Ile Asn Glu Ile Glu Pro Leu Val Leu Phe Ser Ile Val Phe
                245                 250                 255

Phe Phe Phe Ala Ala Leu Asn Pro Gly Thr Gly His Phe Val Thr Asp
                260                 265                 270

Glu Gly Glu Glu Val
                275

<210> SEQ ID NO 47
<211> LENGTH: 269
<212> TYPE: PRT
<213> ORGANISM: Phaseolus vulgaris

<400> SEQUENCE: 47

Met Ala Gln Thr Met Phe Leu Met Ser Ser Val Ser Ser Ser His Ser
1               5                   10                  15

Leu Asp Leu Lys Lys Asp Leu Phe Leu Gln Leu Arg Pro Lys Phe Ser
                20                  25                  30

Gln Leu Ser Phe Ser Pro Leu Pro Ser Ala Ser Phe Ser Ser Ser
            35                  40                  45

Pro Arg Thr Phe Thr Thr Leu Ala Leu Phe Lys Ser Lys Thr Lys Ala
50                  55                  60

Pro Pro Ala Lys Thr Lys Val Thr Lys Ser Lys Pro Lys Val Glu Asp
65                  70                  75                  80

Gly Val Phe Gly Thr Ser Gly Gly Phe Gly Phe Thr Lys Gln Asn Glu
                85                  90                  95

Leu Phe Val Gly Arg Val Ala Met Leu Gly Phe Ala Ala Ser Leu Leu
                100                 105                 110

Gly Glu Ala Val Thr Gly Lys Gly Ile Leu Ser Gln Leu Asn Leu Glu
                115                 120                 125

Thr Gly Ile Pro Ile Tyr Glu Ala Glu Pro Leu Leu Leu Phe Phe Ile
            130                 135                 140

Leu Phe Thr Leu Leu Gly Ala Ile Gly Gly Leu Gly Asp Arg Gly Lys
145                 150                 155                 160

Phe Val Asp Asp Asp Glu Pro Asn Thr Ala Gly Val Ile Pro Ser Gly
                165                 170                 175

Lys Gly Phe Arg Glu Ala Ile Gly Leu Gly Ser Gly Pro Leu Phe Gly
                180                 185                 190

Phe Thr Lys Ala Asn Glu Leu Phe Val Gly Arg Leu Ala Gln Leu Gly
                195                 200                 205

Phe Val Phe Ser Leu Ile Gly Glu Ile Ile Thr Gly Lys Gly Ala Leu
                210                 215                 220
```

```
Ala Gln Leu Asn Ile Glu Thr Gly Val Pro Ile Asn Glu Ile Glu Pro
225                 230                 235                 240

Leu Val Leu Phe Asn Val Leu Phe Phe Val Ala Ala Leu Asn Pro
            245                 250                 255

Gly Thr Gly Lys Phe Val Thr Asp Glu Gly Asp Asp Glu
        260                 265
```

<210> SEQ ID NO 48
<211> LENGTH: 265
<212> TYPE: PRT
<213> ORGANISM: Vigna radiata

<400> SEQUENCE: 48

```
Met Ala Gln Thr Met Leu Leu Met Ser Ser Val Ser Ser Ser His Ser
1               5                   10                  15

Leu Gly Leu Lys Lys Asp Leu Phe Gln Gln Leu Arg Pro Lys Phe Ser
            20                  25                  30

Gln Leu Ser Phe Asn Pro Leu Pro Ser Ser Ser Phe Ser Ser
        35                  40                  45

Pro Arg Thr Phe Thr Thr Leu Ala Leu Phe Lys Ser Lys Thr Lys Ala
50                  55                  60

Pro Pro Ala Lys Val Val Lys Pro Lys Gln Lys Val Glu Asp Gly Ile
65                  70                  75                  80

Phe Gly Thr Ser Gly Gly Phe Gly Phe Thr Lys Gln Asn Glu Leu Phe
                85                  90                  95

Val Gly Arg Val Ala Met Leu Gly Phe Ala Ala Ser Leu Leu Gly Glu
            100                 105                 110

Ala Val Thr Gly Lys Gly Ile Leu Ser Gln Leu Asn Leu Glu Thr Gly
        115                 120                 125

Ile Pro Ile Tyr Glu Ala Glu Pro Leu Leu Leu Phe Ile Leu Phe
    130                 135                 140

Thr Leu Leu Gly Ala Ile Gly Gly Leu Gly Asp Arg Gly Lys Phe Val
145                 150                 155                 160

Asp Asp Glu Pro Asn Thr Gly Gly Val Ile Pro Ser Gly Lys Gly Phe
                165                 170                 175

Arg Glu Ala Leu Gly Leu Gly Ser Gly Arg Leu Phe Gly Phe Thr Lys
            180                 185                 190

Ala Asn Glu Leu Phe Val Gly Arg Leu Ala Gln Leu Gly Phe Val Phe
        195                 200                 205

Ser Leu Ile Gly Glu Ile Ile Thr Gly Lys Gly Ala Leu Ala Gln Leu
    210                 215                 220

Asn Ile Glu Thr Gly Val Pro Ile Asn Glu Ile Glu Pro Leu Val Leu
225                 230                 235                 240

Phe Asn Val Leu Phe Phe Val Ala Ala Leu Asn Pro Gly Thr Gly
                245                 250                 255

Lys Phe Val Thr Asp Glu Glu Asp Asp
            260                 265
```

<210> SEQ ID NO 49
<211> LENGTH: 265
<212> TYPE: PRT
<213> ORGANISM: Vigna angularis

<400> SEQUENCE: 49

```
Met Ala Gln Thr Met Leu Leu Met Ser Ser Val Ser Ser Ser His Ser
1               5                   10                  15
```

Leu Gly Leu Lys Lys Glu Leu Phe Gln Gln Leu Arg Pro Lys Phe Ser
            20                  25                  30

Gln Leu Ser Phe Asn Pro Leu Pro Ser Ser Ser Phe Ser Ser Ser
        35                  40                  45

Pro Arg Thr Phe Thr Thr Leu Ala Leu Phe Lys Ser Lys Thr Lys Ala
 50                  55                  60

Pro Pro Ala Lys Thr Lys Val Thr Lys Pro Lys Val Glu Asp Gly Val
65                  70                  75                  80

Phe Gly Thr Ser Gly Gly Phe Gly Phe Thr Lys Gln Asn Glu Leu Phe
                85                  90                  95

Val Gly Arg Val Ala Met Leu Gly Phe Ala Ala Ser Leu Leu Gly Glu
            100                 105                 110

Ala Val Thr Gly Lys Gly Ile Leu Ser Gln Leu Asn Leu Glu Thr Gly
            115                 120                 125

Ile Pro Ile Tyr Glu Ala Glu Pro Leu Leu Leu Phe Phe Ile Leu Phe
        130                 135                 140

Thr Leu Leu Gly Ala Ile Gly Gly Leu Gly Asp Arg Gly Lys Phe Val
145                 150                 155                 160

Asp Asp Glu Pro Asn Thr Gly Gly Val Ile Pro Ala Gly Lys Gly Phe
                165                 170                 175

Arg Glu Ala Leu Gly Leu Gly Ser Gly Pro Leu Phe Gly Phe Thr Lys
            180                 185                 190

Ala Asn Glu Leu Phe Val Gly Arg Leu Ala Gln Leu Gly Phe Val Phe
        195                 200                 205

Ser Leu Ile Gly Glu Ile Ile Thr Gly Lys Gly Ala Leu Ala Gln Leu
        210                 215                 220

Asn Ile Glu Thr Gly Val Pro Ile Asn Glu Ile Glu Pro Leu Val Leu
225                 230                 235                 240

Phe Asn Val Leu Phe Phe Ile Ala Ala Leu Asn Pro Gly Thr Gly
                245                 250                 255

Lys Phe Val Thr Asp Glu Glu Asp Asp
            260                 265

<210> SEQ ID NO 50
<211> LENGTH: 270
<212> TYPE: PRT
<213> ORGANISM: Cajanus cajan

<400> SEQUENCE: 50

Met Ala Gln Thr Met Leu Leu Met Ser Ser Val Ser Ser Ser Tyr Ser
1               5                   10                  15

Val Ala Leu Asn Lys Asp Val Phe Leu Gln Leu Gln Ala Gln Arg Leu
            20                  25                  30

Arg Pro Lys Phe Ser Asp Leu Ser Phe Asn Pro Leu Pro Ser Asn Ser
        35                  40                  45

Leu Phe Ser Ser Arg Pro Thr Phe Thr Thr Leu Ala Leu Phe Lys Ser
    50                  55                  60

Lys Thr Lys Ala Pro Pro Ala Lys Thr Lys Val Thr Lys Pro Lys Val
65                  70                  75                  80

Glu Asp Gly Ile Phe Gly Thr Ser Gly Gly Phe Gly Phe Thr Lys Gln
                85                  90                  95

Asn Glu Leu Phe Val Gly Arg Val Ala Met Leu Gly Phe Ala Ala Ser
            100                 105                 110

Leu Leu Gly Glu Ala Val Thr Gly Lys Gly Ile Leu Ala Gln Leu Asn
            115                 120                 125

```
Leu Glu Thr Gly Ile Pro Ile Tyr Glu Ala Glu Pro Leu Leu Leu Phe
            130                 135                 140

Phe Ile Leu Phe Thr Leu Leu Gly Ala Ile Gly Gly Leu Gly Asp Arg
145                 150                 155                 160

Gly Arg Phe Val Asp Asp Glu Pro Thr Thr Ala Gly Val Ile Pro Pro
                165                 170                 175

Gly Lys Gly Phe Arg Glu Ala Leu Gly Leu Gly Gln Gly Pro Leu Phe
            180                 185                 190

Gly Phe Thr Lys Ser Asn Glu Leu Phe Val Gly Arg Leu Ala Gln Leu
        195                 200                 205

Gly Phe Val Phe Ser Leu Ile Gly Glu Ile Ile Thr Gly Lys Gly Ala
        210                 215                 220

Leu Ala Gln Leu Asn Ile Glu Thr Gly Val Pro Ile Asn Glu Ile Glu
225                 230                 235                 240

Pro Leu Val Leu Phe Asn Val Leu Phe Phe Ile Ala Ala Leu Asn
                245                 250                 255

Pro Gly Thr Gly Lys Phe Val Thr Asp Glu Glu Ala Asp Asp
            260                 265                 270
```

<210> SEQ ID NO 51
<211> LENGTH: 273
<212> TYPE: PRT
<213> ORGANISM: Abrus precatorius

<400> SEQUENCE: 51

```
Met Ala Gln Thr Met Val Leu Met Ser Ser Val Ser Ser Tyr Ser
1

```
                    225                 230                 235                 240

Glu Ile Glu Pro Leu Val Leu Phe Asn Val Leu Phe Phe Ile Ala
                    245                 250                 255

Ala Leu Asn Pro Gly Thr Gly Lys Phe Leu Thr Asp Glu Glu Asp
                260                 265                 270

Asp

<210> SEQ ID NO 52
<211> LENGTH: 271
<212> TYPE: PRT
<213> ORGANISM: Mucuna pruriens

<400> SEQUENCE: 52

Met Ala Gln Thr Met Leu Leu Met Ser Ser Val Ser Ser Tyr Ser
1               5                   10                  15

Val Asp Leu Lys Lys Asp Leu Phe Leu Gln Leu Gln Ser Gln Arg Leu
                20                  25                  30

Arg Pro Lys Phe Ser His Ile Ser Phe Asn Pro Leu Pro Ser Asn Ser
                35                  40                  45

Phe Phe Ser Ser Pro Arg Thr Phe Thr Thr Gln Ala Leu Phe Lys Ser
50                  55                  60

Lys Thr Lys Ser Pro Pro Lys Thr Lys Val Thr Lys Pro Lys Pro
65                  70                  75                  80

Lys Val Glu Asp Gly Val Phe Gly Thr Ser Gly Gly Phe Gly Phe Thr
                85                  90                  95

Lys Gln Asn Glu Leu Phe Val Gly Arg Val Ala Met Leu Gly Phe Ala
                100                 105                 110

Ala Ser Leu Leu Gly Glu Gly Ile Thr Gly Lys Gly Ile Leu Ala Gln
                115                 120                 125

Leu Asn Leu Glu Thr Gly Ile Pro Ile Tyr Glu Ala Glu Pro Leu Leu
130                 135                 140

Leu Phe Phe Ile Leu Phe Thr Leu Leu Gly Ala Ile Gly Ala Leu Gly
145                 150                 155                 160

Asp Arg Gly Gln Phe Val Asp Asp Glu Pro Thr Thr Gly Gly Val Ile
                165                 170                 175

Pro Pro Gly Lys Gly Leu Arg Glu Ala Leu Gly Leu Gly Gln Gly Pro
                180                 185                 190

Leu Phe Gly Phe Thr Lys Ala Asn Glu Leu Phe Val Gly Arg Leu Ala
                195                 200                 205

Gln Leu Gly Phe Ala Phe Ser Leu Ile Gly Ile Ile Thr Gly Lys
                210                 215                 220

Gly Ala Leu Ala Gln Leu Asn Ile Glu Thr Gly Val Pro Ile Asn Glu
225                 230                 235                 240

Ile Glu Pro Leu Val Leu Phe Asn Val Leu Phe Phe Val Ala Ala
                245                 250                 255

Leu Asn Pro Gly Thr Gly Lys Phe Val Thr Asp Glu Glu Glu Asp
                260                 265                 270

<210> SEQ ID NO 53
<211> LENGTH: 273
<212> TYPE: PRT
<213> ORGANISM: Glycine soja

<400> SEQUENCE: 53

Met Ala Gln Thr Met Leu Leu Met Ser Ser Val Ser Ser Tyr Ser
1               5                   10                  15
```

```
Val Asp Leu Lys Lys Asp Leu Phe Leu Gln Leu Gln Ser Gln Ser Leu
        20                  25                  30

Arg Pro Lys Phe Ser Gln Leu Ser Phe Asn Pro Leu Pro Pro Ser Thr
        35                  40                  45

Ser Ser Phe Ser Ser Pro Arg Thr Phe Thr Thr Leu Ala Leu Phe Lys
 50                  55                  60

Ser Lys Thr Lys Ala Ala Pro Ala Lys Thr Lys Val Thr Lys Pro Lys
 65                  70                  75                  80

Gln Lys Val Glu Asp Gly Ile Phe Gly Thr Ser Gly Gly Phe Gly Phe
                 85                  90                  95

Thr Lys Gln Asn Glu Leu Phe Val Gly Arg Val Ala Met Leu Gly Phe
                100                 105                 110

Ala Ala Ser Leu Leu Gly Glu Gly Ile Thr Gly Lys Gly Ile Leu Ala
                115                 120                 125

Gln Leu Asn Leu Glu Thr Gly Ile Pro Ile Tyr Glu Ala Glu Pro Leu
        130                 135                 140

Leu Leu Phe Phe Ile Leu Phe Thr Leu Leu Gly Ala Ile Gly Gly Leu
145                 150                 155                 160

Gly Asp Arg Gly Lys Phe Val Asp Asp Glu Pro Thr Thr Gly Gly Val
                165                 170                 175

Ile Pro Ser Gly Lys Gly Phe Arg Glu Ala Leu Gly Leu Gly Ser Gly
                180                 185                 190

Pro Leu Phe Gly Phe Thr Lys Ala Asn Glu Leu Phe Val Gly Arg Leu
        195                 200                 205

Ala Gln Leu Gly Phe Val Phe Ser Leu Ile Gly Glu Ile Ile Thr Gly
        210                 215                 220

Lys Gly Ala Leu Ala Gln Leu Asn Ile Glu Thr Gly Val Pro Ile Asn
225                 230                 235                 240

Glu Ile Glu Pro Leu Val Leu Phe Asn Val Leu Phe Phe Ile Ala
                245                 250                 255

Ala Leu Asn Pro Gly Thr Gly Lys Phe Val Thr Asp Asp Gly Glu Asp
                260                 265                 270

Asp

<210> SEQ ID NO 54
<211> LENGTH: 271
<212> TYPE: PRT
<213> ORGANISM: Arachis ipaensis

<400> SEQUENCE: 54

Met Met Ala Gln Thr Met Leu Leu Met Ser Ser Val Ser Thr Thr Tyr
 1               5                  10                  15

Ser Met Asp Leu Lys Lys Asp Thr Leu Leu Gln Leu Gln Asn Gln Arg
                 20                  25                  30

Leu Arg Pro Lys Phe Ser His Leu Pro Phe Asn Pro Ile Pro Ser Asn
         35                 40                  45

Ser Leu Ser Phe Ser Pro Pro Thr Phe Thr Thr Leu Ala Leu Phe Lys
 50                  55                  60

Ser Lys Thr Lys Ala Pro Pro Lys Val Val Lys Pro Lys Pro Lys Val
 65                  70                  75                  80

Glu Asp Gly Ile Phe Gly Thr Ser Gly Gly Phe Gly Phe Thr Lys Gln
                 85                  90                  95

Asn Glu Leu Phe Val Gly Arg Val Ala Met Ile Gly Phe Ala Ala Ser
                100                 105                 110
```

```
Ile Leu Gly Glu Ala Ile Thr Gly Lys Gly Ile Leu Ala Gln Leu Asn
            115                 120                 125

Leu Glu Thr Gly Val Pro Ile Tyr Glu Ala Glu Pro Leu Leu Leu Phe
        130                 135                 140

Phe Ile Leu Phe Thr Leu Leu Gly Ala Ile Gly Ala Leu Gly Asp Arg
145                 150                 155                 160

Gly Lys Phe Val Asp Asp Glu Pro Asn Thr Gly Val Ile Pro
                165                 170                 175

Pro Gly Lys Gly Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
            195                 200                 205

Gln Leu Gly Phe Ala Phe Ser Leu Ile Gly Glu Ile Ile Thr Gly Lys
        210                 215                 220

Gly Ala Leu Ala Gln Leu Asn Ile Glu Thr Gly Val Pro Ile Asn Glu
225                 230                 235                 240

Ile Glu Pro Leu Val Leu Phe Asn Val Ala Phe Phe Ile Ala Ala
                245                 250                 255

Leu Asn Pro Gly Thr Gly Lys Phe Val Thr Asp Glu Glu Asp
            260                 265                 270
```

<210> SEQ ID NO 55
<211> LENGTH: 271
<212> TYPE: PRT
<213> ORGANISM: Arachis hypogaea

<400> SEQUENCE: 55

```
Met Met Ala Gln Thr Met Leu Leu Met Ser Ser Val Ser Thr Thr Tyr
1               5                   10                  15

Ser Met Asp Leu Lys Lys Asp Thr Leu Leu Gln Leu Gln Asn Gln Arg
            20                  25                  30

Leu Arg Pro Lys Phe Ser His Leu Pro Phe Asn Pro Ile Pro Ser Asn
        35                  40                  45

Ser Leu Ser Phe Ser Pro Pro Thr Phe Thr Thr Leu Ala Leu Phe Lys
50                  55                  60

Ser Lys Thr Lys Ala Pro Pro Lys Val Val Lys Pro Lys Pro Lys Val
65                  70                  75                  80

Glu Asp Gly Ile Phe Gly Thr Ser Gly Gly Phe Gly Phe Thr Lys Gln
                85                  90                  95

Asn Glu Leu Phe Val Gly Arg Val Ala Met Leu Gly Phe Ala Ala Ser
            100                 105                 110

Ile Leu Gly Glu Ala Ile Thr Gly Lys Gly Ile Leu Ala Gln Leu Asn
            115                 120                 125

Leu Glu Thr Gly Ile Pro Ile Tyr Glu Ala Glu Pro Leu Leu Leu Phe
        130                 135                 140

Phe Ile Leu Phe Thr Leu Leu Gly Ala Ile Gly Ala Leu Gly Asp Arg
145                 150                 155                 160

Gly Arg Phe Val Asp Asp Glu Pro Asn Thr Gly Val Ile Pro
                165                 170                 175

Pro Gly Lys Gly Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
            195                 200                 205

Gln Leu Gly Phe Ala Phe Ser Leu Ile Gly Glu Ile Ile Thr Gly Lys
```

```
                    210                 215                 220
Gly Ala Leu Ala Gln Leu Asn Ile Glu Thr Gly Val Pro Ile Asn Glu
225                 230                 235                 240

Ile Glu Pro Leu Val Leu Phe Asn Val Ala Phe Phe Phe Ile Ala Ala
                    245                 250                 255

Leu Asn Pro Gly Thr Gly Lys Phe Val Thr Asp Glu Glu Glu Asp
                    260                 265                 270

<210> SEQ ID NO 56
<211> LENGTH: 270
<212> TYPE: PRT
<213> ORGANISM: Pisum sativum

<400> SEQUENCE: 56

Met Ala Gln Thr Met Leu Leu Met Ser Ser Val Ser Ser Thr Tyr Ser
1               5                   10                  15

Val Pro Leu Asn Lys Asp Pro Leu Leu Gln Leu Gln Cys Gln Arg Leu
                20                  25                  30

Lys Pro Arg Phe Ser Asp Ile Ser Phe Ser Pro Leu Ser Ser Asn Ser
                35                  40                  45

Lys Ser Phe Ser Ser Arg Thr Phe Lys Thr Leu Ala Leu Phe Lys Ser
50                  55                  60

Lys Thr Lys Ala Pro Ala Lys Val Val Pro Lys Gln Lys Pro Lys Val
65                  70                  75                  80

Glu Asp Gly Val Phe Gly Thr Ser Gly Gly Phe Gly Phe Thr Lys Gln
                85                  90                  95

Asn Glu Leu Phe Val Gly Arg Val Ala Met Ile Gly Phe Ala Ala Ser
                100                 105                 110

Ile Leu Gly Glu Gly Ile Thr Gly Lys Gly Ile Leu Ser Gln Leu Asn
                115                 120                 125

Leu Glu Thr Gly Ile Pro Ile Tyr Glu Ala Glu Pro Leu Leu Leu Phe
130                 135                 140

Phe Ile Ile Phe Thr Leu Leu Gly Ala Ile Gly Ala Leu Gly Asp Arg
145                 150                 155                 160

Gly Lys Phe Val Asp Asp Glu Pro Thr Thr Gly Val Ile Pro Pro
                165                 170                 175

Gly Lys Gly Phe Arg Gln Ala Leu Gly Leu Ser Glu Gly Pro Leu
                180                 185                 190

Phe Gly Phe Thr Lys Ser Asn Glu Leu Phe Val Gly Arg Leu Ala Gln
                195                 200                 205

Leu Gly Phe Ala Phe Ser Leu Ile Gly Glu Ile Ile Thr Gly Lys Gly
                210                 215                 220

Ala Leu Ala Gln Leu Asn Ile Glu Thr Gly Val Pro Ile Asn Glu Ile
225                 230                 235                 240

Glu Pro Leu Val Leu Phe Asn Val Ala Phe Phe Phe Ile Ala Ala Leu
                245                 250                 255

Asn Pro Gly Thr Gly Lys Phe Val Thr Asp Glu Glu Glu Asp
                260                 265                 270

<210> SEQ ID NO 57
<211> LENGTH: 269
<212> TYPE: PRT
<213> ORGANISM: Cicer arietinum

<400> SEQUENCE: 57

Met Ala Gln Thr Met Leu Leu Met Ser Ser Val Ser Ser Thr Tyr Ser
```

-continued

```
 1               5                  10                 15
Val Asp Leu Lys Lys Asp Pro Leu Leu Gln Leu Gln Cys Gln Arg Leu
            20                  25                  30

Arg Pro Lys Phe Ser Asp Ile Ser Phe Asn Pro Leu Asn Ser Asn Ser
            35                  40                  45

Lys Ser Phe Ser Ser Arg Thr Phe Thr Thr Leu Ala Leu Phe Lys Ser
        50                  55                  60

Lys Ala Lys Ala Pro Pro Lys Val Val Lys Pro Lys Pro Lys Val Glu
65                  70                  75                  80

Asp Gly Val Phe Gly Thr Ser Gly Gly Phe Gly Phe Thr Lys Gln Asn
                85                  90                  95

Glu Leu Phe Val Gly Arg Val Ala Met Ile Gly Phe Ala Ala Ser Ile
            100                 105                 110

Leu Gly Glu Ala Val Thr Gly Lys Gly Ile Leu Ala Gln Leu Asn Leu
        115                 120                 125

Glu Thr Gly Ile Pro Ile Tyr Glu Ala Glu Pro Leu Leu Leu Phe Phe
    130                 135                 140

Ile Ile Phe Thr Leu Leu Gly Ala Ile Gly Ala Leu Gly Asp Arg Gly
145                 150                 155                 160

Lys Phe Val Asp Asp Glu Pro Asn Thr Gly Val Ile Pro Pro Gly
                165                 170                 175

Lys Gly Phe Arg Ser Ala Leu Gly Leu Ser Glu Gly Pro Leu Phe
            180                 185                 190

Gly Phe Thr Lys Ser Asn Glu Leu Phe Val Gly Arg Leu Ala Gln Leu
        195                 200                 205

Gly Phe Ala Phe Ser Leu Ile Gly Glu Ile Ile Thr Gly Lys Gly Ala
    210                 215                 220

Leu Ala Gln Leu Asn Ile Glu Thr Gly Val Pro Ile Asn Glu Ile Glu
225                 230                 235                 240

Pro Leu Val Leu Phe Asn Val Ala Phe Phe Val Ala Ala Leu Asn
                245                 250                 255

Pro Gly Thr Gly Gln Phe Val Lys Asp Glu Asp Asp
            260                 265
```

<210> SEQ ID NO 58
<211> LENGTH: 270
<212> TYPE: PRT
<213> ORGANISM: Medicago truncatula

<400> SEQUENCE: 58

```
Met Ala Gln Thr Met Leu Leu Met Ser Ser Val Ser Ser Thr Tyr Ser
1               5                  10                 15

Val Asp Leu Lys Lys Asp Pro Leu Leu Gln Leu Gln Cys Gln Arg Leu
            20                  25                  30

Arg Pro Arg Phe Ser Asp Val Ser Phe Asn Pro Leu Pro Ser Asn Ser
            35                  40                  45

Lys Cys Phe Ser Ser Arg Thr Phe Thr Thr Leu Ala Leu Phe Lys Ser
        50                  55                  60

Lys Thr Lys Ala Pro Ala Lys Val Val Lys Pro Lys Pro Lys Val
65                  70                  75                  80

Glu Asp Gly Ile Phe Gly Thr Ser Gly Gly Phe Gly Phe Thr Lys Gln
                85                  90                  95

Asn Glu Leu Phe Val Gly Arg Val Ala Met Ile Gly Phe Ala Ala Ser
            100                 105                 110
```

```
Ile Leu Gly Glu Ala Leu Thr Gly Lys Gly Ile Leu Ala Gln Leu Asn
            115                 120                 125

Leu Glu Thr Gly Ile Pro Ile Tyr Glu Ala Glu Pro Leu Leu Leu Phe
        130                 135                 140

Phe Ile Ile Phe Thr Leu Leu Gly Ala Ile Gly Ala Leu Gly Asp Arg
145                 150                 155                 160

Gly Lys Phe Val Asp Asp Glu Pro Asn Thr Gly Gly Val Ile Pro Pro
                165                 170                 175

Gly Lys Gly Phe Arg Ser Ala Leu Gly Leu Ser Glu Gly Gly Pro Leu
            180                 185                 190

Phe Gly Phe Thr Lys Ser Asn Glu Leu Phe Val Gly Arg Leu Ala Gln
        195                 200                 205

Leu Gly Phe Val Phe Ser Leu Ile Gly Glu Ile Ile Thr Gly Lys Gly
    210                 215                 220

Ala Leu Ala Gln Leu Asn Ile Glu Thr Gly Val Pro Ile Thr Glu Ile
225                 230                 235                 240

Glu Pro Leu Val Leu Phe Asn Val Ile Phe Phe Ile Ala Ala Leu
                245                 250                 255

Asn Pro Gly Thr Gly Thr Phe Val Thr Asp Asp Glu Glu Asp
            260                 265                 270

<210> SEQ ID NO 59
<211> LENGTH: 269
<212> TYPE: PRT
<213> ORGANISM: Trifolium pratense

<400> SEQUENCE: 59

Met Ala Gln Thr Met Leu Leu Met Ser Ser Val Ser Ser Thr Tyr Ser
1               5                   10                  15

Val Glu Leu Lys Lys Asp Pro Leu Leu Gln Leu Gln Cys Gln Arg Leu
            20                  25                  30

Arg Pro Arg Ile Ser Asp Val Ser Phe Asn Pro Leu Ser Ser Asn Ser
        35                  40                  45

Lys Arg Leu Ser Ser Arg Thr Phe Thr Thr Leu Ala Leu Phe Lys Ser
    50                  55                  60

Lys Thr Lys Ala Pro Ala Lys Val Val Lys Pro Lys Pro Lys Val Glu
65                  70                  75                  80

Asp Gly Ile Phe Gly Thr Ser Gly Gly Phe Gly Phe Thr Lys Gln Asn
                85                  90                  95

Glu Leu Phe Val Gly Arg Val Ala Met Ile Gly Phe Ala Ala Ser Ile
            100                 105                 110

Leu Gly Glu Ala Leu Thr Gly Lys Gly Ile Leu Ala Gln Leu Asn Leu
        115                 120                 125

Glu Thr Gly Ile Pro Ile Tyr Glu Ala Glu Pro Leu Leu Phe Phe
    130                 135                 140

Ile Ile Phe Thr Leu Leu Gly Ala Ile Gly Ala Leu Gly Asp Arg Gly
145                 150                 155                 160

Lys Phe Val Asp Asp Glu Pro Thr Thr Gly Gly Val Ile Pro Pro Gly
                165                 170                 175

Lys Gly Phe Arg Ala Ala Leu Gly Leu Arg Glu Gly Gly Pro Leu Phe
            180                 185                 190

Gly Phe Thr Lys Ser Asn Glu Leu Phe Val Gly Arg Leu Ala Gln Leu
        195                 200                 205

Gly Phe Val Phe Ser Leu Ile Gly Glu Ile Ile Thr Gly Lys Gly Ala
    210                 215                 220
```

Leu Ala Gln Leu Asn Ile Glu Thr Gly Val Pro Ile Thr Glu Ile Glu
225                 230                 235                 240

Pro Leu Val Leu Phe Asn Val Ile Phe Phe Val Ala Ala Leu Asn
                245                 250                 255

Pro Gly Thr Gly Thr Phe Val Lys Asp Glu Asp Glu Asp
            260                 265

<210> SEQ ID NO 60
<211> LENGTH: 269
<212> TYPE: PRT
<213> ORGANISM: Trifolium subterraneum

<400> SEQUENCE: 60

Met Ala Gln Thr Met Leu Leu Met Ser Ser Val Ser Ser Thr Tyr Ser
1               5                   10                  15

Val Glu Leu Lys Lys Asp Pro Leu Leu Gln Leu Gln Cys Gln Arg Leu
                20                  25                  30

Arg Ser Arg Ile Ser Asp Val Ser Phe Asn Pro Leu Ser Ser Asn Ser
            35                  40                  45

Lys Ser Leu Ser Ser Arg Thr Phe Thr Thr Leu Ala Leu Phe Lys Ser
    50                  55                  60

Lys Thr Lys Ala Pro Ala Lys Val Val Lys Pro Lys Pro Lys Val Glu
65                  70                  75                  80

Asp Gly Ile Phe Gly Thr Ser Gly Gly Phe Gly Phe Thr Lys Gln Asn
                85                  90                  95

Glu Leu Phe Val Gly Arg Val Ala Met Ile Gly Phe Ala Ala Ser Ile
            100                 105                 110

Leu Gly Glu Ala Leu Thr Gly Lys Gly Ile Leu Ala Gln Leu Asn Leu
    115                 120                 125

Glu Thr Gly Ile Pro Ile Tyr Glu Ala Glu Pro Leu Leu Leu Phe Phe
130                 135                 140

Ile Ile Phe Thr Leu Leu Gly Ala Ile Gly Ala Leu Gly Asp Arg Gly
145                 150                 155                 160

Lys Phe Val Asp Asp Glu Pro Thr Thr Gly Gly Val Ile Pro Pro Gly
                165                 170                 175

Lys Gly Phe Arg Ala Ala Leu Gly Leu Arg Glu Gly Gly Pro Leu Phe
            180                 185                 190

Gly Phe Thr Lys Ser Asn Glu Leu Phe Val Gly Arg Leu Ala Gln Leu
    195                 200                 205

Gly Phe Val Phe Ser Leu Ile Gly Glu Ile Ile Thr Gly Lys Gly Ala
210                 215                 220

Leu Ala Gln Leu Asn Val Glu Thr Gly Val Pro Ile Thr Glu Ile Glu
225                 230                 235                 240

Pro Leu Val Leu Phe Asn Val Ile Phe Phe Ile Ala Ala Leu Asn
                245                 250                 255

Pro Gly Thr Gly Thr Phe Val Asp Glu Glu Glu Asp
            260                 265

<210> SEQ ID NO 61
<211> LENGTH: 273
<212> TYPE: PRT
<213> ORGANISM: Lupinus angustifolius

<400> SEQUENCE: 61

Met Ala Gln Ser Ile Met Leu Met Ser Ser Val Ser Ser Ser Tyr Ser
1               5                   10                  15

-continued

Val Ser Leu Lys Lys Asp Pro Leu Leu Gln Leu Gln Ser Gln Lys Leu
            20                  25                  30

Arg Pro Lys Phe Ser His Leu Ser Phe Asn Pro Leu Pro Asn Asn Ser
            35                  40                  45

Leu His Phe Ser Ser His Thr Phe Thr Thr Leu Ala Leu Phe Lys Ser
    50                  55                  60

Lys Thr Lys Ala Pro Pro Lys Lys Val Glu Lys Pro Lys Gln Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Gly Leu Thr Gly Lys Gly Ile Leu Ser Gln Leu Asn
        115                 120                 125

Leu Glu Thr Gly Val Pro Ile Tyr Glu Ala Glu Pro Leu Leu Leu Phe
130                 135                 140

Phe Ile Leu Phe Thr Leu Leu Gly Ala Ile Gly Ala Leu Gly Asp Arg
145                 150                 155                 160

Gly Lys Phe Val Asp Asp Glu Pro Ala Thr Gly Leu Asp Lys Ala Ile
                165                 170                 175

Ile Pro Pro Gly Lys Gly Leu Arg Gly Val Leu Gly Leu Gln Glu Gly
            180                 185                 190

Gly Pro Leu Phe Gly Phe Thr Lys Ser Asn Glu Leu Phe Val Gly Arg
        195                 200                 205

Leu Ala Gln Leu Gly Phe Ala Phe Ser Leu Ile Gly Glu Ile Ile Thr
    210                 215                 220

Gly Lys Gly Ala Leu Ala Gln Leu Asn Ile Glu Thr Gly Val Pro Val
225                 230                 235                 240

Asn Glu Ile Glu Pro Leu Val Leu Phe Asn Val Leu Phe Phe Phe Ile
                245                 250                 255

Ala Ala Leu Asn Pro Gly Thr Gly Lys Phe Val Thr Asp Glu Glu Glu
            260                 265                 270

Asp

<210> SEQ ID NO 62
<211> LENGTH: 273
<212> TYPE: PRT
<213> ORGANISM: Lotus japonicus

<400> SEQUENCE: 62

Met Ala Gln Thr Met Leu Leu Met Ser Ser Val Ser Ser Ser Tyr Ser
1               5                   10                  15

Val Asp Leu Lys Lys Asp Pro Leu Leu His Leu Gln Ser Gln Arg Leu
            20                  25                  30

Arg Pro Lys Phe Ser Gln Leu Ser Phe Asn Pro Leu Pro Ser Asn Ser
            35                  40                  45

Ser Leu Phe Ser Ser Arg Thr Phe Thr Thr Leu Ala Leu Phe Lys Ser
    50                  55                  60

Lys Ala Lys Ala Pro Pro Lys Val Val Lys Gln Lys Pro Lys Val
65                  70                  75                  80

Glu Asp Gly Val Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

```
Leu Leu Gly Glu Ala Leu Thr Gly Lys Gly Ile Leu Ala Gln Leu Asn
            115                 120                 125

Leu Glu Thr Gly Ile Pro Ile Tyr Glu Ala Glu Pro Leu Leu Leu Phe
        130                 135                 140

Phe Ile Leu Phe Thr Leu Leu Gly Ala Ile Gly Ala Leu Gly Asp Arg
145                 150                 155                 160

Gly Lys Phe Val Asp Asp Glu Ser Pro Thr Gly Leu Asp Lys Ala Val
                165                 170                 175

Ile Pro Pro Gly Lys Gly Leu Arg Gly Ala Leu Gly Leu Ser Glu Gly
                180                 185                 190

Gly Pro Leu Phe Gly Phe Thr Lys Ser Asn Glu Leu Phe Val Gly Arg
            195                 200                 205

Leu Ala Gln Leu Gly Phe Ala Phe Ser Leu Ile Gly Glu Ile Ile Thr
        210                 215                 220

Gly Lys Gly Ala Leu Ala Gln Leu Asn Ile Glu Thr Gly Ile Pro Ile
225                 230                 235                 240

Asn Glu Ile Glu Pro Leu Val Leu Phe Asn Val Ala Phe Phe Phe Ile
                245                 250                 255

Ala Ala Leu Asn Pro Gly Thr Gly Lys Phe Val Ser Asp Asp Gly Glu
            260                 265                 270

Asp

<210> SEQ ID NO 63
<211> LENGTH: 274
<212> TYPE: PRT
<213> ORGANISM: Spinacia oleracea

<400> SEQUENCE: 63

Met Ala Gln Ala Met Leu Leu Met Met Pro Gly Val Ser Thr Thr Asn
1               5                   10                  15

Thr Ile Asp Leu Lys Arg Asn Ala Leu Leu Lys Leu Gln Ile Gln Lys
            20                  25                  30

Ile Lys Pro Lys Ser Ser Thr Ser Asn Leu Phe Phe Ser Pro Leu Pro
        35                  40                  45

Ser Ser Ser Ser Ser Ser Ser Thr Val Phe Lys Thr Leu Ala Leu Phe
    50                  55                  60

Lys Ser Lys Ala Lys Ala Pro Lys Lys Val Glu Lys Pro Lys Leu Lys
65                  70                  75                  80

Val Glu Asp Gly Leu Phe Gly Thr Ser Gly Gly Ile Gly Phe Thr Lys
                85                  90                  95

Glu Asn Glu Leu Phe Val Gly Arg Val Ala Met Ile Gly Phe Ala Ala
            100                 105                 110

Ser Leu Leu Gly Glu Gly Ile Thr Gly Lys Gly Ile Leu Ser Gln Leu
        115                 120                 125

Asn Leu Glu Thr Gly Ile Pro Ile Tyr Glu Ala Glu Pro Leu Leu Leu
    130                 135                 140

Phe Phe Ile Leu Phe Thr Leu Leu Gly Ala Ile Gly Ala Leu Gly Asp
145                 150                 155                 160

Arg Gly Arg Phe Val Asp Glu Pro Thr Thr Gly Leu Glu Lys Ala Val
                165                 170                 175

Ile Pro Pro Gly Lys Asp Val Arg Ser Ala Leu Gly Leu Lys Thr Lys
                180                 185                 190

Gly Pro Leu Phe Gly Phe Thr Lys Ser Asn Glu Leu Phe Val Gly Arg
            195                 200                 205
```

```
Leu Ala Gln Leu Gly Phe Ala Phe Ser Leu Ile Gly Glu Ile Ile Thr
    210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Leu Asn Val Val Phe Phe Phe Ile
                245                 250                 255

Ala Ala Ile Asn Pro Gly Thr Gly Lys Phe Ile Thr Asp Asp Glu Glu
            260                 265                 270

Glu Asp

<210> SEQ ID NO 64
<211> LENGTH: 271
<212> TYPE: PRT
<213> ORGANISM: Beta vulgaris

<400> SEQUENCE: 64

Met Ala Gln Ala Met Leu Leu Met Pro Ser Val Ser Thr Thr Asn Thr
1               5                   10                  15

Ile Asp Leu Lys Arg Asn Ala Leu Leu Lys Ile Gln Ile Gln Lys Ile
            20                  25                  30

Lys Pro Lys Ser Ser Ser Ser His Leu Phe Phe Ser Pro Leu Ser Ser
        35                  40                  45

Ser Ser Ser Ser Ser Thr Phe Lys Thr Leu Ala Leu Phe Lys Pro
    50                  55                  60

Lys Thr Lys Ala Pro Val Lys Val Glu Lys Pro Lys Leu Lys Val
65                  70                  75                  80

Glu Asp Gly Leu Phe Gly Thr Ser Gly Gly Ile Gly Phe Thr Lys Glu
                85                  90                  95

Asn Glu Leu Phe Val Gly Arg Val Ala Met Ile Gly Phe Ala Ala Ser
            100                 105                 110

Leu Leu Gly Glu Gly Leu Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Thr Leu Leu Gly Ala Ile Gly Ala Leu Gly Asp Arg
145                 150                 155                 160

Gly Arg Phe Val Asp Asp Pro Pro Thr Gly Leu Glu Lys Ala Val Ile
                165                 170                 175

Pro Pro Gly Lys Asn Val Arg Ser Ala Leu Gly Leu Arg Glu Gly Gly
            180                 185                 190

Pro Leu Phe Gly Phe Thr Lys Ser Asn Glu Leu Phe Val Gly Arg Leu
        195                 200                 205

Ala Gln Leu Gly Phe Ala Phe Ser Leu Ile Gly Glu Ile Ile Thr Gly
    210                 215                 220

Lys Gly Ala Leu Ala Gln Leu Asn Ile Glu Thr Gly Val Pro Val Asn
225                 230                 235                 240

Glu Ile Glu Pro Leu Val Leu Leu Asn Val Leu Phe Phe Phe Ile Ala
                245                 250                 255

Ala Ile Asn Pro Gly Thr Gly Lys Phe Ile Thr Asp Glu Glu Glu
            260                 265                 270

<210> SEQ ID NO 65
<211> LENGTH: 273
<212> TYPE: PRT
<213> ORGANISM: Chenopodium quinoa
```

<400> SEQUENCE: 65

```
Met Ala Gln Ala Met Leu Leu Met Pro Asn Val Ser Thr Asn Thr Val
1               5                   10                  15

Asp Leu Lys Arg Asn Ser Leu Leu Lys Leu Gln Ile Glu Lys Ile Lys
            20                  25                  30

Pro Lys Ser Ser Ser His Leu Phe Phe Ser Pro Leu Pro Ser Leu
        35                  40                  45

Ser Ser Ser Ser Ser Ser Thr Val Leu Lys Thr Phe Ala Leu Phe Lys
    50                  55                  60

Ser Lys Ala Lys Ala Pro Val Lys Val Glu Lys Pro Lys Leu Lys
65                  70                  75                  80

Val Glu Asp Gly Leu Phe Gly Thr Ser Gly Ile Gly Phe Thr Lys
                85                  90                  95

Glu Asn Glu Leu Phe Val Gly Arg Val Ala Met Ile Gly Phe Ala Ala
            100                 105                 110

Ser Leu Leu Gly Glu Ala Val Thr Gly Lys Gly Ile Leu Ala Gln Leu
            115                 120                 125

Asn Leu Glu Thr Gly Ile Pro Ile Tyr Glu Ala Glu Pro Leu Leu Leu
130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Pro Thr Gly Leu Glu Lys Ala Val
                165                 170                 175

Ile Pro Pro Gly Lys Gly Val Arg Ser Ala Leu Gly Leu Lys Glu Gly
            180                 185                 190

Gly Pro Leu Phe Gly Phe Thr Lys Ser Asn Glu Leu Phe Val Gly Arg
        195                 200                 205

Leu Ala Gln Leu Gly Phe Ala Phe Ser Leu Ile Gly Glu Ile Ile Thr
    210                 215                 220

Gly Lys Gly Ala Leu Ser Gln Leu Asn Ile Glu Thr Gly Val Pro Ile
225                 230                 235                 240

Asn Glu Ile Glu Pro Leu Val Leu Leu Asn Val Val Phe Phe Phe Ile
                245                 250                 255

Ala Ala Ile Asn Pro Gly Thr Gly Lys Phe Ile Thr Asp Glu Glu Glu
            260                 265                 270

Asp
```

<210> SEQ ID NO 66
<211> LENGTH: 273
<212> TYPE: PRT
<213> ORGANISM: Chenopodium quinoa

<400> SEQUENCE: 66

```
Met Ala Gln Ala Met Leu Leu Met Pro Asn Val Ser Thr Asn Thr Val
1               5                   10                  15

Asp Leu Lys Arg Asn Ser Leu Leu Lys Leu Gln Ile Glu Lys Ile Lys
            20                  25                  30

Pro Lys Ser Ser Ser His Leu Phe Phe Ser Pro Leu Pro Ser Leu
        35                  40                  45

Ser Ser Ser Ser Ser Ser Asn Val Leu Lys Thr Phe Ala Leu Phe Lys
    50                  55                  60

Ser Lys Ala Lys Ala Pro Ala Lys Lys Val Glu Lys Pro Lys Leu Lys
65                  70                  75                  80
```

```
Val Glu Asp Gly Leu Phe Gly Thr Ser Gly Ile Gly Phe Thr Lys
                85                  90                  95

Glu Asn Glu Leu Phe Val Gly Arg Val Ala Met Ile Gly Phe Ala Ala
            100                 105                 110

Ser Leu Leu Gly Glu Gly Ile Thr Gly Lys Gly Ile Leu Ala Gln Leu
            115                 120                 125

Asn Leu Glu Thr Gly Ile Pro Ile Tyr Glu Ala Glu Pro Leu Leu Leu
            130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Pro Thr Gly Leu Glu Lys Ala Val
                165                 170                 175

Ile Pro Pro Gly Lys Asn Val Arg Ser Ala Leu Gly Leu Lys Glu Gly
            180                 185                 190

Gly Pro Leu Phe Gly Phe Thr Lys Ser Asn Glu Leu Phe Val Gly Arg
            195                 200                 205

Leu Ala Gln Leu Gly Phe Ala Phe Ser Leu Ile Gly Glu Ile Ile Thr
            210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Asn Val Val Phe Phe Phe Ile
                245                 250                 255

Ala Ala Ile Asn Pro Gly Thr Gly Lys Phe Ile Thr Asp Glu Glu
                260                 265                 270

Asp

<210> SEQ ID NO 67
<211> LENGTH: 266
<212> TYPE: PRT
<213> ORGANISM: Eucalyptus grandis

<400> SEQUENCE: 67

Met Ala Gln Thr Met Met Leu Met Pro Ser Val Ser Gly His Ser Val
1               5                   10                  15

Asp Leu Arg Thr Pro Arg Leu Arg Pro Thr Ser Ser Ser Phe Ser Arg
            20                  25                  30

Ser Leu Leu Tyr Asn Pro Leu Pro Ser Pro Ala Ala Ser Ser His Arg
            35                  40                  45

Ser Ser Pro Val Phe Ala Leu Phe Lys Ser Lys Thr Lys Ala Pro Pro
        50                  55                  60

Lys Lys Val Val Lys Glu Lys Pro Lys Val Glu Asp Gly Val Phe Gly
65                  70                  75                  80

Thr Ser Gly Gly Ile Gly Phe Thr Lys Glu Asn Glu Leu Phe Val Gly
                85                  90                  95

Arg Val Ala Met Ile Gly Phe Ala Ala Ser Leu Leu Gly Glu Ala Ile
            100                 105                 110

Thr Gly Lys Gly Ile Leu Ala Gln Leu Asn Leu Glu Thr Gly Val Pro
            115                 120                 125

Ile Tyr Glu Ala Glu Pro Leu Leu Leu Phe Phe Ile Leu Phe Thr Leu
            130                 135                 140

Leu Gly Ala Ile Gly Ala Leu Gly Asp Arg Gly Arg Phe Val Asp Asp
145                 150                 155                 160

Ser Ala Gly Ile Glu Gly Ala Val Ile Pro Pro Gly Lys Gly Phe Leu
                165                 170                 175
```

-continued

```
Ser Ala Leu Gly Leu Lys Glu Gly Gly Pro Leu Phe Gly Phe Thr Lys
            180                 185                 190

Ala Asn Glu Leu Phe Val Gly Arg Leu Ala Gln Leu Gly Phe Ala Phe
        195                 200                 205

Ser Leu Ile Gly Glu Ile Ile Thr Gly Lys Gly Ala Leu Ala Gln Leu
    210                 215                 220

Asn Ile Glu Thr Gly Val Pro Ile Ser Glu Ile Glu Pro Leu Val Leu
225                 230                 235                 240

Phe Asn Val Leu Phe Phe Ile Ala Ala Leu Asn Pro Gly Thr Gly
                245                 250                 255

Lys Phe Leu Thr Asp Glu Asp Leu Glu Asp
            260                 265
```

<210> SEQ ID NO 68
<211> LENGTH: 276
<212> TYPE: PRT
<213> ORGANISM: Rosa chinensis

<400> SEQUENCE: 68

```
Met Ala Gln Thr Met Leu Leu Met Ser Ser Ser Ser Val Ala Lys Thr
1               5                   10                  15

Ser Val Val Asp Leu Lys Ser Ser Asp Pro Leu Leu Gln Leu Gln Val
            20                  25                  30

Gln Arg Leu Arg Pro Lys Ser Phe Ser Gln Leu Val Phe Arg Pro Leu
        35                  40                  45

Pro Ser Ser Thr Thr Ser Leu Arg Ser Ser Gly Val Val Ala Leu Phe
    50                  55                  60

Lys Ser Lys Thr Lys Ala Pro Ala Ser Lys Lys Ala Pro Ser Pro Lys
65                  70                  75                  80

Pro Lys Val Glu Ser Gly Ile Phe Gly Thr Ser Gly Gly Ile Gly Phe
            85                  90                  95

Thr Lys Glu Asn Glu Leu Phe Val Gly Arg Val Ala Met Ile Gly Phe
        100                 105                 110

Ala Ala Ser Leu Leu Gly Glu Ala Ile Thr Gly Lys Gly Ile Leu Ser
    115                 120                 125

Gln Leu Asn Leu Glu Thr Gly Val Pro Ile Tyr Glu Ala Glu Pro Leu
130                 135                 140

Leu Leu Phe Phe Ile Leu Phe Thr Leu Leu Gly Ala Ile Gly Ala Leu
145                 150                 155                 160

Gly Asp Arg Gly Ser Phe Val Asp Asp Pro Pro Thr Gly Ile Glu Gly
            165                 170                 175

Ala Val Ile Pro Pro Gly Lys Gly Ile Arg Gly Ala Leu Gly Leu Lys
        180                 185                 190

Glu Gly Gly Pro Leu Phe Gly Phe Thr Lys Ala Asn Glu Leu Phe Val
    195                 200                 205

Gly Arg Leu Ala Gln Leu Gly Phe Ala Phe Ser Leu Ile Gly Glu Ile
210                 215                 220

Ile Thr Gly Lys Gly Ala Leu Ala Gln Leu Asn Ile Glu Thr Gly Val
225                 230                 235                 240

Pro Ile Asn Glu Ile Glu Pro Leu Val Leu Leu Asn Val Phe Phe
            245                 250                 255

Phe Leu Ala Ala Val Asn Pro Gly Thr Gly Lys Phe Ile Thr Asp Glu
        260                 265                 270

Gly Glu Glu Glu
    275
```

<210> SEQ ID NO 69
<211> LENGTH: 273
<212> TYPE: PRT
<213> ORGANISM: Fragaria vesca

<400> SEQUENCE: 69

```
Met Ala Gln Thr Met Leu Leu Met Ser Ser Ser Val Ala Lys Thr
1               5                   10                  15

Asn Val Val Asp Leu Lys Ser Ser Asp Pro Val Leu Gln Leu Gln Val
                20                  25                  30

Gln Arg Leu Arg Pro Lys Ser Phe Ser Gln Leu Val Phe Arg Pro Leu
            35                  40                  45

Pro Ser Ser Thr Thr Ser Leu Arg Ser Ser Gly Val Val Ala Leu Phe
50                  55                  60

Lys Ser Lys Thr Lys Ala Pro Val Lys Ala Ser Pro Pro Lys Pro
65                  70                  75                  80

Lys Val Glu Ser Gly Ile Phe Gly Thr Ser Gly Ile Gly Phe Thr
                85                  90                  95

Lys Glu Asn Glu Leu Phe Val Gly Arg Val Ala Met Ile Gly Phe Ala
                100                 105                 110

Ala Ser Leu Leu Gly Glu Ala Ile Thr Gly Lys Gly Ile Leu Gln Gln
            115                 120                 125

Leu Asn Leu Glu Thr Gly Ile Pro Ile Tyr Glu Ala Glu Pro Leu Leu
        130                 135                 140

Leu Phe Phe Ile Leu Phe Thr Leu Leu Gly Ala Ile Gly Ala Leu Gly
145                 150                 155                 160

Asp Arg Gly Gln Phe Val Asp Asp Thr Pro Gly Ile Glu Gly Ala Val
                165                 170                 175

Ile Pro Pro Gly Lys Gly Leu Lys Ser Ala Leu Gly Leu Lys Glu Gly
                180                 185                 190

Gly Pro Leu Phe Gly Phe Thr Lys Ala Asn Glu Leu Phe Val Gly Arg
            195                 200                 205

Leu Ala Gln Leu Gly Phe Ala Phe Ser Leu Ile Gly Glu Ile Ile Thr
        210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Leu Asn Val Val Phe Phe Phe Leu
                245                 250                 255

Ala Ala Val Asn Pro Gly Thr Gly Lys Phe Ile Thr Asp Glu Asp Glu
                260                 265                 270

Glu
```

<210> SEQ ID NO 70
<211> LENGTH: 279
<212> TYPE: PRT
<213> ORGANISM: Prunus persica

<400> SEQUENCE: 70

```
Met Ala Gln Thr Met Leu Leu Met Ser Ser Val Ser Ser His
1               5                   10                  15

Val Val Asp Leu Lys Ser Ser Asp Pro Leu Leu Gln Leu Gln Val Gln
                20                  25                  30

Arg Leu Arg Pro Lys Ser Phe Ser Gln Leu Val Phe Arg Pro Leu Pro
            35                  40                  45
```

```
Ser Ser Ser Phe Ala Ser Ser Ser Pro Ala Ile Pro Thr Ile
    50              55              60

Val Ala Leu Phe Lys Ser Lys Thr Lys Ala Pro Val Lys Lys Ala Pro
 65              70              75              80

Ala Pro Lys Pro Lys Val Glu Asp Gly Ile Phe Gly Thr Ser Gly Gly
                 85              90              95

Ile Gly Phe Thr Lys Gln Asn Glu Leu Phe Val Gly Arg Val Ala Met
            100             105             110

Ile Gly Phe Ala Ala Ser Leu Leu Gly Glu Ala Ile Thr Gly Lys Gly
            115             120             125

Ile Leu Ala Gln Leu Asn Leu Glu Thr Gly Val Pro Ile Tyr Glu Ala
        130             135             140

Glu Pro Leu Leu Leu Phe Phe Ile Leu Phe Thr Leu Leu Gly Ala Ile
145             150             155             160

Gly Ala Leu Gly Asp Arg Gly Ser Phe Val Asp Asp Pro Pro Ala Gly
                165             170             175

Ile Glu Arg Ala Val Ile Pro Pro Gly Lys Gly Phe Arg Ser Ala Leu
            180             185             190

Gly Leu Lys Glu Gly Gly Pro Leu Phe Gly Phe Thr Lys Ala Asn Glu
        195             200             205

Leu Phe Val Gly Arg Leu Ala Gln Leu Gly Phe Ala Phe Ser Leu Ile
    210             215             220

Gly Glu Ile Ile Thr Gly Lys Gly Ala Leu Ala Gln Leu Asn Ile Glu
225             230             235             240

Thr Gly Val Pro Ile Asn Glu Ile Glu Pro Leu Val Leu Leu Asn Val
                245             250             255

Val Phe Phe Phe Ile Ala Ala Leu Asn Pro Gly Thr Gly Lys Phe Val
            260             265             270

Thr Asp Glu Gly Glu Glu Glu
            275

<210> SEQ ID NO 71
<211> LENGTH: 279
<212> TYPE: PRT
<213> ORGANISM: Prunus mume

<400> SEQUENCE: 71

Met Ala Gln Thr Met Leu Leu Met Ser Ser Val Ser Ser Arg His
 1               5              10              15

Ala Val Asp Leu Lys Ser Ser Asp Pro Leu Leu Gln Leu Gln Val Gln
            20              25              30

Arg Leu Arg Pro Lys Ser Phe Ser Gln Leu Val Phe Arg Pro Leu Pro
        35              40              45

Ser Ser Ser Phe Ala Ser Ser Ser Pro Ala Ile Pro Thr Val
    50              55              60

Val Ala Leu Phe Lys Ser Lys Thr Lys Ala Pro Val Lys Lys Ala Ser
 65              70              75              80

Pro Pro Lys Pro Lys Val Glu Asp Gly Ile Phe Gly Thr Ser Gly Gly
                 85              90              95

Ile Gly Phe Thr Lys Gln Asn Glu Leu Phe Val Gly Arg Val Ala Met
            100             105             110

Ile Gly Phe Ala Ala Ser Leu Leu Gly Glu Ala Val Thr Gly Lys Gly
            115             120             125

Ile Leu Ala Gln Leu Asn Leu Glu Thr Gly Val Pro Ile Tyr Glu Ala
        130             135             140
```

```
Glu Pro Leu Leu Leu Phe Phe Ile Leu Phe Thr Leu Leu Gly Ala Ile
145                 150                 155                 160

Gly Ala Leu Gly Asp Arg Gly Ser Phe Val Asp Asp Pro Pro Thr Gly
                165                 170                 175

Ile Glu Gly Ala Val Ile Arg Pro Gly Lys Gly Phe Arg Ser Ala Leu
            180                 185                 190

Gly Leu Lys Glu Gly Gly Pro Leu Phe Gly Phe Thr Lys Ala Asn Glu
        195                 200                 205

Leu Phe Val Gly Arg Leu Ala Gln Leu Gly Phe Ala Phe Ser Leu Ile
    210                 215                 220

Gly Glu Ile Ile Thr Gly Lys Gly Ala Leu Ala Gln Leu Asn Ile Glu
225                 230                 235                 240

Thr Gly Val Pro Ile Asn Glu Ile Glu Pro Leu Val Leu Leu Asn Val
                245                 250                 255

Val Phe Phe Phe Ile Ala Ala Leu Asn Pro Gly Thr Gly Lys Phe Val
                260                 265                 270

Thr Asp Glu Gly Glu Glu Glu
        275

<210> SEQ ID NO 72
<211> LENGTH: 279
<212> TYPE: PRT
<213> ORGANISM: Prunus avium

<400> SEQUENCE: 72

Met Ala Gln Thr Met Leu Leu Met Ser Ser Val Ser Ser Ser His
1               5                   10                  15

Val Val Asp Leu Lys Ser Ser Asp Pro Leu Leu Gln Leu Arg Val Gln
                20                  25                  30

Arg Leu Arg Pro Lys Ser Phe Ser Gln Leu Val Phe Arg Pro Leu Pro
            35                  40                  45

Ser Ser Ser Ser Phe Ala Ser Ser Ser Pro Ala Ile Ser Thr Val
    50                  55                  60

Val Ala Leu Phe Lys Ser Lys Thr Lys Ala Pro Val Lys Lys Ala Thr
65                  70                  75                  80

Pro Ala Lys Pro Lys Val Glu Asp Gly Ile Phe Gly Thr Ser Gly Gly
                85                  90                  95

Ile Gly Phe Thr Lys Gln Asn Glu Leu Phe Val Gly Arg Val Ala Met
            100                 105                 110

Ile Gly Phe Ala Ala Ser Leu Leu Gly Glu Ala Val Thr Gly Lys Gly
        115                 120                 125

Ile Leu Ala Gln Leu Asn Leu Glu Thr Gly Val Pro Ile Tyr Glu Ala
    130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Ser Phe Val Asp Asp Pro Pro Thr Gly
                165                 170                 175

Ile Glu Gly Ala Val Ile Arg Pro Gly Lys Gly Phe Arg Ser Ala Leu
            180                 185                 190

Gly Leu Lys Glu Gly Gly Pro Leu Phe Gly Phe Thr Lys Ala Asn Glu
        195                 200                 205

Leu Phe Val Gly Arg Leu Ala Gln Leu Gly Phe Ala Phe Ser Leu Ile
    210                 215                 220

Gly Glu Ile Ile Thr Gly Lys Gly Ala Leu Ala Gln Leu Asn Ile Glu
```

```
                225                 230                 235                 240

Thr Gly Val Pro Ile Asn Glu Ile Glu Pro Leu Val Leu Leu Asn Val
                245                 250                 255

Val Phe Phe Phe Ile Ala Ala Leu Asn Pro Gly Thr Gly Lys Phe Val
                260                 265                 270

Thr Asp Glu Gly Glu Glu Glu
        275

<210> SEQ ID NO 73
<211> LENGTH: 279
<212> TYPE: PRT
<213> ORGANISM: Prunus yedoensis

<400> SEQUENCE: 73

Met Ala Gln Thr Met Leu Leu Met Ser Ser Val Ser Ser Ser His
1               5                   10                  15

Val Val Asp Leu Lys Ser Ser Asp Pro Leu Leu Gln Leu Arg Val Gln
                20                  25                  30

Arg Leu Arg Pro Lys Ser Phe Ser Gln Leu Val Phe Gly Pro Leu Pro
            35                  40                  45

Ser Ser Ser Ser Phe Ala Ser Ser Ser Ser Pro Ala Ile Ser Thr Val
    50                  55                  60

Val Ala Leu Phe Lys Ser Lys Thr Lys Ala Pro Val Lys Lys Ala Ser
65                  70                  75                  80

Pro Ala Lys Pro Lys Val Glu Asp Gly Ile Phe Gly Thr Ser Gly Gly
                85                  90                  95

Ile Gly Phe Thr Lys Gln Asn Glu Leu Phe Val Gly Arg Val Ala Met
                100                 105                 110

Ile Gly Phe Ala Ala Ser Leu Leu Gly Glu Ala Val Thr Gly Lys Gly
            115                 120                 125

Ile Leu Ala Gln Leu Asn Leu Glu Thr Gly Val Pro Ile Tyr Glu Ala
    130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Ser Phe Val Asp Asp Pro Pro Thr Gly
                165                 170                 175

Ile Glu Gly Ala Val Ile Arg Pro Gly Lys Gly Phe Arg Ser Val Leu
                180                 185                 190

Gly Leu Lys Glu Gly Gly Pro Leu Phe Gly Phe Thr Lys Ala Asn Glu
            195                 200                 205

Leu Phe Val Gly Arg Leu Ala Gln Leu Gly Phe Ala Phe Ser Leu Ile
    210                 215                 220

Gly Glu Ile Ile Thr Gly Lys Gly Ala Leu Ala Gln Leu Asn Ile Glu
225                 230                 235                 240

Thr Gly Val Pro Ile Asn Glu Ile Glu Pro Leu Val Leu Leu Asn Val
                245                 250                 255

Val Phe Phe Phe Ile Ala Ala Leu Asn Pro Gly Thr Gly Lys Phe Ile
                260                 265                 270

Thr Asp Glu Gly Glu Glu Glu
        275

<210> SEQ ID NO 74
<211> LENGTH: 279
<212> TYPE: PRT
<213> ORGANISM: Pyrus x bretschneideri
```

<400> SEQUENCE: 74

```
Met Ala Gln Thr Met Leu Leu Met Ser Ser Val Ser Ser Gly His
1               5                   10                  15

Val Val Asp Leu Lys Ser Ser Asp Pro Leu Leu Gln Val Gln Ala Gln
            20                  25                  30

Arg Leu Arg Pro Lys Ser Phe Ser Gln Leu Val Cys Arg Pro Leu Pro
        35                  40                  45

Ser Ser Ser Phe Ala Ala Ser Ser Ser Thr Arg Ile Leu Thr Ile
    50                  55                  60

Val Ala Leu Phe Lys Ser Lys Thr Lys Ala Pro Ala Lys Lys Ala Pro
65                  70                  75                  80

Pro Pro Lys Pro Lys Val Glu Asp Gly Ile Phe Gly Thr Ser Gly Gly
                85                  90                  95

Ile Gly Phe Thr Lys Gln Asn Glu Leu Phe Val Gly Arg Val Ala Met
                100                 105                 110

Ile Gly Phe Ala Ala Ser Leu Leu Gly Glu Ala Ile Thr Gly Lys Gly
            115                 120                 125

Ile Leu Ser Gln Leu Asn Leu Glu Thr Gly Ile Pro Ile Tyr Glu Ala
        130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Arg Phe Val Asp Asp Pro Pro Ala Gly
                165                 170                 175

Ile Glu Gly Ala Val Ile Pro Pro Gly Lys Gly Leu Lys Ser Ala Leu
            180                 185                 190

Gly Leu Lys Glu Gly Gly Pro Leu Phe Gly Phe Thr Lys Ala Asn Glu
        195                 200                 205

Leu Phe Val Gly Arg Leu Ala Gln Leu Gly Phe Ala Phe Ser Leu Ile
    210                 215                 220

Gly Glu Ile Ile Thr Gly Lys Gly Ala Leu Ala Gln Leu Asn Ile Glu
225                 230                 235                 240

Thr Gly Val Pro Ile Ser Glu Ile Glu Pro Leu Val Leu Leu Asn Val
                245                 250                 255

Val Phe Phe Phe Ile Ala Ala Val Asn Pro Gly Thr Gly Lys Phe Ile
            260                 265                 270

Thr Asp Val Asp Glu Glu Asp
        275
```

<210> SEQ ID NO 75
<211> LENGTH: 278
<212> TYPE: PRT
<213> ORGANISM: Malus domestica

<400> SEQUENCE: 75

```
Met Ala Gln Thr Met Leu Leu Met Ser Ser Val Ser Ser Gly His
1               5                   10                  15

Val Val Asp Leu Lys Ser Ser Asp Pro Leu Leu Gln Val Gln Ala Gln
            20                  25                  30

Arg Leu Arg Pro Lys Ser Phe Ser Gln Leu Val Phe Arg Pro Leu Pro
        35                  40                  45

Ser Ser Ser Ser Ala Ser Ser Ser Thr Arg Ile Ser Thr Val Val
    50                  55                  60

Ala Leu Phe Lys Ser Lys Thr Lys Ala Pro Ala Lys Lys Ala Pro Pro
65                  70                  75                  80
```

```
Pro Lys Pro Lys Val Glu Asp Gly Ile Phe Gly Thr Ser Gly Gly Ile
                85                  90                  95

Gly Phe Thr Lys Gln Asn Glu Leu Phe Val Gly Arg Val Ala Met Ile
            100                 105                 110

Gly Phe Ala Ala Ser Leu Leu Gly Glu Ala Ile Thr Gly Lys Gly Ile
            115                 120                 125

Leu Ser Gln Leu Asn Leu Glu Thr Gly Ile Pro Ile Tyr Glu Ala Glu
            130                 135                 140

Pro Leu Leu Leu Phe Phe Ile Leu Phe Thr Leu Leu Gly Ala Ile Gly
145                 150                 155                 160

Ala Leu Gly Asp Arg Gly Arg Phe Val Asp Asp Pro Pro Ala Gly Ile
                165                 170                 175

Glu Gly Ala Val Ile Pro Pro Gly Lys Gly Leu Lys Ser Ala Leu Gly
            180                 185                 190

Leu Lys Glu Gly Gly Pro Leu Phe Gly Phe Thr Lys Ala Asn Glu Leu
            195                 200                 205

Phe Val Gly Arg Leu Ala Gln Leu Gly Phe Ala Phe Ser Leu Ile Gly
            210                 215                 220

Glu Ile Ile Thr Gly Lys Gly Ala Leu Ala Gln Leu Asn Ile Glu Thr
225                 230                 235                 240

Gly Val Pro Ile Ser Glu Ile Glu Pro Leu Val Leu Leu Asn Val Val
                245                 250                 255

Phe Phe Phe Ile Ala Ala Val Asn Pro Gly Thr Gly Lys Phe Ile Thr
            260                 265                 270

Asp Val Asp Glu Glu Asp
            275

<210> SEQ ID NO 76
<211> LENGTH: 278
<212> TYPE: PRT
<213> ORGANISM: Malus domestica

<400> SEQUENCE: 76

Met Ala Gln Thr Met Leu Leu Met Ser Ser Val Ser Ser Gly His
1               5                   10                  15

Val Val Asp Leu Lys Ser Ser Asp Pro Leu Leu Gln Val Gln Ala Gln
                20                  25                  30

Arg Leu Arg Pro Lys Ser Phe Ser Gln Leu Val Phe Arg Ala Leu Pro
            35                  40                  45

Ser Ser Ser Ser Ala Ser Ser Ser Thr Arg Ile Ser Thr Val Val
    50                  55                  60

Ala Leu Phe Lys Ser Lys Thr Lys Ala Pro Lys Lys Ala Pro Pro
65                  70                  75                  80

Pro Lys Pro Lys Val Glu Asp Gly Ile Phe Gly Thr Ser Gly Gly Ile
                85                  90                  95

Gly Phe Thr Lys Gln Asn Glu Leu Phe Val Gly Arg Val Ala Met Ile
            100                 105                 110

Gly Phe Ala Ala Ser Leu Leu Gly Glu Ala Ile Thr Gly Lys Gly Ile
            115                 120                 125

Leu Ser Gln Leu Asn Leu Glu Thr Gly Ile Pro Ile Tyr Glu Ala Glu
            130                 135                 140

Pro Leu Leu Leu Phe Phe Ile Leu Phe Thr Leu Leu Gly Ala Ile Gly
145                 150                 155                 160

Ala Leu Gly Asp Arg Gly Arg Phe Val Asp Asp Pro Pro Ala Gly Ile
                165                 170                 175
```

```
Glu Gly Ala Val Ile Pro Pro Gly Lys Gly Leu Lys Ser Ala Leu Gly
            180                 185                 190

Leu Lys Glu Gly Gly Pro Leu Phe Gly Phe Thr Lys Ala Asn Glu Leu
        195                 200                 205

Phe Val Gly Arg Leu Ala Gln Leu Gly Phe Ala Phe Ser Leu Ile Gly
    210                 215                 220

Glu Ile Ile Thr Gly Lys Gly Ala Leu Ala Gln Leu Asn Ile Glu Thr
225                 230                 235                 240

Gly Val Pro Ile Ser Glu Ile Glu Pro Leu Val Leu Asn Val Val
                245                 250                 255

Phe Phe Phe Ile Ala Ala Val Asn Pro Gly Thr Gly Lys Phe Ile Thr
                260                 265                 270

Asp Val Asp Glu Glu Asp
        275

<210> SEQ ID NO 77
<211> LENGTH: 278
<212> TYPE: PRT
<213> ORGANISM: Malus domestica
<220> FEATURE:
<221> NAME/KEY: VARIANT
<222> LOCATION: (261)..(266)
<223> OTHER INFORMATION: Xaa = Any Amino Acid

<400> SEQUENCE: 77

Met Leu Leu Met Ser Ser Val Ser Ser Gly His Val Val Asp Leu
1               5                   10                  15

Lys Ser Ser Asp Arg Leu Leu Gln Val Gln Val Gln Arg Leu Arg Pro
                20                  25                  30

Lys Ser Phe Ser Gln Leu Val Phe Arg Pro Leu Pro Ser Ser Ser Phe
            35                  40                  45

Ala Ser Ser Ser Thr Val Val Ala Leu Phe Lys Ser Lys Thr Lys
        50                  55                  60

Ala Pro Ala Lys Lys Ala Pro Ser Pro Lys Pro Lys Val Glu Asp Gly
65                  70                  75                  80

Ile Phe Gly Thr Ser Gly Gly Ile Gly Phe Thr Lys Gln Asn Glu Leu
                85                  90                  95

Phe Val Gly Arg Val Ala Met Ile Gly Phe Ala Ala Ser Leu Leu Gly
            100                 105                 110

Glu Ala Ile Thr Gly Lys Gly Ile Leu Ser Gln Leu Asn Leu Glu Thr
        115                 120                 125

Gly Val Pro Ile Tyr Glu Ala Glu Pro Leu Leu Leu Phe Phe Ile Leu
    130                 135                 140

Phe Thr Leu Leu Gly Ala Ile Gly Ala Leu Gly Asp Arg Gly Lys Phe
145                 150                 155                 160

Val Asp Asp Pro Pro Thr Gly Ile Glu Gly Ala Val Ile Pro Pro Gly
                165                 170                 175

Lys Gly Phe Lys Ser Ala Leu Gly Leu Asn Glu Gly Gly Pro Leu Phe
            180                 185                 190

Gly Phe Thr Lys Ala Asn Glu Leu Phe Val Gly Arg Leu Ala Gln Leu
        195                 200                 205

Gly Phe Ala Phe Ser Leu Ile Gly Glu Ile Ile Thr Gly Lys Gly Ala
    210                 215                 220

Leu Ala Gln Leu Asn Ile Glu Thr Gly Val Pro Ile Asn Glu Ile Glu
225                 230                 235                 240
```

Pro Leu Val Leu Leu Asn Val Val Phe Phe Ile Ala Ala Val Asn
              245                 250                 255

Pro Gly Thr Gly Xaa Phe Ile Thr Asp Xaa Met Lys Lys Thr Arg Glu
              260                 265                 270

Arg Glu Thr Ile His His
          275

<210> SEQ ID NO 78
<211> LENGTH: 274
<212> TYPE: PRT
<213> ORGANISM: Pyrus x bretschneideri

<400> SEQUENCE: 78

Met Ala Gln Thr Met Leu Leu Met Ser Ser Ser Val Ser Ser Gly His
1               5                   10                  15

Val Val Asp Leu Lys Ser Ser Asp Pro Leu Leu Lys Val Gln Val Gln
              20                  25                  30

Arg Leu Arg Pro Lys Ser Phe Ser Gln Leu Val Phe Arg Pro Leu Pro
          35                  40                  45

Ser Ser Ser Phe Ala Ser Ser Ser Thr Val Val Ala Leu Phe Lys
      50                  55                  60

Ser Lys Thr Lys Ala Pro Ala Lys Lys Ala Pro Ser Pro Lys Pro Lys
65                  70                  75                  80

Val Glu Asp Gly Ile Phe Gly Thr Ser Gly Ile Gly Phe Thr Lys
              85                  90                  95

Gln Asn Glu Leu Phe Val Gly Arg Val Ala Met Ile Gly Phe Ala Ala
              100                 105                 110

Ser Leu Leu Gly Glu Ala Ile Thr Gly Lys Gly Ile Leu Ser Gln Leu
          115                 120                 125

Asn Leu Glu Thr Gly Val Pro Ile Tyr Glu Ala Glu Pro Leu Leu Leu
      130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Pro Thr Gly Ile Glu Gly Ala Val
              165                 170                 175

Ile Arg Pro Gly Lys Gly Leu Lys Ser Ala Leu Gly Leu Asn Glu Gly
          180                 185                 190

Gly Pro Leu Phe Gly Phe Thr Lys Ala Asn Glu Leu Phe Val Gly Arg
      195                 200                 205

Leu Ala Gln Leu Gly Phe Ala Phe Ser Leu Ile Gly Glu Ile Ile Thr
      210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Leu Asn Val Val Phe Phe Phe Ile
              245                 250                 255

Ala Ala Val Asn Pro Gly Thr Gly Lys Phe Ile Thr Asp Val Asp Glu
              260                 265                 270

Glu Asp

<210> SEQ ID NO 79
<211> LENGTH: 274
<212> TYPE: PRT
<213> ORGANISM: Malus domestica

<400> SEQUENCE: 79

Met Ala Gln Thr Met Leu Leu Met Ser Ser Ser Val Ser Ser Gly His

```
            1               5                  10                 15
Val Val Asp Leu Lys Ser Ser Asp Arg Leu Gln Val Gln Val Gln
                20                  25                  30
Arg Leu Arg Pro Lys Ser Phe Ser Gln Leu Val Phe Arg Pro Leu Pro
                35                  40                  45
Ser Ser Ser Phe Ala Ser Ser Ser Thr Val Val Ala Leu Phe Lys
                50                  55                  60
Ser Lys Thr Lys Ala Pro Ala Lys Lys Ala Pro Ser Pro Lys Pro Lys
65                  70                  75                  80
Val Glu Asp Gly Ile Phe Gly Thr Ser Gly Ile Gly Phe Thr Lys
                85                  90                  95
Gln Asn Glu Leu Phe Val Gly Arg Val Ala Met Ile Gly Phe Ala Ala
                100                 105                 110
Ser Leu Leu Gly Glu Ala Ile Thr Gly Lys Gly Ile Leu Ser Gln Leu
                115                 120                 125
Asn Leu Glu Thr Gly Val Pro Ile Tyr Glu Ala Glu Pro Leu Leu
                130                 135                 140
Phe Phe Ile Leu Phe Thr Leu Leu Gly Ala Ile Gly Ala Leu Gly Asp
145                 150                 155                 160
Arg Gly Lys Phe Val Asp Asp Pro Thr Gly Ile Glu Gly Ala Val
                165                 170                 175
Ile Pro Pro Gly Lys Gly Phe Lys Ser Ala Leu Gly Leu Asn Glu Gly
                180                 185                 190
Gly Pro Leu Phe Gly Phe Thr Lys Ala Asn Glu Leu Phe Val Gly Arg
                195                 200                 205
Leu Ala Gln Leu Gly Phe Ala Phe Ser Leu Ile Gly Glu Ile Ile Thr
                210                 215                 220
Gly Lys Gly Ala Leu Ala Gln Leu Asn Ile Glu Thr Gly Val Pro Ile
225                 230                 235                 240
Asn Glu Ile Glu Pro Leu Val Leu Leu Asn Val Val Phe Phe Ile
                245                 250                 255
Ala Ala Val Asn Pro Gly Thr Gly Lys Phe Ile Thr Asp Val Asp Glu
                260                 265                 270
Glu Asp

<210> SEQ ID NO 80
<211> LENGTH: 280
<212> TYPE: PRT
<213> ORGANISM: Morus notabilis

<400> SEQUENCE: 80

Met Ala Gln Thr Met Leu Leu Ser Ser Ser Val Ser Thr Ser His
1               5                   10                  15
Ala Leu Asp Leu Gln Lys His Pro Leu His Leu Gln Val Gln Ser
                20                  25                  30
Leu Lys Pro Lys Pro Phe Ser His Leu Phe Ser Pro Leu Ser Ser
                35                  40                  45
Arg Asn Pro Ser Leu Ala Ser Ser Ser Arg Gly Ile Ser Thr Val
                50                  55                  60
Phe Ala Leu Phe Lys Ser Lys Thr Lys Ala Ala Pro Thr Lys Lys Val
65                  70                  75                  80
Val Lys Glu Lys Pro Lys Val Glu Asp Gly Ile Phe Gly Thr Ser Gly
                85                  90                  95
Gly Ile Gly Phe Thr Lys Gln Asn Glu Leu Phe Val Gly Arg Val Ala
```

```
                100                 105                 110
Met Ile Gly Phe Ala Ala Leu Leu Gly Glu Ala Ile Thr Gly Lys
                115                 120                 125
Gly Ile Leu Ser Gln Leu Asn Leu Glu Thr Gly Ile Pro Ile Tyr Glu
    130                 135                 140
Ala Glu Pro Leu Leu Leu Phe Phe Ile Leu Phe Thr Leu Leu Gly Ala
145                 150                 155                 160
Ile Gly Ala Leu Gly Asp Arg Gly Arg Phe Val Asp Asp Pro Pro Thr
                165                 170                 175
Gly Ile Glu Gly Ala Val Ile Pro Pro Gly Lys Ser Leu Arg Ser Ala
            180                 185                 190
Leu Gly Leu Lys Glu Gly Pro Leu Phe Gly Phe Thr Lys Ala Asn
            195                 200                 205
Glu Leu Phe Val Gly Arg Leu Ala Gln Leu Gly Phe Ala Phe Ala Leu
            210                 215                 220
Ile Gly Glu Ile Ile Thr Gly Lys Gly Ala Leu Ala Gln Leu Asn Val
225                 230                 235                 240
Glu Thr Gly Val Pro Ile Asn Glu Ile Glu Pro Leu Val Leu Leu Asn
                245                 250                 255
Val Leu Phe Phe Phe Ile Ala Ala Val Asn Pro Gly Thr Gly Lys Phe
                260                 265                 270
Ile Thr Asp Glu Asn Glu Glu Asp
                275                 280

<210> SEQ ID NO 81
<211> LENGTH: 275
<212> TYPE: PRT
<213> ORGANISM: Trema orientale

<400> SEQUENCE: 81

Met Ala Gln Thr Met Leu Leu Ser Ser Ser Val Ser Asn Cys His
1               5                   10                  15
Val Val Asp Leu Lys Arg Asp Pro Leu Leu Gln Ile Arg Val Gln Arg
                20                  25                  30
Leu Lys Thr Thr Lys Pro Phe Ser Gln Ser Leu Thr Phe Asn Pro Leu
            35                  40                  45
Thr Ser Ser Ser Lys Ser Pro Ala Ile Ser Thr Val Phe Ala Leu Phe
    50                  55                  60
Lys Ser Lys Thr Lys Ala Ala Pro Lys Lys Val Val Lys Ser Lys Pro
65                  70                  75                  80
Lys Val Glu Asp Gly Val Phe Gly Thr Ser Gly Gly Ile Gly Phe Thr
                85                  90                  95
Lys Gln Asn Glu Leu Phe Val Gly Arg Val Ala Met Ile Gly Phe Ala
                100                 105                 110
Ala Ser Ile Leu Gly Glu Ala Ile Thr Gly Lys Gly Ile Leu Ala Gln
            115                 120                 125
Leu Asn Leu Glu Thr Gly Ile Pro Ile Tyr Glu Ala Glu Pro Leu Leu
    130                 135                 140
Leu Phe Phe Ile Leu Phe Thr Leu Leu Gly Ala Ile Gly Ala Leu Gly
145                 150                 155                 160
Asp Arg Gly Gln Phe Val Asp Asp Pro Thr Gly Ile Glu Gly Ala
                165                 170                 175
Val Ile Pro Pro Gly Lys Gly Phe Arg Ser Ala Leu Gly Leu Lys Glu
            180                 185                 190
```

```
Gly Gly Pro Leu Phe Gly Phe Thr Lys Ala Asn Glu Leu Phe Val Gly
            195                 200                 205

Arg Leu Ala Gln Leu Gly Phe Ala Phe Ser Leu Ile Gly Glu Ile Ile
210                 215                 220

Thr Gly Lys Gly Ala Leu Ala Gln Leu Asn Ile Glu Thr Gly Val Pro
225                 230                 235                 240

Ile Asn Glu Ile Glu Pro Leu Val Leu Phe Asn Val Leu Phe Phe Phe
                245                 250                 255

Ile Ala Ala Val Asn Pro Gly Thr Gly Lys Phe Val Thr Asp Val Asp
                260                 265                 270

Glu Glu Asp
        275

<210> SEQ ID NO 82
<211> LENGTH: 275
<212> TYPE: PRT
<213> ORGANISM: Parasponia andersonii

<400> SEQUENCE: 82

Met Ala Gln Thr Met Leu Leu Ser Ser Ser Val Ser Asn Cys His
1               5                   10                  15

Val Val Asp Leu Lys Arg Asp Pro Leu Leu Gln Ile Arg Val Gln Arg
                20                  25                  30

Leu Lys Thr Thr Lys Pro Phe Ser Gln Ser Phe Thr Phe Asn Pro Leu
            35                  40                  45

Thr Ser Ser Ser Lys Ser Pro Ala Met Ser Thr Val Phe Ala Leu Phe
    50                  55                  60

Lys Ser Lys Thr Lys Ala Ala Pro Lys Lys Val Val Lys Ser Lys Pro
65                  70                  75                  80

Lys Val Glu Asp Gly Val Phe Gly Thr Ser Gly Gly Ile Gly Phe Thr
                85                  90                  95

Lys Gln Asn Glu Leu Phe Val Gly Arg Val Ala Met Val Gly Phe Ala
            100                 105                 110

Ala Ser Ile Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
130                 135                 140

Leu Phe Phe Ile Leu Phe Thr Leu Leu Gly Ala Ile Gly Ala Leu Gly
145                 150                 155                 160

Asp Arg Gly Gln Phe Val Asp Asp Pro Pro Thr Gly Ile Glu Gly Ala
                165                 170                 175

Val Ile Pro Pro Gly Lys Gly Phe Arg Ser Ala Leu Gly Leu Lys Glu
                180                 185                 190

Gly Gly Pro Leu Phe Gly Phe Thr Lys Ala Asn Glu Leu Phe Val Gly
            195                 200                 205

Arg Leu Ala Gln Leu Gly Phe Ala Phe Ser Leu Ile Gly Glu Ile Val
210                 215                 220

Thr Gly Lys Gly Ala Leu Ala Gln Leu Asn Ile Glu Thr Gly Val Pro
225                 230                 235                 240

Ile Asn Glu Ile Glu Pro Leu Val Leu Phe Asn Val Leu Phe Phe Phe
                245                 250                 255

Ile Ala Ala Val Asn Pro Gly Thr Gly Lys Phe Val Thr Asp Val Asp
                260                 265                 270

Glu Glu Asp
        275
```

<210> SEQ ID NO 83
<211> LENGTH: 277
<212> TYPE: PRT
<213> ORGANISM: Ziziphus jujuba

<400> SEQUENCE: 83

Met Ala Gln Thr Met Leu Leu Met Ser Ser Ser Val Ser Ser
1               5                   10                  15

Val Asp Leu Lys Lys Arg Ser Asp Pro Leu Leu Gln Phe Gln Ile Gln
            20                  25                  30

Arg Leu Arg Pro Thr Lys Pro Leu Ser His Leu Phe Phe Lys Ser Leu
        35                  40                  45

Pro Ser Ser Ser Ser Ser Pro Pro Val Ser Thr Val Ala Leu
    50                  55                  60

Phe Lys Ser Lys Thr Lys Ala Pro Pro Lys Lys Ala Val Lys Ala Pro
65              70                  75                  80

Lys Pro Lys Val Glu Asp Gly Val Phe Gly Thr Ser Gly Gly Ile Gly
                85                  90                  95

Phe Thr Lys Gln Asn Glu Leu Phe Val Gly Arg Val Ala Met Leu Gly
            100                 105                 110

Phe Ala Ala Ser Ile Leu Gly Glu Ala Ile Thr Gly Lys Gly Ile Leu
        115                 120                 125

Ala Gln Leu Asn Leu Glu Thr Gly Ile Pro Ile Tyr Glu Ala Glu Pro
    130                 135                 140

Leu Leu Leu Phe Phe Ile Leu Phe Thr Leu Leu Gly Ala Ile Gly Ala
145                 150                 155                 160

Leu Gly Asp Arg Gly Gln Phe Val Asp Asp Pro Pro Thr Gly Ile Glu
                165                 170                 175

Gly Ala Val Ile Pro Pro Gly Lys Ser Phe Arg Ser Ala Leu Gly Leu
            180                 185                 190

Lys Glu Gly Gly Pro Leu Phe Gly Phe Thr Lys Ala Asn Glu Leu Phe
        195                 200                 205

Val Gly Arg Leu Ala Gln Leu Gly Phe Ala Phe Ser Leu Ile Gly Glu
    210                 215                 220

Ile Ile Thr Gly Lys Gly Ala Leu Ala Gln Leu Asn Ile Glu Thr Gly
225                 230                 235                 240

Val Pro Ile Asn Glu Ile Glu Pro Leu Val Leu Phe Asn Val Ile Phe
                245                 250                 255

Phe Phe Phe Ala Ala Leu Asn Pro Gly Thr Gly Lys Phe Val Thr Asp
            260                 265                 270

Val Asp Glu Glu Asp
        275

<210> SEQ ID NO 84
<211> LENGTH: 271
<212> TYPE: PRT
<213> ORGANISM: Aquilegia coerulea

<400> SEQUENCE: 84

Met Ala Gln Thr Met Met Leu Met Ser Ser Val Ala Gly His Gly Leu
1               5                   10                  15

Asp Leu Lys Arg Val Pro Ser Leu Gln Thr Leu Lys Pro Lys Pro Phe
            20                  25                  30

Ala His Phe Leu Leu Pro Pro Ser Ser Gln Arg Tyr Gln Leu Ala Lys
        35                  40                  45

Tyr Ser Ser Thr Thr Thr Ile Ala Leu Phe Lys Ser Arg Thr Lys
    50                  55                  60

Ala Pro Ala Lys Thr Lys Gln Ala Pro Lys Pro Lys Pro Lys Val Glu
65                  70                  75                  80

Asp Gly Ile Phe Gly Thr Ser Gly Ile Gly Phe Thr Lys Gln Asn
                85                  90                  95

Glu Leu Phe Val Gly Arg Val Ala Met Leu Gly Phe Ala Ala Ser Leu
            100                 105                 110

Leu Gly Glu Gly Ile Thr Gly Lys Gly Ile Leu Ala Gln Leu Asn Ile
        115                 120                 125

Glu Thr Gly Ile Pro Ile Tyr Glu Ala Glu Pro Leu Leu Leu Phe Phe
    130                 135                 140

Ile Leu Phe Thr Leu Leu Gly Ala Ile Gly Ala Leu Gly Asp Arg Gly
145                 150                 155                 160

Arg Phe Val Asp Asp Pro Pro Thr Gly Leu Glu Lys Ala Val Ile Pro
                165                 170                 175

Pro Gly Lys Gly Ile Lys Ser Ala Leu Gly Leu Lys Glu Gly Gly Pro
            180                 185                 190

Leu Phe Gly Phe Thr Lys Ala Asn Glu Leu Phe Val Gly Arg Leu Ala
        195                 200                 205

Gln Leu Gly Phe Val Phe Ser Leu Ile Gly Glu Ile Ile Thr Gly Lys
    210                 215                 220

Gly Ala Leu Ala Gln Leu Asn Ile Glu Thr Gly Val Pro Leu Asn Glu
225                 230                 235                 240

Leu Glu Pro Leu Val Leu Phe Asn Val Ile Phe Phe Phe Ala Ala
                245                 250                 255

Leu Asn Pro Gly Asn Gly Lys Phe Val Thr Asp Glu Asp Glu Glu
            260                 265                 270

<210> SEQ ID NO 85
<211> LENGTH: 273
<212> TYPE: PRT
<213> ORGANISM: Macleaya cordata

<400> SEQUENCE: 85

Met Ala Gln Thr Met Met Leu Met Ser Asn Val Gly Thr Ala Gly Gly
1               5                   10                  15

His Gly Leu Asn Leu Lys Arg Glu Ser Leu Leu Gln Arg Leu Lys Pro
            20                  25                  30

Lys Pro Phe Ser His Leu Leu Leu Pro Pro Leu Ser Thr His Gln Leu
        35                  40                  45

Ser Ser Thr Ser Ser Ser Thr Ser Thr Thr Pro Phe Ala Leu Phe Lys
    50                  55                  60

Ser Lys Thr Lys Ala Pro Val Lys Lys Ala Pro Ala Lys Pro Pro Lys
65                  70                  75                  80

Val Glu Asp Gly Ile Phe Gly Thr Ser Gly Ile Gly Phe Thr Lys
                85                  90                  95

Gln Asn Glu Leu Phe Val Gly Arg Val Ala Met Leu Gly Phe Ala Ala
            100                 105                 110

Ser Leu Leu Gly Glu Ala Ile Thr Gly Lys Gly Ile Leu Ser Gln Leu
        115                 120                 125

Asn Leu Glu Thr Gly Ile Pro Ile Tyr Glu Ala Glu Pro Leu Leu Leu
    130                 135                 140

Phe Phe Ile Leu Phe Thr Leu Leu Gly Ala Ile Gly Ala Leu Gly Asp

```
                145                 150                 155                 160
Arg Gly Lys Phe Val Asp Asp Pro Pro Thr Gly Leu Glu Arg Ala Val
                    165                 170                 175

Ile Pro Pro Gly Lys Ser Phe Arg Ser Ala Leu Gly Leu Lys Glu Gly
                    180                 185                 190

Gly Pro Ile Phe Gly Phe Thr Lys Ser Asn Glu Leu Phe Val Gly Arg
                    195                 200                 205

Leu Ala Gln Leu Gly Ile Ala Phe Ser Ile Ile Gly Glu Ile Ile Thr
                    210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Phe Asn Val Val Phe Phe Phe Ile
                    245                 250                 255

Ala Ala Leu Asn Pro Gly Asn Gly Lys Phe Val Thr Asp Asp Glu Glu
                    260                 265                 270

Glu

<210> SEQ ID NO 86
<211> LENGTH: 272
<212> TYPE: PRT
<213> ORGANISM: Papaver somniferum

<400> SEQUENCE: 86

Met Ala Gln Ser Met Met Leu Met Ser Asn Val Ala Gly Gln Gly Leu
1               5                   10                  15

Asn Phe Lys Arg Glu Ala Leu Val Asp Arg Leu Lys Pro Lys Pro Phe
                    20                  25                  30

Ser His Phe Leu Leu Pro Ser Ser Leu Ser Ser Pro Ser Thr Ser Ser
                    35                  40                  45

Ser Ser Lys Ala Phe Thr Ile Phe Ala Leu Phe Lys Ser Lys Thr Lys
            50                  55                  60

Ala Pro Ala Lys Lys Ala Ala Pro Ala Pro Lys Pro Lys Val Glu Asp
65                  70                  75                  80

Gly Ile Phe Gly Thr Ser Gly Gly Ile Gly Phe Thr Lys Gln Asn Glu
                    85                  90                  95

Leu Phe Val Gly Arg Val Ala Met Leu Gly Phe Ala Ala Ser Leu Leu
                    100                 105                 110

Gly Glu Ala Ile Thr Gly Lys Gly Ile Leu Ser Gln Leu Asn Leu Glu
                    115                 120                 125

Thr Gly Ile Pro Ile Tyr Glu Ala Glu Pro Leu Leu Leu Phe Phe Ile
                    130                 135                 140

Leu Phe Thr Leu Leu Gly Ala Ile Gly Ala Leu Gly Asp Arg Gly Lys
145                 150                 155                 160

Phe Val Asp Asp Ala Pro Ala Thr Gly Ile Asp Arg Ala Val Ile Pro
                    165                 170                 175

Pro Gly Lys Gly Phe Arg Ala Ala Leu Gly Leu Lys Glu Gly Gly Pro
                    180                 185                 190

Val Phe Gly Phe Thr Lys Ser Asn Glu Leu Phe Val Gly Arg Leu Ala
                    195                 200                 205

Gln Leu Gly Val Ala Phe Ser Ile Ile Gly Glu Ile Ile Thr Gly Lys
                    210                 215                 220

Gly Ala Leu Ala Gln Leu Asn Ile Glu Thr Gly Val Pro Ile Gly Glu
225                 230                 235                 240

Ile Glu Pro Leu Val Leu Phe Asn Val Val Phe Phe Ile Ala Ala
```

<210> SEQ ID NO 87
<211> LENGTH: 272
<212> TYPE: PRT
<213> ORGANISM: Papaver somniferum

<400> SEQUENCE: 87

Met Ala Gln Ser Met Met Leu Met Ser Asn Val Ala Gln Gly Leu
1               5                   10                  15

Asn Phe Lys Arg Glu Ala Leu Val Asp Arg Leu Lys Pro Lys Pro Phe
            20                  25                  30

Ser His Phe Leu Leu Pro Ser Ser Leu Ser Ser Pro Ser Thr Ser Ser
        35                  40                  45

Ser Ser Lys Thr Phe Thr Thr Phe Ala Leu Phe Lys Ser Lys Thr Lys
    50                  55                  60

Ala Pro Ala Lys Lys Ala Ala Pro Ala Pro Lys Pro Lys Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Leu Gly Phe Ala Ala Ser Leu Leu
            100                 105                 110

Gly Glu Ala Ile Thr Gly Lys Gly Ile Leu Ser Gln Leu Asn Leu Glu
        115                 120                 125

Thr Gly Ile Pro Ile Tyr Glu Ala Glu Pro Leu Leu Leu Phe Phe Ile
    130                 135                 140

Leu Phe Thr Leu Leu Gly Ala Ile Gly Ala Leu Gly Asp Arg Gly Lys
145                 150                 155                 160

Phe Val Asp Asp Ala Pro Ala Thr Gly Ile Asp Arg Ala Val Ile Pro
                165                 170                 175

Pro Gly Lys Gly Phe Arg Ala Ala Leu Gly Leu Lys Glu Gly Gly Pro
            180                 185                 190

Val Phe Gly Phe Thr Lys Ser Asn Glu Leu Phe Val Gly Arg Leu Ala
        195                 200                 205

Gln Leu Gly Val Ala Phe Ser Ile Ile Gly Glu Ile Ile Thr Gly Lys
    210                 215                 220

Gly Ala Leu Ala Gln Leu Asn Ile Glu Thr Gly Val Pro Ile Gly Glu
225                 230                 235                 240

Ile Glu Pro Leu Val Leu Phe Asn Val Val Phe Phe Ile Ala Ala
                245                 250                 255

Leu Asn Pro Gly Ser Gly Lys Phe Val Thr Asp Asp Gly Glu Glu Glu
            260                 265                 270

<210> SEQ ID NO 88
<211> LENGTH: 272
<212> TYPE: PRT
<213> ORGANISM: Daucus carota

<400> SEQUENCE: 88

Met Ala Gln Thr Met Leu Leu Met Ser Ser Ser Thr Cys Val Ser Gly
1               5                   10                  15

His Ala Ala Asp Asn Leu Lys Ser Pro Ala Leu Pro Leu Leu Gln Arg
            20                  25                  30

Leu Lys Pro Lys Pro Phe Ser His Ser Leu Leu Pro His Leu Ala Asn

```
            35                  40                  45
Ile Ser Lys Ser Ser Thr Phe Thr Thr Tyr Ala Leu Phe Lys Ser
 50                  55                  60

Lys Ala Lys Ala Pro Ala Lys Lys Val Val Ala Pro Lys Pro Lys Val
 65                  70                  75                  80

Glu Asp Gly Ile Phe Gly Thr Ser Gly Gly Ile Gly Phe Thr Lys Gln
                 85                  90                  95

Asn Glu Leu Phe Val Gly Arg Val Ala Met Ile Gly Phe Ala Ala Ser
                100                 105                 110

Leu Leu Gly Glu Ala Val Thr Gly Lys Gly Ile Leu Ala Gln Leu Asn
                115                 120                 125

Leu Glu Thr Gly Ile Pro Ile Tyr Glu Ala Glu Pro Leu Leu Leu Phe
130                 135                 140

Phe Ile Leu Phe Thr Leu Leu Gly Ala Ile Gly Ala Leu Gly Asp Arg
145                 150                 155                 160

Gly Arg Phe Val Asp Asp Pro Pro Thr Gly Leu Glu Lys Ala Val Ile
                165                 170                 175

Lys Pro Gly Lys Gly Phe Arg Gly Ala Leu Gly Leu Ser Glu Gly Gly
                180                 185                 190

Pro Leu Phe Gly Phe Thr Lys Ser Asn Glu Leu Phe Val Gly Arg Leu
                195                 200                 205

Ala Gln Leu Gly Ile Ala Phe Ser Leu Ile Gly Glu Ile Ile Thr Gly
                210                 215                 220

Lys Gly Ala Leu Ala Gln Leu Asn Ile Glu Thr Gly Ile Pro Ile Ser
225                 230                 235                 240

Asp Ile Glu Pro Leu Val Leu Asn Val Val Phe Phe Val Ala
                245                 250                 255

Ala Leu Asn Pro Gly Thr Gly Lys Phe Ile Thr Asp Glu Glu Glu Asp
                260                 265                 270

<210> SEQ ID NO 89
<211> LENGTH: 259
<212> TYPE: PRT
<213> ORGANISM: Actinidia chinensis

<400> SEQUENCE: 89

Met Ala Gln Thr Met Phe Leu Thr Ser Ser Val Cys Gly His Ala Leu
 1               5                  10                  15

Val Gln Arg Leu Arg Pro Lys Ser Phe Ser His Ile Ser Gln Ser Pro
                20                  25                  30

Ile Pro Thr Ser Ser Ser Ile Lys Pro Asn Thr Ile Val Ala Leu Phe
                35                  40                  45

Lys Ser Lys Thr Lys Ala Pro Leu Pro Ala Lys Lys Ala Pro Lys Thr
 50                  55                  60

Ala Ser Lys Val Glu Asp Gly Ile Phe Gly Thr Ser Gly Gly Ile Gly
 65                  70                  75                  80

Phe Thr Lys Gln Asn Glu Leu Phe Val Gly Arg Val Ala Met Ile Gly
                 85                  90                  95

Phe Ala Ala Ser Leu Leu Gly Glu Ala Ile Thr Gly Lys Gly Ile Leu
                100                 105                 110

Ala Gln Leu Asn Leu Glu Thr Gly Ile Pro Ile Tyr Glu Ala Glu Pro
                115                 120                 125

Leu Leu Leu Phe Phe Ile Leu Phe Thr Leu Leu Gly Ala Ile Gly Ala
                130                 135                 140
```

```
Leu Gly Asp Arg Gly Arg Phe Val Asp Asp Pro Thr Gly Leu Glu
145                 150                 155                 160

Lys Ala Val Ile Pro Pro Gly Lys Gly Val Arg Ser Ala Leu Gly Leu
                165                 170                 175

Lys Glu Gly Gly Pro Leu Phe Gly Phe Thr Lys Ala Asn Glu Leu Phe
                180                 185                 190

Val Gly Arg Leu Ala Gln Leu Gly Ile Ala Phe Ser Leu Ile Gly Glu
            195                 200                 205

Ile Ile Thr Gly Lys Gly Ala Leu Ala Gln Leu Asn Ile Glu Thr Gly
        210                 215                 220

Val Pro Ile Ser Glu Ile Glu Pro Leu Leu Phe Asn Val Ala Phe
225                 230                 235                 240

Phe Phe Phe Ala Ala Leu Asn Pro Gly Thr Gly Lys Phe Val Thr Asp
                245                 250                 255

Glu Glu Glu

<210> SEQ ID NO 90
<211> LENGTH: 260
<212> TYPE: PRT
<213> ORGANISM: Actinidia chinensis

<400> SEQUENCE: 90

Met Ala Gln Thr Met Phe Leu Thr Ser Ser Val Cys Gly His Ala Leu
1               5                   10                  15

Val Gln Arg Leu Arg Pro Lys Ser Phe Ser His Ile Ser Gln Ser Pro
            20                  25                  30

Ile Pro Thr Ser Ser Ser Ile Lys Thr Asn Thr Ile Val Ala Leu
            35                  40                  45

Phe Lys Ser Lys Thr Lys Ala Pro Pro Ala Lys Lys Ala Pro Lys
50                  55                  60

Val Ala Ser Lys Val Glu Asp Gly Ile Phe Gly Thr Ser Gly Gly Ile
65                  70                  75                  80

Gly Phe Thr Lys Gln Asn Glu Leu Phe Val Gly Arg Val Ala Met Ile
                85                  90                  95

Gly Phe Ala Ala Ser Leu Leu Gly Glu Ala Ile Thr Gly Lys Gly Ile
                100                 105                 110

Leu Ala Gln Leu Asn Leu Glu Thr Gly Ile Pro Ile Tyr Glu Ala Glu
            115                 120                 125

Pro Leu Leu Leu Phe Phe Ile Leu Phe Thr Leu Leu Gly Ala Ile Gly
        130                 135                 140

Ala Leu Gly Asp Arg Gly Arg Phe Val Asp Asp Pro Thr Gly Leu
145                 150                 155                 160

Glu Lys Ala Val Ile Pro Pro Gly Lys Gly Ile Arg Ser Ala Leu Gly
                165                 170                 175

Leu Lys Glu Gly Gly Pro Leu Phe Gly Phe Thr Lys Ala Asn Glu Leu
                180                 185                 190

Phe Val Gly Arg Leu Ala Gln Leu Gly Ile Ala Phe Ser Leu Ile Gly
            195                 200                 205

Glu Ile Ile Thr Gly Lys Gly Ala Leu Ala Gln Leu Asn Ile Glu Thr
        210                 215                 220

Gly Val Pro Ile Ser Glu Ile Glu Pro Leu Leu Leu Phe Asn Val Ala
225                 230                 235                 240

Phe Phe Phe Phe Ala Ala Leu Asn Pro Gly Thr Gly Lys Phe Leu Thr
                245                 250                 255
```

-continued

```
Asp Glu Glu Glu
        260

<210> SEQ ID NO 91
<211> LENGTH: 262
<212> TYPE: PRT
<213> ORGANISM: Lactuca sativa

<400> SEQUENCE: 91

Met Ala Gln Ala Met Leu Leu Thr Ser Asn Thr Ile Leu Ser Gly Gln
1               5                   10                  15

Pro Leu Gln Ser Leu Lys Pro Lys Pro Phe Ser Tyr His Leu Leu
            20                  25                  30

Pro Arg Asn Leu Pro Asn Leu Ser Pro Ala Thr Lys Phe Thr Ser Pro
        35                  40                  45

Val Ala Leu Phe Lys Ser Lys Ala Lys Ala Pro Val Lys Lys Ala Val
    50                  55                  60

Val Ser Lys Pro Lys Val Glu Asp Gly Ile Phe Gly Thr Ser Gly Gly
65                  70                  75                  80

Ile Gly Phe Thr Lys Gln Asn Glu Leu Phe Val Gly Arg Val Ala Met
                85                  90                  95

Ile Gly Phe Ala Ala Ser Leu Leu Gly Glu Gly Ile Thr Gly Lys Gly
            100                 105                 110

Ile Leu Gln Gln Leu Asn Leu Glu Thr Gly Ile Pro Ile Tyr Glu Ala
        115                 120                 125

Glu Pro Leu Leu Leu Phe Phe Ile Leu Phe Thr Leu Leu Gly Ala Ile
    130                 135                 140

Gly Ala Leu Gly Asp Arg Gly Arg Phe Val Asp Glu Pro Thr Thr Gly
145                 150                 155                 160

Leu Asp Lys Ala Val Ile Pro Pro Gly Lys Gly Val Arg Gly Ala Leu
                165                 170                 175

Gly Leu Lys Glu Gly Gly Pro Leu Phe Gly Phe Thr Lys Ala Asn Glu
            180                 185                 190

Leu Phe Val Gly Arg Leu Ala Gln Leu Gly Ile Ala Phe Ser Leu Ile
        195                 200                 205

Gly Glu Ile Ile Thr Gly Lys Gly Ala Leu Ala Gln Leu Asn Ile Glu
    210                 215                 220

Thr Gly Ile Pro Ile Ser Asp Ile Glu Pro Leu Val Leu Phe Asn Val
225                 230                 235                 240

Ala Phe Phe Phe Ile Ala Ala Leu Asn Pro Gly Thr Gly Lys Phe Val
                245                 250                 255

Thr Asp Glu Glu Glu Asp
            260

<210> SEQ ID NO 92
<211> LENGTH: 264
<212> TYPE: PRT
<213> ORGANISM: Artemisia annua

<400> SEQUENCE: 92

Met Ala Gln Thr Met Leu Leu Thr Ser Asn Thr Ile Ile Ser Gly Ser
1               5                   10                  15

Pro Leu Leu Gln Ser Leu Arg Pro Lys Pro Phe Ala His Leu Leu Leu
            20                  25                  30

Pro Pro Ser Leu Ala Ser Ser Ser Thr Arg Thr Tyr Thr Ser Pro
        35                  40                  45
```

```
Ile Ala Leu Phe Lys Ser Lys Ala Lys Ala Pro Ala Lys Lys Ala
    50                  55                  60

Ala Pro Ala Pro Lys Pro Lys Val Glu Asp Gly Ile Phe Gly Thr Ser
65              70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Ile Thr Gly
            100                 105                 110

Lys Gly Ile Leu Gln Gln Leu Asn Leu Glu Thr Gly Ile Pro Ile Tyr
            115                 120                 125

Glu Ala Glu Pro Leu Leu Leu Phe Phe Ile Leu Phe Thr Leu Leu Gly
130                 135                 140

Ala Ile Gly Ala Leu Gly Asp Arg Gly Arg Phe Val Asp Asp Ala Pro
145                 150                 155                 160

Thr Gly Leu Asp Lys Ala Val Ile Ala Pro Gly Lys Gly Phe Arg Ser
            165                 170                 175

Ala Leu Gly Leu Ser Glu Gly Gly Pro Leu Phe Gly Phe Thr Lys Ser
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
210                 215                 220

Ile Glu Thr Gly Leu Pro Ile Ser Glu Ile Glu Pro Leu Val Leu Phe
225                 230                 235                 240

Asn Val Ala Phe Phe Val Ala Ala Leu Asn Pro Gly Thr Gly Lys
            245                 250                 255

Phe Val Thr Asp Glu Asp Glu Asp
            260

<210> SEQ ID NO 93
<211> LENGTH: 264
<212> TYPE: PRT
<213> ORGANISM: Helianthus annuus

<400> SEQUENCE: 93

Met Ala Gln Thr Met Leu Leu Thr Ser Asn Thr Ile Ile Ser Gly Gln
1               5                   10                  15

Pro Leu Leu Arg Ser Leu Arg Pro Lys Pro Phe Ser Tyr Ile Val Leu
            20                  25                  30

Pro Pro Ser Leu Leu Pro Lys Ser Ser Pro Thr Ser Thr Thr Phe Ser
        35                  40                  45

Ser Pro Val Ala Leu Phe Lys Pro Lys Thr Lys Ala Ala Pro Lys Lys
50                  55                  60

Ala Ala Pro Ala Pro Lys Pro Lys Val Glu Asp Gly Ile Phe Gly Thr
65                  70                  75                  80

Ser Gly Gly Ile Gly Phe Thr Lys Gln Asn Glu Leu Phe Val Gly Arg
                85                  90                  95

Val Ala Met Ile Gly Phe Ala Ala Ser Leu Leu Gly Glu Ala Ile Thr
            100                 105                 110

Gly Lys Gly Ile Leu Ser Gln Leu Asn Leu Glu Thr Gly Ile Pro Ile
            115                 120                 125

Tyr Glu Ala Glu Pro Leu Leu Leu Phe Phe Ile Leu Phe Thr Leu Leu
130                 135                 140

Gly Ala Ile Gly Ala Leu Gly Asp Arg Gly Arg Phe Val Asp Glu Pro
145                 150                 155                 160
```

Thr Gly Leu Asp Lys Ala Val Ile Pro Pro Gly Lys Gly Phe Arg Ser
            165                 170                 175

Ala Leu Gly Leu Ser Glu Gly Gly Pro Leu Phe Gly Phe Thr Lys Ala
            180                 185                 190

Asn Glu Leu Phe Val Gly Arg Leu Ala Gln Leu Gly Ile Ala Phe Ser
            195                 200                 205

Leu Ile Gly Glu Ile Ile Thr Gly Lys Gly Ala Leu Ala Gln Leu Asn
            210                 215                 220

Ile Glu Thr Gly Leu Pro Ile Ser Glu Ile Glu Pro Leu Val Leu Phe
225                 230                 235                 240

Asn Val Ala Phe Phe Val Ala Ala Leu Asn Pro Gly Thr Gly Lys
            245                 250                 255

Phe Val Thr Asp Glu Glu Glu Asp
            260

<210> SEQ ID NO 94
<211> LENGTH: 271
<212> TYPE: PRT
<213> ORGANISM: Phalaenopsis equestris

<400> SEQUENCE: 94

Met Ala Gln Ser Met Leu Met Ser Ser Phe Gly Gly His Leu Val Asp
1               5                   10                  15

Cys Asn Arg Asp Pro Leu Leu Arg Thr Gln Ile Arg Arg Leu Arg Pro
            20                  25                  30

Ser Pro Leu Ser His Leu Phe Leu Ser Arg Pro Ser Pro Ser Gln Ser
            35                  40                  45

Thr Ser Pro Ser Ser Tyr Ala Pro Pro Leu Ala Val Phe Lys Ser Lys
            50                  55                  60

Thr Lys Ala Pro Ser Arg Lys Val Glu Lys Asp Arg Pro Lys Val Glu
65                  70                  75                  80

Asp Gly Ile Phe Gly Thr Ser Gly Gly Ile Gly Phe Thr Lys Ala Asn
            85                  90                  95

Glu Leu Phe Val Gly Arg Val Ala Met Leu Gly Phe Ala Ala Ser Leu
            100                 105                 110

Ile Gly Glu Gly Ile Thr Gly Lys Gly Ile Leu Ala Gln Leu Asn Leu
            115                 120                 125

Glu Thr Gly Ile Pro Ile Tyr Glu Ala Glu Pro Leu Leu Leu Phe Phe
            130                 135                 140

Ile Leu Phe Thr Leu Leu Gly Ala Ile Gly Ala Leu Gly Asp Arg Gly
145                 150                 155                 160

Ser Phe Val Asp Asp Pro Pro Thr Gly Leu Asp Lys Ala Val Ile Ala
            165                 170                 175

Pro Gly Lys Gly Phe Arg Ser Ala Leu Gly Leu Lys Glu Gly Gly Pro
            180                 185                 190

Leu Phe Gly Phe Thr Lys Ala Asn Glu Leu Phe Val Gly Arg Leu Ala
            195                 200                 205

Gln Leu Gly Ile Val Phe Ser Leu Ile Gly Glu Ile Ile Thr Gly Lys
            210                 215                 220

Gly Ala Leu Ala Gln Leu Asn Ile Glu Thr Gly Val Pro Leu Asn Glu
225                 230                 235                 240

Leu Glu Pro Leu Val Leu Phe Asn Val Phe Phe Phe Ala Ala
            245                 250                 255

Leu Asn Pro Gly Ser Gly Lys Phe Val Thr Asp Glu Asp Val Glu

<210> SEQ ID NO 95
<211> LENGTH: 273
<212> TYPE: PRT
<213> ORGANISM: Musa acuminata

<400> SEQUENCE: 95

Met Ala Gln Ser Val Leu Leu Ala Ser Thr Gly Gly Arg Ser Leu Ser
1               5                   10                  15

Ser Thr Met Glu Pro Leu Leu Gln Ala Gln Ile His Arg Leu Arg Pro
            20                  25                  30

Thr Arg Phe Ser Asp Leu Ile Leu Pro Arg Thr Pro Arg Arg His Leu
        35                  40                  45

Pro Ala Thr Ser Ser Ser Phe Phe Pro Thr Leu Ala Leu Phe Lys
    50                  55                  60

Ala Lys Thr Lys Ala Pro Pro Ala Lys Val Glu Thr Lys Lys Pro Lys
65                  70                  75                  80

Val Glu Asp Gly Ile Phe Gly Thr Ser Gly Ile Gly Phe Thr Lys
                85                  90                  95

Gln Asn Glu Leu Phe Val Gly Arg Val Ala Met Leu Gly Phe Ala Ala
            100                 105                 110

Ser Leu Leu Gly Glu Gly Ile Thr Gly Lys Gly Ile Leu Ala Gln Leu
        115                 120                 125

Asn Leu Glu Thr Gly Ile Pro Ile Tyr Glu Ala Glu Pro Leu Leu Leu
    130                 135                 140

Phe Phe Ile Leu Phe Thr Leu Leu Gly Ala Ile Gly Ala Leu Gly Asp
145                 150                 155                 160

Arg Gly Gln Phe Val Asp Asp Ser Pro Thr Gly Leu Gly Lys Ala Val
                165                 170                 175

Ile Pro Pro Gly Lys Gly Phe Arg Ala Ala Leu Gly Leu Glu Glu Gly
            180                 185                 190

Gly Pro Leu Phe Gly Phe Thr Lys Ala Asn Glu Leu Phe Val Gly Arg
        195                 200                 205

Leu Ala Gln Leu Gly Ile Ala Phe Ser Ile Ile Gly Glu Ile Ile Thr
    210                 215                 220

Gly Lys Gly Ala Leu Ala Gln Leu Asn Ile Glu Thr Gly Val Pro Val
225                 230                 235                 240

Ser Glu Leu Glu Pro Leu Val Leu Phe Asn Val Ala Phe Phe Phe
                245                 250                 255

Ala Ala Leu Asn Pro Gly Thr Gly Lys Phe Val Thr Asp Glu Val Glu
            260                 265                 270

Glu

<210> SEQ ID NO 96
<211> LENGTH: 273
<212> TYPE: PRT
<213> ORGANISM: Cinnamomum micranthum f. kanehirae

<400> SEQUENCE: 96

Met Ala Gln Ser Met Leu Met Ser Val Ser Gly Gln Leu Val Pro
1               5                   10                  15

Ser Arg Thr Glu Ala Leu Leu Gln Phe Gln Ile Arg Arg Leu Cys Pro
            20                  25                  30

Thr Pro Phe Ser His Ile Leu Leu Ser Pro Ser Thr His Gln Arg Pro
        35                  40                  45

```
Pro Ser Pro Ser Thr Ser Ile Ser Thr Pro Thr Leu Ala Leu Phe Lys
    50                  55                  60

Ser Lys Thr Lys Ala Pro Ala Lys Lys Val Glu Lys Pro Lys
65                  70                  75                  80

Val Glu Asp Gly Ile Phe Gly Thr Ser Gly Ile Gly Phe Thr Lys
                    85                  90                  95

Gln Asn Glu Leu Phe Val Gly Arg Val Ala Met Ile Gly Phe Ala Ala
                100                 105                 110

Ser Leu Leu Gly Glu Gly Ile Thr Gly Lys Gly Ile Leu Ala Gln Leu
            115                 120                 125

Asn Leu Glu Thr Gly Ile Pro Ile Tyr Glu Ala Glu Pro Leu Leu Leu
            130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Thr Gly Leu Glu Arg Ala Val
                165                 170                 175

Ile Pro Pro Gly Lys Ser Ile Arg Ser Ala Leu Gly Leu Lys Glu Gly
                180                 185                 190

Gly Pro Leu Phe Gly Phe Thr Lys Ser Asn Glu Leu Phe Val Gly Arg
            195                 200                 205

Leu Ala Gln Leu Gly Ile Ala Phe Ser Ile Ile Gly Glu Ile Ile Thr
210                 215                 220

Gly Lys Gly Ala Leu Ala Gln Leu Asn Ile Glu Thr Gly Val Pro Leu
225                 230                 235                 240

Gln Asp Ile Glu Pro Leu Val Leu Phe Asn Val Ile Phe Phe Phe
                245                 250                 255

Ala Ala Leu Asn Pro Gly Asn Gly Lys Phe Val Thr Asp Glu Glu Asp
            260                 265                 270

Lys

<210> SEQ ID NO 97
<211> LENGTH: 274
<212> TYPE: PRT
<213> ORGANISM: Phoenix dactylifera

<400> SEQUENCE: 97

Met Val His Ala Val Phe Thr Ser Gly Leu Gly Ala His Leu Pro Asp
1               5                   10                  15

Ser Lys Arg Glu Pro Leu Leu Gln Ser Gln Leu Arg Arg Leu Arg Pro
                20                  25                  30

Thr Pro Phe Ser His Leu Leu Leu Ser Gln Pro Ser His Lys Gln Leu
            35                  40                  45

Pro Ser Pro Ser Tyr Ser Ser Tyr Thr Pro Val Leu Ala Leu Phe Lys
    50                  55                  60

Ser Lys Thr Lys Ala Pro Pro Lys Lys Val Glu Lys Ala Lys Pro Lys
65                  70                  75                  80

Val Glu Asp Gly Ile Phe Gly Thr Ser Gly Ile Gly Phe Thr Lys
                    85                  90                  95

Gln Asn Glu Leu Phe Val Gly Arg Val Ala Met Ile Gly Phe Ala Ala
                100                 105                 110

Ser Leu Leu Gly Glu Ala Ile Thr Gly Lys Gly Ile Leu Ala Gln Leu
            115                 120                 125

Asn Leu Glu Thr Gly Ile Pro Ile Tyr Glu Ala Glu Pro Leu Leu Leu
            130                 135                 140
```

```
Phe Phe Ile Leu Phe Thr Leu Leu Gly Ala Ile Gly Ala Leu Gly Asp
145                 150                 155                 160

Arg Gly Arg Phe Val Asp Asp Pro Thr Gly Leu Asp Lys Ala Val
                165                 170                 175

Ile Pro Pro Gly Lys Gly Ile Arg Ser Ala Leu Gly Leu Lys Glu Gly
                180                 185                 190

Gly Pro Leu Phe Gly Phe Thr Lys Ser Asn Glu Leu Phe Val Gly Arg
                195                 200                 205

Leu Ala Gln Leu Gly Ile Ala Phe Ser Ile Ile Gly Glu Ile Val Thr
                210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Phe Asn Val Ile Phe Phe Phe Ile
                245                 250                 255

Ala Ala Leu Asn Pro Gly Asn Gly Lys Phe Val Thr Asp Val Asp Glu
                260                 265                 270

Glu Glu

<210> SEQ ID NO 98
<211> LENGTH: 273
<212> TYPE: PRT
<213> ORGANISM: Elaeis guineensis

<400> SEQUENCE: 98

Met Ala Gln Ala Val Phe Thr Ser Arg Leu Gly Ser Gln Leu Leu Asp
1               5                   10                  15

Ser Lys Thr Glu Pro Leu Leu Gln Ser Gln Leu Arg Arg Leu Arg Pro
                20                  25                  30

Thr Pro Phe Ser His Leu Leu Leu Ser Gln Pro Ser His Lys Gln Ile
                35                  40                  45

Pro Ser Pro Ser Tyr Ser Ser Tyr Thr Pro Val Leu Ala Leu Phe Lys
                50                  55                  60

Ser Lys Thr Lys Ala Pro Pro Lys Lys Val Glu Lys Thr Lys Pro Lys
65                  70                  75                  80

Ile Glu Asp Gly Ile Phe Gly Thr Ser Gly Gly Ile Gly Phe Thr Lys
                85                  90                  95

Gln Asn Glu Leu Phe Val Gly Arg Val Ala Met Ile Gly Phe Ala Ala
                100                 105                 110

Ser Leu Leu Gly Glu Ala Ile Thr Gly Lys Gly Ile Leu Ala Gln Leu
                115                 120                 125

Asn Leu Glu Thr Gly Ile Pro Ile Tyr Glu Ala Glu Pro Leu Leu Leu
                130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Ser Thr Gly Leu Gly Lys Ala Val
                165                 170                 175

Ile Pro Pro Gly Lys Gly Phe Arg Ser Ala Leu Gly Leu Lys Glu Gly
                180                 185                 190

Gly Pro Leu Phe Gly Phe Thr Lys Ala Asn Glu Leu Phe Val Gly Arg
                195                 200                 205

Leu Ala Gln Leu Gly Ile Ala Phe Ser Ile Ile Gly Glu Ile Ile Thr
                210                 215                 220

Gly Lys Gly Ala Leu Ala Gln Leu Asn Ile Glu Thr Gly Val Pro Ile
225                 230                 235                 240
```

Asn Glu Ile Glu Pro Leu Val Leu Phe Asn Val Ile Phe Phe Phe
            245                 250                 255

Ala Ala Leu Asn Pro Gly Thr Gly Lys Phe Leu Thr Asp Glu Asp Glu
            260                 265                 270

Glu

<210> SEQ ID NO 99
<211> LENGTH: 279
<212> TYPE: PRT
<213> ORGANISM: Punica granatum

<400> SEQUENCE: 99

Met Ala Gln Ala Met Leu Val Met Pro Ser Ala Ser Gly His Ser Val
1               5                   10                  15

Asp Val Lys Arg Asp Gly Leu Leu Arg Phe Gln Ile Gln Arg Leu Arg
            20                  25                  30

Pro Lys Ser Ser Phe Pro Ser Leu Leu Gly Phe Asn Pro Leu Leu Thr
            35                  40                  45

Pro Ala Ser Leu Asp Ser Arg Arg Pro Val Ser Ser Pro Ala Val Ala
        50                  55                  60

Leu Phe Lys Ser Lys Thr Lys Ala Pro Pro Lys Val Ala Lys Glu
65              70                  75                  80

Pro Pro Lys Pro Lys Val Glu Asp Gly Ile Phe Gly Thr Ser Gly Gly
                85                  90                  95

Ile Gly Phe Thr Lys Glu Asn Glu Leu Phe Val Gly Arg Val Ala Met
            100                 105                 110

Leu Gly Phe Ala Ala Ser Leu Leu Gly Glu Gly Ile Thr Gly Lys Gly
        115                 120                 125

Ile Leu Ala Gln Leu Asn Leu Glu Thr Gly Ile Pro Ile Tyr Glu Ala
    130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Lys Phe Val Asp Asp Pro Ala Thr Gly
                165                 170                 175

Ile Glu Gly Ala Val Ile Pro Pro Gly Lys Ser Phe Arg Ala Ala Val
            180                 185                 190

Gly Leu Lys Glu Gly Gly Pro Leu Phe Gly Phe Thr Lys Ala Asn Glu
        195                 200                 205

Leu Phe Val Gly Arg Leu Ala Gln Leu Gly Phe Ala Phe Ser Leu Ile
    210                 215                 220

Gly Glu Ile Ile Thr Gly Lys Gly Ala Leu Ala Gln Leu Asn Val Glu
225                 230                 235                 240

Thr Gly Val Pro Ile Asn Glu Ile Glu Pro Leu Val Leu Phe Asn Val
                245                 250                 255

Leu Phe Phe Phe Ile Ala Ala Ile Asn Pro Gly Thr Gly Lys Phe Val
            260                 265                 270

Thr Asp Glu Asp Gln Glu Asn
        275

<210> SEQ ID NO 100
<211> LENGTH: 272
<212> TYPE: PRT
<213> ORGANISM: Carica papaya

<400> SEQUENCE: 100

Met Ala Gln Thr Met Leu Leu Met His Ser Thr His Ala Ala Leu Asp
1               5                   10                  15

Leu Lys Lys Gln Ser Leu Leu His Thr Gln Leu Arg Ile Lys Pro Phe
        20                  25                  30

Ser Pro Leu Phe Phe Ser Pro Leu Pro Pro Ser Ser Ser Ser Ser Ser
            35                  40                  45

Ser Ser Ser Ser Lys Pro Phe Thr Thr Leu Ala Leu Phe Lys Ser Lys
    50                  55                  60

Thr Lys Ala Ala Pro Ala Lys Lys Val Glu Pro Lys Leu Lys Thr
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Leu Gly Phe Ala Ala Ser
            100                 105                 110

Leu Leu Gly Glu Ala Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Thr Leu Leu Gly Ala Ile Gly Ala Leu Gly Asp Arg
145                 150                 155                 160

Gly Arg Phe Val Asp Asp Pro Pro Thr Gly Leu Glu Gly Ala Val Ile
                165                 170                 175

Arg Pro Gly Lys Gly Ile Arg Gly Ala Leu Gly Leu Asn Glu Gly Gly
            180                 185                 190

Pro Leu Phe Gly Phe Thr Lys Ala Asn Glu Leu Phe Val Gly Arg Leu
        195                 200                 205

Ala Gln Leu Gly Ile Ala Phe Ser Leu Ile Gly Glu Ile Ile Thr Gly
    210                 215                 220

Lys Gly Ala Leu Ala Gln Leu Asn Phe Glu Thr Gly Ile Pro Ile Ser
225                 230                 235                 240

Asp Ile Glu Pro Ile Val Leu Phe Asn Val Ala Phe Phe Phe Ala
                245                 250                 255

Ala Ile Asn Pro Gly Thr Gly Lys Phe Ile Thr Asp Glu Asp Glu Glu
            260                 265                 270

<210> SEQ ID NO 101
<211> LENGTH: 278
<212> TYPE: PRT
<213> ORGANISM: Corchorus capsularis

<400> SEQUENCE: 101

Met Ala Gln Thr Met Leu Leu Met Ser Ser Thr Ser Val Ser Thr Gly
1               5                   10                  15

His Ala Val Leu Asn Leu Lys Lys Glu His Pro Leu Phe Gln Leu Gln
            20                  25                  30

Ala His Gly Leu Lys Pro Lys Pro Phe Ser His Phe Leu Phe Asn Pro
        35                  40                  45

Leu Ser Thr Asn Thr Val Ser Thr Ser Ser Lys Gly Phe Thr Thr Phe
    50                  55                  60

Ala Ile Phe Lys Pro Arg Thr Lys Ala Ala Pro Lys Lys Ala Ala Pro
65                  70                  75                  80

Lys Pro Lys Leu Gln Val Glu Asp Gly Ile Phe Gly Thr Ser Gly Gly
                85                  90                  95

Ile Gly Phe Thr Lys Gln Asn Glu Leu Phe Val Gly Arg Val Ala Met
            100                 105                 110

```
Ile Gly Phe Ala Ala Ser Leu Leu Gly Glu Ala Ile Thr Gly Lys Gly
        115                 120                 125

Ile Leu Ala Gln Leu Asn Leu Glu Thr Gly Ile Pro Ile Tyr Glu Ala
        130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Arg Phe Val Asp Asp Pro Pro Thr Gly
                165                 170                 175

Ile Glu Gly Ala Val Ile Pro Pro Gly Lys Gly Ile Arg Gly Ala Leu
                180                 185                 190

Gly Leu Lys Glu Gly Gly Pro Leu Phe Gly Phe Thr Lys Ser Asn Glu
        195                 200                 205

Leu Phe Val Gly Arg Leu Ala Gln Leu Gly Ile Ala Phe Ser Leu Ile
        210                 215                 220

Gly Glu Ile Ile Thr Gly Lys Gly Ala Leu Ala Gln Leu Asn Ile Glu
225                 230                 235                 240

Thr Gly Ile Pro Val Asn Glu Ile Glu Pro Leu Val Leu Leu Asn Val
                245                 250                 255

Val Phe Phe Phe Leu Ala Ala Ile Asn Pro Gly Thr Gly Lys Phe Val
                260                 265                 270

Thr Asp Glu Glu Asp Asp
        275

<210> SEQ ID NO 102
<211> LENGTH: 278
<212> TYPE: PRT
<213> ORGANISM: Corchorus olitorius

<400> SEQUENCE: 102

Met Ala Gln Thr Met Leu Leu Met Ser Ser Thr Ser Val Ser Thr Gly
1               5                   10                  15

His Ala Val Leu Asn Leu Lys Lys Glu His Pro Leu Phe Gln Leu Gln
            20                  25                  30

Ala His Gly Leu Lys Pro Lys Pro Phe Ser Arg Phe Leu Phe Asn Pro
        35                  40                  45

Leu Ser Thr Asn Thr Val Ser Thr Ser Ser Lys Gly Phe Thr Thr Phe
50                  55                  60

Ala Ile Phe Lys Pro Arg Thr Lys Ala Ala Pro Lys Lys Ala Ala Pro
65                  70                  75                  80

Lys Pro Lys Leu Gln Val Glu Asp Gly Ile Phe Gly Thr Ser Gly Gly
            85                  90                  95

Ile Gly Phe Thr Lys Gln Asn Glu Leu Phe Val Gly Arg Val Ala Met
        100                 105                 110

Ile Gly Phe Ala Ala Ser Leu Leu Gly Glu Ala Ile Thr Gly Lys Gly
        115                 120                 125

Ile Leu Ala Gln Leu Asn Leu Glu Thr Gly Ile Pro Ile Tyr Glu Ala
        130                 135                 140

Glu Pro Leu Leu Leu Phe Phe Ile Leu Phe Thr Leu Leu Gly Ala Ile
145                 150                 155                 160

Gly Ala Leu Gly Asp Arg Gly Arg Phe Val Asp Asp Pro Pro Thr Gly
                165                 170                 175

Ile Glu Gly Ala Val Ile Pro Pro Gly Lys Gly Ile Arg Gly Ala Leu
                180                 185                 190

Gly Leu Lys Glu Gly Gly Pro Leu Phe Gly Phe Thr Lys Ser Asn Glu
```

```
                195                 200                 205
Leu Phe Val Gly Arg Leu Ala Gln Leu Gly Ile Ala Phe Ser Leu Ile
    210                 215                 220
Gly Glu Ile Ile Thr Gly Lys Gly Ala Leu Ala Gln Leu Asn Ile Glu
225                 230                 235                 240
Thr Gly Ile Pro Val Asn Glu Ile Glu Pro Leu Val Leu Leu Asn Val
                245                 250                 255
Val Phe Phe Phe Leu Ala Ala Ile Asn Pro Gly Thr Gly Lys Phe Val
                260                 265                 270
Thr Asp Glu Glu Glu Asp
            275

<210> SEQ ID NO 103
<211> LENGTH: 269
<212> TYPE: PRT
<213> ORGANISM: Gossypium arboreum

<400> SEQUENCE: 103

Met Ala Gln Thr Met Leu Leu Met Ser Ser His Ala Val Ser Leu Lys
1               5                   10                  15
Arg Asp His Pro Leu Leu His Phe Gln Ala Gln Gly Leu Lys Pro Lys
                20                  25                  30
Pro Val Ser His Leu Phe Phe Asn Pro Leu Ser Asn Gly Val His Thr
            35                  40                  45
Ser Ser Lys Ala Phe Thr Thr Leu Ala Met Phe Lys Ser Lys Thr Lys
        50                  55                  60
Ala Ala Pro Lys Arg Val Glu Pro Lys Ser Lys Pro Lys Val Glu Asp
65                  70                  75                  80
Gly Ile Phe Gly Thr Ser Gly Gly Ile Gly Phe Thr Lys Gln Asn Glu
                85                  90                  95
Leu Phe Val Gly Arg Val Ala Met Leu Gly Phe Ala Ala Ser Leu Leu
                100                 105                 110
Gly Glu Ala Ile Thr Gly Lys Gly Ile Leu Ala Gln Leu Asn Leu Glu
            115                 120                 125
Thr Gly Ile Pro Ile Tyr Glu Ala Glu Pro Leu Leu Phe Phe Phe Ile
        130                 135                 140
Leu Phe Thr Leu Leu Gly Ala Ile Gly Ala Leu Gly Asp Arg Gly Arg
145                 150                 155                 160
Phe Val Asp Asp Pro Pro Thr Gly Ile Glu Gly Ala Val Ile Pro Pro
                165                 170                 175
Gly Lys Gly Ile Arg Gly Ala Leu Gly Leu Lys Glu Gly Gly Pro Leu
                180                 185                 190
Phe Gly Phe Thr Lys Ala Asn Glu Leu Phe Val Gly Arg Leu Ala Gln
            195                 200                 205
Leu Gly Ile Ala Phe Ser Leu Ile Gly Glu Ile Ile Thr Gly Lys Gly
        210                 215                 220
Ala Leu Ala Gln Leu Asn Ile Glu Thr Gly Ile Pro Ile Ser Asp Ile
225                 230                 235                 240
Glu Pro Leu Val Leu Phe Asn Val Ala Phe Phe Phe Ala Ala Ile
                245                 250                 255
Asn Pro Gly Thr Gly Lys Phe Leu Thr Asp Glu Glu Glu
                260                 265

<210> SEQ ID NO 104
<211> LENGTH: 269
```

```
<212> TYPE: PRT
<213> ORGANISM: Gossypium arboreum

<400> SEQUENCE: 104

Met Ala Gln Thr Met Leu Leu Met Ser Ser His Ala Val Ser Leu Lys
1               5                   10                  15

Arg Asp His Pro Leu Leu His Phe Gln Ala Gln Gly Leu Lys Pro Lys
            20                  25                  30

Pro Val Ser His Leu Phe Phe Asn Pro Leu Ser Asn Gly Val His Thr
        35                  40                  45

Ser Ser Lys Ala Phe Thr Thr Leu Ala Ile Phe Lys Ser Lys Thr Lys
    50                  55                  60

Ala Ala Pro Lys Arg Val Glu Pro Lys Ser Lys Pro Lys Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Leu Gly Phe Ala Ala Ser Leu Leu
            100                 105                 110

Gly Glu Ala Ile Thr Gly Lys Gly Ile Leu Ala Gln Leu Asn Leu Glu
        115                 120                 125

Thr Gly Ile Pro Ile Tyr Glu Ala Glu Pro Leu Leu Leu Phe Phe Ile
    130                 135                 140

Leu Phe Thr Leu Leu Gly Ala Ile Gly Ala Leu Gly Asp Arg Gly Arg
145                 150                 155                 160

Phe Val Asp Asp Pro Pro Thr Gly Ile Glu Gly Ala Val Ile Pro Pro
                165                 170                 175

Gly Lys Gly Ile Arg Gly Ala Leu Gly Leu Lys Glu Gly Gly Pro Leu
            180                 185                 190

Phe Gly Phe Thr Lys Ala Asn Glu Leu Phe Val Gly Arg Leu Ala Gln
        195                 200                 205

Leu Gly Ile Ala Phe Ser Leu Ile Gly Glu Ile Ile Thr Gly Lys Gly
    210                 215                 220

Ala Leu Ala Gln Leu Asn Ile Glu Thr Gly Ile Pro Ile Ser Asp Ile
225                 230                 235                 240

Glu Pro Leu Val Leu Phe Asn Val Ala Phe Phe Phe Ala Ala Ile
                245                 250                 255

Asn Pro Gly Thr Gly Lys Phe Leu Thr Asp Glu Glu Glu
            260                 265

<210> SEQ ID NO 105
<211> LENGTH: 268
<212> TYPE: PRT
<213> ORGANISM: Gossypium hirsutum

<400> SEQUENCE: 105

Met Ala Gln Thr Met Leu Leu Met Ser Ser His Ala Val Ser Leu Lys
1               5                   10                  15

Arg Asp His Pro Leu Leu His Phe Gln Ala Gln Gly Leu Lys Pro Lys
            20                  25                  30

Pro Ala Ser His Leu Phe Phe Asn Pro Leu Ser Asn Gly Val His Thr
        35                  40                  45

Ser Pro Lys Ala Phe Thr Thr Leu Ala Val Phe Lys Ser Lys Thr Lys
    50                  55                  60

Ala Ala Pro Lys Arg Val Glu Pro Lys Pro Lys Val Glu Asp Gly Ile
65                  70                  75                  80
```

```
Phe Gly Thr Ser Gly Ile Gly Phe Thr Lys Gln Asn Glu Leu Phe
            85                  90                  95

Val Gly Arg Val Ala Met Leu Gly Phe Ala Ala Ser Leu Leu Gly Glu
            100                 105                 110

Ala Ile Thr Gly Lys Gly Ile Leu Ala Gln Leu Asn Leu Glu Thr Gly
            115                 120                 125

Ile Pro Ile Tyr Glu Ala Glu Pro Leu Leu Leu Phe Phe Ile Leu Phe
            130                 135                 140

Thr Leu Leu Gly Ala Ile Gly Ala Leu Gly Asp Arg Gly Arg Phe Val
145                 150                 155                 160

Asp Asp Pro Pro Thr Gly Ile Glu Gly Ala Val Ile Pro Pro Gly Lys
                165                 170                 175

Gly Ile Arg Gly Ala Leu Gly Leu Lys Glu Gly Pro Leu Phe Gly
            180                 185                 190

Phe Thr Lys Ala Asn Glu Leu Phe Val Gly Arg Leu Ala Gln Leu Gly
            195                 200                 205

Ile Ala Phe Ser Leu Ile Gly Glu Ile Ile Thr Gly Lys Gly Ala Leu
            210                 215                 220

Ala Gln Leu Asn Ile Glu Thr Gly Ile Pro Ile Ser Asp Ile Glu Pro
225                 230                 235                 240

Leu Val Leu Phe Asn Val Ala Phe Phe Phe Ala Ala Ile Asn Pro
                245                 250                 255

Gly Thr Gly Lys Phe Leu Thr Asp Glu Glu Glu
            260                 265

<210> SEQ ID NO 106
<211> LENGTH: 276
<212> TYPE: PRT
<213> ORGANISM: Theobroma cacao

<400> SEQUENCE: 106

Met Ala Gln Thr Met Leu Leu Met Ser Ser Thr Ser Val Ser Thr Ser
1               5                   10                  15

His Val Val Asn Leu Lys Arg Gly His Pro Leu Leu Gln Phe Gln Ala
            20                  25                  30

Gln Gly Leu Lys Pro Lys Pro Phe His Phe Leu Leu Asn Pro Phe
        35                  40                  45

Ser Asp Ser Val Ala Thr Ser Ser Arg Gly Phe Thr Thr Phe Ala Val
    50                  55                  60

Phe Lys Pro Lys Thr Lys Ala Ala Pro Lys Arg Ala Ala Ala Pro Pro
65                  70                  75                  80

Lys Leu Lys Val Glu Asp Gly Ile Phe Gly Thr Ser Gly Gly Ile Gly
            85                  90                  95

Phe Thr Lys Gln Asn Glu Leu Phe Val Gly Arg Val Ala Met Leu Gly
            100                 105                 110

Phe Ala Ala Ser Leu Leu Gly Glu Ala Ile Thr Gly Lys Gly Ile Leu
            115                 120                 125

Ala Gln Leu Asn Leu Glu Thr Gly Ile Pro Ile Tyr Glu Ala Glu Pro
            130                 135                 140

Leu Leu Leu Phe Phe Ile Leu Phe Thr Leu Leu Gly Ala Ile Gly Ala
145                 150                 155                 160

Leu Gly Asp Arg Gly Ser Phe Val Asp Asp Pro Pro Ser Gly Ile Glu
                165                 170                 175

Gly Ala Val Ile Pro Pro Gly Arg Gly Ile Arg Gly Ala Leu Gly Leu
            180                 185                 190
```

```
Lys Glu Gly Gly Pro Leu Phe Gly Phe Thr Lys Ala Asn Glu Leu Phe
            195                 200                 205

Val Gly Arg Leu Ala Gln Leu Gly Ile Ala Phe Ser Leu Ile Gly Glu
        210                 215                 220

Ile Ile Thr Gly Lys Gly Ala Leu Ala Gln Leu Asn Ile Glu Thr Gly
225                 230                 235                 240

Ile Pro Ile Ser Asp Ile Glu Pro Leu Val Leu Phe Asn Val Ala Phe
                245                 250                 255

Phe Phe Phe Ala Ala Ile Asn Pro Gly Thr Gly Lys Phe Val Thr Asp
            260                 265                 270

Glu Asp Glu Lys
        275

<210> SEQ ID NO 107
<211> LENGTH: 276
<212> TYPE: PRT
<213> ORGANISM: Theobroma cacao

<400> SEQUENCE: 107

Met Ala Gln Thr Met Leu Leu Met Ser Ser Thr Ser Val Ser Thr Ser
1               5                   10                  15

His Val Val Asn Leu Lys Arg Gly His Pro Leu Leu Gln Phe Gln Ala
            20                  25                  30

Gln Gly Leu Lys Pro Lys Pro Phe His Phe Leu Leu Asn Pro Phe
        35                  40                  45

Ser Asp Ser Val Ala Thr Ser Ser Arg Gly Phe Thr Thr Phe Ala Val
    50                  55                  60

Phe Lys Pro Lys Thr Lys Ala Ala Pro Lys Arg Val Ala Ala Pro Pro
65                  70                  75                  80

Lys Leu Lys Val Glu Asp Gly Ile Phe Gly Thr Ser Gly Gly Ile Gly
                85                  90                  95

Phe Thr Lys Gln Asn Glu Leu Phe Val Gly Arg Val Ala Met Leu Gly
            100                 105                 110

Phe Ala Ala Ser Leu Leu Gly Glu Ala Ile Thr Gly Lys Gly Ile Leu
        115                 120                 125

Ala Gln Leu Asn Leu Glu Thr Gly Ile Pro Ile Tyr Glu Ala Glu Pro
130                 135                 140

Leu Leu Leu Phe Phe Ile Leu Phe Thr Leu Leu Gly Ala Ile Gly Ala
145                 150                 155                 160

Leu Gly Asp Arg Gly Ser Phe Val Asp Asp Pro Pro Ser Gly Ile Glu
                165                 170                 175

Gly Ala Val Ile Pro Pro Gly Arg Gly Ile Arg Gly Ala Leu Gly Leu
            180                 185                 190

Lys Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Leu Ile Gly Glu
    210                 215                 220

Ile Ile Thr Gly Lys Gly Ala Leu Ala Gln Leu Asn Ile Glu Thr Gly
225                 230                 235                 240

Ile Pro Ile Ser Asp Ile Glu Pro Leu Val Leu Phe Asn Val Ala Phe
                245                 250                 255

Phe Phe Phe Ala Ala Ile Asn Pro Gly Thr Gly Lys Phe Val Thr Asp
            260                 265                 270

Glu Asp Glu Glu
```

<210> SEQ ID NO 108
<211> LENGTH: 277
<212> TYPE: PRT
<213> ORGANISM: Gossypioides kirkii

<400> SEQUENCE: 108

```
Met Ala Gln Thr Met Leu Val Met Ser Ser Thr Ser Val Ser Ala Ser
1               5                   10                  15

His Val Val Asn Leu Lys Arg Asp His Pro Leu Leu His Phe Gln Ala
            20                  25                  30

Gln Gly Leu Lys Pro Lys Pro Phe Ser His Phe Leu Phe Asn Pro Leu
        35                  40                  45

Ser Asn Ala Val Ala Ala Ser Ser Ser Lys Ala Phe Thr Thr Phe Ala
    50                  55                  60

Leu Phe Lys Ser Lys Thr Lys Ala Ala Pro Lys Lys Ala Glu Pro Lys
65                  70                  75                  80

Pro Lys Pro Lys Val Glu Asp Gly Ile Phe Gly Thr Ser Gly Gly Ile
                85                  90                  95

Gly Phe Thr Lys Gln Asn Glu Leu Phe Val Gly Arg Val Ala Met Ile
            100                 105                 110

Gly Phe Ala Ala Ser Leu Leu Gly Glu Ala Ile Thr Gly Lys Gly Ile
        115                 120                 125

Leu Ala Gln Leu Asn Leu Glu Thr Gly Ile Pro Ile Tyr Glu Ala Glu
    130                 135                 140

Pro Leu Leu Leu Phe Phe Ile Leu Phe Thr Leu Leu Gly Ala Ile Gly
145                 150                 155                 160

Ala Leu Gly Asp Arg Gly Arg Phe Val Asp Glu Pro Thr Gly Val
                165                 170                 175

Glu Gly Ala Val Ile Pro Pro Gly Lys Gly Val Arg Gly Ala Leu Gly
            180                 185                 190

Leu Lys Glu Gly Gly Pro Leu Phe Gly Phe Thr Lys Ala Asn Glu Leu
        195                 200                 205

Phe Val Gly Arg Leu Ala Gln Leu Gly Ile Ala Phe Ser Leu Ile Gly
    210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Val Leu Phe Asn Val Ala
                245                 250                 255

Phe Phe Phe Ala Ala Ile Asn Pro Gly Thr Gly Lys Phe Val Thr
            260                 265                 270

Asp Glu Glu Asp
        275
```

<210> SEQ ID NO 109
<211> LENGTH: 278
<212> TYPE: PRT
<213> ORGANISM: Gossypium hirsutum

<400> SEQUENCE: 109

```
Met Ala Gln Thr Met Leu Val Met Ser Ser Thr Ser Val Ser Thr Ser
1               5                   10                  15

His Val Val Asn Leu Lys Arg Asp His Pro Leu Leu His Phe Gln Ala
            20                  25                  30

Gln Gly Leu Lys Pro Lys Pro Ser Ser His Phe Leu Phe Asn Pro His
```

```
                35                  40                  45
Ser Asn Thr Val Ala Ala Ser Ser Lys Ala Phe Thr Thr Phe Ala
 50                  55                  60

Leu Phe Lys Pro Lys Thr Lys Ala Ala Pro Lys Ala Ala Pro Lys
 65                  70                  75                  80

Pro Lys Pro Lys Val Glu Asp Gly Ile Phe Gly Thr Ser Gly Gly Ile
                 85                  90                  95

Gly Phe Thr Lys Gln Asn Glu Leu Phe Val Gly Arg Val Ala Met Ile
                100                 105                 110

Gly Phe Ala Ala Ser Leu Leu Gly Glu Ala Ile Thr Gly Lys Gly Ile
                115                 120                 125

Leu Ala Gln Leu Asn Leu Glu Thr Gly Ile Pro Ile Tyr Glu Ala Glu
130                 135                 140

Pro Leu Leu Leu Phe Phe Ile Leu Phe Thr Leu Gly Ala Ile Gly
145                 150                 155                 160

Ala Leu Gly Asp Arg Gly Lys Phe Val Asp Glu Pro Pro Thr Gly Ile
                165                 170                 175

Glu Gly Ala Val Ile Pro Pro Gly Lys Gly Ile Arg Gly Thr Leu Gly
                180                 185                 190

Leu Lys Glu Gly Gly Pro Leu Phe Gly Phe Thr Lys Ala Asn Glu Leu
                195                 200                 205

Phe Val Gly Arg Leu Ala Gln Leu Gly Ile Ala Ile Ser Leu Ile Gly
                210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Ala Leu Phe Asn Val Ala
                245                 250                 255

Phe Phe Phe Phe Ala Ala Ile Asn Pro Gly Thr Gly Lys Phe Val Thr
                260                 265                 270

Asp Glu Ala Glu Glu Asp
                275

<210> SEQ ID NO 110
<211> LENGTH: 278
<212> TYPE: PRT
<213> ORGANISM: Gossypium arboreum

<400> SEQUENCE: 110

Met Ala Gln Thr Met Leu Val Met Ser Ser Thr Ser Val Ser Thr Ser
 1               5                  10                  15

His Val Val Asn Leu Lys Arg Asp His Pro Leu Leu His Phe Gln Ala
                 20                  25                  30

Gln Gly Leu Lys Pro Lys Pro Ser Ser His Phe Leu Phe Asn Pro His
                 35                  40                  45

Ser Asn Thr Val Ala Ala Ser Ser Lys Ala Phe Thr Thr Phe Ala
 50                  55                  60

Leu Phe Lys Pro Lys Thr Lys Ala Ala Pro Lys Ala Ala Pro Lys
 65                  70                  75                  80

Pro Lys Pro Lys Val Glu Asp Gly Ile Phe Gly Thr Ser Gly Gly Ile
                 85                  90                  95

Gly Phe Thr Lys Gln Asn Glu Leu Phe Val Gly Arg Val Ala Met Ile
                100                 105                 110

Gly Phe Ala Ala Ser Leu Leu Gly Glu Ala Ile Thr Gly Lys Gly Ile
                115                 120                 125
```

```
Leu Ala Gln Leu Asn Leu Glu Thr Gly Ile Pro Ile Tyr Glu Ala Glu
        130                 135                 140

Pro Leu Leu Phe Phe Ile Leu Phe Thr Leu Leu Gly Ala Ile Gly
145                 150                 155                 160

Ala Leu Gly Asp Arg Gly Lys Phe Val Asp Glu Pro Pro Thr Gly Ile
                165                 170                 175

Glu Gly Ala Val Ile Pro Pro Gly Lys Gly Ile Arg Gly Ala Leu Gly
                180                 185                 190

Leu Lys Glu Gly Gly Pro Leu Phe Gly Phe Thr Lys Ala Asn Glu Leu
                195                 200                 205

Phe Val Gly Arg Leu Ala Gln Leu Gly Ile Ala Phe Ser Leu Ile Gly
210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Val Leu Asn Val Ala
                245                 250                 255

Phe Phe Phe Phe Ala Ala Ile Asn Pro Gly Thr Gly Lys Phe Val Thr
                260                 265                 270

Asp Glu Ala Glu Glu Asp
            275

<210> SEQ ID NO 111
<211> LENGTH: 274
<212> TYPE: PRT
<213> ORGANISM: Gossypium hirsutum

<400> SEQUENCE: 111

Met Leu Val Met Ser Ser Thr Ser Val Ser Thr Ser His Val Val Asn
1               5                   10                  15

Leu Lys Arg Asp His Pro Leu Leu His Phe Gln Ala Gln Gly Leu Lys
                20                  25                  30

Pro Lys Pro Ser Ser His Phe Leu Phe Asn Pro His Ser Asn Thr Val
            35                  40                  45

Ala Ala Ser Ser Ser Lys Ala Phe Thr Thr Phe Ala Leu Phe Lys Pro
50                  55                  60

Lys Thr Lys Ala Ala Pro Lys Lys Ala Pro Lys Pro Lys Pro Lys
65                  70                  75                  80

Val Glu Asp Gly Ile Phe Gly Thr Ser Gly Ile Gly Phe Thr Lys
                85                  90                  95

Gln Asn Glu Leu Phe Val Gly Arg Val Ala Met Ile Gly Phe Ala Ala
            100                 105                 110

Ser Leu Leu Gly Glu Ala Ile Thr Gly Lys Gly Ile Leu Ala Gln Leu
        115                 120                 125

Asn Leu Glu Thr Gly Ile Pro Ile Tyr Glu Ala Glu Pro Leu Leu Leu
    130                 135                 140

Phe Phe Ile Leu Phe Thr Leu Leu Gly Ala Ile Gly Ala Leu Gly Asp
145                 150                 155                 160

Arg Gly Lys Phe Val Asp Glu Pro Pro Thr Gly Ile Glu Gly Ala Val
                165                 170                 175

Ile Pro Pro Gly Lys Gly Ile Arg Gly Ala Leu Gly Leu Lys Glu Gly
            180                 185                 190

Gly Pro Leu Phe Gly Phe Thr Lys Ala Asn Glu Leu Phe Val Gly Arg
        195                 200                 205

Leu Ala Gln Leu Gly Ile Ala Phe Ser Leu Ile Gly Glu Ile Ile Thr
    210                 215                 220
```

```
Gly Lys Gly Ala Leu Ala Gln Leu Asn Ile Glu Thr Gly Ile Pro Ile
225                 230                 235                 240

Ser Asp Ile Glu Pro Leu Val Leu Phe Asn Val Ala Phe Phe Phe
                245                 250                 255

Ala Ala Ile Asn Pro Gly Thr Gly Lys Phe Val Thr Asp Glu Ala Glu
            260                 265                 270

Glu Asp

<210> SEQ ID NO 112
<211> LENGTH: 278
<212> TYPE: PRT
<213> ORGANISM: Gossypium hirsutum

<400> SEQUENCE: 112

Met Ala Gln Thr Met Leu Val Met Ser Ser Thr Ser Val Ser Thr Ser
1               5                   10                  15

His Val Val Asn Leu Lys Arg Asp His Pro Leu Leu His Phe Gln Ala
                20                  25                  30

Gln Gly Leu Lys Pro Lys Pro Ser Ser His Phe Leu Phe Asn Pro His
            35                  40                  45

Ser Asn Thr Val Ala Ala Ser Ser Ser Lys Ala Phe Thr Thr Phe Ala
        50                  55                  60

Leu Phe Lys Pro Lys Thr Lys Ala Ala Pro Lys Lys Ala Ala Pro Lys
65                  70                  75                  80

Pro Lys Pro Lys Val Glu Asp Gly Ile Phe Gly Thr Ser Gly Gly Ile
                85                  90                  95

Gly Phe Thr Lys Gln Asn Glu Leu Phe Val Gly Arg Val Ala Met Ile
                100                 105                 110

Gly Phe Ala Ala Ser Leu Leu Gly Glu Ala Ile Thr Gly Lys Gly Ile
            115                 120                 125

Leu Ala Gln Leu Asn Leu Glu Thr Gly Ile Pro Ile Tyr Glu Ala Glu
130                 135                 140

Pro Leu Leu Leu Phe Phe Ile Leu Phe Thr Leu Leu Gly Ala Ile Gly
145                 150                 155                 160

Ala Leu Gly Asp Arg Gly Lys Phe Val Asp Glu Pro Pro Thr Gly Ile
                165                 170                 175

Glu Gly Ala Val Ile Pro Pro Gly Lys Gly Ile Arg Gly Ala Leu Gly
            180                 185                 190

Leu Lys Glu Gly Gly Pro Leu Phe Gly Phe Thr Lys Ala Asn Glu Leu
        195                 200                 205

Phe Val Gly Arg Leu Ala Gln Leu Gly Ile Ala Phe Ser Leu Ile Gly
210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Val Leu Phe Asn Val Ala
                245                 250                 255

Phe Phe Phe Phe Ala Ala Ile Asn Pro Gly Thr Gly Lys Phe Val Thr
            260                 265                 270

Asp Glu Ala Glu Glu Asp
        275

<210> SEQ ID NO 113
<211> LENGTH: 278
<212> TYPE: PRT
<213> ORGANISM: Gossypium hirsutum
```

```
<400> SEQUENCE: 113

Met Ala Gln Thr Met Leu Val Met Ser Ser Thr Arg Val Ser Thr Ser
1               5                   10                  15

His Val Val Asn Leu Lys Arg Asp His Thr Leu Leu His Phe Gln Ala
            20                  25                  30

Gln Gly Leu Lys Pro Lys Pro Ser Ser His Phe Leu Phe Asn Pro His
        35                  40                  45

Ser Asn Thr Val Ala Ala Ser Ser Ser Lys Ala Phe Thr Thr Phe Ala
    50                  55                  60

Leu Phe Lys Pro Lys Thr Lys Ala Ala Pro Lys Lys Ala Ala Pro Lys
65                  70                  75                  80

Pro Lys Pro Lys Val Glu Asp Gly Ile Phe Gly Thr Ser Gly Gly Ile
                85                  90                  95

Gly Phe Thr Lys Gln Asn Glu Leu Phe Val Gly Arg Val Ala Met Ile
            100                 105                 110

Gly Phe Ala Ala Ser Leu Leu Gly Glu Ala Ile Thr Gly Lys Gly Ile
        115                 120                 125

Leu Ala Gln Leu Asn Leu Glu Thr Gly Ile Pro Ile Tyr Glu Ala Glu
    130                 135                 140

Pro Leu Leu Leu Phe Phe Ile Leu Phe Thr Leu Leu Gly Ala Ile Gly
145                 150                 155                 160

Ala Leu Gly Asp Arg Gly Lys Phe Val Asp Glu Pro Thr Gly Ile
                165                 170                 175

Glu Gly Ala Val Ile Pro Pro Gly Lys Gly Ile Arg Gly Ala Leu Gly
        180                 185                 190

Leu Lys Glu Gly Gly Pro Leu Phe Gly Phe Thr Lys Ala Asn Glu Leu
    195                 200                 205

Phe Val Gly Arg Leu Ala Gln Leu Gly Ile Ala Phe Ser Leu Ile Gly
210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Val Leu Phe Asn Val Ala
            245                 250                 255

Phe Phe Phe Phe Ala Ala Ile Asn Pro Gly Thr Gly Lys Phe Val Thr
        260                 265                 270

Asp Glu Ala Glu Glu Asp
        275

<210> SEQ ID NO 114
<211> LENGTH: 278
<212> TYPE: PRT
<213> ORGANISM: Gossypium raimondii

<400> SEQUENCE: 114

Met Ala Gln Thr Met Leu Val Met Ser Ser Thr Ser Val Ser Thr Ser
1               5                   10                  15

His Val Val Asn Leu Lys Arg Asp His Thr Leu Leu His Phe Gln Ala
            20                  25                  30

Gln Gly Leu Lys Pro Lys Pro Ser Ser His Phe Leu Phe Asn Pro His
        35                  40                  45

Ser Asn Thr Val Ala Ala Ser Ser Ser Lys Ala Phe Thr Thr Phe Ala
    50                  55                  60

Leu Phe Lys Pro Lys Thr Lys Ala Ala Pro Lys Lys Ala Ala Pro Lys
65                  70                  75                  80
```

-continued

Pro Lys Pro Lys Val Glu Asp Gly Ile Phe Gly Thr Ser Gly Gly Ile
            85                  90                  95

Gly Phe Thr Lys Gln Asn Glu Leu Phe Val Gly Arg Val Ala Met Ile
                100                 105                 110

Gly Phe Ala Ala Ser Leu Leu Gly Glu Ala Ile Thr Gly Lys Gly Ile
            115                 120                 125

Leu Ala Gln Leu Asn Leu Glu Thr Gly Ile Pro Ile Tyr Glu Ala Glu
        130                 135                 140

Pro Leu Leu Leu Phe Phe Ile Leu Phe Thr Leu Leu Gly Ala Ile Gly
145                 150                 155                 160

Ala Leu Gly Asp Arg Gly Lys Phe Val Asp Glu Pro Pro Thr Gly Ile
                165                 170                 175

Glu Gly Ala Val Ile Pro Pro Gly Lys Gly Ile Arg Gly Ala Leu Gly
                180                 185                 190

Leu Lys Glu Gly Gly Pro Leu Phe Gly Phe Thr Lys Ala Asn Glu Leu
        195                 200                 205

Phe Val Gly Arg Leu Ala Gln Leu Gly Ile Ala Phe Ser Leu Ile Gly
210                 215                 220

Glu Ile Ile Thr Gly Lys Gly Ala Leu Ala Gln Leu Asn Ile Glu Thr
225                 230                 235                 240

Gly Ile Pro Ile Ser Asp Ile Glu Pro Leu Val Leu Phe Asn Val Ala
                245                 250                 255

Phe Phe Phe Phe Ala Ala Ile Asn Pro Gly Thr Gly Lys Phe Val Thr
                260                 265                 270

Asp Glu Ala Glu Glu Asp
        275

<210> SEQ ID NO 115
<211> LENGTH: 274
<212> TYPE: PRT
<213> ORGANISM: Durio zibethinus

<400> SEQUENCE: 115

Met Ala Gln Thr Val Leu Leu Met Ser Ser Thr Ser Val Ser Thr Ser
1               5                   10                  15

His Val Asn Leu Lys Arg Asn Gln Pro Leu Leu His Phe Gln Pro
            20                  25                  30

Gln Gly Leu Lys Pro Lys Pro Phe Ser His Phe Leu Phe Asn Pro Pro
        35                  40                  45

Ser Asn Gly Val Ala Thr Ser Ser Lys Ala Phe Thr Thr Phe Ala Ile
    50                  55                  60

Phe Lys Ser Lys Thr Lys Ala Val Pro Lys Lys Val Ala Gln Lys Pro
65                  70                  75                  80

Lys Val Glu Asp Gly Ile Phe Gly Thr Ser Gly Gly Ile Gly Phe Thr
                85                  90                  95

Lys Gln Asn Glu Leu Phe Val Gly Arg Val Ala Met Leu Gly Phe Ala
            100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
    130                 135                 140

Leu Phe Phe Ile Leu Phe Thr Leu Leu Gly Ala Ile Gly Ala Leu Gly
145                 150                 155                 160

Asp Arg Gly Arg Phe Val Asp Asp Pro Pro Thr Gly Ile Glu Gly Ala

```
                    165                 170                 175
Val Ile Pro Pro Gly Lys Gly Ile Arg Gly Ala Leu Gly Leu Lys Glu
                180                 185                 190

Gly Gly Pro Leu Phe Gly Phe Thr Lys Ser Asn Glu Leu Phe Val Gly
            195                 200                 205

Arg Leu Ala Gln Leu Gly Ile Val Phe Ser Leu Ile Gly Glu Ile Ile
        210                 215                 220

Thr Gly Lys Gly Ala Leu Ala Gln Leu Asn Ile Glu Thr Gly Ile Pro
225                 230                 235                 240

Ile Asn Asp Ile Glu Pro Leu Val Leu Phe Asn Val Ala Phe Phe
                245                 250                 255

Phe Ala Ala Ile Asn Pro Gly Thr Gly Lys Phe Leu Thr Asp Glu Asp
                260                 265                 270

Glu Glu

<210> SEQ ID NO 116
<211> LENGTH: 276
<212> TYPE: PRT
<213> ORGANISM: Durio zibethinus

<400> SEQUENCE: 116

Met Ala Gln Thr Met Leu Leu Met Ser Ser Thr Cys Val Ser Thr Ser
1               5                   10                  15

His Val Val Asn Leu Lys Arg Asp Leu Pro Leu Leu His Phe Gln Ala
                20                  25                  30

Gln Gly Leu Lys Pro Lys Pro Phe Ser His Phe Leu Phe Asn Pro Leu
            35                  40                  45

Ser Asn Gly Val Ala Thr Ser Ser Lys Ala Phe Thr Thr Phe Ala Val
        50                  55                  60

Phe Lys Ser Arg Thr Lys Ala Ala Pro Lys Lys Val Glu Pro Lys Pro
65                  70                  75                  80

Lys Pro Lys Val Glu Asp Gly Ile Phe Gly Thr Ser Gly Gly Ile Gly
                85                  90                  95

Phe Thr Lys Gln Asn Glu Leu Phe Val Gly Arg Val Ala Met Leu Gly
                100                 105                 110

Phe Ala Ala Ser Leu Leu Gly Glu Ala Ile Thr Gly Lys Gly Ile Leu
            115                 120                 125

Ala Gln Leu Asn Leu Glu Thr Gly Ile Pro Ile Tyr Glu Ala Glu Pro
        130                 135                 140

Leu Leu Leu Phe Phe Ile Leu Phe Thr Leu Leu Gly Ala Ile Gly Ala
145                 150                 155                 160

Leu Gly Asp Arg Gly Ser Phe Val Asp Asp Pro Pro Thr Gly Val Glu
                165                 170                 175

Gly Ala Val Ile Pro Pro Gly Lys Gly Ile Arg Gly Ala Leu Gly Leu
                180                 185                 190

Lys Glu Gly Gly Pro Leu Phe Gly Phe Thr Lys Ala Asn Glu Leu Phe
            195                 200                 205

Val Gly Arg Leu Ala Gln Leu Gly Ile Ala Phe Ser Leu Ile Gly Glu
        210                 215                 220

Ile Ile Thr Gly Lys Gly Ala Leu Ala Gln Leu Asn Ile Glu Thr Gly
225                 230                 235                 240

Ile Pro Ile Asn Asp Ile Glu Pro Leu Val Leu Phe Asn Val Ala Phe
                245                 250                 255

Phe Phe Phe Ala Ala Ile Asn Pro Gly Thr Gly Lys Phe Val Thr Asp
```

```
            260                 265                 270
Glu Asp Glu Glu
        275

<210> SEQ ID NO 117
<211> LENGTH: 273
<212> TYPE: PRT
<213> ORGANISM: Nelumbo nucifera

<400> SEQUENCE: 117

Met Ala Gln Ser Met Met Leu Met Ser Arg Val Ala Gly His Val Leu
1               5                   10                  15

Asp Leu Lys Arg Glu Pro Val Leu Gln Ser Gln Val Gln Arg Leu Arg
            20                  25                  30

Pro Lys Pro Phe Ser His Leu Val Leu Pro Pro Leu Ser Thr Arg Pro
        35                  40                  45

His Ser Thr Ser Ser Ser Ala Ser Thr Val Val Ser Leu Phe Lys Ala
    50                  55                  60

Arg Thr Lys Ala Ala Pro Ala Lys Val Glu Lys Pro Lys Glu Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Leu Gly Phe Ala Ala Ser
            100                 105                 110

Leu Leu Gly Glu Gly Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Thr Leu Leu Gly Ala Ile Gly Ala Leu Gly Asp Arg
145                 150                 155                 160

Gly Arg Phe Val Asp Asp Pro Thr Gly Leu Glu Arg Ala Val Ile
                165                 170                 175

Pro Pro Gly Lys Ser Phe Arg Ala Ala Leu Gly Leu Asn Glu Gly Gly
            180                 185                 190

Pro Leu Phe Gly Phe Thr Lys Ala Asn Glu Leu Phe Val Gly Arg Leu
        195                 200                 205

Ala Gln Leu Gly Ile Ala Phe Ser Leu Ile Gly Glu Ile Ile Thr Gly
    210                 215                 220

Lys Gly Ala Leu Ala Gln Leu Asn Ile Glu Thr Gly Val Pro Ile Asn
225                 230                 235                 240

Glu Leu Glu Pro Leu Leu Leu Phe Asn Val Ala Phe Phe Phe Ala
                245                 250                 255

Ala Ile Asn Pro Gly Thr Gly Lys Phe Leu Thr Asp Glu Glu Asp
            260                 265                 270

Glu

<210> SEQ ID NO 118
<211> LENGTH: 270
<212> TYPE: PRT
<213> ORGANISM: Vitis vinifera

<400> SEQUENCE: 118

Met Ala Gln Thr Met Leu Ile Thr Pro Ser Val Ser Gly His Ser Val
1               5                   10                  15

Leu Asp Leu Lys Arg Gln Pro Leu Leu Gln Arg Leu Arg Pro Lys Pro
            20                  25                  30
```

```
Phe Ser His Leu Leu Pro Pro Leu Pro Thr Ser Ser Thr Ser
            35                  40                  45

Ser Pro Ala Phe Thr Thr Leu Ala Leu Phe Lys Ser Lys Thr Lys Ala
 50                  55                  60

Ala Pro Ser Lys Lys Val Thr Lys Pro Lys Pro Gln Val Glu Asp Gly
 65                  70                  75                  80

Ile Phe Gly Thr Ser Gly Gly Ile Gly Phe Thr Lys Lys Asn Glu Leu
                    85                  90                  95

Phe Val Gly Arg Val Ala Met Leu Gly Phe Ala Ala Ser Leu Leu Gly
                100                 105                 110

Glu Ala Ile Thr Gly Lys Gly Ile Leu Ala Gln Leu Asn Leu Glu Thr
                115                 120                 125

Gly Ile Pro Ile Tyr Glu Ala Glu Pro Leu Leu Leu Phe Phe Ile Leu
130                 135                 140

Phe Thr Leu Leu Gly Ala Ile Gly Ala Leu Gly Asp Arg Gly Arg Phe
145                 150                 155                 160

Val Asp Asp Asp Pro Pro Thr Gly Ile Glu Gly Ala Val Ile Pro Pro
                165                 170                 175

Gly Lys Gly Leu Arg Ser Ala Leu Gly Leu Arg Glu Gly Gly Pro Leu
                180                 185                 190

Phe Gly Phe Thr Lys Ser Asn Glu Leu Phe Val Gly Arg Leu Ala Gln
                195                 200                 205

Leu Gly Ile Val Phe Ser Ile Ile Gly Glu Ile Ile Thr Gly Lys Gly
                210                 215                 220

Ala Leu Ala Gln Leu Asn Ile Glu Thr Gly Val Pro Ile Ser Asp Ile
225                 230                 235                 240

Glu Pro Leu Val Leu Phe Asn Val Ile Phe Phe Phe Ala Ala Leu
                245                 250                 255

Asn Pro Gly Ser Gly Lys Phe Val Thr Asp Asp Glu Glu
                260                 265                 270

<210> SEQ ID NO 119
<211> LENGTH: 270
<212> TYPE: PRT
<213> ORGANISM: Vitis vinifera

<400> SEQUENCE: 119

Met Ala Gln Thr Met Leu Ile Thr Pro Ser Val Ser Gly His Ser Val
  1               5                  10                  15

Leu Asp Leu Lys Arg Gln Pro Leu Leu Gln Arg Leu Arg Pro Lys Pro
                 20                  25                  30

Phe Ser His Leu Leu Leu Pro Pro Leu Pro Thr Ser Ser Ser Thr Ser
            35                  40                  45

Ser Pro Ala Phe Thr Thr Leu Ala Leu Phe Lys Ser Lys Thr Lys Ala
 50                  55                  60

Ala Pro Pro Lys Lys Val Thr Lys Pro Lys Pro Gln Val Glu Asp Gly
 65                  70                  75                  80

Ile Phe Gly Thr Ser Gly Gly Ile Gly Phe Thr Lys Lys Asn Glu Leu
                    85                  90                  95

Phe Val Gly Arg Val Ala Met Leu Gly Phe Ala Ala Ser Leu Leu Gly
                100                 105                 110

Glu Ala Ile Thr Gly Lys Gly Ile Leu Ala Gln Leu Asn Leu Glu Thr
                115                 120                 125

Gly Ile Pro Ile Tyr Glu Ala Glu Pro Leu Leu Leu Phe Phe Ile Leu
```

```
              130                 135                 140
Phe Thr Leu Leu Gly Ala Ile Gly Ala Leu Gly Asp Arg Gly Arg Phe
145                 150                 155                 160

Val Asp Asp Pro Pro Thr Gly Ile Glu Gly Ala Val Ile Pro Pro
                165                 170                 175

Gly Lys Gly Leu Arg Ser Ala Leu Gly Leu Arg Glu Gly Gly Pro Leu
                180                 185                 190

Phe Gly Phe Thr Lys Ser Asn Glu Leu Phe Val Gly Arg Leu Ala Gln
                195                 200                 205

Leu Gly Ile Val Phe Ser Ile Ile Gly Glu Ile Ile Thr Gly Lys Gly
                210                 215                 220

Ala Leu Ala Gln Leu Asn Ile Glu Thr Gly Val Pro Ile Ser Asp Ile
225                 230                 235                 240

Glu Pro Leu Val Leu Phe Asn Val Ile Phe Phe Phe Ala Ala Leu
                245                 250                 255

Asn Pro Gly Ser Gly Lys Phe Val Thr Asp Asp Glu Glu Glu
                260                 265                 270

<210> SEQ ID NO 120
<211> LENGTH: 281
<212> TYPE: PRT
<213> ORGANISM: Citrus sinensis

<400> SEQUENCE: 120

Met Ala Gln Thr Met Leu Leu Met Ser Gly Val Ser Thr Ser His Ala
1               5                   10                  15

Gly Asn Leu Lys Arg Asp Ser Leu Val Thr Phe Gln Thr Gln Met Leu
                20                  25                  30

Arg Pro Lys Pro Phe Ser His Leu Met Phe Asn Pro Leu Ser Asn Glu
                35                  40                  45

Ser Leu Thr Ala Ala Ala Ala Ser Ser Ser Lys Ala Phe Ser Thr
50                  55                  60

Val Ala Leu Phe Lys Ser Lys Thr Lys Ala Pro Pro Lys Thr Lys Lys
65                  70                  75                  80

Val Glu Ser Lys Pro Lys Val Glu Asp Gly Ile Phe Gly Thr Ser Gly
                85                  90                  95

Gly Phe Gly Phe Thr Lys Gln Asn Glu Leu Phe Val Gly Arg Val Ala
                100                 105                 110

Met Ile Gly Phe Ala Ala Ser Leu Leu Gly Glu Gly Ile Thr Gly Lys
                115                 120                 125

Gly Ile Leu Ala Gln Leu Asn Leu Glu Thr Gly Ile Pro Ile Tyr Glu
                130                 135                 140

Ala Glu Pro Leu Leu Leu Phe Phe Ile Leu Phe Thr Leu Leu Gly Ala
145                 150                 155                 160

Ile Gly Ala Leu Gly Asp Arg Gly Lys Phe Val Asp Glu Pro Asp Glu
                165                 170                 175

Pro Thr Gly Leu Gly Gly Ala Val Ile Pro Pro Gly Lys Gly Leu Arg
                180                 185                 190

Ser Ala Leu Gly Leu Lys Glu Gly Pro Ile Phe Gly Phe Thr Lys
                195                 200                 205

Ser Asn Glu Leu Phe Val Gly Arg Leu Ala Gln Leu Gly Ile Ala Phe
                210                 215                 220

Ser Leu Ile Gly Glu Ile Ile Thr Gly Lys Gly Ala Leu Ala Gln Leu
225                 230                 235                 240
```

Asn Ile Glu Thr Gly Ile Pro Ile Asn Glu Ile Glu Pro Leu Val Leu
            245                 250                 255

Phe Asn Val Ile Phe Phe Phe Val Ala Ala Leu Asn Pro Gly Thr Gly
            260                 265                 270

Lys Phe Val Thr Asp Glu Asp Glu Glu
        275                 280

<210> SEQ ID NO 121
<211> LENGTH: 281
<212> TYPE: PRT
<213> ORGANISM: Citrus clementina

<400> SEQUENCE: 121

Met Ala Gln Thr Met Leu Leu Met Ser Gly Val Ser Thr Ser His Ala
1               5                   10                  15

Gly Asn Leu Lys Arg Asp Ser Leu Val Thr Phe Gln Thr Gln Met Leu
            20                  25                  30

Arg Pro Lys Pro Phe Ser His Leu Met Phe Asn Pro Leu Ser Asn Glu
        35                  40                  45

Ser Leu Thr Ala Ala Ala Ser Ser Ser Lys Ala Phe Ser Thr
50                  55                  60

Val Ala Leu Phe Lys Ser Lys Thr Lys Ala Pro Lys Thr Lys Lys
65                  70                  75                  80

Val Glu Ser Lys Pro Lys Val Glu Asp Gly Ile Phe Gly Thr Ser Gly
                85                  90                  95

Gly Phe Gly Phe Thr Lys Gln Asn Glu Leu Phe Val Gly Arg Val Ala
            100                 105                 110

Met Ile Gly Phe Ala Ala Ser Leu Leu Gly Glu Gly Ile Thr Gly Lys
        115                 120                 125

Gly Ile Leu Ala Gln Leu Asn Leu Glu Thr Gly Ile Pro Ile Tyr Glu
130                 135                 140

Ala Glu Pro Leu Leu Leu Phe Phe Ile Leu Phe Thr Leu Leu Gly Ala
145                 150                 155                 160

Ile Gly Ala Leu Gly Asp Arg Gly Lys Phe Val Asp Glu Pro Asp Glu
                165                 170                 175

Pro Thr Gly Leu Gly Gly Ala Val Ile Pro Pro Gly Lys Ser Leu Arg
            180                 185                 190

Ser Ala Leu Gly Leu Lys Glu Gly Pro Ile Phe Gly Phe Thr Lys
        195                 200                 205

Ser Asn Glu Leu Phe Val Gly Arg Leu Ala Gln Leu Gly Ile Ala Phe
210                 215                 220

Ser Leu Ile Gly Glu Ile Ile Thr Gly Lys Gly Ala Leu Ala Gln Leu
225                 230                 235                 240

Asn Ile Glu Thr Gly Ile Pro Ile Asn Glu Ile Glu Pro Leu Val Leu
                245                 250                 255

Phe Asn Val Ile Phe Phe Phe Val Ala Ala Leu Asn Pro Gly Thr Gly
            260                 265                 270

Lys Phe Val Thr Asp Glu Asp Glu Glu
        275                 280

<210> SEQ ID NO 122
<211> LENGTH: 274
<212> TYPE: PRT
<213> ORGANISM: Cephalotus follicularis

<400> SEQUENCE: 122

```
Met Ala Gln Thr Met Leu Leu Met Cys Gly Ile Ser Thr Ser His Val
1               5                   10                  15

Val Asp Leu Arg Arg Asp Pro Leu Phe His Val Gln Ile Gln Lys Leu
            20                  25                  30

Arg Pro Lys Ser Phe Ser His Leu Phe Phe Asn Pro Leu Ser Asn Asn
            35                  40                  45

Gly Phe Ser Leu Ala Gln Lys Phe Asn Thr Leu Ala Leu Phe Lys Ser
        50                  55                  60

Lys Thr Lys Ala Ala Pro Lys Lys Val Ala Thr Ala Lys Pro Lys
65                  70                  75                  80

Val Glu Asp Gly Leu Phe Gly Thr Ser Gly Gly Ile Gly Phe Thr Lys
                85                  90                  95

Gln Asn Glu Leu Phe Val Gly Arg Val Ala Met Ile Gly Phe Ala Ala
                100                 105                 110

Ser Leu Leu Gly Glu Ala Val Thr Gly Lys Gly Ile Leu Ser Gln Leu
            115                 120                 125

Asn Leu Glu Thr Gly Ile Pro Ile Tyr Glu Ala Glu Pro Leu Leu Leu
        130                 135                 140

Phe Phe Ile Leu Phe Thr Leu Leu Gly Ala Ile Gly Ala Leu Gly Asp
145                 150                 155                 160

Arg Gly Arg Phe Val Asp Asp Glu Pro Thr Gly Leu Glu Arg Ala Val
                165                 170                 175

Ile Pro Pro Gly Lys Gly Ile Arg Gly Ala Leu Gly Leu Arg Glu Gly
                180                 185                 190

Gly Pro Leu Phe Gly Phe Thr Lys Ser Asn Glu Leu Phe Val Gly Arg
            195                 200                 205

Leu Ala Gln Leu Gly Ile Ala Phe Ser Leu Ile Gly Glu Ile Ile Thr
        210                 215                 220

Gly Lys Gly Ala Leu Ala Gln Leu Asn Ile Glu Thr Gly Ile Pro Ile
225                 230                 235                 240

Asn Glu Ile Glu Pro Leu Val Leu Phe Asn Val Ile Phe Phe Phe Phe
                245                 250                 255

Ala Ala Leu Asn Pro Gly Thr Gly Lys Phe Val Thr Asp Glu Glu Ala
            260                 265                 270

Glu Asp

<210> SEQ ID NO 123
<211> LENGTH: 273
<212> TYPE: PRT
<213> ORGANISM: Juglans regia

<400> SEQUENCE: 123

Met Ala Gln Thr Ile Leu Leu Met Ser Gly Val Ser Ser Ser His Val
1               5                   10                  15

Val Asp Leu Lys Arg Asp Ala Leu Leu Asn Phe Gln Leu Gln Lys Leu
            20                  25                  30

Arg Pro Lys Pro Phe Ser His Leu Leu Leu Pro His Leu Pro Ala Asn
            35                  40                  45

Thr Thr Ser Ser Ser Pro Val Phe Thr Phe Ala Leu Phe Lys Ala
        50                  55                  60

Lys Thr Lys Ala Pro Pro Lys Lys Val Ala Pro Lys Pro Lys Glu Lys
65                  70                  75                  80

Val Glu Asp Gly Ile Phe Gly Thr Ser Gly Gly Ile Gly Phe Thr Lys
                85                  90                  95
```

Gln Asn Glu Leu Phe Val Gly Arg Val Ala Met Ile Gly Phe Ala Ala
                100                 105                 110

Ser Leu Leu Gly Glu Gly Ile Thr Gly Lys Gly Ile Leu Ser Gln Leu
            115                 120                 125

Asn Leu Glu Thr Gly Ile Pro Ile Tyr Glu Ala Glu Pro Leu Leu Leu
            130                 135                 140

Phe Ile Leu Phe Thr Leu Leu Gly Ala Ile Gly Ala Leu Gly Asp
145                 150                 155                 160

Arg Gly Lys Phe Val Asp Asp Thr Thr Gly Leu Glu Lys Ala Val
                165                 170                 175

Ile Pro Pro Gly Lys Gly Leu Arg Ser Ala Leu Gly Leu Lys Glu Gly
                180                 185                 190

Gly Pro Leu Phe Gly Phe Thr Lys Ser Asn Glu Leu Phe Val Gly Arg
            195                 200                 205

Leu Ala Gln Leu Gly Ile Ala Phe Ser Leu Ile Gly Glu Ile Ile Thr
            210                 215                 220

Gly Lys Gly Ala Leu Ala Gln Leu Asn Ile Glu Thr Gly Ile Pro Ile
225                 230                 235                 240

Asn Glu Ile Glu Pro Leu Val Leu Phe Asn Val Ile Phe Phe Phe
                245                 250                 255

Ala Ala Leu Asn Pro Gly Thr Gly Lys Phe Val Thr Asp Glu Glu Asp
            260                 265                 270

Asn

<210> SEQ ID NO 124
<211> LENGTH: 273
<212> TYPE: PRT
<213> ORGANISM: Populus tomentosa

<400> SEQUENCE: 124

Met Ala Gln Thr Met Val Leu Met Ser Gly Val Ser Thr Arg Gln Val
1               5                   10                  15

Val Asp Leu Lys Arg Asp Pro Leu Leu Gln Phe Gln Val Gln Arg Leu
                20                  25                  30

Arg Pro Ala Pro Phe Ser Arg Leu Leu Tyr Asn Pro Leu Pro Ser Lys
            35                  40                  45

Ala Ser Ser Ser Asn Ala Phe Thr Thr Leu Ala Leu Phe Lys Pro Arg
50                  55                  60

Thr Lys Ala Val Pro Lys Ala Ala Pro Pro Lys Pro Lys Val
65                  70                  75                  80

Glu Asp Gly Ile Phe Gly Thr Ser Gly Ile Gly Phe Thr Lys Gln
                85                  90                  95

Asn Glu Leu Phe Val Gly Arg Val Ala Met Ile Gly Phe Ala Ala Ser
                100                 105                 110

Leu Leu Gly Glu Ala Ile Thr Gly Lys Gly Ile Leu Ser Gln Leu Asn
            115                 120                 125

Leu Glu Thr Gly Ile Pro Ile Tyr Glu Ala Glu Pro Leu Leu Leu Phe
            130                 135                 140

Phe Ile Leu Phe Thr Leu Leu Gly Ala Ile Gly Ala Leu Gly Asp Arg
145                 150                 155                 160

Gly Arg Phe Val Asp Asp Pro Thr Gly Ile Glu Gly Ala Val Ile
                165                 170                 175

Pro Pro Gly Lys Ser Leu Arg Ala Ala Leu Gly Leu Lys Glu Gly Gly
            180                 185                 190

```
Ser Pro Leu Phe Gly Phe Thr Lys Ser Asn Glu Leu Phe Val Gly Arg
            195                 200                 205

Leu Ala Gln Leu Gly Ile Ala Phe Ser Leu Ile Gly Glu Ile Ile Thr
    210                 215                 220

Gly Lys Gly Ala Leu Ala Gln Leu Asn Ile Glu Thr Gly Ile Pro Val
225                 230                 235                 240

Ser Glu Ile Glu Pro Leu Val Leu Phe Asn Val Leu Phe Phe Phe Val
                245                 250                 255

Ala Ala Leu Asn Pro Gly Thr Gly Lys Phe Val Thr Asp Glu Asp Glu
            260                 265                 270

Glu

<210> SEQ ID NO 125
<211> LENGTH: 272
<212> TYPE: PRT
<213> ORGANISM: Populus trichocarpa

<400> SEQUENCE: 125

Met Ala Gln Thr Met Val Leu Met Ser Gly Val Ser Thr Arg Gln Val
1               5                   10                  15

Val Asp Leu Lys Arg Asp Pro Leu Leu Gln Phe Gln Val Gln Arg Leu
            20                  25                  30

Arg Pro Ala Pro Phe Ser Arg Leu Leu Tyr Asn Pro Leu Pro Ser Lys
        35                  40                  45

Ala Ser Ser Ser Asn Ala Phe Thr Thr Leu Ala Leu Phe Lys Pro Arg
    50                  55                  60

Thr Lys Ala Val Pro Lys Lys Ala Ala Pro Pro Lys Pro Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Ala Ile Thr Gly Lys Gly Ile Leu Ser Gln Leu Asn
        115                 120                 125

Leu Glu Thr Gly Ile Pro Ile Tyr Glu Ala Pro Leu Leu Leu Phe
    130                 135                 140

Phe Ile Leu Phe Thr Leu Leu Gly Ala Ile Gly Ala Leu Gly Asp Arg
145                 150                 155                 160

Gly Arg Phe Val Asp Asp Pro Thr Thr Gly Ile Glu Gly Ala Val Ile
                165                 170                 175

Pro Pro Gly Lys Ser Phe Arg Ala Ala Leu Gly Leu Lys Glu Gly Gly
            180                 185                 190

Pro Leu Phe Gly Phe Thr Lys Ser Asn Glu Leu Phe Val Gly Arg Leu
        195                 200                 205

Ala Gln Leu Gly Ile Ala Phe Ser Leu Ile Gly Glu Ile Ile Thr Gly
    210                 215                 220

Lys Gly Ala Leu Ala Gln Leu Asn Ile Glu Thr Gly Ile Pro Val Asn
225                 230                 235                 240

Glu Ile Glu Pro Leu Val Leu Phe Asn Val Leu Phe Phe Phe Ile Ala
                245                 250                 255

Ala Leu Asn Pro Gly Thr Gly Lys Phe Val Thr Asp Glu Asp Glu Glu
            260                 265                 270

<210> SEQ ID NO 126
<211> LENGTH: 272
```

```
<212> TYPE: PRT
<213> ORGANISM: Populus euphratica

<400> SEQUENCE: 126

Met Ala Gln Thr Met Val Leu Met Ser Gly Val Pro Thr Arg Gln Val
1               5                   10                  15

Val Asp Leu Lys Arg Asp Pro Leu Leu Gln Phe Gln Val Gln Arg Leu
            20                  25                  30

Arg Pro Ala Pro Phe Ser Arg Leu Leu Tyr Asn Pro Leu Pro Ser Lys
        35                  40                  45

Ala Ser Ser Asn Ala Phe Thr Thr Leu Ala Leu Phe Lys Pro Arg
50                  55                  60

Thr Lys Ala Val Pro Lys Lys Ala Ala Pro Pro Lys Pro Lys Val
65                  70                  75                  80

Glu Asp Gly Ile Phe Gly Thr Ser Gly Gly Ile Gly Phe Thr Lys Gln
                    85                  90                  95

Asn Glu Leu Phe Val Gly Arg Val Ala Met Ile Gly Phe Ala Ala Ser
                100                 105                 110

Leu Leu Gly Glu Ala Ile Thr Gly Lys Gly Ile Leu Ser Gln Leu Asn
            115                 120                 125

Leu Glu Thr Gly Ile Pro Ile Tyr Glu Ala Glu Pro Leu Leu Leu Phe
130                 135                 140

Phe Ile Leu Phe Thr Leu Leu Gly Ala Ile Gly Ala Leu Gly Asp Arg
145                 150                 155                 160

Gly Arg Phe Ile Asp Asp Pro Thr Thr Gly Ile Glu Gly Ala Val Ile
                165                 170                 175

Pro Pro Gly Lys Ser Phe Arg Ala Ala Leu Gly Leu Lys Glu Gly Gly
                180                 185                 190

Pro Leu Phe Gly Phe Thr Lys Ser Asn Glu Leu Phe Val Gly Arg Leu
            195                 200                 205

Ala Gln Leu Gly Ile Ala Phe Ser Leu Ile Gly Glu Ile Ile Thr Gly
        210                 215                 220

Lys Gly Ala Leu Ala Gln Leu Asn Ile Glu Thr Gly Ile Pro Val Asn
225                 230                 235                 240

Glu Ile Glu Pro Leu Val Leu Phe Asn Val Leu Phe Phe Val Ala
                245                 250                 255

Ala Leu Asn Pro Gly Thr Gly Lys Phe Val Thr Asp Glu Asp Glu Glu
            260                 265                 270

<210> SEQ ID NO 127
<211> LENGTH: 275
<212> TYPE: PRT
<213> ORGANISM: Hevea brasiliensis

<400> SEQUENCE: 127

Met Ala Gln Thr Met Leu Leu Met Ser Gly Val Ser Thr Arg His Val
1               5                   10                  15

Val His Phe Lys Arg Asp Pro Leu Leu Gln Phe Gln Val Glu Arg Leu
            20                  25                  30

Arg Pro Lys Pro Phe Ser His Leu Leu Leu Ser Arg Leu Ser Ala Asn
        35                  40                  45

Tyr Thr Cys Phe Ser Ser Arg Ala Phe Ser Thr Leu Ala Leu Phe Lys
    50                  55                  60

Ser Lys Thr Lys Ala Pro Pro Lys Lys Ala Ala Val Pro Lys Pro
65                  70                  75                  80
```

```
Lys Val Glu Asp Gly Ile Phe Gly Thr Ser Gly Gly Ile Gly Phe Thr
             85                  90                  95

Lys Gln Asn Glu Leu Phe Val Gly Arg Val Ala Met Leu Gly Phe Ala
        100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
    130                 135                 140

Leu Phe Phe Ile Leu Phe Thr Leu Leu Gly Ala Ile Gly Ala Leu Gly
145                 150                 155                 160

Asp Arg Gly Lys Phe Val Asp Asp Thr Ser Thr Gly Leu Glu Gly Ala
                165                 170                 175

Val Ile Pro Pro Gly Lys Ser Phe Arg Thr Ala Leu Gly Leu Lys Glu
            180                 185                 190

Gly Gly Pro Leu Phe Gly Phe Thr Lys Ala Asn Glu Leu Phe Val Gly
        195                 200                 205

Arg Leu Ala Gln Leu Gly Ile Ala Phe Ser Leu Ile Gly Glu Ile Ile
    210                 215                 220

Thr Gly Lys Gly Ala Leu Ala Gln Leu Asn Ile Glu Thr Gly Ile Pro
225                 230                 235                 240

Ile Asn Glu Ile Glu Pro Leu Val Leu Phe Asn Val Val Phe Phe Phe
                245                 250                 255

Ile Ala Ala Val Asn Pro Gly Asn Gly Lys Phe Val Thr Asp Glu Asp
            260                 265                 270

Glu Asp Asp
        275

<210> SEQ ID NO 128
<211> LENGTH: 275
<212> TYPE: PRT
<213> ORGANISM: Ricinus communis

<400> SEQUENCE: 128

Met Ala Gln Thr Met Leu Phe Met Ser Gly Val Ser Thr Arg His Val
1               5                   10                  15

Val Asp Leu Lys Arg Asp Pro Leu Leu Gln Phe Gln Val Asp Arg Leu
            20                  25                  30

Arg Pro Lys Pro Phe Ser Ser Leu Leu Phe Ser Pro Leu Pro Thr Asn
        35                  40                  45

Ser Ser Ser Phe Ala Pro Ser Lys Thr Phe Thr Thr Phe Ala Leu Phe
    50                  55                  60

Lys Ser Lys Ala Lys Ala Ala Pro Lys Lys Thr Val Val Lys Pro Lys
65                  70                  75                  80

Gln Lys Val Glu Asp Gly Val Phe Gly Thr Ser Gly Gly Ile Gly Phe
                85                  90                  95

Thr Lys Gln Asn Glu Leu Phe Val Gly Arg Val Ala Met Leu Gly Phe
            100                 105                 110

Ala Ala Ser Leu Leu Gly Glu Gly Leu Thr Gly Lys Gly Ile Leu Ala
        115                 120                 125

Gln Leu Asn Leu Glu Thr Gly Ile Pro Ile Tyr Glu Ala Glu Pro Leu
    130                 135                 140

Leu Leu Phe Phe Ile Leu Phe Thr Leu Leu Gly Ala Ile Gly Ala Leu
145                 150                 155                 160

Gly Asp Arg Gly Lys Phe Val Asp Asp Pro Pro Thr Gly Ile Glu Gly
                165                 170                 175
```

```
Ala Val Ile Pro Pro Gly Lys Gly Phe Arg Ala Ala Leu Gly Leu Lys
            180                 185                 190

Glu Gly Gly Pro Leu Phe Gly Phe Thr Lys Ser Asn Glu Leu Phe Val
            195                 200                 205

Gly Arg Leu Ala Gln Leu Gly Ile Ala Phe Ser Leu Ile Gly Glu Ile
            210                 215                 220

Ile Thr Gly Lys Gly Ala Leu Ala Gln Leu Asn Ile Glu Thr Gly Ile
225                 230                 235                 240

Pro Val Asn Glu Ile Glu Pro Leu Val Leu Phe Asn Val Ile Phe Phe
                245                 250                 255

Phe Phe Ala Ala Leu Asn Pro Gly Thr Gly Lys Phe Val Thr Asp Glu
            260                 265                 270

Glu Asp Glu
        275
```

<210> SEQ ID NO 129
<211> LENGTH: 274
<212> TYPE: PRT
<213> ORGANISM: Jatropha curcas

<400> SEQUENCE: 129

```
Met Ala Gln Thr Met Leu Phe Ile Ser Gly Val Ser Thr Arg His Val
1               5                   10                  15

Val Asp Leu Lys Arg Asp Pro Leu Leu Gln Phe Gln Val Glu Arg Leu
            20                  25                  30

Arg Pro Lys Pro Phe Ser Asn Leu Val Phe Asn Pro Ile Ser Ile Ser
            35                  40                  45

Lys Thr Ser Phe Ser Thr Ser Lys Pro Phe Thr Thr Leu Ala Leu Phe
50                  55                  60

Lys Ser Lys Ala Lys Ala Pro Pro Lys Lys Val Glu Lys Pro Lys Glu
65                  70                  75                  80

Lys Val Glu Asp Gly Ile Phe Gly Thr Ser Gly Gly Ile Gly Phe Thr
            85                  90                  95

Lys Gln Asn Glu Leu Phe Val Gly Arg Val Ala Met Leu Gly Phe Ala
            100                 105                 110

Ala Ser Leu Leu Gly Glu Ala Val Thr Gly Lys Gly Ile Leu Ala Gln
            115                 120                 125

Leu Asn Leu Glu Thr Gly Ile Pro Ile Tyr Glu Ala Glu Pro Leu Leu
            130                 135                 140

Leu Phe Phe Ile Leu Phe Thr Leu Leu Gly Ala Ile Gly Ala Leu Gly
145                 150                 155                 160

Asp Arg Gly Lys Phe Val Asp Asp Pro Pro Thr Gly Ile Glu Gly Ala
                165                 170                 175

Val Ile Pro Pro Gly Lys Ser Phe Arg Ala Ala Leu Gly Leu Lys Glu
            180                 185                 190

Gly Gly Pro Leu Phe Gly Phe Thr Lys Ala Asn Glu Leu Phe Val Gly
            195                 200                 205

Arg Leu Ala Gln Leu Gly Ile Ala Phe Ser Leu Ile Gly Glu Ile Ile
            210                 215                 220

Thr Gly Lys Gly Ala Leu Ala Gln Leu Asn Ile Glu Thr Gly Ile Pro
225                 230                 235                 240

Ile Asn Glu Leu Glu Pro Leu Val Leu Phe Asn Ile Ile Phe Phe Phe
                245                 250                 255

Ile Ala Ala Leu Asn Pro Gly Thr Gly Lys Phe Val Thr Asp Glu Glu
```

260                 265                 270

Glu Asp

<210> SEQ ID NO 130
<211> LENGTH: 279
<212> TYPE: PRT
<213> ORGANISM: Physcomitrella patens

<400> SEQUENCE: 130

Met Ala Gln Ala Ala Leu Ile Ser Arg Ile Gly Ala Gln Ala Leu
1               5                   10                  15

Gly Gly Val Ala Gln Ser Gln Thr Leu Ser Thr Arg Arg Leu Ser Ser
                20                  25                  30

Leu Phe Ala Ala Ser Ser Ser Thr Leu Pro Val Gly Leu Gly Leu
            35                  40                  45

Asn Arg Asn Ala Glu Arg Val Ser Ser Gly Ala Val Lys Thr Phe Ala
        50                  55                  60

Leu Phe Gly Lys Thr Lys Pro Ala Ala Lys Ala Pro Ala Pro Thr Lys
65                  70                  75                  80

Gly Lys Ala Lys Val Glu Asp Gly Ile Phe Gly Thr Ser Gly Gly Ile
                85                  90                  95

Gly Phe Thr Lys Ala Asn Glu Leu Phe Val Gly Arg Val Ala Met Leu
            100                 105                 110

Gly Phe Ala Ala Ser Ile Leu Gly Glu Ala Leu Thr Gly Lys Gly Thr
            115                 120                 125

Leu Ala Gln Phe Asp Ile Glu Thr Gly Ile Pro Leu Thr Glu Thr Glu
130                 135                 140

Pro Leu Leu Leu Phe Phe Ile Leu Phe Thr Leu Leu Gly Ala Ile Gly
145                 150                 155                 160

Ala Leu Gly Asp Arg Gly Lys Phe Val Asp Asp Ala Pro Val Ala Gly
                165                 170                 175

Leu Asp Ser Thr Ile Ile Lys Pro Gly Lys Gly Val Lys Gly Ala Leu
            180                 185                 190

Gly Leu Asn Glu Lys Gly Pro Val Phe Gly Phe Thr Lys Ser Asn Glu
            195                 200                 205

Leu Phe Val Gly Arg Leu Ala Gln Leu Gly Ile Ala Phe Ala Ile Ile
210                 215                 220

Gly Glu Ile Ile Thr Gly Lys Gly Ala Leu Ala Gln Leu Asn Ile Glu
225                 230                 235                 240

Thr Gly Val Pro Ile Thr Glu Leu Glu Pro Leu Ile Leu Phe Asn Val
                245                 250                 255

Ile Phe Phe Leu Phe Ala Ala Val Asn Pro Gly Thr Gly Lys Phe Val
            260                 265                 270

Asn Asp Asp Asp Ile Glu Asp
        275

<210> SEQ ID NO 131
<211> LENGTH: 282
<212> TYPE: PRT
<213> ORGANISM: Marchantia polymorpha

<400> SEQUENCE: 131

Met Ala Gln Ala Thr Met Leu Ala Arg Ser Leu Ala Thr Val Ala Leu
1               5                   10                  15

Ser Arg Asn Val Gln Val Ser Glu Ser Ser Leu Lys Val Gln Pro Phe
                20                  25                  30

Ser Ala Arg Gln Leu Ser Ser Leu His Gly Ser Ser Val Ser Ser Phe
            35                  40                  45

Ala Ala Gly Ser Ala Ser Gln Val Gly Val Ala Arg Ser Gly Lys Val
        50                  55                  60

Phe Ala Leu Phe Lys Ser Ala Lys Lys Glu Ala Pro Lys Lys Gln Asp
65                  70                  75                  80

Lys Lys Pro Val Lys Ser Ser Thr Glu Asp Gly Ile Phe Gly Thr Ser
                85                  90                  95

Gly Gly Ile Gly Phe Thr Lys Ala Asn Glu Leu Phe Val Gly Arg Val
            100                 105                 110

Ala Met Leu Gly Phe Ser Ala Ser Ile Leu Gly Glu Ala Leu Thr Gly
        115                 120                 125

Lys Gly Thr Leu Ala Gln Phe Asp Val Glu Thr Gly Ile Pro Leu Asn
130                 135                 140

Glu Thr Glu Pro Leu Leu Leu Phe Phe Ile Leu Phe Thr Leu Leu Gly
145                 150                 155                 160

Ala Ile Gly Ala Leu Gly Asp Arg Gly Lys Phe Val Asp Asp Val
            165                 170                 175

Asp Glu Ala Asn Thr Gly Val Ile Pro Pro Gly Lys Gly Phe Lys
            180                 185                 190

Ala Ala Leu Gly Leu Asn Gln Lys Gly Pro Thr Phe Gly Phe Thr Lys
        195                 200                 205

Ala Asn Glu Leu Phe Val Gly Arg Leu Ala Gln Leu Gly Ile Ala Phe
        210                 215                 220

Ser Ile Ile Gly Glu Ile Thr Gly Lys Gly Thr Leu Ala Gln Leu
225                 230                 235                 240

Asn Ile Glu Thr Gly Leu Pro Ile Thr Glu Leu Glu Pro Leu Ile Leu
            245                 250                 255

Phe Asn Val Ile Phe Phe Phe Leu Ala Ala Ile Asn Pro Gly Thr Gly
            260                 265                 270

Lys Phe Ile Asn Asp Asp Asp Ile Glu Glu
            275                 280

<210> SEQ ID NO 132
<211> LENGTH: 281
<212> TYPE: PRT
<213> ORGANISM: Marchantia polymorpha

<400> SEQUENCE: 132

Met Ala Gln Ala Thr Met Leu Ala Arg Ser Leu Ala Thr Val Ala Leu
1               5                   10                  15

Ser Arg Asn Val Gln Val Ser Glu Ser Ser Leu Lys Val Gln Pro Phe
            20                  25                  30

Ser Ala Arg Gln Leu Ser Ser Leu His Gly Ser Ser Val Ser Ser Phe
            35                  40                  45

Ala Ala Gly Ser Ala Ser Gln Val Gly Val Ala Arg Ser Gly Lys Val
        50                  55                  60

Phe Ala Leu Phe Lys Ser Ala Lys Lys Glu Ala Pro Lys Lys Asp Lys
65                  70                  75                  80

Lys Pro Val Lys Ser Ser Thr Glu Asp Gly Ile Phe Gly Thr Ser Gly
                85                  90                  95

Gly Ile Gly Phe Thr Lys Ala Asn Glu Leu Phe Val Gly Arg Val Ala
            100                 105                 110

Met Leu Gly Phe Ser Ala Ser Ile Leu Gly Glu Ala Leu Thr Gly Lys

```
            115                 120                 125
Gly Thr Leu Ala Gln Phe Asp Val Glu Thr Gly Ile Pro Leu Asn Glu
        130                 135                 140

Thr Glu Pro Leu Leu Leu Phe Phe Ile Leu Phe Thr Leu Leu Gly Ala
145                 150                 155                 160

Ile Gly Ala Leu Gly Asp Arg Gly Lys Phe Val Asp Asp Val Asp
                165                 170                 175

Glu Ala Asn Thr Gly Gly Val Ile Pro Pro Gly Lys Gly Phe Lys Ala
            180                 185                 190

Ala Leu Gly Leu Asn Gln Lys Gly Pro Thr Phe Gly Phe Thr Lys Ala
        195                 200                 205

Asn Glu Leu Phe Val Gly Arg Leu Ala Gln Leu Gly Ile Ala Phe Ser
    210                 215                 220

Ile Ile Gly Glu Ile Ile Thr Gly Lys Gly Thr Leu Ala Gln Leu Asn
225                 230                 235                 240

Ile Glu Thr Gly Leu Pro Ile Thr Glu Leu Glu Pro Leu Ile Leu Phe
                245                 250                 255

Asn Val Ile Phe Phe Phe Leu Ala Ala Ile Asn Pro Gly Thr Gly Lys
            260                 265                 270

Phe Ile Asn Asp Asp Asp Ile Glu Glu
        275                 280

<210> SEQ ID NO 133
<211> LENGTH: 266
<212> TYPE: PRT
<213> ORGANISM: Selaginella moellendorffii

<400> SEQUENCE: 133

Met Ala Gln Ala Ala Leu Leu Ser Arg Val Thr Thr Ala Leu Asn Gly
1               5                   10                  15

Ile Ala Gln Gln Arg Leu Ser Ser Thr Arg Ser Asn Ala Ile Gly Gly
            20                  25                  30

Ser Ser Gln Gln Leu Leu Gly Gln Arg Leu Gly Val Val Thr Pro
        35                  40                  45

Gln His Phe Ser Ser Ala Ser Arg Ile Val Arg Thr Phe Ala Leu Lys
    50                  55                  60

Ser Lys Ala Pro Ala Thr Ser Lys Lys Ser Lys Ser Thr Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Ile Gly Phe Ala Ala Ser Leu Leu
            100                 105                 110

Gly Glu Ala Ile Thr Gly Lys Gly Val Leu Ala Gln Phe Asp Leu Glu
        115                 120                 125

Thr Gly Ile Pro Leu Asn Glu Thr Glu Pro Leu Leu Leu Phe Phe Ile
    130                 135                 140

Leu Phe Thr Leu Leu Gly Ala Ile Gly Ala Leu Gly Asp Arg Gly Lys
145                 150                 155                 160

Phe Val Asp Glu Thr Pro Gly Pro Ile Ile Glu Pro Gly Lys Gly Phe
                165                 170                 175

Lys Ser Ala Ile Gly Leu Lys Glu Lys Gly Pro Val Phe Gly Phe Thr
            180                 185                 190

Lys Ser Asn Glu Leu Phe Val Gly Arg Leu Ala Gln Leu Gly Ile Ala
        195                 200                 205
```

```
Phe Ser Ile Ile Gly Glu Leu Ile Thr Gly Lys Gly Ala Leu Ala Gln
    210                 215                 220

Leu Asn Ile Glu Thr Gly Val Pro Ile Thr Glu Ile Glu Pro Leu Leu
225                 230                 235                 240

Leu Phe Asn Ile Ile Phe Phe Phe Ile Ala Ala Ile Asn Pro Gly Thr
                245                 250                 255

Gly Arg Phe Ile Ala Asp Asn Glu Glu Glu
                260                 265
```

<210> SEQ ID NO 134
<211> LENGTH: 266
<212> TYPE: PRT
<213> ORGANISM: Selaginella moellendorffii

<400> SEQUENCE: 134

```
Met Ala Gln Ala Ala Leu Leu Ser Arg Val Thr Thr Ala Leu Asn Gly
1               5                   10                  15

Ile Ala Gln Gln Arg Leu Ser Ser Thr Arg Ser Asn Ala Ile Gly Gly
            20                  25                  30

Ser Ser Gln Gln Leu Leu Gly Gln Arg Leu Gly Val Val Val Ala Pro
        35                  40                  45

Gln His Phe Ser Ser Ala Ser Arg Ile Val Arg Thr Phe Ala Leu Lys
    50                  55                  60

Ser Lys Ala Pro Ala Thr Ser Lys Lys Ser Lys Ser Thr Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Ile Gly Phe Ala Ala Ser Leu Leu
            100                 105                 110

Gly Glu Ala Ile Thr Gly Lys Gly Val Leu Ala Gln Phe Asp Leu Glu
        115                 120                 125

Thr Gly Ile Pro Leu Asn Glu Thr Glu Pro Leu Leu Leu Phe Phe Ile
    130                 135                 140

Leu Phe Thr Leu Leu Gly Ala Ile Gly Ala Leu Gly Asp Arg Gly Lys
145                 150                 155                 160

Phe Val Asp Glu Thr Pro Gly Pro Ile Ile Glu Pro Gly Lys Gly Phe
                165                 170                 175

Lys Ser Ala Ile Gly Leu Lys Glu Lys Gly Pro Val Phe Gly Phe Thr
            180                 185                 190

Lys Ser Asn Glu Leu Phe Val Gly Arg Leu Ala Gln Leu Gly Ile Ala
        195                 200                 205

Phe Ser Ile Ile Gly Glu Leu Ile Thr Gly Lys Gly Ala Leu Ala Gln
    210                 215                 220

Leu Asn Ile Glu Thr Gly Val Pro Ile Thr Glu Ile Glu Pro Leu Leu
225                 230                 235                 240

Leu Phe Asn Ile Ile Phe Phe Phe Ile Ala Ala Ile Asn Pro Gly Thr
                245                 250                 255

Gly Arg Phe Ile Ala Asp Asn Glu Glu Glu
                260                 265
```

<210> SEQ ID NO 135
<211> LENGTH: 294
<212> TYPE: PRT
<213> ORGANISM: Picea sitchensis

<400> SEQUENCE: 135

-continued

Met Ala Gln Ser Val Leu Pro Ser Arg Ser Val Arg Ser Tyr Val Gly
1               5                   10                  15

Gly Ile Ala Ala Phe Ser Gln Arg Pro Leu Pro Ala Pro Pro Ala Leu
                20                  25                  30

Pro Val Ala Arg Gly Leu Arg Ile Arg Pro Pro Asn Ala Ala Glu Thr
            35                  40                  45

Ser Trp Ser Pro Leu Arg Glu Leu Pro Ser Ala Asn Ala Ala Gly Leu
    50                  55                  60

Asn Ala Arg Thr Ala Asn Thr Val Ala Leu Phe Arg Pro Lys Glu Lys
65                  70                  75                  80

Ala Ala Ala Pro Pro Lys Lys Gly Arg Thr Gly Arg Val Ser Val Pro
                85                  90                  95

Glu Glu Lys Pro Lys Val Glu Asp Gly Ile Phe Gly Thr Ser Gly Gly
                100                 105                 110

Ile Gly Phe Thr Lys Ala Asn Glu Leu Phe Val Gly Arg Val Ala Met
            115                 120                 125

Ile Gly Phe Ala Ala Ser Leu Leu Gly Glu Ala Ile Thr Gly Lys Gly
            130                 135                 140

Ile Leu Ala Gln Leu Asn Leu Glu Thr Gly Ile Pro Ile Tyr Glu Ala
145                 150                 155                 160

Glu Pro Leu Leu Leu Phe Phe Ile Leu Phe Thr Leu Gly Ala Ile
                165                 170                 175

Gly Ala Leu Gly Asp Arg Gly Lys Phe Val Asp Glu Ala Pro Thr Pro
            180                 185                 190

Asp Ser Leu Val Asp Pro Gly Lys Gly Phe Arg Ser Ala Val Gly Leu
            195                 200                 205

Lys Asp Ser Gly Pro Leu Phe Gly Phe Thr Lys Ser Asn Glu Leu Phe
210                 215                 220

Val Gly Arg Leu Ala Gln Leu Gly Ile Ala Phe Ser Ile Ile Gly Glu
225                 230                 235                 240

Ile Ile Thr Gly Lys Gly Ala Leu Ala Gln Leu Asn Ile Glu Thr Gly
                245                 250                 255

Val Pro Val Ser Glu Ile Glu Pro Leu Val Leu Phe Asn Val Ala Phe
            260                 265                 270

Phe Leu Phe Ala Ala Leu Asn Pro Gly Asn Gly Lys Phe Val Thr Asp
    275                 280                 285

Val Asp Glu Glu Glu Glu
    290

<210> SEQ ID NO 136
<211> LENGTH: 297
<212> TYPE: PRT
<213> ORGANISM: Picea sitchensis

<400> SEQUENCE: 136

Met Ala Gln Ser Val Leu Ala Ser Gly Gly Leu Ser Ser Cys Val Ala
1               5                   10                  15

Gly Ile Ala Gly Phe Asn Gln Arg Pro Leu Pro Ser Pro Pro Ala Leu
                20                  25                  30

Pro Val Ala Arg Gly Leu Arg Ile Arg Pro Pro Asn Ala Ala Gln Ile
            35                  40                  45

Ser Trp Ser Pro Leu Thr Glu Leu Pro Ser Ala Asn Ala Ala Gly Leu
    50                  55                  60

Asn Ala Arg Ile Ala Arg Thr Glu Ala Leu Phe Arg Pro Lys Glu Lys
65                  70                  75                  80

Ala Ala Ala Pro Pro Lys Lys Gly Arg Thr Gly Arg Val Ala Leu Pro
                85                  90                  95

Glu Glu Lys Pro Lys Val Glu Asp Gly Ile Phe Gly Thr Ser Gly Gly
            100                 105                 110

Ile Gly Phe Thr Lys Ala Asn Glu Leu Phe Val Gly Arg Val Ala Met
        115                 120                 125

Ile Gly Phe Ala Ala Ser Leu Leu Gly Glu Ala Ile Thr Gly Lys Gly
    130                 135                 140

Ile Leu Ser Gln Leu Asn Leu Glu Thr Gly Ile Pro Ile Tyr Glu Ala
145                 150                 155                 160

Glu Pro Leu Leu Leu Phe Phe Ile Leu Phe Thr Leu Leu Gly Ala Ile
                165                 170                 175

Gly Ala Leu Gly Asp Arg Gly Lys Phe Val Asp Asp Gln Thr Pro Thr
            180                 185                 190

Thr Gly Leu Glu Lys Ala Val Ile Pro Pro Gly Lys Gly Phe Arg Ser
        195                 200                 205

Ala Val Gly Leu Asn Glu Ser Gly Pro Leu Phe Gly Phe Thr Lys Ser
    210                 215                 220

Asn Glu Leu Phe Val Gly Arg Leu Ala Gln Leu Gly Ile Ala Phe Ser
225                 230                 235                 240

Ile Ile Gly Glu Ile Ile Thr Gly Lys Gly Ala Leu Ala Gln Leu Asn
                245                 250                 255

Ile Glu Thr Gly Val Pro Val Ser Glu Ile Glu Pro Leu Val Leu Phe
            260                 265                 270

Asn Val Ala Phe Phe Leu Phe Ala Leu Asn Pro Gly Asn Gly Lys
        275                 280                 285

Phe Val Thr Asp Glu Glu Glu Glu
    290                 295

<210> SEQ ID NO 137
<211> LENGTH: 271
<212> TYPE: PRT
<213> ORGANISM: Zea mays

<400> SEQUENCE: 137

Met Ala Gln Ser Met Ile Thr Ser Ser Val Leu Gly Cys Leu Ser Ser
1               5                   10                  15

Ser Thr Val Arg Lys Asp Thr Leu Leu Gln Phe Gln Ile Gln Arg Leu
            20                  25                  30

Arg Pro Thr Ser Ser Ser Thr Leu Phe Leu Ser Pro Lys Ser Ser Pro
        35                  40                  45

Gly Arg Ser Thr Gln Ser Thr Leu Phe Phe Gln Pro Leu Ala Leu Phe
    50                  55                  60

Lys Ser Lys Ala Lys Thr Ile Pro Lys Lys Val Val Lys Pro Lys
65                  70                  75                  80

Val Glu Ser Gly Ile Phe Gly Thr Ser Gly Gly Ile Gly Phe Thr Lys
                85                  90                  95

Glu Asn Glu Leu Phe Val Gly Arg Val Ala Met Leu Gly Phe Ala Ala
            100                 105                 110

Ser Leu Leu Gly Glu Gly Leu Thr Gly Lys Gly Ile Leu Ser Gln Leu
        115                 120                 125

Asn Leu Glu Thr Gly Ile Pro Ile Tyr Glu Ala Glu Pro Leu Leu Leu
    130                 135                 140

Phe Phe Ile Leu Phe Thr Leu Leu Gly Ala Ile Gly Ala Leu Gly Asp

```
145                 150                 155                 160
Arg Gly Arg Phe Glu Asp Glu Ala Thr Gly Leu Asp Lys Ala Val Ile
                165                 170                 175

Ala Pro Gly Lys Asn Leu Arg Thr Ser Phe Gly Leu Lys Glu Gly Gly
                180                 185                 190

Pro Leu Phe Gly Phe Thr Lys Ala Asn Glu Leu Phe Val Gly Arg Met
                195                 200                 205

Ala Gln Leu Gly Ile Ala Phe Ser Ile Ile Gly Glu Ile Ile Thr Gly
                210                 215                 220

Lys Gly Ala Leu Ala Gln Leu Asn Ile Glu Thr Gly Val Pro Ile Thr
225                 230                 235                 240

Glu Ile Glu Pro Leu Val Leu Phe Asn Val Val Phe Phe Ile Ala
                245                 250                 255

Ala Leu Asn Pro Gly Ser Gly Lys Phe Lys Thr Asp Asp Glu Glu
                260                 265                 270

<210> SEQ ID NO 138
<211> LENGTH: 273
<212> TYPE: PRT
<213> ORGANISM: Sedum alfredii

<400> SEQUENCE: 138

Met Ala Gln Ser Thr Leu Leu Met Phe Asn Gly Ala Leu Pro Thr Phe
1               5                  10                  15

Lys Thr His Ser Ser Leu Gln Ser Gln Ile Gln Arg Leu Val Lys Pro
                20                  25                  30

Asn Asn Asn Pro Phe Leu Gln Thr Pro Leu Leu His Ser Lys Ala Ser
                35                  40                  45

Ser Pro Leu Gly Leu Gly Phe Thr Thr Val Ala Leu Phe Lys Ala Lys
            50                  55                  60

Ala Lys Ala Pro Ala Lys Lys Glu Thr Lys Ser Lys Pro Lys Leu Lys
65              70                  75                  80

Val Glu Asp Gly Val Phe Gly Thr Ser Gly Gly Ile Gly Phe Thr Lys
                85                  90                  95

Gln Asn Glu Leu Phe Val Gly Arg Val Ala Met Ile Gly Phe Ala Ala
                100                 105                 110

Ser Ile Leu Gly Glu Ala Val Thr Gly Lys Gly Ile Leu Ala Gln Leu
            115                 120                 125

Asn Leu Glu Thr Gly Ile Pro Ile Tyr Glu Ala Glu Pro Leu Leu Leu
130                 135                 140

Phe Phe Ile Leu Phe Thr Leu Leu Gly Ala Ile Gly Ala Leu Gly Asp
145                 150                 155                 160

Arg Gly Arg Phe Val Asp Asp Pro Pro Thr Gly Leu Glu Lys Ala Val
                165                 170                 175

Ile Pro Pro Gly Lys Gly Leu Arg Ser Ala Phe Gly Leu Ser Glu Gly
                180                 185                 190

Gly Pro Leu Phe Gly Phe Thr Lys Ser Asn Glu Leu Phe Val Gly Arg
                195                 200                 205

Leu Ala Gln Leu Gly Phe Ala Phe Ser Leu Ile Gly Glu Ile Ile Thr
                210                 215                 220

Gly Lys Gly Ala Leu Ala Gln Leu Asn Ile Glu Thr Gly Val Pro Ile
225                 230                 235                 240

Asn Glu Ile Glu Pro Leu Val Leu Phe Asn Val Ile Phe Phe Phe
                245                 250                 255
```

```
Ala Ala Leu Asn Pro Gly Thr Gly Lys Phe Val Thr Asp Asp Glu Glu
            260                 265                 270

Asp

<210> SEQ ID NO 139
<211> LENGTH: 268
<212> TYPE: PRT
<213> ORGANISM: Dorcoceras hygrometricum

<400> SEQUENCE: 139

Met Ala Ala Gln Thr Thr Met Leu Ile Ser Thr Gly Asn Arg Val Ser
1               5                   10                  15

Gly His Glu Pro Leu Val Arg Gly Leu Lys Pro Asn Pro Phe Pro Arg
            20                  25                  30

Phe Leu Phe Pro Ser Ile Pro Thr Val Asp Arg Pro Ala Ser Ser Ser
        35                  40                  45

Ser Ala Thr Thr Arg Tyr Val Ile Glu Ser Met Ala Lys Ala Pro Pro
    50                  55                  60

Ala Val Lys Lys Ala Pro Ala Val Lys Lys Ser Thr Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Ile Gly Phe Ala Ala Ser Leu Leu
            100                 105                 110

Gly Glu Ala Ile Thr Gly Lys Gly Ile Leu Ala Gln Leu Asn Leu Glu
        115                 120                 125

Thr Gly Ile Pro Ile Tyr Glu Ala Glu Pro Leu Leu Leu Phe Phe Ile
    130                 135                 140

Leu Phe Asn Leu Leu Gly Ala Ile Gly Ala Leu Gly Asp Arg Gly Arg
145                 150                 155                 160

Phe Val Asp Asp Ala Thr Gly Leu Asp Lys Thr Val Val Ala Pro Gly
                165                 170                 175

Lys Gly Leu Arg Ala Ala Leu Gly Leu Gly Gln Gly Gly Arg Leu Phe
            180                 185                 190

Gly Phe Thr Lys Ala Asn Glu Leu Phe Val Gly Arg Leu Ala Gln Leu
        195                 200                 205

Gly Ile Ala Phe Ser Ile Ile Gly Glu Ile Ile Thr Gly Lys Gly Ala
    210                 215                 220

Leu Ala Gln Leu Asn Ile Glu Thr Gly Val Pro Ile Asn Glu Ile Glu
225                 230                 235                 240

Pro Leu Leu Leu Phe Asn Ile Val Phe Phe Val Ala Ala Ile Asn
                245                 250                 255

Pro Gly Ser Gly Lys Phe Val Thr Asp Asp Glu Glu
            260                 265

<210> SEQ ID NO 140
<211> LENGTH: 271
<212> TYPE: PRT
<213> ORGANISM: Erythranthe guttata

<400> SEQUENCE: 140

Met Ala Gln Thr Met Leu Leu Asn Ala Ser Asn Val Ser Ser Val Val
1               5                   10                  15

Arg Thr Thr Thr Asn Glu Pro Leu Leu Gln Arg Leu Lys Pro Lys Ser
            20                  25                  30

Phe Ser Gln Phe Leu Leu Thr Pro Arg Thr Thr Ser Ala Thr Ser Thr
```

```
                35                  40                  45
Pro Ala Phe Ser Ser Thr Leu Ala Leu Phe Lys Pro Lys Thr Lys Ala
 50                  55                  60
Pro Pro Lys Lys Ala Pro Val Val Lys Glu Lys Ser Lys Val Glu
 65                  70                  75                  80
Asp Gly Ile Phe Gly Thr Ser Gly Gly Ile Gly Phe Thr Lys Gln Asn
                 85                  90                  95
Glu Leu Phe Val Gly Arg Val Ala Met Ile Gly Phe Ala Ala Ser Leu
            100                 105                 110
Leu Gly Glu Ala Leu Thr Gly Lys Gly Ile Leu Ala Gln Leu Asn Leu
            115                 120                 125
Glu Thr Gly Ile Pro Ile Tyr Glu Ala Glu Pro Leu Leu Leu Phe Phe
130                 135                 140
Ile Leu Phe Asn Leu Leu Gly Ala Ile Gly Ala Leu Gly Asp Arg Gly
145                 150                 155                 160
Arg Phe Val Asp Glu Pro Thr Thr Gly Leu Asp Lys Ala Val Ile Ala
                165                 170                 175
Pro Gly Lys Gly Phe Arg Thr Ala Ile Gly Leu Gly Glu Gly Gly Pro
            180                 185                 190
Leu Phe Gly Phe Thr Lys Ser Asn Glu Leu Phe Val Gly Arg Leu Ala
            195                 200                 205
Gln Leu Gly Ile Ala Phe Ser Ile Ile Gly Glu Ile Val Thr Gly Lys
            210                 215                 220
Gly Ala Leu Ala Gln Leu Asn Ile Glu Thr Gly Val Pro Ile Ser Glu
225                 230                 235                 240
Ile Glu Pro Leu Leu Leu Phe Asn Val Ala Phe Phe Phe Ala Ala
                245                 250                 255
Ile Asn Pro Gly Thr Gly Lys Phe Val Thr Asp Asp Gly Asp Glu
            260                 265                 270

<210> SEQ ID NO 141
<211> LENGTH: 270
<212> TYPE: PRT
<213> ORGANISM: Erythranthe guttata

<400> SEQUENCE: 141

Met Ala Ala Gln Thr Met Leu Leu Thr Gly Ser Ser Ser His Val Val
 1               5                  10                  15
Lys Gly Glu Thr Asn Thr Leu Leu Ile Gln Lys Leu Lys Pro Met Pro
                 20                  25                  30
Leu Ser Gln Phe Leu Phe Pro Gln Arg Thr Asn His Ser Ser Phe Ser
                 35                  40                  45
Ser Ser Ser Ala Ser Ile Val Ser Leu Phe Lys Pro Lys Thr Lys Ala
 50                  55                  60
Pro Pro Lys Lys Ala Ala Pro Val Val Lys Glu Lys Ser Lys Val Glu
 65                  70                  75                  80
Asp Gly Ile Phe Gly Thr Ser Gly Gly Ile Gly Phe Thr Lys Gln Asn
                 85                  90                  95
Glu Leu Phe Val Gly Arg Val Ala Met Ile Gly Phe Ala Ala Ser Leu
            100                 105                 110
Leu Gly Glu Ala Leu Thr Gly Lys Gly Ile Leu Ala Gln Leu Asn Leu
            115                 120                 125
Glu Thr Gly Ile Pro Ile Tyr Glu Ala Glu Pro Leu Leu Leu Phe Phe
130                 135                 140
```

Ile Leu Phe Thr Leu Leu Gly Ala Ile Gly Ala Leu Gly Asp Arg Gly
145                 150                 155                 160

Arg Phe Val Asp Glu Glu Pro Ala Gly Leu Gly Lys Ala Val Ile Ala
                165                 170                 175

Pro Gly Lys Gly Phe Arg Ala Ala Leu Gly Leu Gly Glu Gly Gly Pro
            180                 185                 190

Leu Leu Gly Phe Thr Lys Ser Asn Glu Leu Phe Val Gly Arg Leu Ala
            195                 200                 205

Gln Leu Gly Ile Ala Phe Ser Ile Ile Gly Glu Ile Thr Gly Lys
            210                 215                 220

Gly Gly Leu Ala Gln Leu Asn Ile Glu Thr Gly Val Pro Ile Asn Glu
225                 230                 235                 240

Leu Glu Pro Leu Leu Leu Phe Asn Val Ala Phe Phe Phe Ala Ala
                245                 250                 255

Ile Asn Pro Gly Ser Gly Lys Phe Val Thr Asp Asp Glu Asp
            260                 265                 270

<210> SEQ ID NO 142
<211> LENGTH: 265
<212> TYPE: PRT
<213> ORGANISM: Cynara cardunculus

<400> SEQUENCE: 142

Met Ala Gln Thr Met Leu Leu Thr Ser Asn Thr Val Val Ser Gly His
1               5                   10                  15

Pro Leu Leu Gln Ser Leu Arg Pro Lys Pro Phe Ser His Leu Leu Leu
                20                  25                  30

Pro Pro Ser Leu Val Asn Ala Ser Ser Thr Ser Pro Ala Arg Thr Tyr
            35                  40                  45

Thr Ser Pro Val Ala Leu Phe Lys Ala Lys Thr Lys Ala Pro Ala Lys
50                  55                  60

Lys Ala Ala Pro Lys Glu Lys Ile Lys Val Glu Asp Gly Ile Phe Gly
65                  70                  75                  80

Thr Ser Gly Gly Ile Gly Phe Thr Lys Gln Asn Glu Leu Phe Val Gly
                85                  90                  95

Arg Val Ala Met Ile Gly Phe Ala Ala Ser Leu Leu Gly Glu Gly Leu
                100                 105                 110

Thr Gly Lys Gly Ile Leu Gln Gln Leu Asn Leu Glu Thr Gly Ile Pro
            115                 120                 125

Ile Tyr Glu Ala Glu Pro Leu Leu Leu Phe Phe Ile Leu Phe Thr Leu
130                 135                 140

Leu Gly Ala Ile Gly Ala Leu Gly Asp Arg Gly Arg Phe Val Asp Glu
145                 150                 155                 160

Pro Thr Gly Leu Asp Lys Ala Val Ile Pro Pro Gly Lys Gly Leu Arg
                165                 170                 175

Ser Ala Leu Gly Leu Ser Glu Gly Gly Pro Leu Phe Gly Phe Thr Lys
            180                 185                 190

Ser Asn Glu Leu Phe Val Gly Arg Leu Ala Gln Leu Gly Ile Ala Phe
            195                 200                 205

Ser Leu Ile Gly Glu Ile Ile Thr Gly Lys Gly Ala Leu Ala Gln Leu
            210                 215                 220

Asn Ile Glu Thr Gly Ile Pro Ile Ser Asp Ile Glu Pro Leu Val Leu
225                 230                 235                 240

Phe Asn Val Ala Phe Phe Val Ala Ala Leu Asn Pro Gly Thr Gly
                245                 250                 255

```
Lys Phe Val Thr Asp Asp Glu Glu Asp
            260                 265

<210> SEQ ID NO 143
<211> LENGTH: 262
<212> TYPE: PRT
<213> ORGANISM: Helianthus annuus

<400> SEQUENCE: 143

Met Ala Gln Thr Met Leu Leu Thr Ser Asn Thr Ile Ile Ser Asp Gln
1               5                   10                  15

Pro Leu Leu Arg Ser Leu Arg Pro Lys Pro Phe Ser His Arg Val Leu
            20                  25                  30

Ala Pro Gly Leu Leu Pro Asn Ser Ser Thr Thr Phe Leu Ser Pro Val
        35                  40                  45

Ala Leu Phe Lys Pro Lys Thr Lys Ala Ala Pro Lys Lys Ala Val Thr
    50                  55                  60

Pro Pro Pro Lys Leu Lys Val Glu Asp Gly Ile Phe Gly Thr Ser Gly
65                  70                  75                  80

Gly Ile Gly Phe Thr Lys Gln Asn Glu Leu Phe Val Gly Arg Val Ala
                85                  90                  95

Met Leu Gly Phe Ala Ala Ser Leu Leu Gly Glu Gly Ile Thr Gly Lys
            100                 105                 110

Gly Ile Leu Ser Gln Leu Asn Leu Glu Thr Gly Ile Pro Ile Tyr Glu
        115                 120                 125

Ala Glu Pro Leu Leu Leu Phe Phe Ile Leu Phe Thr Leu Leu Gly Ala
    130                 135                 140

Ile Gly Ala Leu Gly Asp Arg Gly Arg Phe Val Asp Glu Pro Thr Gly
145                 150                 155                 160

Leu Asp Lys Ala Ile Ile Pro Pro Gly Lys Gly Phe Arg Ser Ala Leu
                165                 170                 175

Gly Leu Ser Glu Gly Gly Pro Leu Phe Gly Phe Thr Lys Ala Asn Glu
            180                 185                 190

Leu Phe Val Gly Arg Leu Ala Gln Leu Gly Ile Ala Phe Ser Leu Ile
        195                 200                 205

Gly Glu Ile Ile Thr Gly Lys Gly Ala Leu Ala Gln Leu Asn Ile Glu
    210                 215                 220

Thr Gly Leu Pro Val Ser Glu Ile Glu Pro Leu Val Leu Phe Asn Val
225                 230                 235                 240

Ala Phe Phe Phe Ile Ala Ala Leu Asn Pro Gly Thr Gly Lys Phe Val
                245                 250                 255

Thr Asp Glu Glu Glu Asp
            260

<210> SEQ ID NO 144
<211> LENGTH: 264
<212> TYPE: PRT
<213> ORGANISM: Dorcoceras hygrometricum

<400> SEQUENCE: 144

Met Ala Ala Gln Thr Met Leu Thr Ala Asn Ala Ile Asn Ala Gly
1               5                   10                  15

Gly Glu Ala Leu Ile Arg Arg Leu Lys Pro Lys Pro Phe Ser His Phe
            20                  25                  30

Leu Leu Pro Ser Lys Ala Gly Ser Ala Pro Ser Ser Ala Cys Gly Ile
        35                  40                  45
```

```
Val Ala Ile Phe Lys Ala Lys Pro Lys Ala Asp Pro Val Lys Lys Gly
            50                  55                  60

Pro Ala Ala Lys Glu Lys Leu Lys Val Glu Asp Gly Ile Phe Gly Thr
 65                  70                  75                  80

Ser Gly Gly Ile Gly Phe Thr Lys Gln Asn Glu Leu Phe Val Gly Arg
                85                  90                  95

Val Ala Met Ile Gly Phe Ala Ala Ser Leu Leu Gly Glu Ala Ile Thr
               100                 105                 110

Gly Lys Gly Ile Leu Ala Gln Leu Asn Leu Glu Thr Gly Ile Pro Ile
           115                 120                 125

Tyr Glu Ala Glu Pro Leu Leu Leu Phe Phe Ile Leu Phe Asn Leu Leu
       130                 135                 140

Gly Ala Ile Gly Ala Leu Gly Asp Arg Gly Arg Phe Val Asp Asp Thr
145                 150                 155                 160

Thr Gly Leu Asp Lys Ala Val Ile Ser Pro Gly Lys Gly Phe Arg Ser
               165                 170                 175

Ala Leu Gly Leu Gly Glu Gly Gly Pro Leu Phe Gly Phe Thr Lys Ala
           180                 185                 190

Asn Glu Leu Phe Val Gly Arg Leu Ala Gln Leu Gly Ile Ala Phe Ser
       195                 200                 205

Ile Ile Gly Glu Ile Ile Thr Gly Lys Gly Ala Leu Ala Gln Leu Asn
   210                 215                 220

Phe Glu Thr Gly Val Pro Ile Thr Glu Ile Glu Pro Leu Ile Leu Phe
225                 230                 235                 240

Asn Val Ala Phe Phe Ile Ala Ala Ile Asn Pro Gly Thr Gly Lys
               245                 250                 255

Phe Val Thr Asp Asp Gly Asp Asp
           260

<210> SEQ ID NO 145
<211> LENGTH: 269
<212> TYPE: PRT
<213> ORGANISM: Olea europaea

<400> SEQUENCE: 145

Met Ala Gln Thr Met Leu Leu Ser Ala Gly Ser Thr Val Ser Gly His
1               5                   10                  15

Ala Leu Asp Leu Lys Lys Asp Pro Leu Met Met Gln Arg Leu Lys Pro
               20                  25                  30

Lys Pro Phe Ser His Phe Val Leu Pro Pro Lys Thr Ser Ser Pro Leu
           35                  40                  45

Ser Ser Ser Thr Thr Thr Val Ala Leu Phe Lys Ser Lys Thr Lys Ala
       50                  55                  60

Pro Ala Lys Lys Val Pro Val Lys Glu Lys Pro Lys Val Glu Asp
 65                  70                  75                  80

Gly Ile Phe Gly Thr Ser Gly Phe Gly Phe Thr Lys Glu Asn Glu
               85                  90                  95

Leu Phe Val Gly Arg Val Ala Met Ile Gly Phe Ala Ala Ser Leu Leu
               100                 105                 110

Gly Glu Ala Val Thr Gly Lys Gly Ile Leu Ala Gln Leu Asn Leu Glu
           115                 120                 125

Thr Gly Ile Pro Leu Tyr Glu Ala Glu Pro Leu Leu Leu Phe Phe Ile
       130                 135                 140

Leu Phe Asn Leu Leu Gly Ala Ile Gly Ala Leu Gly Asp Arg Gly Arg
```

```
                145                 150                 155                 160
        Phe Val Asp Asp Pro Thr Gly Leu Asp Lys Ala Val Ile Ala Pro
                        165                 170                 175

Gly Lys Gly Ile Arg Gly Ala Leu Gly Leu Gly Asp Gly Pro Leu Phe
                        180                 185                 190

Gly Phe Thr Lys Ser Asn Glu Leu Phe Val Gly Arg Leu Ala Gln Leu
                        195                 200                 205

Gly Ile Val Phe Ser Ile Ile Gly Glu Ile Val Thr Gly Lys Gly Ala
                        210                 215                 220

Leu Ala Gln Leu Asn Ile Glu Thr Gly Val Pro Ile Asn Glu Leu Glu
        225                 230                 235                 240

Pro Leu Leu Leu Phe Asn Ile Val Phe Phe Ile Ala Ala Ile Asn
                        245                 250                 255

Pro Gly Thr Gly Lys Phe Val Thr Asp Glu Glu Glu Ala
                        260                 265

<210> SEQ ID NO 146
<211> LENGTH: 269
<212> TYPE: PRT
<213> ORGANISM: Olea europaea

<400> SEQUENCE: 146

Met Val Gln Thr Met Leu Phe Ser Ala Ser Thr Val Ser Gly His
        1               5                   10                  15

Ala Leu Asp Leu Lys Lys Glu Gln Leu Met Ile Gln Arg Leu Lys Pro
                        20                  25                  30

Lys Pro Phe Ser His Phe Leu Pro Pro Lys Thr Ser Ser Pro Leu
                        35                  40                  45

Ser Ser Ser Thr Thr Thr Val Ala Leu Phe Lys Ser Lys Ala Lys Ala
        50                  55                  60

Pro Ala Lys Lys Ile Ala Val Val Lys Glu Lys Thr Lys Val Glu Asp
        65                  70                  75                  80

Gly Ile Phe Gly Thr Ser Gly Gly Phe Gly Phe Thr Lys Glu Asn Glu
                        85                  90                  95

Leu Phe Val Gly Arg Val Ala Met Ile Gly Phe Ala Ala Ser Leu Leu
                        100                 105                 110

Gly Glu Ala Val Thr Gly Lys Gly Ile Leu Ser Gln Leu Asn Leu Glu
                        115                 120                 125

Thr Gly Ile Pro Ile Tyr Glu Ala Glu Pro Leu Leu Leu Phe Phe Ile
        130                 135                 140

Leu Phe Asn Leu Leu Gly Ala Ile Gly Ala Leu Gly Asp Arg Gly Arg
        145                 150                 155                 160

Phe Val Asp Glu Thr Pro Thr Gly Leu Asp Lys Ala Val Ile Ala Pro
                        165                 170                 175

Gly Lys Gly Phe Arg Gly Ala Leu Gly Leu Gly Asp Gly Pro Leu Phe
                        180                 185                 190

Gly Phe Thr Lys Ser Asn Glu Leu Phe Val Gly Arg Leu Ala Gln Leu
                        195                 200                 205

Gly Ile Val Phe Ser Ile Ile Gly Glu Ile Val Thr Gly Lys Gly Ala
                        210                 215                 220

Leu Ala Gln Leu Asn Ile Glu Thr Gly Val Pro Ile Asn Glu Leu Glu
        225                 230                 235                 240

Pro Leu Leu Leu Phe Asn Ile Val Phe Phe Ile Ala Ala Ile Asn
                        245                 250                 255
```

-continued

Pro Gly Thr Gly Lys Phe Val Thr Asp Glu Glu Glu Ala
         260                 265

<210> SEQ ID NO 147
<211> LENGTH: 260
<212> TYPE: PRT
<213> ORGANISM: Handroanthus impetiginosus

<400> SEQUENCE: 147

Met Ala Gln Thr Met Leu Leu Thr Ala Asn Val Ser Gly Glu Pro Leu
1               5                   10                  15

Leu Ile Gln Lys Leu Arg Lys Pro Phe Ala His Gln Phe Leu Leu Pro
            20                  25                  30

Lys Arg Ser Phe Ser Arg Phe Ser Thr Ser Thr Thr Tyr Ala Phe
        35                  40                  45

Phe Lys Ser Lys Thr Lys Ala Ala Pro Pro Lys Lys Ala Val Val Val
    50                  55                  60

Lys Glu Lys Ser Lys Val Glu Asp Gly Ile Phe Gly Thr Ser Gly Gly
65                  70                  75                  80

Ile Gly Phe Thr Lys Gln Asn Glu Leu Phe Val Gly Arg Val Ala Met
                85                  90                  95

Ile Gly Phe Ala Ala Ser Leu Leu Gly Glu Ala Ile Thr Gly Lys Gly
            100                 105                 110

Ile Leu Ala Gln Leu Asn Leu Glu Thr Gly Ile Pro Ile Tyr Glu Ala
            115                 120                 125

Glu Pro Leu Leu Leu Phe Phe Ile Leu Phe Asn Leu Leu Gly Ala Ile
        130                 135                 140

Gly Ala Leu Gly Asp Arg Gly Arg Phe Val Asp Glu Pro Ala Gly Leu
145                 150                 155                 160

Glu Lys Ala Val Ile Pro Pro Gly Lys Gly Phe Arg Ala Ala Leu Gly
                165                 170                 175

Leu Gly Glu Gly Pro Leu Phe Gly Phe Thr Lys Ala Asn Glu Leu Phe
            180                 185                 190

Val Gly Arg Leu Ala Gln Leu Gly Ile Ala Phe Ser Ile Ile Gly Glu
        195                 200                 205

Ile Ile Thr Gly Lys Gly Ala Leu Ala Gln Leu Asn Phe Glu Thr Gly
    210                 215                 220

Val Pro Ile Asn Glu Ile Glu Pro Leu Leu Leu Phe Asn Ile Leu Phe
225                 230                 235                 240

Phe Phe Val Ala Ala Ile Asn Pro Gly Thr Gly Lys Phe Val Thr Asp
                245                 250                 255

Glu Glu Glu Asp
            260

<210> SEQ ID NO 148
<211> LENGTH: 262
<212> TYPE: PRT
<213> ORGANISM: Plantago major

<400> SEQUENCE: 148

Met Ala Gln Thr Met Leu Leu Ser Ala Asn Val Ser Ala His Leu Lys
1               5                   10                  15

Ser Glu Gln Pro Leu Ile Lys Thr Phe Lys Pro Lys Ala Phe Ser Asn
            20                  25                  30

Phe Val Leu Pro Pro Arg Thr Asn Val Ser Arg Ser Leu Pro Phe Thr
        35                  40                  45

Thr Tyr Ala Leu Phe Lys Ser Lys Thr Lys Ala Pro Thr Lys Ala Pro
    50                  55                  60

Val Val Lys Glu Lys Pro Lys Val Glu Asp Gly Ile Phe Gly Thr Ser
65                  70                  75                  80

Gly Gly Ile Gly Phe Thr Lys Gln Asn Glu Leu Phe Val Gly Arg Val
                85                  90                  95

Ala Met Ile Gly Phe Ala Ala Ser Leu Leu Gly Glu Ala Ile Thr Gly
            100                 105                 110

Lys Gly Ile Leu Ala Gln Leu Asn Leu Glu Thr Gly Ile Pro Ile Phe
        115                 120                 125

Glu Ala Glu Pro Leu Leu Leu Phe Phe Ile Leu Phe Asn Leu Leu Gly
130                 135                 140

Ala Ile Gly Ala Leu Gly Asp Arg Gly Arg Phe Val Asp Glu Pro Thr
145                 150                 155                 160

Gly Leu Asp Lys Ala Val Ile Ala Pro Gly Lys Gly Phe Arg Ala Ala
                165                 170                 175

Leu Gly Leu Gly Ser Gly Pro Leu Phe Gly Phe Thr Lys Ala Asn Glu
            180                 185                 190

Leu Phe Val Gly Arg Leu Ala Gln Leu Gly Ile Ala Phe Ser Ile Ile
        195                 200                 205

Gly Glu Ile Val Thr Gly Lys Gly Ala Leu Ala Gln Leu Asn Val Glu
210                 215                 220

Thr Gly Val Pro Ile Gly Glu Leu Glu Pro Leu Leu Leu Phe Asn Ile
225                 230                 235                 240

Val Phe Phe Phe Val Ala Ala Ile Asn Pro Gly Thr Gly Lys Phe Val
                245                 250                 255

Thr Asp Glu Glu Glu Asp
            260

<210> SEQ ID NO 149
<211> LENGTH: 264
<212> TYPE: PRT
<213> ORGANISM: Sesamum indicum

<400> SEQUENCE: 149

Met Ala Gln Thr Met Leu Leu Thr Ala Asn Val Ser Gly His Val Lys
1               5                   10                  15

Gly Glu Gln Leu Leu Ile His Thr Leu Lys Pro Lys Pro Phe Ser His
            20                  25                  30

Phe Leu Leu Pro Pro Arg Thr Arg Thr Thr Ser Ser His Leu Pro
        35                  40                  45

Ser Ser Thr Thr Val Ala Leu Phe Lys Ser Lys Thr Lys Ala Pro Pro
50                  55                  60

Ala Lys Lys Val Val Glu Lys Pro Lys Val Glu Asp Gly Ile Phe Gly
65                  70                  75                  80

Thr Ser Gly Gly Ile Gly Phe Thr Lys Gln Asn Glu Leu Phe Val Gly
                85                  90                  95

Arg Val Ala Met Ile Gly Phe Ala Ala Ser Leu Leu Gly Glu Ala Ile
            100                 105                 110

Thr Gly Lys Gly Ile Leu Ala Gln Leu Asn Leu Glu Thr Gly Ile Pro
        115                 120                 125

Ile Tyr Glu Ala Glu Pro Leu Leu Leu Phe Phe Ile Leu Phe Asn Leu
130                 135                 140

Leu Gly Ala Ile Gly Ala Leu Gly Asp Arg Gly Arg Phe Val Asp Glu
145                 150                 155                 160

```
Pro Thr Gly Leu Glu Lys Ala Val Ile Pro Pro Gly Lys Gly Phe Arg
                165                 170                 175

Ala Ala Leu Gly Leu Gly Asp Gly Pro Leu Phe Gly Phe Thr Lys Ala
            180                 185                 190

Asn Glu Leu Phe Val Gly Arg Leu Ala Gln Leu Gly Ile Ala Phe Ser
        195                 200                 205

Ile Ile Gly Glu Ile Val Thr Gly Lys Gly Ala Leu Ala Gln Leu Asn
    210                 215                 220

Ile Glu Thr Gly Val Pro Ile Asn Glu Ile Glu Pro Leu Leu Leu Phe
225                 230                 235                 240

Asn Ile Leu Phe Phe Val Ala Ala Ile Asn Pro Gly Thr Gly Lys
                245                 250                 255

Phe Val Thr Asp Glu Glu Glu Asp
                260

<210> SEQ ID NO 150
<211> LENGTH: 271
<212> TYPE: PRT
<213> ORGANISM: Arabidopsis thaliana

<400> SEQUENCE: 150

Met Pro Gln Ser Leu Leu Met Ser Gly Ala Ala Ile Asp Phe Lys Arg
1               5                   10                  15

Asp Asn Ala Leu Leu Gln Phe Gln Ser Thr His Ser Leu Leu Arg Pro
            20                  25                  30

Ala Pro Phe Ser His Ser Val Arg Pro Pro Leu Pro Pro Arg Arg Cys
        35                  40                  45

Leu Val Leu Gly Thr Pro Phe Pro Leu Ala Leu Phe Lys Ser Lys Thr
    50                  55                  60

Lys Ala Ala Pro Val Lys Lys Val Ala Glu Ser Lys Pro Lys Val Glu
65                  70                  75                  80

Asp Gly Ile Phe Gly Thr Ser Gly Gly Ile Gly Phe Thr Lys Gln Asn
                85                  90                  95

Glu Leu Phe Val Gly Arg Val Ala Met Ile Gly Phe Ala Ala Ser Ile
            100                 105                 110

Leu Gly Glu Ala Ile Thr Gly Lys Gly Ile Leu Ala Gln Leu Asn Leu
        115                 120                 125

Glu Thr Gly Ile Pro Ile Tyr Glu Ala Glu Pro Leu Leu Leu Phe Phe
    130                 135                 140

Ile Leu Phe Thr Leu Leu Gly Ala Ile Gly Ala Leu Gly Asp Arg Gly
145                 150                 155                 160

Arg Phe Val Asp Asp Ser Pro Thr Gly Leu Asp Lys Ala Val Ile Pro
                165                 170                 175

Pro Gly Lys Gly Ile Arg Ser Ala Leu Gly Leu Pro Glu Gly Gly Pro
            180                 185                 190

Leu Phe Gly Phe Thr Lys Ala Asn Glu Leu Phe Val Gly Arg Leu Ala
        195                 200                 205

Gln Leu Gly Ile Ala Phe Ser Ile Ile Gly Glu Ile Val Thr Gly Lys
    210                 215                 220

Gly Ala Leu Ala Gln Leu Asn Ile Glu Thr Gly Val Pro Leu Ser Asp
225                 230                 235                 240

Ile Glu Pro Leu Val Leu Phe Asn Val Leu Phe Phe Val Ala Ala
                245                 250                 255

Leu Asn Pro Gly Ser Gly Lys Phe Val Thr Asp Glu Asp Lys Asp
```

<210> SEQ ID NO 151
<211> LENGTH: 272
<212> TYPE: PRT
<213> ORGANISM: Musa acuminata

<400> SEQUENCE: 151

Met Ala Gln Ser Met Leu Val Ser Ser Ile Gly Gly Lys Glu Ala Ala
1               5                   10                  15
Leu Leu Gln Ser Gln Thr His Arg Leu Arg Pro Thr Pro Phe Ser His
                20                  25                  30
Leu Leu Leu Pro Arg Val Pro His Gly Arg Gln Leu Pro Pro Pro Ala
            35                  40                  45
Ala Ser Phe Phe Pro Thr Leu Ala Ile Phe Lys Pro Lys Thr Lys Ala
        50                  55                  60
Pro Ala Lys Lys Gln Val Ala Lys Pro Lys Pro Lys Arg Lys Val Glu
65                  70                  75                  80
Asp Gly Ile Phe Gly Thr Ser Gly Gly Ile Gly Phe Thr Lys Gln Asn
                85                  90                  95
Glu Leu Phe Val Gly Arg Val Ala Met Ile Gly Phe Ala Ala Ser Ile
            100                 105                 110
Leu Gly Glu Ala Ile Thr Gly Lys Gly Ile Leu Ala Gln Leu Asn Leu
        115                 120                 125
Glu Thr Gly Ile Pro Ile Tyr Glu Ala Glu Pro Leu Leu Leu Phe Phe
    130                 135                 140
Ile Leu Phe Thr Leu Leu Gly Ala Ile Gly Ala Leu Gly Asp Arg Gly
145                 150                 155                 160
Ser Phe Val Asp Asp Pro Pro Thr Gly Leu Glu Gly Ala Val Ile Pro
                165                 170                 175
Pro Gly Lys Gly Phe Arg Ser Ala Leu Gly Leu Lys Glu Gly Gly Pro
            180                 185                 190
Leu Phe Gly Phe Thr Lys Ala Asn Glu Leu Phe Val Gly Arg Leu Ala
        195                 200                 205
Gln Leu Gly Ile Ala Phe Ser Ile Ile Gly Glu Ile Val Thr Gly Lys
    210                 215                 220
Gly Ala Leu Ala Gln Leu Asn Ile Glu Thr Gly Val Pro Ile Ser Asp
225                 230                 235                 240
Ile Glu Pro Leu Val Leu Phe Asn Val Val Phe Phe Phe Ala Ala
                245                 250                 255
Leu Asn Pro Gly Thr Gly Lys Phe Val Thr Asp Val Glu Glu Glu Glu
            260                 265                 270

<210> SEQ ID NO 152
<211> LENGTH: 274
<212> TYPE: PRT
<213> ORGANISM: Ensete ventricosum

<400> SEQUENCE: 152

Met Met Ala Gln Ser Met Leu Val Ser Ser Ile Gly Gly Lys Glu Ala
1               5                   10                  15
Ala Leu Leu Gln Ser Gln Thr His Arg Leu Arg Pro Thr Pro Phe Ser
                20                  25                  30
His Leu Leu Leu Pro Arg Val Pro His Gly Arg Gln Leu Pro Pro Pro
            35                  40                  45
Ala Ala Ser Phe Phe Pro Thr Leu Ala Ile Phe Lys Pro Arg Thr Lys

```
            50                  55                  60
Ala Pro Ala Lys Lys Gln Val Ala Ser Phe Pro Lys Pro Lys Gln Lys
 65                  70                  75                  80

Val Glu Asp Gly Ile Phe Gly Thr Ser Gly Ile Gly Phe Thr Lys
                     85                  90                  95

Gln Asn Glu Leu Phe Val Gly Arg Val Ala Met Leu Gly Phe Ala Ala
                    100                 105                 110

Ser Ile Leu Gly Glu Ala Ile Thr Gly Lys Gly Ile Leu Ala Gln Leu
                    115                 120                 125

Asn Leu Glu Thr Gly Ile Pro Ile Tyr Glu Ala Glu Pro Leu Leu Leu
                    130                 135                 140

Phe Phe Ile Leu Phe Thr Leu Leu Gly Ala Ile Gly Ala Leu Gly Asp
145                 150                 155                 160

Arg Gly Ser Phe Val Asp Asp Pro Pro Thr Gly Leu Glu Gly Ala Val
                    165                 170                 175

Ile Pro Pro Gly Lys Gly Phe Arg Ser Ala Leu Gly Leu Lys Glu Gly
                    180                 185                 190

Gly Pro Leu Phe Gly Phe Thr Lys Ala Asn Glu Leu Phe Val Gly Arg
                    195                 200                 205

Leu Ala Gln Leu Gly Ile Ala Phe Ser Ile Ile Gly Glu Ile Val Thr
                    210                 215                 220

Gly Lys Gly Ala Leu Ala Gln Leu Asn Ile Glu Thr Gly Val Pro Ile
225                 230                 235                 240

Gly Glu Ile Glu Pro Leu Val Leu Phe Asn Val Leu Phe Phe Phe
                    245                 250                 255

Ala Ala Leu Asn Pro Gly Thr Gly Lys Phe Val Thr Asp Val Glu Glu
                    260                 265                 270

Glu Glu

<210> SEQ ID NO 153
<211> LENGTH: 274
<212> TYPE: PRT
<213> ORGANISM: Ensete ventricosum

<400> SEQUENCE: 153

Met Met Ala Gln Ser Met Leu Val Ser Ser Ile Gly Gly Lys Glu Ala
 1               5                  10                  15

Ala Leu Leu Gln Ser Gln Thr His Arg Leu Arg Pro Thr Pro Phe Ser
                    20                  25                  30

His Leu Leu Leu Pro Arg Val Pro His Gly Arg Gln Leu Pro Pro Pro
                    35                  40                  45

Ala Ala Ser Phe Phe Pro Thr Leu Ala Ile Phe Lys Pro Arg Thr Lys
                    50                  55                  60

Ala Pro Ala Lys Lys Gln Val Ala Ser Phe Pro Lys Pro Lys Gln Lys
 65                  70                  75                  80

Val Glu Asp Gly Ile Phe Gly Thr Ser Gly Ile Gly Phe Thr Lys
                     85                  90                  95

Gln Asn Glu Leu Phe Val Gly Arg Val Ala Met Leu Gly Phe Ala Ala
                    100                 105                 110

Ser Ile Leu Gly Glu Ala Ile Thr Gly Lys Gly Ile Leu Ala Gln Leu
                    115                 120                 125

Asn Leu Glu Thr Gly Ile Pro Ile Tyr Glu Ala Glu Pro Leu Leu Leu
                    130                 135                 140

Phe Phe Ile Leu Phe Thr Leu Leu Gly Ala Ile Gly Ala Leu Gly Asp
```

```
145                 150                 155                 160
Arg Gly Ser Phe Val Asp Asp Pro Thr Gly Leu Glu Gly Ala Val
                165                 170                 175

Ile Pro Pro Gly Lys Gly Phe Arg Ser Ala Leu Gly Leu Lys Asp Gly
                180                 185                 190

Gly Pro Leu Phe Gly Phe Thr Lys Ser Asn Glu Leu Phe Val Gly Arg
                195                 200                 205

Leu Ala Gln Leu Gly Ile Ala Phe Ser Ile Ile Gly Glu Ile Val Thr
    210                 215                 220

Gly Lys Gly Ala Leu Ala Gln Leu Asn Ile Glu Thr Gly Val Pro Ile
225                 230                 235                 240

Ser Glu Ile Glu Pro Leu Val Leu Phe Asn Val Leu Phe Phe Phe
                    245                 250                 255

Ala Ala Leu Asn Pro Gly Thr Gly Lys Phe Val Thr Asp Val Glu Glu
                260                 265                 270

Glu Glu

<210> SEQ ID NO 154
<211> LENGTH: 268
<212> TYPE: PRT
<213> ORGANISM: Sorghum bicolor

<400> SEQUENCE: 154

Met Ala Gln Ser Met Leu Met Ser Thr Ser Val Asn Gly Gly Arg Ala
1               5                   10                  15

Leu Pro Ser Leu Gln Ala Gly Arg Pro Ala Pro Tyr Pro Arg Leu Pro
                20                  25                  30

Leu Pro Ser Ser Ser Ser Gly Tyr Arg His Ser Lys Ser Val Ser Val
            35                  40                  45

Lys Thr Leu Ala Leu Phe Gly Lys Ser Lys Val Lys Thr Ala Pro Ser
    50                  55                  60

Lys Lys Ala Ala Ala Pro Lys Pro Lys Pro Lys Val Glu Asp Gly Ile
65                  70                  75                  80

Phe Gly Thr Ser Gly Gly Ile Gly Phe Thr Lys Glu Asn Glu Leu Phe
                85                  90                  95

Val Gly Arg Val Ala Met Leu Gly Phe Ala Ala Ser Leu Leu Gly Glu
                100                 105                 110

Ala Ile Thr Gly Lys Gly Ile Leu Ala Gln Leu Asn Leu Glu Thr Gly
            115                 120                 125

Ile Pro Ile Tyr Glu Ala Glu Pro Leu Leu Phe Phe Ile Leu Phe
    130                 135                 140

Thr Leu Leu Gly Ala Ile Gly Ala Leu Gly Asp Arg Gly Arg Phe Val
145                 150                 155                 160

Asp Glu Glu Val Thr Gly Leu Asp Lys Ala Val Ile Gln Pro Gly Lys
                165                 170                 175

Gly Phe Arg Gly Ala Leu Gly Leu Ser Glu Gly Gly Pro Leu Phe Gly
                180                 185                 190

Phe Thr Lys Ser Asn Glu Leu Phe Val Gly Arg Leu Ala Gln Leu Gly
                195                 200                 205

Val Ala Phe Ser Ile Ile Gly Glu Ile Thr Gly Lys Gly Ala Leu
                210                 215                 220

Ala Gln Leu Asn Ile Glu Thr Gly Val Pro Ile Asn Glu Ile Glu Pro
225                 230                 235                 240

Leu Val Ile Phe Asn Val Leu Phe Phe Val Ala Ala Ile Asn Pro
```

```
                    245                 250                 255

Gly Asn Gly Arg Phe Ile Ile Gly Glu Asp Glu Glu
            260                 265

<210> SEQ ID NO 155
<211> LENGTH: 268
<212> TYPE: PRT
<213> ORGANISM: Saccharum hybrid

<400> SEQUENCE: 155

Met Ala Gln Ser Met Leu Met Ser Thr Ser Val Asn Gly Gly Arg Ala
1               5                   10                  15

Leu Pro Ser Leu Gln Ala Gly Arg Pro Ala Pro Tyr Pro Arg Leu Pro
            20                  25                  30

Gln Pro Ser Ser Ser Ser Gly Tyr Arg His Ser Lys Ser Val Ser Val
        35                  40                  45

Lys Thr Leu Ala Leu Phe Gly Lys Ser Lys Val Lys Thr Ala Pro Ser
    50                  55                  60

Lys Lys Ala Ala Ala Pro Lys Pro Lys Pro Lys Val Glu Asp Gly Ile
65                  70                  75                  80

Phe Gly Thr Ser Gly Gly Ile Gly Phe Thr Lys Glu Asn Glu Leu Phe
                85                  90                  95

Val Gly Arg Val Ala Met Leu Gly Phe Ala Ala Ser Leu Leu Gly Glu
            100                 105                 110

Ala Ile Thr Gly Lys Gly Ile Leu Ala Gln Leu Asn Leu Glu Thr Gly
        115                 120                 125

Ile Pro Ile Tyr Glu Ala Glu Pro Leu Leu Leu Phe Phe Ile Leu Phe
    130                 135                 140

Thr Leu Leu Gly Ala Ile Gly Ala Leu Gly Asp Arg Gly Arg Phe Val
145                 150                 155                 160

Asp Glu Glu Val Thr Gly Leu Asp Lys Ala Val Ile Gln Pro Gly Lys
                165                 170                 175

Gly Phe Arg Gly Ala Leu Gly Leu Ser Glu Gly Gly Pro Leu Phe Gly
            180                 185                 190

Phe Thr Lys Ser Asn Glu Leu Phe Val Gly Arg Leu Ala Gln Leu Gly
        195                 200                 205

Val Ala Phe Ser Ile Ile Gly Glu Ile Ile Thr Gly Lys Gly Ala Leu
    210                 215                 220

Ala Gln Leu Asn Ile Glu Thr Gly Val Pro Ile Asn Glu Ile Glu Pro
225                 230                 235                 240

Leu Val Ile Phe Asn Val Leu Phe Phe Phe Val Ala Ala Ile Asn Pro
                245                 250                 255

Gly Asn Gly Arg Phe Ile Ile Gly Glu Asp Glu Glu
            260                 265

<210> SEQ ID NO 156
<211> LENGTH: 265
<212> TYPE: PRT
<213> ORGANISM: Dichanthelium oligosanthes

<400> SEQUENCE: 156

Met Ala Gln Ser Met Ile Met Ser Thr Ser Val Ser Gly Gly Arg Ala
1               5                   10                  15

Leu Pro Ser Leu Gln Ala Val Arg Pro Ala Pro Tyr Pro Arg Leu
            20                  25                  30

Pro Leu Pro Ser Val Tyr Arg His Ser Lys Ser Val Ser Val Lys Thr
```

```
            35                  40                  45
Leu Ala Leu Phe Gly Gly Lys Ser Lys Ala Ala Lys Ala Ala Pro Val
 50                  55                  60
Lys Lys Ala Pro Ala Pro Lys Pro Lys Val Glu Asp Gly Ile Phe Gly
 65                  70                  75                  80
Thr Ser Gly Gly Ile Gly Phe Thr Lys Glu Asn Glu Leu Phe Val Gly
                     85                  90                  95
Arg Val Ala Met Leu Gly Phe Ala Ala Ser Leu Leu Gly Glu Ala Ile
                    100                 105                 110
Thr Gly Lys Gly Ile Leu Ala Gln Leu Asn Leu Glu Thr Gly Ile Pro
                115                 120                 125
Ile Tyr Glu Ala Glu Pro Leu Leu Leu Phe Phe Ile Leu Phe Thr Leu
            130                 135                 140
Leu Gly Ala Ile Gly Ala Leu Gly Asp Arg Gly Thr Phe Val Asp Asp
145                 150                 155                 160
Val Thr Gly Leu Asp Lys Ala Val Ile Gln Pro Gly Lys Gly Phe Arg
                165                 170                 175
Gly Ala Leu Gly Leu Ser Glu Gly Gly Pro Leu Phe Gly Phe Thr Lys
                180                 185                 190
Ser Asn Glu Leu Phe Val Gly Arg Leu Ala Gln Leu Gly Val Ala Phe
            195                 200                 205
Ser Ile Ile Gly Glu Ile Ile Thr Gly Lys Gly Ala Leu Ala Gln Leu
        210                 215                 220
Asn Ile Glu Thr Gly Val Pro Ile Asn Glu Ile Glu Pro Leu Val Leu
225                 230                 235                 240
Phe Asn Val Leu Phe Phe Ile Ala Ala Val Asn Pro Gly Thr Gly
                245                 250                 255
Lys Phe Ile Ile Ser Glu Glu Glu
                260                 265

<210> SEQ ID NO 157
<211> LENGTH: 265
<212> TYPE: PRT
<213> ORGANISM: Setaria italica

<400> SEQUENCE: 157

Met Ala Gln Ser Met Leu Met Ser Thr Ser Val Ser Gly Gly Arg Ala
 1               5                  10                  15
Leu Pro Ser Leu Gln Ala Ala Arg Pro Ala Ala Ala Tyr Pro Arg Leu
                20                  25                  30
Ala Leu Pro Ser Val Asn Arg His Ser Lys Ser Val Ser Val Lys Thr
            35                  40                  45
Leu Ala Leu Phe Gly Lys Ser Lys Ala Ala Lys Ala Ala Pro Ala Lys
 50                  55                  60
Lys Val Ala Ala Pro Lys Pro Lys Val Glu Asp Gly Ile Phe Gly Thr
 65                  70                  75                  80
Ser Gly Gly Ile Gly Phe Thr Lys Glu Asn Glu Leu Phe Val Gly Arg
                 85                  90                  95
Val Ala Met Leu Gly Phe Ala Ala Ser Leu Leu Gly Glu Ala Ile Thr
                100                 105                 110
Gly Lys Gly Ile Leu Ala Gln Leu Asn Leu Glu Thr Gly Ile Pro Ile
            115                 120                 125
Tyr Glu Ala Glu Pro Leu Leu Leu Phe Phe Ile Leu Phe Thr Leu Leu
        130                 135                 140
```

```
Gly Ala Ile Gly Ala Leu Gly Asp Arg Gly Thr Phe Val Asp Asp Val
145                 150                 155                 160

Thr Gly Leu Asp Lys Ala Val Ile Gln Pro Gly Lys Gly Phe Arg Gly
            165                 170                 175

Ala Leu Gly Leu Ser Glu Gly Gly Pro Leu Phe Gly Phe Thr Lys Ser
        180                 185                 190

Asn Glu Leu Phe Val Gly Arg Leu Ala Gln Leu Gly Val Ala Phe Ser
    195                 200                 205

Ile Ile Gly Glu Ile Ile Thr Gly Lys Gly Ala Leu Ala Gln Leu Asn
210                 215                 220

Ile Glu Thr Gly Val Pro Ile Asn Glu Ile Glu Pro Leu Val Leu Phe
225                 230                 235                 240

Asn Val Leu Phe Phe Phe Ile Ala Ala Ile Asn Pro Gly Thr Gly Lys
                245                 250                 255

Phe Ile Ile Gly Asp Asp Glu Lys Glu
            260                 265

<210> SEQ ID NO 158
<211> LENGTH: 262
<212> TYPE: PRT
<213> ORGANISM: Panicum miliaceum

<400> SEQUENCE: 158

Met Ala Gln Ser Met Leu Met Ser Thr Ser Val Ser Gly Gly Arg Ala
1               5                   10                  15

Leu Pro Ser Leu Gln Ala Gly Arg Pro Ala Pro Tyr Leu Arg Leu Ala
            20                  25                  30

Leu Pro Ser Ala Tyr Arg His Ser Arg Ser Val Ser Val Lys Thr Leu
        35                  40                  45

Ala Leu Phe Gly Lys Ser Lys Ala Ala Lys Ala Pro Ala Lys Lys Ala
    50                  55                  60

Pro Ala Pro Lys Pro Lys Val Glu Asp Gly Ile Phe Gly Thr Ser Gly
65                  70                  75                  80

Gly Ile Gly Phe Thr Lys Glu Asn Glu Leu Phe Val Gly Arg Val Ala
                85                  90                  95

Met Leu Gly Phe Ala Ala Ser Leu Leu Gly Glu Ala Ile Thr Gly Lys
            100                 105                 110

Gly Ile Leu Ala Gln Leu Asn Leu Glu Thr Gly Ile Pro Ile Tyr Glu
        115                 120                 125

Ala Glu Pro Leu Leu Leu Phe Phe Ile Leu Phe Thr Leu Leu Gly Ala
    130                 135                 140

Ile Gly Ala Leu Gly Asp Arg Gly Thr Phe Val Asp Asp Val Thr Gly
145                 150                 155                 160

Leu Asp Lys Ala Val Ile Pro Pro Gly Lys Gly Phe Arg Gly Ala Leu
                165                 170                 175

Gly Leu Ser Glu Gly Gly Pro Leu Phe Gly Phe Thr Lys Ser Asn Glu
            180                 185                 190

Leu Phe Val Gly Arg Leu Ala Gln Leu Gly Val Ala Phe Ser Ile Ile
        195                 200                 205

Gly Glu Ile Ile Thr Gly Lys Gly Ala Leu Ala Gln Leu Asn Ile Glu
    210                 215                 220

Thr Gly Val Pro Ile Asn Glu Ile Glu Pro Leu Val Leu Phe Asn Val
225                 230                 235                 240

Leu Phe Phe Phe Ile Ala Ala Ile Asn Pro Gly Thr Gly Lys Phe Ile
                245                 250                 255
```

```
Ile Gly Glu Asp Glu Glu
            260

<210> SEQ ID NO 159
<211> LENGTH: 262
<212> TYPE: PRT
<213> ORGANISM: Panicum hallii

<400> SEQUENCE: 159

Met Ala Arg Ser Met Leu Met Ser Thr Ser Val Ser Gly Gly Arg Ala
1               5                   10                  15

Leu Pro Ser Leu Gln Ala Gly Arg Pro Ala Pro Tyr Leu Arg Leu Ala
            20                  25                  30

Leu Pro Ser Ala Tyr Arg His Ser Arg Ser Val Ser Val Lys Thr Leu
        35                  40                  45

Ala Leu Phe Gly Lys Ser Lys Ala Lys Ala Pro Ala Lys Lys Ala
    50                  55                  60

Pro Ala Pro Lys Pro Lys Val Glu Asp Gly Ile Phe Gly Thr Ser Gly
65                  70                  75                  80

Gly Ile Gly Phe Thr Lys Glu Asn Glu Leu Phe Val Gly Arg Val Ala
                85                  90                  95

Met Leu Gly Phe Ala Ala Ser Leu Leu Gly Glu Ala Ile Thr Gly Lys
            100                 105                 110

Gly Ile Leu Ala Gln Leu Asn Leu Glu Thr Gly Ile Pro Ile Tyr Glu
        115                 120                 125

Ala Glu Pro Leu Leu Leu Phe Phe Ile Leu Phe Thr Leu Leu Gly Ala
    130                 135                 140

Ile Gly Ala Leu Gly Asp Arg Gly Thr Phe Val Asp Asp Val Thr Gly
145                 150                 155                 160

Leu Asp Lys Ala Val Ile Pro Pro Gly Lys Gly Phe Arg Gly Ala Leu
                165                 170                 175

Gly Leu Ser Glu Gly Gly Pro Leu Phe Gly Phe Thr Lys Ser Asn Glu
            180                 185                 190

Leu Phe Val Gly Arg Leu Ala Gln Leu Gly Val Ala Phe Ser Ile Ile
        195                 200                 205

Gly Glu Ile Ile Thr Gly Lys Gly Ala Leu Ala Gln Leu Asn Ile Glu
    210                 215                 220

Thr Gly Val Pro Ile Asn Glu Ile Glu Pro Leu Val Leu Phe Asn Val
225                 230                 235                 240

Leu Phe Phe Phe Ile Ala Ala Ile Asn Pro Gly Thr Gly Lys Phe Ile
                245                 250                 255

Ile Gly Glu Asp Glu Glu
            260

<210> SEQ ID NO 160
<211> LENGTH: 269
<212> TYPE: PRT
<213> ORGANISM: Brachypodium distachyon

<400> SEQUENCE: 160

Met Ala Gln Ser Met Leu Met Ser Val Asn Gly Val Ala Ser Ser
1               5                   10                  15

Gly Arg Ser Leu Leu Gln Ala Ala Arg Pro Ala Ala Thr Pro Phe Ser
            20                  25                  30

Arg Leu Ala Leu Pro Ala Ser Pro Ser Tyr Tyr Lys His Met Pro Ser
        35                  40                  45
```

```
Leu Ser Val Arg Thr Met Ala Ile Phe Gly Lys Ser Lys Ala
    50                  55                  60

Ala Pro Ala Lys Lys Val Ala Ala Pro Lys Pro Lys Thr Glu Asp Gly
65                  70                  75                  80

Ile Phe Gly Thr Ser Gly Gly Ile Gly Phe Thr Lys Glu Asn Glu Leu
                85                  90                  95

Phe Val Gly Arg Val Ala Met Ile Gly Phe Ala Ala Ser Ile Leu Gly
                100                 105                 110

Glu Ala Ile Thr Gly Lys Gly Ile Leu Ser Gln Leu Asn Leu Glu Thr
            115                 120                 125

Gly Ile Pro Ile Tyr Glu Ala Glu Pro Leu Leu Phe Phe Ile Leu
            130                 135                 140

Phe Thr Leu Leu Gly Ala Ile Gly Ala Leu Gly Asp Arg Gly Lys Phe
145                 150                 155                 160

Val Asp Glu Gln Pro Thr Gly Leu Asp Lys Ala Val Ile Ala Pro Gly
                165                 170                 175

Lys Gly Phe Arg Ser Ala Leu Gly Leu Ser Glu Gly Gly Pro Leu Phe
                180                 185                 190

Gly Phe Thr Lys Ser Asn Glu Leu Phe Val Gly Arg Leu Ala Gln Leu
                195                 200                 205

Gly Ile Ala Phe Ser Ile Ile Gly Glu Ile Ile Thr Gly Lys Gly Ala
            210                 215                 220

Leu Ala Gln Leu Asn Ile Glu Thr Gly Val Pro Ile Ser Glu Ile Glu
225                 230                 235                 240

Pro Leu Val Leu Phe Asn Val Val Phe Phe Val Ala Ala Ile Asn
                245                 250                 255

Pro Gly Thr Gly Lys Phe Ile Ser Gly Glu Glu Asp Asp
                260                 265

<210> SEQ ID NO 161
<211> LENGTH: 271
<212> TYPE: PRT
<213> ORGANISM: Mycobacteroides abscessus

<400> SEQUENCE: 161

Met Ala Gln Ser Met Leu Met Ser Gly Val Asn Gly Val Ala Ser Gly
1               5                   10                  15

Arg Ser Leu Leu Gln Ala Ala Arg Pro Ser Ser Ala Ser Thr Pro Phe
                20                  25                  30

Ser Arg Leu Ala Leu Ser Ser Ser Ala Ala Tyr Tyr Lys His Met
            35                  40                  45

Pro Ser Leu Ser Val Arg Thr Met Ala Leu Phe Gly Lys Ser Lys Thr
    50                  55                  60

Lys Ala Ala Pro Ala Lys Lys Val Val Ala Pro Lys Pro Lys Thr Glu
65                  70                  75                  80

Asp Gly Ile Phe Gly Thr Ser Gly Gly Ile Gly Phe Thr Lys Glu Asn
                85                  90                  95

Glu Leu Phe Val Gly Arg Val Ala Met Ile Gly Phe Ala Ala Ser Ile
                100                 105                 110

Leu Gly Glu Ala Ile Thr Gly Lys Gly Ile Leu Ser Gln Leu Asn Leu
            115                 120                 125

Glu Thr Gly Ile Pro Ile Tyr Glu Ala Glu Pro Leu Leu Phe Phe
            130                 135                 140

Ile Leu Phe Thr Leu Leu Gly Ala Ile Gly Ala Leu Gly Asp Arg Gly
```

```
145                 150                 155                 160
Arg Phe Val Asp Glu Gln Pro Thr Gly Leu Asp Lys Ala Val Ile Ala
                165                 170                 175

Pro Gly Lys Gly Phe Arg Ser Ala Leu Gly Leu Ser Glu Gly Gly Pro
            180                 185                 190

Leu Phe Gly Phe Thr Lys Ser Asn Glu Leu Phe Val Gly Arg Leu Ala
        195                 200                 205

Gln Leu Gly Ile Ala Phe Ser Ile Ile Gly Glu Ile Ile Thr Gly Lys
    210                 215                 220

Gly Ala Leu Ala Gln Leu Asn Ile Glu Thr Gly Val Pro Ile Ser Glu
225                 230                 235                 240

Ile Glu Pro Leu Val Leu Phe Asn Val Val Phe Phe Ile Ala Ala
                245                 250                 255

Ile Asn Pro Gly Thr Gly Lys Phe Ile Ser Gly Glu Asp Asp
            260                 265                 270

<210> SEQ ID NO 162
<211> LENGTH: 272
<212> TYPE: PRT
<213> ORGANISM: Triticum aestivum

<400> SEQUENCE: 162

Met Ala Gln Ser Met Leu Met Ser Gly Val Asn Gly Val Ala Ser Gly
1               5                   10                  15

Arg Ser Leu Leu Gln Ala Ala Arg Pro Ser Thr Ala Ser Thr Pro Phe
            20                  25                  30

Ser Arg Leu Ala Leu Ser Ser Ser Ala Ala Tyr Tyr Lys His Met
        35                  40                  45

Pro Ser Leu Ser Val Arg Thr Met Ala Leu Phe Gly Lys Ser Lys Thr
    50                  55                  60

Lys Ala Ala Pro Ala Lys Lys Val Ala Ala Pro Lys Pro Lys Thr Glu
65                  70                  75                  80

Asp Gly Ile Phe Gly Thr Ser Gly Gly Ile Gly Phe Thr Lys Glu Asn
                85                  90                  95

Glu Leu Phe Val Gly Arg Val Ala Met Ile Gly Phe Ala Ala Ser Ile
            100                 105                 110

Leu Gly Glu Ala Ile Thr Gly Lys Gly Ile Leu Ser Gln Leu Asn Leu
        115                 120                 125

Glu Thr Gly Ile Pro Ile Tyr Glu Ala Glu Pro Leu Leu Leu Phe Phe
    130                 135                 140

Ile Leu Phe Thr Leu Leu Gly Ala Ile Gly Ala Leu Gly Asp Arg Gly
145                 150                 155                 160

Arg Phe Val Asp Glu Gln Pro Thr Thr Gly Leu Asp Lys Ala Val Ile
                165                 170                 175

Ala Pro Gly Lys Gly Phe Arg Ser Ala Leu Gly Leu Ser Glu Gly Gly
            180                 185                 190

Pro Leu Phe Gly Phe Thr Lys Ser Asn Glu Leu Phe Val Gly Arg Leu
        195                 200                 205

Ala Gln Leu Gly Ile Ala Phe Ser Ile Ile Gly Glu Ile Ile Thr Gly
    210                 215                 220

Lys Gly Ala Leu Ala Gln Leu Asn Ile Glu Thr Gly Val Pro Ile Ser
225                 230                 235                 240

Glu Ile Glu Pro Leu Val Leu Phe Asn Val Val Phe Phe Ile Ala
                245                 250                 255
```

```
Ala Ile Asn Pro Gly Thr Gly Lys Phe Ile Ser Gly Glu Glu Asp Asp
            260                 265                 270

<210> SEQ ID NO 163
<211> LENGTH: 273
<212> TYPE: PRT
<213> ORGANISM: Aegilops tauschii

<400> SEQUENCE: 163

Met Ala Gln Ser Met Leu Met Ser Gly Val Asn Gly Val Ala Ser Gly
1               5                   10                  15

Arg Ser Leu Leu Gln Ala Ala Arg Pro Ser Ser Ala Ser Thr Pro Phe
            20                  25                  30

Ser Arg Leu Ala Leu Ser Ser Ser Ser Ala Ala Tyr Tyr Lys
        35                  40                  45

His Met Pro Ser Leu Ser Val Arg Thr Met Ala Leu Phe Gly Lys Lys
50                  55                  60

Thr Lys Ala Ala Pro Ala Lys Lys Val Val Ala Pro Lys Pro Lys Thr
65                  70                  75                  80

Glu Asp Gly Ile Phe Gly Thr Ser Gly Ile Gly Phe Thr Lys Glu
                85                  90                  95

Asn Glu Leu Phe Val Gly Arg Val Ala Met Ile Gly Phe Ala Ala Ser
            100                 105                 110

Ile Leu Gly Glu Ala Ile Thr Gly Lys Gly Ile Leu Ser Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Thr Leu Leu Gly Ala Ile Gly Ala Leu Gly Asp Arg
145                 150                 155                 160

Gly Arg Phe Val Asp Glu Gln Pro Thr Thr Gly Leu Asp Lys Ala Val
                165                 170                 175

Ile Ala Pro Gly Lys Gly Phe Arg Ser Ala Leu Gly Leu Ser Glu Gly
            180                 185                 190

Gly Pro Leu Phe Gly Phe Thr Lys Ser Asn Glu Leu Phe Val Gly Arg
        195                 200                 205

Leu Ala Gln Leu Gly Ile Ala Phe Ser Ile Ile Gly Glu Ile Ile Thr
    210                 215                 220

Gly Lys Gly Ala Leu Ala Gln Leu Asn Ile Glu Thr Gly Val Pro Ile
225                 230                 235                 240

Ser Glu Ile Glu Pro Leu Val Leu Phe Asn Val Val Phe Phe Phe Ile
                245                 250                 255

Ala Ala Ile Asn Pro Gly Thr Gly Lys Phe Ile Ser Gly Glu Glu Asp
            260                 265                 270

Asp

<210> SEQ ID NO 164
<211> LENGTH: 271
<212> TYPE: PRT
<213> ORGANISM: Triticum urartu

<400> SEQUENCE: 164

Met Ala Gln Ser Met Leu Met Ser Gly Val Asn Gly Val Ala Ser Gly
1               5                   10                  15

Arg Ser Leu Leu Gln Ala Ala Arg Pro Ser Ser Ala Ser Thr Pro Phe
            20                  25                  30

Ser Arg Leu Ala Leu Ser Ser Ser Ser Ser Ala Ala Tyr Tyr Lys His
```

```
                35                  40                  45
Met Pro Ser Leu Ser Val Arg Thr Met Ala Leu Phe Gly Lys Lys Thr
 50                  55                  60

Lys Ala Ala Pro Ala Lys Val Ala Pro Lys Pro Lys Thr Glu
 65                  70                  75                  80

Asp Gly Ile Phe Gly Thr Ser Gly Gly Ile Gly Phe Thr Lys Glu Asn
                     85                  90                  95

Glu Leu Phe Val Gly Arg Val Ala Met Ile Gly Phe Ala Ala Ser Ile
                100                 105                 110

Leu Gly Glu Ala Ile Thr Gly Lys Gly Ile Leu Ser Gln Leu Asn Leu
            115                 120                 125

Glu Thr Gly Ile Pro Ile Tyr Glu Ala Glu Pro Leu Leu Leu Phe Phe
130                 135                 140

Ile Leu Phe Thr Leu Leu Gly Ala Ile Gly Ala Leu Gly Asp Arg Gly
145                 150                 155                 160

Arg Phe Val Asp Glu Gln Pro Thr Gly Leu Asp Lys Ala Val Ile Ala
                165                 170                 175

Pro Gly Lys Gly Phe Arg Ser Ala Leu Gly Leu Ser Glu Gly Gly Pro
                180                 185                 190

Leu Phe Gly Phe Thr Lys Ser Asn Glu Leu Phe Val Gly Arg Leu Ala
            195                 200                 205

Gln Leu Gly Ile Ala Phe Ser Ile Ile Gly Glu Ile Ile Thr Gly Lys
        210                 215                 220

Gly Ala Leu Ala Gln Leu Asn Ile Glu Thr Gly Val Pro Ile Ser Glu
225                 230                 235                 240

Ile Glu Pro Leu Val Leu Phe Asn Val Val Phe Phe Ile Ala Ala
                245                 250                 255

Ile Asn Pro Gly Thr Gly Lys Phe Ile Ser Gly Glu Glu Asp Asp
                260                 265                 270

<210> SEQ ID NO 165
<211> LENGTH: 269
<212> TYPE: PRT
<213> ORGANISM: Phyllostachys edulis

<400> SEQUENCE: 165

Met Ala Arg Ser Met Leu Met Ser Ser Val Ser Gly Val Ala Ser Ala
  1               5                  10                  15

Ser Gly Arg Ser Leu Leu His Ala Val Arg Pro Thr Pro Leu Ser Arg
                 20                  25                  30

Phe Val Leu Ser Ser Gln Pro Ser Tyr Cys Lys Arg Met Ala Pro Leu
             35                  40                  45

Ser Val Lys Thr Val Ala Leu Phe Gly Lys Ser Lys Ala Lys Ala
 50                  55                  60

Ala Pro Ala Arg Lys Ala Glu Thr Lys Pro Lys Phe Lys Thr Glu Asp
 65                  70                  75                  80

Gly Ile Phe Gly Thr Ser Gly Gly Ile Gly Phe Thr Lys Glu Asn Glu
                 85                  90                  95

Leu Phe Val Gly Arg Val Ala Met Leu Gly Phe Ala Ala Ser Ile Leu
                100                 105                 110

Gly Glu Ala Ile Thr Gly Lys Gly Ile Leu Ala Gln Leu Asn Leu Glu
            115                 120                 125

Thr Gly Ile Pro Ile Tyr Glu Ala Glu Pro Leu Leu Leu Phe Phe Ile
        130                 135                 140
```

```
Leu Phe Thr Leu Leu Gly Ala Ile Gly Ala Leu Gly Asp Arg Gly Ser
145                 150                 155                 160

Phe Val Asp Glu Pro Thr Gly Leu Asp Lys Ala Ile Val Pro Pro Gly
                165                 170                 175

Lys Gly Leu Arg Ser Ala Leu Gly Leu Gly Glu Gly Gly Pro Leu Phe
            180                 185                 190

Gly Phe Thr Lys Ala Asn Glu Leu Phe Val Gly Arg Leu Ala Gln Leu
        195                 200                 205

Gly Ile Ala Phe Ser Ile Ile Gly Glu Ile Ile Thr Gly Lys Gly Ala
    210                 215                 220

Leu Ala Gln Leu Asn Ile Glu Thr Gly Val Pro Ile Ser Glu Ile Glu
225                 230                 235                 240

Pro Leu Val Leu Phe Asn Val Ile Phe Phe Val Ala Ala Ile Asn
                245                 250                 255

Pro Gly Thr Gly Lys Phe Val Thr Thr Asp Asp Glu Glu
                260                 265
```

```
<210> SEQ ID NO 166
<211> LENGTH: 250
<212> TYPE: PRT
<213> ORGANISM: Oryza brachyantha

<400> SEQUENCE: 166

Met Tyr Met Tyr Met Gln Gln Ala Met Pro Met Val Val Cys Gly Arg
1               5                   10                  15

Pro Ser Trp Gly Glu Lys Gln Met Met Met Arg Gly Arg Arg Arg Gln
            20                  25                  30

Val Met Val Val Ala Ala Phe Lys Ser Arg Ser Lys Ala Ala Pro
        35                  40                  45

Ala Pro Ala Lys Arg Gln Lys Val Ala Val Glu Asp Gly Ile Phe Gly
    50                  55                  60

Thr Ser Gly Gly Ile Gly Phe Thr Lys Glu Asn Glu Leu Phe Val Gly
65                  70                  75                  80

Arg Val Ala Met Leu Gly Phe Ala Ala Ser Leu Leu Gly Glu Ala Val
                85                  90                  95

Thr Gly Lys Gly Ile Leu Ala Gln Leu Asn Leu Glu Thr Gly Ile Pro
            100                 105                 110

Ile Tyr Glu Ala Glu Pro Leu Leu Leu Phe Phe Ile Leu Phe Thr Leu
        115                 120                 125

Leu Gly Ala Ile Gly Ala Leu Gly Asp Arg Gly Arg Phe Val Asp Asp
    130                 135                 140

Ala Thr Gly Ile Glu Arg Ala Val Ile Pro Pro Gly Lys Gly Phe Arg
145                 150                 155                 160

Ala Ala Leu Gly Leu Arg Glu Gly Gly Pro Leu Phe Gly Phe Thr Lys
                165                 170                 175

Ala Asn Glu Leu Phe Val Gly Arg Leu Ala Gln Leu Gly Ile Ala Phe
            180                 185                 190

Ser Leu Ile Gly Glu Ile Ile Thr Gly Lys Gly Ala Leu Ala Gln Leu
        195                 200                 205

Asn Ile Glu Thr Gly Val Pro Val Asn Glu Ile Glu Pro Leu Leu Leu
    210                 215                 220

Phe Ser Ile Leu Phe Phe Phe Ala Ala Ile Asn Pro Gly Thr Gly
225                 230                 235                 240

Lys Phe Val Thr Asp Asn Asp Gln Asp Gln
                245                 250
```

<210> SEQ ID NO 167
<211> LENGTH: 270
<212> TYPE: PRT
<213> ORGANISM: Apostasia shenzhenica

<400> SEQUENCE: 167

Met Ala Gln Ser Met Leu Ile Ser Ser Phe Ala Ala Gly Gln Leu Val
1               5                   10                  15

Gly Cys Asn Asn Ser Arg Val Gly Ala Pro Ser Leu Ser Lys Leu
            20                  25                  30

Phe Leu Leu Glu Asn Ser Ser Ser Arg Arg Gln Pro Ser Ser Ser
        35                  40                  45

Ala Ser Pro His Ala Pro Thr Leu Ala Val Phe Lys Pro Lys Thr Lys
    50                  55                  60

Ala Pro Val Lys Lys Ile Glu Lys Thr Ser Lys Pro Lys Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Leu Gly Phe Ala Ala Ser Leu Leu
            100                 105                 110

Gly Glu Gly Leu Thr Gly Lys Gly Ile Leu Ala Gln Leu Asn Leu Glu
        115                 120                 125

Thr Gly Ile Pro Ile Tyr Glu Ala Glu Pro Leu Leu Leu Phe Phe Ile
    130                 135                 140

Leu Phe Thr Val Leu Gly Ala Ile Gly Ala Leu Gly Asp Arg Gly Lys
145                 150                 155                 160

Phe Val Asp Asp Pro Pro Ala Gly Leu Asp Lys Ala Val Ile Pro Pro
                165                 170                 175

Gly Lys Gly Leu Arg Ser Ala Leu Gly Leu Lys Glu Gly Gly Pro Leu
            180                 185                 190

Phe Gly Phe Thr Lys Ala Asn Glu Leu Phe Val Gly Arg Leu Ala Gln
        195                 200                 205

Leu Gly Ile Ala Phe Ser Ile Ile Gly Glu Ile Thr Gly Lys Gly
    210                 215                 220

Ala Leu Ala Gln Leu Asn Ile Glu Thr Gly Val Pro Ile Asn Glu Val
225                 230                 235                 240

Glu Pro Leu Val Ile Phe Asn Val Ile Phe Phe Leu Ala Ala Leu
                245                 250                 255

Asn Pro Gly Ser Gly Arg Phe Val Thr Asp Glu Gly Glu Glu
            260                 265                 270

<210> SEQ ID NO 168
<211> LENGTH: 271
<212> TYPE: PRT
<213> ORGANISM: Tarenaya hassleriana

<400> SEQUENCE: 168

Met Ala Gln Thr Met Leu Leu Thr Ser Gly Val Ser Ala Gly Ser Leu
1               5                   10                  15

Leu Asn His Asn Arg Asn Pro Leu Ser Gly Pro Glu Leu Arg Pro Arg
            20                  25                  30

His Gly Leu Phe Ser Ser Ala Asp Ser Pro Ala Leu Pro Ser Arg Arg
        35                  40                  45

Leu Ser Ser Pro Ala Leu Val Pro Leu Ala Ile Phe Lys Pro Lys Thr
    50                  55                  60

```
Lys Ala Pro Ala Lys Ala Pro Pro Lys Pro Lys Val Glu
 65                  70                  75                  80

Asp Gly Ile Phe Gly Thr Ser Gly Gly Ile Gly Phe Thr Lys Gln Asn
                 85                  90                  95

Glu Leu Phe Val Gly Arg Val Ala Met Ile Gly Phe Ala Ala Ser Leu
            100                 105                 110

Leu Gly Glu Ala Val Thr Gly Lys Gly Ile Leu Ala Gln Leu Asn Leu
        115                 120                 125

Glu Thr Gly Ile Pro Ile Tyr Glu Ala Glu Pro Leu Leu Leu Phe Phe
    130                 135                 140

Ile Leu Phe Thr Leu Leu Gly Ala Ile Gly Ala Leu Gly Asp Arg Gly
145                 150                 155                 160

Gln Phe Val Asp Asp Pro Pro Thr Gly Leu Asp Lys Ala Val Ile Pro
                165                 170                 175

Pro Gly Lys Ser Phe Arg Ser Ala Ile Gly Leu Pro Glu Gln Gly Pro
            180                 185                 190

Leu Phe Gly Phe Thr Lys Ala Asn Glu Leu Phe Val Gly Arg Leu Ala
        195                 200                 205

Gln Leu Gly Ile Ala Phe Ser Leu Ile Gly Glu Ile Ile Thr Gly Lys
    210                 215                 220

Gly Ala Leu Ala Gln Leu Asn Phe Glu Thr Gly Ile Pro Ile Thr Glu
225                 230                 235                 240

Ile Glu Pro Ile Val Leu Phe Asn Val Ala Phe Phe Phe Ala Ala
                245                 250                 255

Ile Asn Pro Gly Thr Gly Lys Phe Ile Thr Asp Asp Glu Glu Asp
            260                 265                 270

<210> SEQ ID NO 169
<211> LENGTH: 271
<212> TYPE: PRT
<213> ORGANISM: Coffea arabica

<400> SEQUENCE: 169

Met Ala Gln Ala Met Leu Leu Thr Ala Ser Val Pro Ser Ser His Ala
1               5                   10                  15

Gly Asp Leu Lys Gly Ser Glu Pro Leu Leu Gln Arg Ile Arg Pro Lys
            20                  25                  30

Pro Ile Ser His Leu Phe Phe Ser Pro Leu Pro Thr Ser Ser Ser Ser
        35                  40                  45

Ser Tyr Cys Pro Leu Thr Thr Val Ala Val Phe Lys Ser Lys Thr Lys
    50                  55                  60

Ala Pro Ala Lys Lys Pro Ala Ala Ala Thr Lys Pro Lys Glu Lys Val
65                  70                  75                  80

Glu Asp Gly Ile Phe Gly Thr Ser Gly Gly Ile Gly Phe Thr Lys Glu
                85                  90                  95

Asn Glu Leu Phe Val Gly Arg Val Ala Met Leu Gly Phe Ala Ala Ser
            100                 105                 110

Ile Leu Gly Glu Ala Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Asn Leu Leu Gly Ala Ile Gly Ala Leu Gly Asp Arg
145                 150                 155                 160

Gly Arg Phe Val Asp Asp Ala Pro Gly Ile Glu Gly Ala Val Val Pro
```

```
                165                 170                 175
Pro Gly Lys Gly Leu Arg Gly Ala Leu Gly Leu Arg Glu Gly Gly Pro
            180                 185                 190

Leu Phe Gly Phe Thr Lys Ala Asn Glu Leu Phe Val Gly Arg Leu Ala
        195                 200                 205

Gln Leu Gly Ile Ala Phe Ser Ile Ile Gly Glu Ile Ile Thr Gly Lys
    210                 215                 220

Gly Ala Leu Ala Gln Leu Asn Ile Glu Thr Gly Val Pro Ile Thr Glu
225                 230                 235                 240

Ile Glu Pro Leu Ile Ile Phe Asn Val Val Phe Phe Val Ala Ala
                245                 250                 255

Ile Asn Pro Gly Thr Gly Lys Phe Val Thr Asp Glu Glu Asp Ala
            260                 265                 270

<210> SEQ ID NO 170
<211> LENGTH: 271
<212> TYPE: PRT
<213> ORGANISM: Coffea arabica

<400> SEQUENCE: 170

Met Ala Gln Ala Met Leu Leu Thr Ala Ser Val Pro Ser Ser His Ala
1               5                   10                  15

Gly Asp Leu Lys Arg Ser Glu Pro Leu Leu Gln Arg Ile Arg Pro Lys
            20                  25                  30

Pro Ile Ser His Leu Phe Phe Ser Pro Leu Pro Thr Ser Ser Ser Ser
        35                  40                  45

Ser Tyr Cys Pro Leu Thr Thr Val Ala Val Phe Lys Ser Lys Thr Lys
    50                  55                  60

Ala Pro Ala Lys Lys Pro Ala Ala Thr Lys Pro Lys Glu Lys Val
65                  70                  75                  80

Glu Asp Gly Ile Phe Gly Thr Ser Gly Ile Gly Phe Thr Lys Glu
                85                  90                  95

Asn Glu Leu Phe Val Gly Arg Val Ala Met Leu Gly Phe Ala Ala Ser
            100                 105                 110

Ile Leu Gly Glu Ala Ile Thr Gly Lys Gly Ile Leu Ala Gln Leu Asn
        115                 120                 125

Leu Glu Thr Gly Ile Pro Ile Tyr Glu Ala Glu Pro Leu Leu Leu Phe
    130                 135                 140

Phe Ile Leu Phe Asn Leu Leu Gly Ala Ile Gly Ala Leu Gly Asp Arg
145                 150                 155                 160

Gly Arg Phe Val Asp Asp Ala Pro Gly Ile Glu Gly Ala Val Val Pro
                165                 170                 175

Pro Gly Lys Gly Leu Arg Ser Ala Leu Gly Leu Arg Glu Gly Gly Pro
            180                 185                 190

Leu Phe Gly Phe Thr Lys Ala Asn Glu Leu Phe Val Gly Arg Leu Ala
        195                 200                 205

Gln Leu Gly Ile Ala Phe Ser Ile Ile Gly Glu Ile Ile Thr Gly Lys
    210                 215                 220

Gly Ala Leu Ala Gln Leu Asn Ile Glu Thr Gly Val Pro Ile Thr Glu
225                 230                 235                 240

Ile Glu Pro Leu Ile Ile Phe Asn Val Val Phe Phe Val Ala Ala
                245                 250                 255

Ile Asn Pro Gly Thr Gly Lys Phe Val Thr Asp Glu Glu Asp Ala
            260                 265                 270
```

<210> SEQ ID NO 171
<211> LENGTH: 271
<212> TYPE: PRT
<213> ORGANISM: Coffea canephora

<400> SEQUENCE: 171

Met Ala Gln Ala Met Leu Leu Thr Ala Ser Val Pro Ser Ser His Ala
1               5                   10                  15

Gly Asp Leu Lys Arg Ser Glu Pro Leu Leu Gln Arg Ile Arg Pro Lys
            20                  25                  30

Pro Ile Ser His Leu Phe Phe Ser Pro Leu Pro Thr Ser Ser Ser Ser
        35                  40                  45

Ser Tyr Cys Pro Leu Thr Thr Val Ala Val Phe Lys Ser Lys Thr Lys
50                  55                  60

Ala Pro Ala Lys Lys Pro Ala Ala Thr Lys Pro Lys Glu Lys Val
65                  70                  75                  80

Glu Asp Gly Ile Phe Gly Thr Ser Gly Gly Ile Gly Phe Thr Lys Glu
            85                  90                  95

Asn Glu Leu Phe Val Gly Arg Val Ala Met Leu Gly Phe Ala Ala Ser
        100                 105                 110

Ile Leu Gly Glu Ala Ile Thr Gly Lys Gly Ile Leu Ala Gln Leu Asn
    115                 120                 125

Leu Glu Thr Gly Ile Pro Ile Tyr Glu Ala Glu Pro Leu Leu Leu Phe
130                 135                 140

Phe Ile Leu Phe Asn Leu Leu Gly Ala Ile Gly Ala Leu Gly Asp Arg
145                 150                 155                 160

Gly Arg Phe Val Asp Asp Ala Pro Gly Ile Glu Gly Ala Val Val Pro
            165                 170                 175

Pro Gly Lys Gly Leu Arg Gly Ala Leu Gly Leu Arg Glu Gly Pro
        180                 185                 190

Leu Phe Gly Phe Thr Lys Ala Asn Glu Leu Phe Val Gly Arg Leu Ala
    195                 200                 205

Gln Leu Gly Ile Ala Phe Ser Ile Ile Gly Glu Ile Ile Thr Gly Lys
210                 215                 220

Gly Ala Leu Ala Gln Leu Asn Ile Glu Thr Gly Val Pro Ile Thr Glu
225                 230                 235                 240

Ile Glu Pro Leu Ile Ile Phe Asn Val Val Phe Phe Val Ala Ala
            245                 250                 255

Ile Asn Pro Gly Thr Gly Lys Phe Val Thr Asp Glu Glu Asp Ala
        260                 265                 270

<210> SEQ ID NO 172
<211> LENGTH: 269
<212> TYPE: PRT
<213> ORGANISM: Ananas comosus

<400> SEQUENCE: 172

Met Ala Gln Ser Met Leu Leu Ser Ser Leu Ser Gly His Pro Leu Ala
1               5                   10                  15

Ser Lys Arg Asp Pro Leu Leu Gln Ser Leu Arg Pro Thr Pro Phe Ser
            20                  25                  30

His Leu Ile Phe Ser Gln Thr Pro Arg Lys Glu Leu Ser Pro Ser Ser
        35                  40                  45

Ser Ser Ser Phe Thr Pro Thr Leu Ala Val Phe Lys Ser Lys Ala Lys
50                  55                  60

```
Ala Pro Pro Lys Lys Leu Glu Lys Asp Ala Lys Val Glu Asp
 65              70                  75                  80

Gly Ile Phe Gly Thr Ser Gly Gly Ile Gly Phe Thr Lys Gln Asn Glu
                 85                  90                  95

Leu Phe Val Gly Arg Val Ala Met Ile Gly Phe Ala Ala Ser Leu Leu
                100                 105                 110

Gly Glu Ala Ile Thr Gly Lys Gly Ile Leu Ala Gln Leu Asn Leu Glu
            115                 120                 125

Thr Gly Ile Pro Ile Tyr Glu Ala Glu Pro Leu Leu Leu Phe Phe Ile
    130                 135                 140

Leu Phe Thr Leu Leu Gly Ala Ile Gly Ala Leu Gly Asp Arg Gly Gln
145                 150                 155                 160

Phe Val Asp Glu Thr Ala Gly Leu Glu Lys Ala Val Ile Pro Pro Gly
                165                 170                 175

Lys Gly Phe Lys Ser Ala Leu Gly Leu Lys Glu Gly Gly Pro Leu Phe
                180                 185                 190

Gly Phe Thr Lys Ala Asn Glu Leu Phe Val Gly Arg Leu Ala Gln Leu
            195                 200                 205

Gly Ile Ala Phe Ser Leu Ile Gly Glu Ile Ile Thr Gly Lys Gly Ala
    210                 215                 220

Leu Ala Gln Leu Asn Ile Glu Thr Gly Val Pro Ile Asn Glu Ile Glu
225                 230                 235                 240

Pro Leu Leu Leu Phe Asn Ile Ala Phe Phe Phe Ala Ala Ile Asn
                245                 250                 255

Pro Gly Thr Gly Lys Phe Ile Thr Asp Glu Glu Glu Ala
                260                 265

<210> SEQ ID NO 173
<211> LENGTH: 281
<212> TYPE: PRT
<213> ORGANISM: Diospyros kaki

<400> SEQUENCE: 173

Met Ala Ala Gln Ala Met Leu Leu Thr Ser Ser Thr Val Asp Leu Lys
  1               5                  10                  15

Arg Gln Gln Leu Pro Leu Ile Glu Arg Leu Arg Pro Lys Pro Tyr Phe
                 20                  25                  30

Ser His Phe Leu Leu Pro Pro Leu Ser Ser Ser Thr Ser Ser Pro
             35                  40                  45

Ser Ser Ser Ser Ser Ser Ser Ser Ser Val His Tyr Asn Ser Ser
         50                  55                  60

Pro Thr Ile Ala Leu Phe Lys Ser Lys Ala Lys Ala Ala Pro Pro Lys
 65                  70                  75                  80

Lys Val Ala Thr Pro Lys Pro Lys Val Glu Asp Gly Leu Phe Gly Thr
                 85                  90                  95

Ser Gly Gly Ile Gly Phe Thr Lys Gln Asn Glu Leu Phe Val Gly Arg
                100                 105                 110

Val Ala Met Leu Gly Phe Ala Ala Ser Leu Leu Gly Glu Ala Ile Thr
             115                 120                 125

Gly Lys Gly Ile Leu Ala Gln Leu Asn Leu Glu Thr Gly Ile Pro Ile
    130                 135                 140

Tyr Glu Ala Glu Pro Leu Leu Leu Phe Phe Ile Leu Phe Thr Leu Leu
145                 150                 155                 160

Gly Ala Ile Gly Ala Leu Gly Asp Arg Gly Lys Phe Val Asp Glu Ser
                165                 170                 175
```

```
Pro Thr Gly Leu Asp Lys Ala Val Ile Pro Gly Lys Gly Phe Arg
            180                 185                 190

Ser Ser Leu Gly Leu Lys Glu Gly Pro Leu Phe Gly Phe Thr Lys
            195                 200                 205

Ala Asn Glu Leu Phe Val Gly Arg Leu Ala Gln Leu Gly Ile Ala Phe
210                 215                 220

Ser Ile Ile Gly Glu Ile Ile Thr Gly Lys Gly Ala Leu Ala Gln Leu
225                 230                 235                 240

Asn Ile Glu Thr Gly Val Pro Ile Ser Asp Ile Glu Pro Leu Val Leu
                245                 250                 255

Phe Asn Val Ala Phe Phe Ile Ala Ala Leu Asn Pro Gly Thr Gly
            260                 265                 270

Lys Phe Val Thr Asp Glu Glu Glu
            275                 280

<210> SEQ ID NO 174
<211> LENGTH: 274
<212> TYPE: PRT
<213> ORGANISM: Ipomoea nil

<400> SEQUENCE: 174

Met Ala Gln Thr Met Leu Leu Thr Ala Ser Ala Ser Ser Pro Ala Leu
1               5                   10                  15

Asp Leu Lys Arg Gln Ser Thr Phe Leu Gln Thr Leu Lys Pro Lys Pro
            20                  25                  30

Ser Ile Gln Gln His Phe Leu Leu Pro Leu Pro Ser Ser Ser Ser Ser
            35                  40                  45

Ser Ser Ser Phe Ser Ser Thr Arg Ile Val Ala Leu Phe Lys Ser Lys
50                  55                  60

Ala Lys Ala Ala Pro Ala Lys Lys Val Val Gln Pro Lys Pro Lys Val
65                  70                  75                  80

Glu Asp Gly Ile Phe Gly Thr Ser Gly Gly Ile Gly Phe Thr Lys Gln
                85                  90                  95

Asn Glu Leu Phe Val Gly Arg Val Ala Met Ile Gly Phe Ala Ala Ser
            100                 105                 110

Leu Leu Gly Glu Ala Ile Thr Gly Lys Gly Ile Leu Ser Gln Leu Asn
            115                 120                 125

Leu Glu Thr Gly Ile Pro Ile Tyr Glu Ala Glu Pro Leu Leu Leu Phe
            130                 135                 140

Phe Ile Leu Phe Asn Leu Leu Gly Ala Ile Gly Ala Leu Gly Asp Arg
145                 150                 155                 160

Gly Lys Phe Val Asp Asp Pro Ala Pro Pro Thr Gly Leu Asp Arg Ala
                165                 170                 175

Val Ile Pro Pro Gly Lys Ser Phe Arg Ser Ala Leu Gly Leu Ser Glu
            180                 185                 190

Gly Gly Pro Leu Phe Gly Phe Thr Lys Ser Asn Glu Leu Phe Val Gly
            195                 200                 205

Arg Leu Ala Gln Leu Gly Ile Ala Phe Ser Ile Ile Gly Glu Ile Ile
210                 215                 220

Thr Gly Lys Gly Ala Leu Ala Gln Leu Asn Ile Glu Thr Gly Val Pro
225                 230                 235                 240

Ile Gly Glu Ile Glu Pro Leu Ile Leu Phe Asn Val Ala Phe Phe
                245                 250                 255

Phe Ala Ala Ile Asn Pro Gly Thr Gly Lys Phe Val Thr Asp Glu Glu
```

-continued

```
                    260                 265                 270

Glu Asp

<210> SEQ ID NO 175
<211> LENGTH: 272
<212> TYPE: PRT
<213> ORGANISM: Nicotiana tomentosiformis

<400> SEQUENCE: 175

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Phe Phe Leu Pro Ser Leu Pro Leu Lys Tyr Pro Ser Ala Ser Ser Ser
        35                  40                  45

Ser His Phe Ala Ser Thr Thr Val Ala Leu Phe Lys Ser Lys Ala Lys
    50                  55                  60

Ala Pro Ala Lys Lys Ala Val Pro Lys Pro Lys Glu Lys Val Glu Asp
65                  70                  75                  80

Gly Ile Phe Gly Thr Ser Gly Gly Ile Gly Phe Thr Lys Gln Asn Glu
                85                  90                  95

Leu Phe Val Gly Arg Val Ala Met Ile Gly Phe Ala Ala Ser Leu Leu
            100                 105                 110

Gly Glu Ala Val Thr Gly Lys Gly Ile Leu Ala Gln Leu Asn Leu Glu
        115                 120                 125

Thr Gly Ile Pro Ile Tyr Glu Ala Glu Pro Leu Leu Leu Phe Phe Ile
    130                 135                 140

Leu Phe Asn Leu Leu Gly Ala Ile Gly Ala Leu Gly Asp Arg Gly Lys
145                 150                 155                 160

Phe Ile Asp Asp Pro Ala Pro Ala Thr Gly Leu Asp Lys Ala Val Ile
                165                 170                 175

Pro Pro Gly Lys Gly Phe Lys Ala Ala Leu Gly Leu Arg Glu Gly Gly
            180                 185                 190

Pro Leu Phe Gly Phe Thr Lys Ala Asn Glu Leu Phe Val Gly Arg Leu
        195                 200                 205

Ala Gln Leu Gly Ile Ala Phe Ser Ile Ile Gly Glu Ile Ile Thr Gly
    210                 215                 220

Lys Gly Ala Leu Ala Gln Leu Asn Phe Glu Thr Gly Val Pro Ile Asn
225                 230                 235                 240

Glu Ile Glu Pro Leu Leu Leu Phe Asn Ile Val Phe Phe Ile Ala
                245                 250                 255

Ala Ile Asn Pro Gly Thr Gly Lys Phe Val Thr Asp Glu Glu Glu Glu
            260                 265                 270

<210> SEQ ID NO 176
<211> LENGTH: 272
<212> TYPE: PRT
<213> ORGANISM: Nicotiana attenuata

<400> SEQUENCE: 176

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Phe Phe Leu Pro Ser Leu Pro Leu Lys Tyr Pro Ser Ala Ser Ser Ser
        35                  40                  45
```

Ser His Phe Thr Ser Thr Thr Val Ala Leu Phe Lys Ser Lys Ala Lys
 50                  55                  60

Ala Pro Ala Lys Lys Val Val Pro Lys Pro Lys Glu Lys Val Glu Asp
 65                  70                  75                  80

Gly Ile Phe Gly Thr Ser Gly Gly Ile Gly Phe Thr Lys Gln Asn Glu
                 85                  90                  95

Leu Phe Val Gly Arg Val Ala Met Ile Gly Phe Ala Ala Ser Leu Leu
                100                 105                 110

Gly Glu Ala Val Thr Gly Lys Gly Ile Leu Ala Gln Leu Asn Leu Glu
                115                 120                 125

Thr Gly Ile Pro Ile Tyr Glu Ala Glu Pro Leu Leu Leu Phe Phe Ile
130                 135                 140

Leu Phe Asn Leu Leu Gly Ala Ile Gly Ala Leu Gly Asp Arg Gly Lys
145                 150                 155                 160

Phe Val Asp Asp Pro Ala Pro Ala Thr Gly Leu Asp Lys Ala Val Ile
                165                 170                 175

Pro Pro Gly Lys Gly Phe Lys Ala Ala Leu Gly Leu Arg Glu Gly Gly
                180                 185                 190

Pro Leu Phe Gly Phe Thr Lys Ala Asn Glu Leu Phe Val Gly Arg Leu
                195                 200                 205

Ala Gln Leu Gly Ile Ala Phe Ser Ile Gly Glu Ile Ile Thr Gly
210                 215                 220

Lys Gly Ala Leu Ala Gln Leu Asn Phe Glu Thr Gly Val Pro Ile Asn
225                 230                 235                 240

Glu Ile Glu Pro Leu Leu Phe Asn Ile Val Phe Phe Ile Ala
                245                 250                 255

Ala Ile Asn Pro Gly Thr Gly Lys Phe Val Thr Asp Glu Glu Glu Glu
                260                 265                 270

<210> SEQ ID NO 177
<211> LENGTH: 274
<212> TYPE: PRT
<213> ORGANISM: Nicotiana sylvestris

<400> SEQUENCE: 177

Met Ala Gln Thr Met Leu Leu Thr Ala Asn Ala Lys Val Asp Leu Arg
1                5                  10                  15

Ser Lys Glu Ser Leu Val Glu Arg Leu Lys Pro Lys Pro Leu Ser Ser
                20                  25                  30

Phe Phe Leu Pro Ser Leu Pro Leu Lys Tyr Pro Ser Ala Ser Ala Ser
                35                  40                  45

Ala Ser Ser His Phe Thr Ser Thr Thr Val Ala Leu Phe Lys Ser Lys
                50                  55                  60

Ala Lys Ala Pro Ala Lys Lys Val Val Pro Lys Pro Lys Glu Lys Val
 65                  70                  75                  80

Glu Asp Gly Ile Phe Gly Thr Ser Gly Gly Ile Gly Phe Thr Lys Gln
                 85                  90                  95

Asn Glu Leu Phe Val Gly Arg Val Ala Met Ile Gly Phe Ala Ala Ser
                100                 105                 110

Leu Leu Gly Glu Ala Ile Thr Gly Lys Gly Ile Leu Ala Gln Leu Asn
                115                 120                 125

Leu Glu Thr Gly Ile Pro Ile Tyr Glu Ala Glu Pro Leu Leu Leu Phe
130                 135                 140

Phe Ile Leu Phe Asn Leu Leu Gly Ala Ile Gly Ala Leu Gly Asp Arg

-continued

```
                145                 150                 155                 160
Gly Lys Phe Ile Asp Asp Pro Ala Pro Pro Thr Gly Leu Asp Lys Ala
                    165                 170                 175

Val Ile Pro Pro Gly Lys Gly Phe Lys Ser Ala Leu Gly Leu Ser Glu
                180                 185                 190

Gly Gly Pro Leu Phe Gly Phe Thr Lys Ala Asn Glu Leu Phe Val Gly
            195                 200                 205

Arg Leu Ala Gln Leu Gly Ile Ala Phe Ser Ile Ile Gly Glu Ile Ile
        210                 215                 220

Thr Gly Lys Gly Ala Leu Ala Gln Leu Asn Phe Glu Thr Gly Val Pro
225                 230                 235                 240

Ile Asn Glu Ile Glu Pro Leu Leu Leu Phe Asn Ile Val Phe Phe Phe
                245                 250                 255

Val Ala Ala Ile Asn Pro Gly Thr Gly Lys Phe Val Thr Asp Glu Glu
                260                 265                 270

Glu Glu

<210> SEQ ID NO 178
<211> LENGTH: 277
<212> TYPE: PRT
<213> ORGANISM: Capsicum annuum

<400> SEQUENCE: 178

Met Ala Gln Thr Met Leu Leu Thr Ala Asn Ala Lys Val Asp Leu Arg
1               5                   10                  15

Ser Lys Gly Ser Leu Val Glu Arg Leu Lys Pro Lys Pro Leu Ser Ser
            20                  25                  30

Leu Phe Leu Pro Ser Leu Pro Leu Lys Phe Ser Thr Thr Ala Thr Asn
        35                  40                  45

Ala Ser Ser Ser Lys Phe Thr Ser Thr Thr Val Ala Met Phe Lys Ser
    50                  55                  60

Lys Ala Lys Ala Ala Pro Ala Lys Lys Ala Ala Pro Lys Pro Lys Glu
65                  70                  75                  80

Lys Val Glu Asp Gly Ile Phe Gly Thr Ser Gly Gly Ile Gly Phe Thr
                85                  90                  95

Lys Gln Asn Glu Leu Phe Val Gly Arg Val Ala Met Ile Gly Phe Ala
            100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
    130                 135                 140

Leu Phe Phe Ile Leu Phe Asn Leu Leu Gly Ala Ile Gly Ala Leu Gly
145                 150                 155                 160

Asp Arg Gly Lys Phe Val Asp Asp Pro Ala Pro Pro Thr Gly Leu Glu
                165                 170                 175

Lys Ala Val Ile Pro Pro Gly Arg Ser Phe Lys Ser Ala Leu Gly Leu
            180                 185                 190

Ser Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Ile Ile Gly Glu
    210                 215                 220

Ile Ile Thr Gly Lys Gly Ala Leu Ala Gln Leu Asn Ile Glu Thr Gly
225                 230                 235                 240

Val Pro Ile Asn Glu Ile Glu Pro Leu Leu Leu Phe Asn Val Ala Phe
```

-continued

```
                245                 250                 255
Phe Phe Phe Ala Ala Ile Asn Pro Gly Thr Gly Lys Phe Ile Thr Asp
            260                 265                 270
Gly Glu Glu Glu Asp
        275

<210> SEQ ID NO 179
<211> LENGTH: 277
<212> TYPE: PRT
<213> ORGANISM: Capsicum baccatum

<400> SEQUENCE: 179

Met Ala Gln Thr Met Leu Leu Thr Ala Asn Ala Lys Val Asp Leu Arg
1               5                   10                  15
Ser Lys Gly Ser Leu Val Glu Arg Leu Lys Pro Lys Pro Leu Ser Ser
            20                  25                  30
Leu Phe Leu Pro Ser Leu Pro Leu Lys Phe Ser Thr Thr Ala Thr Asn
        35                  40                  45
Ala Ser Ser Ser Lys Ser Thr Ser Thr Thr Val Ala Met Phe Lys Ser
    50                  55                  60
Lys Ala Lys Ala Pro Ala Lys Lys Ala Ala Pro Lys Pro Lys Glu
65                  70                  75                  80
Lys Val Glu Asp Gly Ile Phe Gly Thr Ser Gly Gly Ile Gly Phe Thr
                85                  90                  95
Lys Gln Asn Glu Leu Phe Val Gly Arg Val Ala Met Ile Gly Phe Ala
            100                 105                 110
Ala Ser Leu Leu Gly Glu Ala Ile Thr Gly Lys Gly Ile Leu Ala Gln
        115                 120                 125
Leu Asn Leu Glu Thr Gly Ile Pro Ile Tyr Glu Ala Glu Pro Leu Leu
    130                 135                 140
Leu Phe Phe Ile Leu Phe Asn Leu Leu Gly Ala Ile Gly Ala Leu Gly
145                 150                 155                 160
Asp Arg Gly Lys Phe Val Asp Pro Ala Pro Ser Thr Gly Leu Glu
                165                 170                 175
Lys Ala Val Ile Pro Pro Gly Arg Ser Phe Lys Ser Ala Leu Gly Leu
            180                 185                 190
Ser Glu Gly Gly Pro Leu Phe Gly Phe Thr Lys Ala Asn Glu Leu Phe
        195                 200                 205
Val Gly Arg Leu Ala Gln Leu Gly Ile Ala Phe Ser Ile Ile Gly Glu
    210                 215                 220
Ile Ile Thr Gly Lys Gly Ala Leu Ala Gln Leu Asn Ile Glu Thr Gly
225                 230                 235                 240
Val Pro Ile Asn Glu Ile Glu Pro Leu Leu Leu Phe Asn Val Ala Phe
                245                 250                 255
Phe Phe Phe Ala Ala Ile Asn Pro Gly Thr Gly Lys Phe Ile Thr Asp
            260                 265                 270
Gly Glu Glu Glu Asp
        275

<210> SEQ ID NO 180
<211> LENGTH: 276
<212> TYPE: PRT
<213> ORGANISM: Solanum sogarandinum

<400> SEQUENCE: 180

Met Ala Gln Thr Met Leu Leu Thr Ala Asn Ala Lys Val Asp Leu Arg
```

```
          1               5                  10                 15
        Ser Lys Glu Ser Leu Val Glu Arg Leu Lys Pro Lys Pro Leu Ser Ser
                         20                 25                 30

Leu Phe Leu Pro Ser Leu Pro Leu Arg Phe Ser Ser Thr Thr Asn
                     35                 40                 45

Phe Ser Ser Ser Lys Phe Thr Ser Thr Thr Val Ala Leu Phe Lys Ser
                     50                 55                 60

Lys Ala Lys Ala Pro Pro Lys Lys Val Ala Pro Pro Lys Glu Lys Gln
         65                 70                 75                 80

Lys Val Glu Asp Gly Ile Phe Gly Thr Ser Gly Gly Ile Gly Phe Thr
                             85                 90                 95

Lys Gln Asn Glu Leu Phe Val Gly Arg Val Ala Met Ile Gly Phe Ala
                        100                105                110

Ala Ser Leu Leu Gly Glu Ala Ile Thr Gly Lys Gly Ile Leu Ala Gln
                        115                120                125

Leu Asn Leu Glu Thr Gly Ile Pro Ile Tyr Glu Ala Glu Pro Leu Leu
                130                135                140

Leu Phe Phe Ile Leu Phe Asn Leu Leu Gly Ala Ile Gly Ala Leu Gly
        145                150                155                160

Asp Arg Gly Arg Phe Ile Asp Asp Pro Ala Pro Ala Thr Gly Leu Glu
                        165                170                175

Lys Ala Val Ile Pro Pro Gly Lys Ser Phe Lys Ser Ala Leu Gly Leu
                        180                185                190

Ser Glu Gly Gly Pro Leu Phe Gly Phe Thr Lys Ala Asn Glu Leu Phe
                        195                200                205

Val Gly Arg Leu Ala Gln Leu Gly Ile Ala Phe Ser Ile Ile Gly Glu
                210                215                220

Ile Ile Thr Gly Lys Gly Ala Leu Ala Gln Leu Asn Phe Glu Thr Gly
        225                230                235                240

Val Pro Ile Asn Glu Ile Glu Pro Leu Leu Leu Phe Asn Ile Ala Phe
                        245                250                255

Phe Phe Phe Ala Ala Ile Asn Pro Gly Thr Gly Lys Phe Ile Thr Asp
                        260                265                270

Glu Glu Glu Asp
                275

<210> SEQ ID NO 181
<211> LENGTH: 276
<212> TYPE: PRT
<213> ORGANISM: Solanum tuberosum

<400> SEQUENCE: 181

Met Ala Gln Thr Met Leu Leu Thr Ala Asn Ala Lys Val Asp Leu Arg
        1               5                  10                 15

Ser Lys Glu Ser Leu Val Glu Arg Leu Lys Pro Lys Pro Leu Ser Ser
                         20                 25                 30

Leu Phe Leu Pro Ser Leu Pro Leu Arg Phe Ser Ser Thr Thr Asn
                     35                 40                 45

Val Ser Ser Ser Lys Phe Thr Ser Thr Thr Val Ala Leu Phe Lys Ser
                     50                 55                 60

Lys Ala Lys Ala Pro Pro Lys Lys Val Ala Pro Pro Lys Glu Lys Gln
         65                 70                 75                 80

Lys Val Glu Asp Gly Ile Phe Gly Thr Ser Gly Gly Ile Gly Phe Thr
                             85                 90                 95
```

```
Lys Gln Asn Glu Leu Phe Val Gly Arg Val Ala Met Ile Gly Phe Ala
            100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
    130                 135                 140

Leu Phe Phe Ile Leu Phe Asn Leu Leu Gly Ala Ile Gly Ala Leu Gly
145                 150                 155                 160

Asp Arg Gly Lys Phe Ile Asp Asp Pro Ser Pro Ala Thr Gly Leu Glu
                165                 170                 175

Lys Ala Val Ile Pro Pro Gly Lys Ser Phe Lys Ser Ala Leu Gly Leu
            180                 185                 190

Thr Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Ile Ile Gly Glu
    210                 215                 220

Ile Ile Thr Gly Lys Gly Ala Leu Ala Gln Leu Asn Phe Glu Thr Gly
225                 230                 235                 240

Val Pro Ile Asn Glu Ile Glu Pro Leu Leu Leu Phe Asn Ile Ala Phe
                245                 250                 255

Phe Phe Phe Ala Ala Ile Asn Pro Gly Thr Gly Lys Phe Ile Thr Asp
            260                 265                 270

Glu Glu Glu Asp
        275

<210> SEQ ID NO 182
<211> LENGTH: 276
<212> TYPE: PRT
<213> ORGANISM: Solanum nigrum

<400> SEQUENCE: 182

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Leu Phe Leu Pro Ser Leu Pro Leu Arg Phe Ser Ser Ser Ser Thr Asn
        35                  40                  45

Ala Ser Ser Ser Lys Phe Thr Ser Thr Thr Val Ala Leu Phe Lys Ser
    50                  55                  60

Lys Ala Lys Ala Pro Pro Lys Lys Val Ala Pro Pro Lys Gln Lys Glu
65                  70                  75                  80

Lys Val Glu Asp Gly Ile Phe Gly Thr Ser Gly Ile Gly Phe Thr
                85                  90                  95

Lys Gln Asn Glu Leu Phe Val Gly Arg Val Ala Met Ile Gly Phe Ala
            100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
    130                 135                 140

Leu Phe Phe Ile Leu Phe Asn Leu Leu Gly Ala Ile Gly Ala Leu Gly
145                 150                 155                 160

Asp Arg Gly Lys Phe Val Asp Asp Pro Ala Pro Thr Gly Leu Glu
                165                 170                 175

Lys Ala Val Ile Pro Pro Gly Arg Ser Phe Lys Ser Ala Leu Gly Leu
            180                 185                 190
```

```
Ser Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Ile Ile Gly Glu
210                 215                 220

Ile Ile Thr Gly Lys Gly Ala Leu Ala Gln Leu Asn Phe Glu Thr Gly
225                 230                 235                 240

Val Pro Ile Asn Glu Ile Glu Pro Leu Leu Leu Phe Asn Ile Ala Phe
                245                 250                 255

Phe Phe Phe Ala Ala Ile Asn Pro Gly Thr Gly Lys Phe Ile Thr Asp
                260                 265                 270

Glu Glu Glu Asp
        275

<210> SEQ ID NO 183
<211> LENGTH: 276
<212> TYPE: PRT
<213> ORGANISM: Solanum pennellii

<400> SEQUENCE: 183

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
                20                  25                  30

Leu Phe Leu Pro Ser Leu Pro Leu Arg Phe Ser Ser Ser Thr Thr Asn
            35                  40                  45

Val Ser Ser Ser Lys Phe Thr Ser Thr Thr Val Ala Leu Phe Lys Ser
50                  55                  60

Lys Ala Lys Ala Pro Pro Lys Lys Val Ala Pro Pro Lys Glu Lys Gln
65                  70                  75                  80

Lys Val Glu Asp Gly Ile Phe Gly Thr Ser Gly Ile Gly Phe Thr
                85                  90                  95

Lys Gln Asn Glu Leu Phe Val Gly Arg Val Ala Met Ile Gly Phe Ala
                100                 105                 110

Ala Ser Leu Leu Gly Glu Ala Ile Thr Gly Lys Gly Ile Leu Ala Gln
            115                 120                 125

Leu Asn Leu Glu Thr Gly Ile Pro Ile Tyr Glu Ala Glu Pro Leu Leu
130                 135                 140

Leu Phe Phe Ile Leu Phe Asn Leu Leu Gly Ala Ile Gly Ala Leu Gly
145                 150                 155                 160

Asp Arg Gly Lys Phe Val Asp Asp Pro Thr Pro Thr Gly Leu Glu
                165                 170                 175

Lys Ala Val Ile Pro Pro Gly Lys Ser Phe Lys Ser Ala Leu Gly Leu
            180                 185                 190

Ser Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Ile Ile Gly Glu
210                 215                 220

Ile Ile Thr Gly Lys Gly Ala Leu Ala Gln Leu Asn Phe Glu Thr Gly
225                 230                 235                 240

Val Pro Ile Asn Glu Ile Glu Pro Leu Leu Leu Phe Asn Ile Ala Phe
                245                 250                 255

Phe Phe Phe Ala Ala Ile Asn Pro Gly Thr Gly Lys Phe Ile Thr Asp
                260                 265                 270

Glu Glu Glu Asp
```

<210> SEQ ID NO 184
<211> LENGTH: 276
<212> TYPE: PRT
<213> ORGANISM: Solanum lycopersicum

<400> SEQUENCE: 184

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
                20                  25                  30

Leu Phe Leu Pro Ser Leu Pro Leu Arg Phe Ser Ser Ser Thr Asn
            35                  40                  45

Ala Ser Ser Ser Lys Phe Thr Ser Thr Thr Val Ala Leu Phe Lys Ser
    50                  55                  60

Lys Ala Lys Ala Pro Pro Lys Lys Val Ala Pro Pro Lys Glu Lys Gln
65                  70                  75                  80

Lys Val Glu Asp Gly Ile Phe Gly Thr Ser Gly Gly Ile Gly Phe Thr
                85                  90                  95

Lys Gln Asn Glu Leu Phe Val Gly Arg Val Ala Met Ile Gly Phe Ala
            100                 105                 110

Ala Ser Leu Leu Gly Glu Ala Ile Thr Gly Lys Gly Ile Leu Ala Gln
        115                 120                 125

Leu Asn Leu Glu Thr Gly Ile Pro Ile Tyr Glu Ala Glu Pro Leu Leu
130                 135                 140

Leu Phe Phe Ile Leu Phe Asn Leu Leu Gly Ala Ile Gly Ala Leu Gly
145                 150                 155                 160

Asp Arg Gly Lys Phe Val Asp Asp Pro Thr Pro Pro Thr Gly Leu Glu
                165                 170                 175

Lys Ala Val Ile Pro Pro Gly Lys Ser Phe Lys Ser Ala Leu Gly Leu
            180                 185                 190

Ser Glu Gly Gly Pro Leu Phe Gly Phe Thr Lys Ala Asn Glu Leu Phe
        195                 200                 205

Val Gly Arg Leu Ala Gln Leu Gly Ile Ala Phe Ser Ile Ile Gly Glu
210                 215                 220

Ile Ile Thr Gly Lys Gly Ala Leu Ala Gln Leu Asn Phe Glu Thr Gly
225                 230                 235                 240

Val Pro Ile Asn Glu Ile Glu Pro Leu Leu Leu Phe Asn Ile Ala Phe
                245                 250                 255

Phe Phe Phe Ala Ala Ile Asn Pro Gly Thr Gly Lys Phe Ile Thr Asp
            260                 265                 270

Glu Glu Glu Asp
        275

<210> SEQ ID NO 185
<211> LENGTH: 29
<212> TYPE: PRT
<213> ORGANISM: Oryza sativa

<400> SEQUENCE: 185

Met Ala Leu Gln Gln Ser Met Ala Met Pro Met Val Val Ser Asp
1               5                   10                  15

Leu Gly Thr Ala Pro Arg Ser Ser Pro Met Val Gln Leu
                20                  25

-continued

<210> SEQ ID NO 186
<211> LENGTH: 23
<212> TYPE: PRT
<213> ORGANISM: Oryza sativa

<400> SEQUENCE: 186

Met Ala Met Pro Met Met Val Val Ser Asp Leu Gly Thr Ala Pro Arg
1               5                   10                  15

Ser Ser Pro Met Val Gln Leu
            20

<210> SEQ ID NO 187
<211> LENGTH: 23
<212> TYPE: PRT
<213> ORGANISM: Oryza sativa

<400> SEQUENCE: 187

Met Ala Met Pro Met Met Val Val Ser Asp Leu Gly Thr Ala Pro Arg
1               5                   10                  15

Ser Ser Pro Met Val Gln Leu
            20

<210> SEQ ID NO 188
<211> LENGTH: 29
<212> TYPE: PRT
<213> ORGANISM: Oryza sativa

<400> SEQUENCE: 188

Met Ala Leu Gln Gln Ser Met Ala Met Pro Met Met Val Val Ser Asp
1               5                   10                  15

Leu Gly Thr Ala Pro Arg Ser Ser Pro Met Val Gln Leu
            20                  25

<210> SEQ ID NO 189
<211> LENGTH: 41
<212> TYPE: PRT
<213> ORGANISM: Oryza sativa

<400> SEQUENCE: 189

Met Ala Gln Ser Met Leu Val Ser Gly Ala Asn Gly Thr Val Ala Ala
1               5                   10                  15

Ala Ser Thr Ser Arg Leu Gln Pro Val Arg Pro Thr Pro Phe Ser Arg
            20                  25                  30

Leu Val Leu Ser Gln Pro Ser Ser Ser
            35                  40

<210> SEQ ID NO 190
<211> LENGTH: 40
<212> TYPE: PRT
<213> ORGANISM: Zea mays

<400> SEQUENCE: 190

Met Ala Ala Gln Ser Met Leu Met Ser Thr Ser Val Asn Gly Gly Arg
1               5                   10                  15

Ala Leu Pro Ser Leu Gln Ala Val Arg Pro Ala Pro Tyr Pro Arg Leu
            20                  25                  30

Pro Leu Pro Ser Ser Ser Ser Ser
            35                  40

<210> SEQ ID NO 191
<211> LENGTH: 41
<212> TYPE: PRT

<213> ORGANISM: Zea mays

<400> SEQUENCE: 191

Met Ala Ala Gln Ser Met Leu Met Ser Thr Ser Val Asn Gly Gly Arg
1               5                   10                  15

Ala Leu Pro Ser Leu Gln Ala Val Arg Pro Ala Pro Tyr Pro Arg Leu
            20                  25                  30

Pro Leu Pro Ser Ser Ser Ser Ser
        35                  40

<210> SEQ ID NO 192
<211> LENGTH: 34
<212> TYPE: PRT
<213> ORGANISM: Zea mays

<400> SEQUENCE: 192

Met Ser Thr Ser Val Asn Gly Gly Arg Ala Leu Pro Ser Leu Gln Ala
1               5                   10                  15

Val Arg Pro Ala Pro Tyr Pro Arg Leu Pro Leu Pro Ser Ser Ser Ser
            20                  25                  30

Ser Ser

<210> SEQ ID NO 193
<211> LENGTH: 47
<212> TYPE: PRT
<213> ORGANISM: Nicotiana benthamiana

<400> SEQUENCE: 193

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Phe Phe Leu Pro Ser Leu Ser Leu Lys Tyr Pro Ser Ala Ser Ser
        35                  40                  45

<210> SEQ ID NO 194
<211> LENGTH: 47
<212> TYPE: PRT
<213> ORGANISM: Nicotiana tabacum

<400> SEQUENCE: 194

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Phe Phe Leu Pro Ser Leu Ser Leu Lys Tyr Pro Ser Ala Ser Ser
        35                  40                  45

<210> SEQ ID NO 195
<211> LENGTH: 47
<212> TYPE: PRT
<213> ORGANISM: Nicotiana tabacum

<400> SEQUENCE: 195

Met Ala Gln Thr Met Leu Leu Thr Ala Asn Ala Lys Val Asp Leu Arg
1               5                   10                  15

Ser Lys Glu Ser Leu Val Glu Arg Leu Lys Pro Lys Pro Leu Ser Ser
            20                  25                  30

Phe Phe Leu Pro Ser Leu Ser Leu Lys Tyr Pro Ser Ala Ser Ser
        35                  40                  45

<210> SEQ ID NO 196
<211> LENGTH: 47
<212> TYPE: PRT
<213> ORGANISM: Nicotiana benthamiana

<400> SEQUENCE: 196

Met Ala Gln Thr Met Leu Leu Thr Ala Asn Ala Lys Val Asp Leu Arg
1               5                   10                  15

Asn Lys Glu Pro Leu Val Glu Arg Leu Lys Pro Lys Pro Leu Ser Ser
            20                  25                  30

Phe Phe Leu Pro Ser Leu Ser Leu Lys Tyr Pro Ser Ala Ser Ser
        35                  40                  45

<210> SEQ ID NO 197
<211> LENGTH: 37
<212> TYPE: PRT
<213> ORGANISM: Arabidopsis thaliana

<400> SEQUENCE: 197

Met Ala Gln Thr Met Leu Leu Thr Ser Gly Val Thr Ala Gly His Phe
1               5                   10                  15

Leu Arg Asn Lys Ser Pro Leu Ala Gln Pro Lys Val His His Leu Phe
            20                  25                  30

Leu Ser Gly Asn Ser
        35

<210> SEQ ID NO 198
<211> LENGTH: 47
<212> TYPE: PRT
<213> ORGANISM: Hevea brasiliensis

<400> SEQUENCE: 198

Met Ala Gln Thr Ile Leu Phe Met Ser Gly Val Ser Thr Lys His Val
1               5                   10                  15

Val Asn Leu Lys Arg Asp Pro Leu Leu Gln Phe Gln Val Glu Arg Leu
            20                  25                  30

Arg Pro Lys Pro Phe Ser Arg Leu Phe Phe Asn Pro Leu Pro Ser
        35                  40                  45

<210> SEQ ID NO 199
<211> LENGTH: 47
<212> TYPE: PRT
<213> ORGANISM: Manihot esculenta

<400> SEQUENCE: 199

Met Ala Gln Thr Thr Met Phe Met Ser Gly Val Ser Thr Lys His Val
1               5                   10                  15

Val Asn Leu Lys Arg Asp Pro Leu Leu Gln Phe Gln Val Glu Arg Leu
            20                  25                  30

Arg Pro Lys Pro Leu Ser Pro Ile Phe Tyr Asn Pro Leu Pro Ser
        35                  40                  45

<210> SEQ ID NO 200
<211> LENGTH: 41
<212> TYPE: PRT
<213> ORGANISM: Vigna unguiculata

<400> SEQUENCE: 200

Met Ala Gln Thr Met Leu Leu Met Ser Ser Val Ser Ser Ser His Ser
1               5                   10                  15

```
Leu Gly Leu Lys Lys Asp Leu Phe Leu Gln Leu Arg Pro Lys Phe Ser
            20                  25                  30

Gln Leu Ser Phe Asn Pro Leu Pro Ser
            35                  40
```

<210> SEQ ID NO 201
<211> LENGTH: 46
<212> TYPE: PRT
<213> ORGANISM: Glycine max

<400> SEQUENCE: 201

```
Met Ala Gln Thr Met Leu Leu Met Ser Ser Val Ser Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Ser
            35                  40                  45
```

<210> SEQ ID NO 202
<211> LENGTH: 46
<212> TYPE: PRT
<213> ORGANISM: Glycine max

<400> SEQUENCE: 202

```
Met Ala Gln Thr Met Leu Leu Met Ser Ser Val Ser Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Ser
            35                  40                  45
```

<210> SEQ ID NO 203
<211> LENGTH: 46
<212> TYPE: PRT
<213> ORGANISM: Glycine max

<400> SEQUENCE: 203

```
Met Ala Gln Thr Met Leu Leu Met Ser Ser Val Ser Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Pro
            35                  40                  45
```

<210> SEQ ID NO 204
<211> LENGTH: 46
<212> TYPE: PRT
<213> ORGANISM: Glycine max

<400> SEQUENCE: 204

```
Met Ala Gln Thr Met Leu Leu Met Ser Ser Val Ser Ser Ser Tyr Ser
1               5                   10                  15

Val Asp Leu Lys Lys Asp Leu Phe Leu Gln Leu Gln Ser Gln Ser Leu
            20                  25                  30

Arg Pro Lys Phe Ser Gln Leu Ser Phe Asn Pro Leu Pro Pro
            35                  40                  45
```

<210> SEQ ID NO 205
<211> LENGTH: 54
<212> TYPE: PRT

<213> ORGANISM: Oryza sativa

<400> SEQUENCE: 205

Gln Arg Met Lys Lys His Leu Val Val Ala Ala Phe Lys Ser Arg
1               5                   10                  15

Thr Lys Ala Ser Pro Lys Val Asp Lys Ser Asn Lys Asn Lys Ser Ile
            20                  25                  30

Val Glu Asp Gly Ile Phe Gly Thr Ser Gly Gly Ile Gly Phe Thr Lys
        35                  40                  45

Glu Asn Glu Leu Phe Val
    50

<210> SEQ ID NO 206
<211> LENGTH: 54
<212> TYPE: PRT
<213> ORGANISM: Oryza sativa

<400> SEQUENCE: 206

Gln Arg Met Lys Lys His Leu Val Val Ala Ala Phe Lys Ser Arg
1               5                   10                  15

Thr Lys Ala Ser Pro Lys Val Asp Lys Ser Asn Lys Asn Lys Ser Ile
            20                  25                  30

Val Glu Asp Gly Ile Phe Gly Thr Ser Gly Gly Ile Gly Phe Thr Lys
        35                  40                  45

Glu Asn Glu Leu Phe Val
    50

<210> SEQ ID NO 207
<211> LENGTH: 54
<212> TYPE: PRT
<213> ORGANISM: Oryza sativa

<400> SEQUENCE: 207

Gln Arg Met Lys Lys His Leu Val Val Ala Ala Phe Lys Ser Arg
1               5                   10                  15

Thr Lys Ala Ser Pro Lys Val Asp Lys Ser Asn Lys Asn Lys Ser Ile
            20                  25                  30

Val Glu Asp Gly Ile Phe Gly Thr Ser Gly Gly Ile Gly Phe Thr Lys
        35                  40                  45

Glu Asn Glu Leu Phe Val
    50

<210> SEQ ID NO 208
<211> LENGTH: 54
<212> TYPE: PRT
<213> ORGANISM: Oryza sativa

<400> SEQUENCE: 208

Gln Arg Met Lys Lys His Leu Val Val Ala Ala Phe Lys Ser Arg
1               5                   10                  15

Thr Lys Ala Ser Pro Lys Val Asp Lys Ser Asn Lys Asn Lys Ser Ile
            20                  25                  30

Val Glu Asp Gly Ile Phe Gly Thr Ser Gly Gly Ile Gly Phe Thr Lys
        35                  40                  45

Glu Asn Glu Leu Phe Val
    50

<210> SEQ ID NO 209
<211> LENGTH: 55

```
<212> TYPE: PRT
<213> ORGANISM: Oryza sativa

<400> SEQUENCE: 209

Leu Gly Arg Ala Val Ser Val Lys Thr Val Ala Leu Phe Gly Arg Ser
1               5                   10                  15

Lys Thr Lys Ala Ala Pro Ala Arg Lys Ala Glu Pro Lys Pro Lys Phe
                20                  25                  30

Lys Thr Glu Asp Gly Ile Phe Gly Thr Ser Gly Gly Ile Gly Phe Thr
            35                  40                  45

Lys Glu Asn Glu Leu Phe Val
        50                  55

<210> SEQ ID NO 210
<211> LENGTH: 60
<212> TYPE: PRT
<213> ORGANISM: Zea mays

<400> SEQUENCE: 210

Ser Gly Tyr Arg His Ser Lys Ser Val Ser Val Lys Thr Leu Ala Leu
1               5                   10                  15

Phe Gly Lys Ser Lys Val Lys Thr Ala Pro Ala Lys Lys Ala Ala Ala
                20                  25                  30

Pro Lys Pro Lys Pro Lys Val Glu Asp Gly Ile Phe Gly Thr Ser Gly
            35                  40                  45

Gly Ile Gly Phe Thr Lys Glu Asn Glu Leu Phe Val
        50                  55                  60

<210> SEQ ID NO 211
<211> LENGTH: 60
<212> TYPE: PRT
<213> ORGANISM: Zea mays

<400> SEQUENCE: 211

Ala Gly Tyr Arg His Ser Lys Ser Val Ser Val Lys Thr Leu Ala Leu
1               5                   10                  15

Phe Gly Lys Ser Lys Val Lys Thr Ala Pro Ala Lys Lys Ala Ala Ala
                20                  25                  30

Pro Lys Pro Lys Pro Lys Val Glu Asp Gly Ile Phe Gly Thr Ser Gly
            35                  40                  45

Gly Ile Gly Phe Thr Lys Glu Asn Glu Leu Phe Val
        50                  55                  60

<210> SEQ ID NO 212
<211> LENGTH: 60
<212> TYPE: PRT
<213> ORGANISM: Zea mays

<400> SEQUENCE: 212

Ala Gly Tyr Arg His Ser Lys Ser Val Ser Val Lys Thr Leu Ala Leu
1               5                   10                  15

Phe Gly Lys Ser Lys Val Lys Thr Ala Pro Ala Lys Lys Ala Ala Ala
                20                  25                  30

Pro Lys Pro Lys Pro Lys Val Glu Asp Gly Ile Phe Gly Thr Ser Gly
            35                  40                  45

Gly Ile Gly Phe Thr Lys Glu Asn Glu Leu Phe Val
        50                  55                  60

<210> SEQ ID NO 213
```

```
<211> LENGTH: 57
<212> TYPE: PRT
<213> ORGANISM: Nicotiana benthamiana

<400> SEQUENCE: 213

Ser Ser Ser Ser Ser Ser His Phe Thr Ser Thr Thr Val Ala Leu
1               5                   10                  15

Phe Lys Ser Lys Ala Lys Ala Pro Ala Lys Lys Val Val Pro Lys Pro
                20              25                  30

Lys Glu Lys Val Glu Asp Gly Ile Phe Gly Thr Ser Gly Gly Ile Gly
            35                  40                  45

Phe Thr Lys Gln Asn Glu Leu Phe Val
    50                  55

<210> SEQ ID NO 214
<211> LENGTH: 54
<212> TYPE: PRT
<213> ORGANISM: Nicotiana tabacum

<400> SEQUENCE: 214

Ser Ala Ser Ser His Phe Thr Ser Thr Thr Val Ala Leu Phe Lys Ser
1               5                   10                  15

Lys Ala Lys Ala Pro Ala Lys Lys Val Val Pro Lys Pro Lys Glu Lys
                20              25                  30

Val Glu Asp Gly Ile Phe Gly Thr Ser Gly Gly Ile Gly Phe Thr Lys
            35                  40                  45

Gln Asn Glu Leu Phe Val
    50

<210> SEQ ID NO 215
<211> LENGTH: 54
<212> TYPE: PRT
<213> ORGANISM: Nicotiana tabacum

<400> SEQUENCE: 215

Ser Ser Ser Ser His Phe Ala Ser Thr Thr Val Ala Leu Phe Lys Ser
1               5                   10                  15

Lys Ala Lys Ala Pro Ala Lys Lys Val Val Pro Lys Pro Lys Glu Lys
                20              25                  30

Val Glu Asp Gly Ile Phe Gly Thr Ser Gly Gly Ile Gly Phe Thr Lys
            35                  40                  45

Gln Asn Glu Leu Phe Val
    50

<210> SEQ ID NO 216
<211> LENGTH: 54
<212> TYPE: PRT
<213> ORGANISM: Nicotiana benthamiana

<400> SEQUENCE: 216

Ser Ser Ser Ser His Phe Thr Ser Thr Thr Val Ala Leu Phe Lys Ser
1               5                   10                  15

Lys Ala Lys Ala Pro Ala Lys Lys Val Val Pro Lys Pro Lys Glu Lys
                20              25                  30

Val Glu Asp Gly Ile Phe Gly Thr Ser Gly Gly Ile Gly Phe Thr Lys
            35                  40                  45

Gln Asn Glu Leu Phe Val
    50
```

```
<210> SEQ ID NO 217
<211> LENGTH: 56
<212> TYPE: PRT
<213> ORGANISM: Arabidopsis thaliana

<400> SEQUENCE: 217

Pro Val Ala Leu Pro Ser Arg Arg Gln Ser Phe Val Pro Leu Ala Leu
1               5                   10                  15

Phe Lys Pro Lys Thr Lys Ala Ala Pro Lys Lys Val Glu Lys Pro Lys
            20                  25                  30

Ser Lys Val Glu Asp Gly Ile Phe Gly Thr Ser Gly Gly Ile Gly Phe
        35                  40                  45

Thr Lys Ala Asn Glu Leu Phe Val
    50                  55

<210> SEQ ID NO 218
<211> LENGTH: 54
<212> TYPE: PRT
<213> ORGANISM: Hevea brasiliensis

<400> SEQUENCE: 218

Asn Ser Ser Phe Ser Ser Lys Thr Phe Thr Thr Leu Ala Leu Phe Lys
1               5                   10                  15

Ser Lys Thr Lys Ala Pro Leu Lys Lys Ala Ala Glu Pro Lys Pro Lys
            20                  25                  30

Val Glu Asp Gly Ile Phe Gly Thr Ser Gly Gly Ile Gly Phe Thr Lys
        35                  40                  45

Gln Asn Glu Leu Phe Val
    50

<210> SEQ ID NO 219
<211> LENGTH: 54
<212> TYPE: PRT
<213> ORGANISM: Manihot esculenta

<400> SEQUENCE: 219

Cys Ser Ala Ser Ser Ser Lys Thr Phe Thr Thr Val Ala Leu Phe Arg
1               5                   10                  15

Ser Lys Thr Lys Ala Pro Val Lys Lys Val Ala Glu Pro Lys Pro Lys
            20                  25                  30

Val Glu Asp Gly Ile Phe Gly Thr Ser Gly Gly Ile Gly Phe Thr Lys
        35                  40                  45

Gln Asn Glu Leu Phe Val
    50

<210> SEQ ID NO 220
<211> LENGTH: 58
<212> TYPE: PRT
<213> ORGANISM: Vigna unguiculata

<400> SEQUENCE: 220

Ser Thr Pro Phe Pro Ser Ser Pro Arg Thr Phe Thr Thr Leu Ala Leu
1               5                   10                  15

Phe Lys Ser Lys Thr Lys Ala Pro Pro Ala Lys Thr Lys Val Val Lys
            20                  25                  30

Pro Lys Gln Lys Val Glu Asp Gly Ile Phe Gly Thr Ser Gly Gly Phe
        35                  40                  45

Gly Phe Thr Lys Gln Asn Glu Leu Phe Val
    50                  55
```

```
<210> SEQ ID NO 221
<211> LENGTH: 58
<212> TYPE: PRT
<213> ORGANISM: Glycine max

<400> SEQUENCE: 221

Ser Thr Ser Ser Phe Ser Ser Pro Arg Thr Phe Thr Thr Leu Ala Leu
1               5                   10                  15

Phe Lys Ser Lys Thr Lys Ala Ala Pro Ala Lys Thr Lys Val Thr Lys
            20                  25                  30

Pro Lys Gln Lys Val Glu Asp Gly Ile Phe Gly Thr Ser Gly Gly Phe
        35                  40                  45

Gly Phe Thr Lys Gln Asn Glu Leu Phe Val
    50                  55

<210> SEQ ID NO 222
<211> LENGTH: 58
<212> TYPE: PRT
<213> ORGANISM: Glycine max

<400> SEQUENCE: 222

Ser Thr Ser Ser Phe Ser Ser Pro Arg Thr Phe Thr Thr Leu Ala Leu
1               5                   10                  15

Phe Lys Ser Lys Thr Lys Ala Ala Pro Ala Lys Thr Lys Val Thr Lys
            20                  25                  30

Pro Lys Gln Lys Val Glu Asp Gly Ile Phe Gly Thr Ser Gly Gly Phe
        35                  40                  45

Gly Phe Thr Lys Gln Asn Glu Leu Phe Val
    50                  55

<210> SEQ ID NO 223
<211> LENGTH: 58
<212> TYPE: PRT
<213> ORGANISM: Glycine max

<400> SEQUENCE: 223

Ser Thr Ser Ser Phe Ser Ser Pro Arg Thr Phe Thr Thr Leu Ala Leu
1               5                   10                  15

Phe Lys Ser Lys Thr Lys Ala Ala Pro Ala Lys Thr Lys Val Thr Lys
            20                  25                  30

Pro Lys Gln Lys Val Glu Asp Gly Ile Phe Gly Thr Ser Gly Gly Phe
        35                  40                  45

Gly Phe Thr Lys Gln Asn Glu Leu Phe Val
    50                  55

<210> SEQ ID NO 224
<211> LENGTH: 58
<212> TYPE: PRT
<213> ORGANISM: Glycine max

<400> SEQUENCE: 224

Ser Thr Ser Ser Phe Ser Ser Pro Arg Thr Phe Thr Thr Leu Ala Leu
1               5                   10                  15

Phe Lys Ser Lys Thr Lys Ala Ala Pro Ala Lys Thr Lys Val Thr Lys
            20                  25                  30

Pro Lys Gln Lys Val Glu Asp Gly Ile Phe Gly Thr Ser Gly Gly Phe
        35                  40                  45

Gly Phe Thr Lys Gln Asn Glu Leu Phe Val
    50                  55
```

<210> SEQ ID NO 225
<211> LENGTH: 60
<212> TYPE: PRT
<213> ORGANISM: Oryza sativa

<400> SEQUENCE: 225

Gly Arg Val Ala Met Leu Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 226
<211> LENGTH: 60
<212> TYPE: PRT
<213> ORGANISM: Oryza sativa

<400> SEQUENCE: 226

Gly Arg Val Ala Met Leu Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 227
<211> LENGTH: 60
<212> TYPE: PRT
<213> ORGANISM: Oryza sativa

<400> SEQUENCE: 227

Gly Arg Val Ala Met Leu Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 228
<211> LENGTH: 60
<212> TYPE: PRT
<213> ORGANISM: Oryza sativa

<400> SEQUENCE: 228

Gly Arg Val Ala Met Leu Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly

<210> SEQ ID NO 229
<211> LENGTH: 60
<212> TYPE: PRT
<213> ORGANISM: Oryza sativa

<400> SEQUENCE: 229

Gly Arg Val Ala Met Leu Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 230
<211> LENGTH: 60
<212> TYPE: PRT
<213> ORGANISM: Zea mays

<400> SEQUENCE: 230

Gly Arg Val Ala Met Leu Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 231
<211> LENGTH: 60
<212> TYPE: PRT
<213> ORGANISM: Zea mays

<400> SEQUENCE: 231

Gly Arg Val Ala Met Leu Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 232
<211> LENGTH: 60
<212> TYPE: PRT
<213> ORGANISM: Zea mays

<400> SEQUENCE: 232

Gly Arg Val Ala Met Leu Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
        50                  55                  60

<210> SEQ ID NO 233
<211> LENGTH: 60
<212> TYPE: PRT
<213> ORGANISM: Nicotiana benthamiana

<400> SEQUENCE: 233

Gly Arg Val Ala Met Ile Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Asn
        35                  40                  45

Leu Leu Gly Ala Ile Gly Ala Leu Gly Asp Arg Gly
        50                  55                  60

<210> SEQ ID NO 234
<211> LENGTH: 60
<212> TYPE: PRT
<213> ORGANISM: Nicotiana tabacum

<400> SEQUENCE: 234

Gly Arg Val Ala Met Ile Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Asn
        35                  40                  45

Leu Leu Gly Ala Ile Gly Ala Leu Gly Asp Arg Gly
        50                  55                  60

<210> SEQ ID NO 235
<211> LENGTH: 60
<212> TYPE: PRT
<213> ORGANISM: Nicotiana tabacum

<400> SEQUENCE: 235

Gly Arg Val Ala Met Ile Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Asn
        35                  40                  45

Leu Leu Gly Ala Ile Gly Ala Leu Gly Asp Arg Gly
        50                  55                  60

<210> SEQ ID NO 236
<211> LENGTH: 60
<212> TYPE: PRT
<213> ORGANISM: Nicotiana benthamiana

<400> SEQUENCE: 236

Gly Arg Val Ala Met Ile Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Asn
        35                  40                  45

Leu Leu Gly Ala Ile Gly Ala Leu Gly Asp Arg Gly
    50                  55                  60

<210> SEQ ID NO 237
<211> LENGTH: 60
<212> TYPE: PRT
<213> ORGANISM: Arabidopsis thaliana

<400> SEQUENCE: 237

Gly Arg Val Ala Met Ile Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 238
<211> LENGTH: 60
<212> TYPE: PRT
<213> ORGANISM: Hevea brasiliensis

<400> SEQUENCE: 238

Gly Arg Val Ala Met Leu Gly Phe Ala Ala Ser Leu Leu Gly Glu Ala
1               5                   10                  15

Ile Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr
        35                  40                  45

Leu Leu Gly Ala Ile Gly Ala Leu Gly Asp Arg Gly
    50                  55                  60

<210> SEQ ID NO 239
<211> LENGTH: 59
<212> TYPE: PRT
<213> ORGANISM: Manihot esculenta

<400> SEQUENCE: 239

Gly Arg Val Ala Met Leu Gly Phe Ala Ser Leu Leu Gly Glu Ala Ile
1               5                   10                  15

Thr Gly Lys Gly Ile Leu Ala Gln Leu Asn Leu Glu Thr Gly Ile Pro
            20                  25                  30

Ile Tyr Glu Ala Glu Pro Leu Leu Leu Phe Phe Ile Leu Phe Thr Leu
        35                  40                  45

Leu Gly Ala Ile Gly Ala Leu Gly Asp Arg Gly
    50                  55

<210> SEQ ID NO 240
<211> LENGTH: 60
<212> TYPE: PRT
<213> ORGANISM: Vigna unguiculata

<400> SEQUENCE: 240

Gly Arg Val Ala Met Leu Gly Phe Ala Ala Ser Leu Leu Gly Glu Ala
1               5                   10                  15

Val Thr Gly Lys Gly Ile Leu Ala Gln Leu Asn Leu Glu Thr Gly Ile
            20                  25                  30

Pro Ile Tyr Glu Ala Glu Pro Leu Leu Leu Phe Phe Ile Leu Phe Thr

```
                35                  40                  45
Leu Leu Gly Ala Ile Gly Gly Leu Gly Asp Arg Gly
 50                  55                  60

<210> SEQ ID NO 241
<211> LENGTH: 60
<212> TYPE: PRT
<213> ORGANISM: Glycine max

<400> SEQUENCE: 241

Gly Arg Val Ala Met Leu Gly Phe Ala Ala Ser Leu Leu Gly Glu Ala
  1               5                  10                  15

Ile Thr Gly Lys Gly Ile Leu Ala Gln Leu Asn Leu Glu Thr Gly Ile
                20                  25                  30

Pro Ile Tyr Glu Ala Glu Pro Leu Leu Leu Phe Phe Ile Leu Phe Thr
                35                  40                  45

Leu Leu Gly Ala Ile Gly Gly Leu Gly Asp Arg Gly
 50                  55                  60

<210> SEQ ID NO 242
<211> LENGTH: 60
<212> TYPE: PRT
<213> ORGANISM: Glycine max

<400> SEQUENCE: 242

Gly Arg Val Ala Met Leu Gly Phe Ala Ala Ser Leu Leu Gly Glu Ala
  1               5                  10                  15

Ile Thr Gly Lys Gly Ile Leu Ala Gln Leu Asn Leu Glu Thr Gly Ile
                20                  25                  30

Pro Ile Tyr Glu Ala Glu Pro Leu Leu Leu Phe Phe Ile Leu Phe Thr
                35                  40                  45

Leu Leu Gly Ala Ile Gly Gly Leu Gly Asp Arg Gly
 50                  55                  60

<210> SEQ ID NO 243
<211> LENGTH: 60
<212> TYPE: PRT
<213> ORGANISM: Glycine max

<400> SEQUENCE: 243

Gly Arg Val Ala Met Leu Gly Phe Ala Ala Ser Leu Leu Gly Glu Ala
  1               5                  10                  15

Ile Thr Gly Lys Gly Ile Leu Ala Gln Leu Asn Leu Glu Thr Gly Ile
                20                  25                  30

Pro Ile Tyr Glu Ala Glu Pro Leu Leu Leu Phe Phe Ile Leu Phe Thr
                35                  40                  45

Leu Leu Gly Ala Ile Gly Gly Leu Gly Asp Arg Gly
 50                  55                  60

<210> SEQ ID NO 244
<211> LENGTH: 60
<212> TYPE: PRT
<213> ORGANISM: Glycine max

<400> SEQUENCE: 244

Gly Arg Val Ala Met Leu Gly Phe Ala Ala Ser Leu Leu Gly Glu Ala
  1               5                  10                  15

Ile Thr Gly Lys Gly Ile Leu Ala Gln Leu Asn Leu Glu Thr Gly Ile
                20                  25                  30
```

Pro Ile Tyr Glu Ala Glu Pro Leu Leu Phe Phe Ile Leu Phe Thr
         35                  40                  45

Leu Leu Gly Ala Ile Gly Gly Leu Gly Asp Arg Gly
 50                  55                  60

<210> SEQ ID NO 245
<211> LENGTH: 57
<212> TYPE: PRT
<213> ORGANISM: Oryza sativa

<400> SEQUENCE: 245

Arg Phe Val Asp Asp Ala Thr Gly Leu Glu Arg Ala Val Ile Pro Pro
 1               5                  10                  15

Gly Lys Gly Phe Arg Ala Ala Leu Gly Leu Ser Glu Gly Gly Pro Leu
             20                  25                  30

Phe Gly Phe Thr Lys Ala Asn Glu Leu Phe Val Gly Arg Leu Ala His
         35                  40                  45

Val Gly Ile Ala Phe Ser Leu Ile Gly
 50                  55

<210> SEQ ID NO 246
<211> LENGTH: 57
<212> TYPE: PRT
<213> ORGANISM: Oryza sativa

<400> SEQUENCE: 246

Arg Phe Val Asp Asp Ala Thr Gly Leu Glu Arg Ala Val Ile Pro Pro
 1               5                  10                  15

Gly Lys Gly Phe Arg Ala Ala Leu Gly Leu Ser Glu Gly Gly Pro Leu
             20                  25                  30

Phe Gly Phe Thr Lys Ala Asn Glu Leu Phe Val Gly Arg Leu Ala Gln
         35                  40                  45

Leu Gly Ile Ala Phe Ser Leu Ile Gly
 50                  55

<210> SEQ ID NO 247
<211> LENGTH: 57
<212> TYPE: PRT
<213> ORGANISM: Oryza sativa

<400> SEQUENCE: 247

Arg Phe Val Asp Asp Ala Thr Gly Leu Glu Arg Ala Val Ile Pro Pro
 1               5                  10                  15

Gly Lys Gly Phe Arg Ala Ala Leu Gly Leu Ser Glu Gly Gly Pro Leu
             20                  25                  30

Phe Gly Phe Thr Lys Ala Asn Glu Leu Phe Val Gly Arg Leu Ala Gln
         35                  40                  45

Leu Gly Ile Ala Phe Ser Leu Ile Gly
 50                  55

<210> SEQ ID NO 248
<211> LENGTH: 57
<212> TYPE: PRT
<213> ORGANISM: Oryza sativa

<400> SEQUENCE: 248

Arg Phe Val Asp Asp Ala Thr Gly Leu Glu Arg Ala Val Ile Pro Pro
 1               5                  10                  15

Gly Lys Gly Phe Arg Ala Ala Leu Gly Leu Ser Glu Gly Gly Pro Leu
             20                  25                  30

Phe Gly Phe Thr Lys Ala Asn Glu Leu Phe Val Gly Arg Leu Ala Gln
        35                  40                  45

Leu Gly Ile Ala Phe Ser Leu Ile Gly
    50                  55

<210> SEQ ID NO 249
<211> LENGTH: 59
<212> TYPE: PRT
<213> ORGANISM: Oryza sativa

<400> SEQUENCE: 249

Ser Phe Val Asp Asp Gln Pro Val Thr Gly Leu Asp Lys Ala Val Ile
1               5                   10                  15

Ala Pro Gly Lys Gly Phe Arg Ser Ala Leu Gly Leu Ser Glu Gly Gly
            20                  25                  30

Pro Leu Phe Gly Phe Thr Lys Ala Asn Glu Leu Phe Val Gly Arg Leu
        35                  40                  45

Ala Gln Leu Gly Ile Ala Phe Ser Ile Ile Gly
    50                  55

<210> SEQ ID NO 250
<211> LENGTH: 58
<212> TYPE: PRT
<213> ORGANISM: Zea mays

<400> SEQUENCE: 250

Arg Phe Val Asp Glu Glu Val Thr Gly Leu Asp Lys Ala Val Ile Gln
1               5                   10                  15

Pro Gly Lys Gly Phe Arg Gly Ala Leu Gly Leu Ser Glu Gly Gly Pro
            20                  25                  30

Leu Phe Gly Phe Thr Lys Ser Asn Glu Leu Phe Val Gly Arg Met Ala
        35                  40                  45

Gln Leu Gly Val Ala Phe Ser Ile Ile Gly
    50                  55

<210> SEQ ID NO 251
<211> LENGTH: 58
<212> TYPE: PRT
<213> ORGANISM: Zea mays

<400> SEQUENCE: 251

Arg Phe Val Asp Glu Glu Val Thr Gly Leu Asp Lys Ala Val Ile Gln
1               5                   10                  15

Pro Gly Lys Gly Phe Arg Gly Ala Leu Gly Leu Ser Glu Gly Gly Pro
            20                  25                  30

Leu Phe Gly Phe Thr Lys Ser Asn Glu Leu Phe Val Gly Arg Met Ala
        35                  40                  45

Gln Leu Gly Val Ala Phe Ser Ile Ile Gly
    50                  55

<210> SEQ ID NO 252
<211> LENGTH: 58
<212> TYPE: PRT
<213> ORGANISM: Zea mays

<400> SEQUENCE: 252

Arg Phe Val Asp Glu Glu Val Thr Gly Leu Asp Lys Ala Val Ile Gln
1               5                   10                  15

Pro Gly Lys Gly Phe Arg Gly Ala Leu Gly Leu Ser Glu Gly Gly Pro

```
            20                  25                  30

Leu Phe Gly Phe Thr Lys Ser Asn Glu Leu Phe Val Gly Arg Met Ala
            35                  40                  45

Gln Leu Gly Val Ala Phe Ser Ile Ile Gly
            50                  55

<210> SEQ ID NO 253
<211> LENGTH: 60
<212> TYPE: PRT
<213> ORGANISM: Nicotiana benthamiana

<400> SEQUENCE: 253

Lys Phe Ile Asp Asp Pro Thr Pro Pro Thr Gly Leu Asp Lys Ala Val
1               5                   10                  15

Ile Pro Pro Gly Lys Gly Phe Lys Ser Ala Leu Gly Leu Ser Glu Gly
            20                  25                  30

Gly Pro Leu Phe Gly Phe Thr Lys Ala Asn Glu Leu Phe Val Gly Arg
            35                  40                  45

Leu Ala Gln Leu Gly Ile Ala Phe Ser Ile Ile Gly
            50                  55                  60

<210> SEQ ID NO 254
<211> LENGTH: 60
<212> TYPE: PRT
<213> ORGANISM: Nicotiana tabacum

<400> SEQUENCE: 254

Lys Phe Ile Asp Asp Pro Ala Pro Pro Thr Gly Leu Asp Lys Ala Val
1               5                   10                  15

Ile Pro Pro Gly Lys Gly Phe Lys Ser Ala Leu Gly Leu Ser Glu Gly
            20                  25                  30

Gly Pro Leu Phe Glu Phe Thr Lys Ala Asn Glu Leu Phe Val Gly Arg
            35                  40                  45

Leu Ala Gln Leu Gly Ile Ala Phe Ser Ile Ile Gly
            50                  55                  60

<210> SEQ ID NO 255
<211> LENGTH: 60
<212> TYPE: PRT
<213> ORGANISM: Nicotiana tabacum

<400> SEQUENCE: 255

Lys Phe Ile Asp Asp Pro Ala Pro Ala Thr Gly Leu Asp Lys Ala Val
1               5                   10                  15

Ile Pro Pro Gly Lys Gly Phe Lys Ala Ala Leu Gly Leu Arg Glu Gly
            20                  25                  30

Gly Pro Leu Phe Gly Phe Thr Lys Ala Asn Glu Leu Phe Val Gly Arg
            35                  40                  45

Leu Ala Gln Leu Gly Ile Ala Phe Ser Ile Ile Gly
            50                  55                  60

<210> SEQ ID NO 256
<211> LENGTH: 60
<212> TYPE: PRT
<213> ORGANISM: Nicotiana benthamiana

<400> SEQUENCE: 256

Lys Phe Ile Asp Asp Pro Val Pro Ala Thr Gly Leu Asp Lys Ala Val
1               5                   10                  15
```

Ile Pro Pro Gly Lys Gly Phe Lys Ser Ala Leu Gly Leu Ser Glu Gly
                20                  25                  30

Gly Pro Leu Phe Gly Phe Thr Lys Ala Asn Glu Leu Phe Val Gly Arg
            35                  40                  45

Leu Ala Gln Leu Gly Ile Ala Phe Ser Ile Ile Gly
        50                  55                  60

<210> SEQ ID NO 257
<211> LENGTH: 58
<212> TYPE: PRT
<213> ORGANISM: Arabidopsis thaliana

<400> SEQUENCE: 257

Lys Phe Val Asp Asp Pro Pro Thr Gly Leu Glu Lys Ala Val Ile Pro
1               5                   10                  15

Pro Gly Lys Asn Val Arg Ser Ala Leu Gly Leu Lys Glu Gln Gly Pro
            20                  25                  30

Leu Phe Gly Phe Thr Lys Ala Asn Glu Leu Phe Val Gly Arg Leu Ala
        35                  40                  45

Gln Leu Gly Ile Ala Phe Ser Leu Ile Gly
    50                  55

<210> SEQ ID NO 258
<211> LENGTH: 58
<212> TYPE: PRT
<213> ORGANISM: Hevea brasiliensis

<400> SEQUENCE: 258

Lys Phe Val Asp Asp Pro Pro Thr Gly Ile Glu Gly Ala Val Ile Pro
1               5                   10                  15

Pro Gly Lys Gly Phe Arg Ser Ala Leu Gly Leu Lys Glu Gly Gly Pro
            20                  25                  30

Leu Phe Gly Phe Thr Lys Ala Asn Glu Leu Phe Val Gly Arg Leu Ala
        35                  40                  45

Gln Leu Gly Ile Ala Phe Ser Leu Ile Gly
    50                  55

<210> SEQ ID NO 259
<211> LENGTH: 58
<212> TYPE: PRT
<213> ORGANISM: Manihot esculenta

<400> SEQUENCE: 259

Lys Phe Val Asp Asp Pro Pro Thr Gly Leu Glu Gly Ala Val Ile Pro
1               5                   10                  15

Pro Gly Lys Ser Phe Arg Ser Ala Leu Gly Leu Lys Glu Gly Gly Pro
            20                  25                  30

Leu Phe Gly Phe Thr Lys Ala Asn Glu Leu Phe Val Gly Arg Leu Ala
        35                  40                  45

Gln Leu Gly Ile Ala Phe Ser Leu Ile Gly
    50                  55

<210> SEQ ID NO 260
<211> LENGTH: 56
<212> TYPE: PRT
<213> ORGANISM: Vigna unguiculata

<400> SEQUENCE: 260

Lys Phe Val Asp Asp Glu Glu Pro Asn Thr Gly Gly Val Ile Pro Gly
1               5                   10                  15

Gly Lys Gly Phe Arg Glu Ala Leu Gly Leu Gly Ser Gly Pro Leu Phe
            20                  25                  30

Gly Phe Thr Lys Ala Asn Glu Leu Phe Val Gly Arg Leu Ala Gln Leu
        35                  40                  45

Gly Phe Val Phe Ser Leu Ile Gly
    50                  55

<210> SEQ ID NO 261
<211> LENGTH: 55
<212> TYPE: PRT
<213> ORGANISM: Glycine max

<400> SEQUENCE: 261

Lys Phe Val Asp Asp Glu Pro Thr Thr Gly Gly Val Ile Pro Pro Gly
1               5                   10                  15

Lys Gly Phe Arg Glu Ala Leu Gly Leu Gly Ser Gly Pro Leu Phe Gly
            20                  25                  30

Phe Thr Lys Ala Asn Glu Leu Phe Val Gly Arg Leu Ala Gln Leu Gly
        35                  40                  45

Phe Val Phe Ser Leu Ile Gly
    50                  55

<210> SEQ ID NO 262
<211> LENGTH: 55
<212> TYPE: PRT
<213> ORGANISM: Glycine max

<400> SEQUENCE: 262

Lys Phe Val Asp Asp Glu Pro Thr Thr Gly Gly Val Ile Pro Pro Gly
1               5                   10                  15

Lys Gly Phe Arg Glu Ala Leu Gly Leu Gly Ser Gly Pro Leu Phe Gly
            20                  25                  30

Phe Thr Lys Ala Asn Glu Pro Phe Val Gly Arg Leu Ala Gln Leu Gly
        35                  40                  45

Phe Val Phe Ser Leu Ile Gly
    50                  55

<210> SEQ ID NO 263
<211> LENGTH: 55
<212> TYPE: PRT
<213> ORGANISM: Glycine max

<400> SEQUENCE: 263

Lys Phe Val Asp Asp Glu Pro Thr Thr Gly Gly Val Ile Pro Ser Gly
1               5                   10                  15

Lys Gly Phe Arg Glu Ala Leu Gly Leu Gly Ser Gly Pro Leu Phe Gly
            20                  25                  30

Phe Thr Lys Ala Asn Glu Leu Phe Val Gly Arg Leu Ala Gln Leu Gly
        35                  40                  45

Phe Val Phe Ser Leu Ile Gly
    50                  55

<210> SEQ ID NO 264
<211> LENGTH: 55
<212> TYPE: PRT
<213> ORGANISM: Glycine max

<400> SEQUENCE: 264

Lys Phe Val Asp Asp Glu Pro Thr Thr Gly Gly Val Ile Pro Ser Gly

-continued

```
                1               5                  10                  15
Lys Gly Phe Arg Glu Ala Leu Gly Leu Gly Ser Gly Pro Leu Phe Gly
              20                  25                  30
Phe Thr Lys Ala Asn Glu Leu Phe Val Gly Arg Leu Ala Gln Leu Gly
              35                  40                  45
Phe Val Ser Ser Leu Ile Gly
              50                  55
```

<210> SEQ ID NO 265
<211> LENGTH: 54
<212> TYPE: PRT
<213> ORGANISM: Oryza sativa

<400> SEQUENCE: 265

```
Glu Ile Ile Thr Gly Lys Gly Ala Leu Ala Gln Leu Asn Ile Glu Thr
1               5                  10                  15
Gly Val Pro Ile Asn Glu Ile Glu Pro Leu Leu Leu Phe Asn Ile Leu
              20                  25                  30
Phe Phe Phe Phe Ala Ala Ile Asn Pro Gly Thr Gly Lys Phe Val Thr
              35                  40                  45
Asp Asp Asn Asp Asp Gln
              50
```

<210> SEQ ID NO 266
<211> LENGTH: 54
<212> TYPE: PRT
<213> ORGANISM: Oryza sativa

<400> SEQUENCE: 266

```
Glu Ile Ile Thr Gly Lys Gly Ala Leu Ala Gln Leu Asn Ile Glu Thr
1               5                  10                  15
Gly Val Pro Ile Asn Glu Ile Glu Pro Leu Leu Leu Phe Asn Ile Leu
              20                  25                  30
Phe Phe Phe Phe Ala Ala Ile Asn Pro Gly Thr Gly Lys Phe Val Thr
              35                  40                  45
Asp Asp Asn Asp Asp Gln
              50
```

<210> SEQ ID NO 267
<211> LENGTH: 54
<212> TYPE: PRT
<213> ORGANISM: Oryza sativa

<400> SEQUENCE: 267

```
Glu Ile Ile Thr Gly Lys Gly Ala Leu Ala Gln Leu Asn Ile Glu Thr
1               5                  10                  15
Gly Val Pro Ile Asn Glu Ile Glu Pro Leu Leu Leu Phe Asn Ile Leu
              20                  25                  30
Phe Phe Phe Phe Ala Ala Ile Asn Pro Gly Thr Gly Lys Phe Val Thr
              35                  40                  45
Asp Asp Asn Asp Asp Gln
              50
```

<210> SEQ ID NO 268
<211> LENGTH: 54
<212> TYPE: PRT
<213> ORGANISM: Oryza sativa

<400> SEQUENCE: 268

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Leu Leu Phe Asn Ile Leu
            20                  25                  30

Phe Phe Phe Phe Ala Ala Ile Asn Pro Gly Thr Gly Lys Phe Val Thr
        35                  40                  45

Asp Asp Asn Asp Asp Gln
        50

<210> SEQ ID NO 269
<211> LENGTH: 53
<212> TYPE: PRT
<213> ORGANISM: Oryza sativa

<400> SEQUENCE: 269

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Val
            20                  25                  30

Phe Phe Phe Ile Ala Ala Ile Asn Pro Gly Thr Gly Lys Phe Val Ser
        35                  40                  45

Asp Asp Asp Glu Glu
        50

<210> SEQ ID NO 270
<211> LENGTH: 53
<212> TYPE: PRT
<213> ORGANISM: Zea mays

<400> SEQUENCE: 270

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Ile Phe Asn Val Leu
            20                  25                  30

Phe Phe Phe Ile Ala Ala Ile Asn Pro Gly Asn Gly Arg Phe Ile Ile
        35                  40                  45

Gly Glu Glu Glu Glu
        50

<210> SEQ ID NO 271
<211> LENGTH: 53
<212> TYPE: PRT
<213> ORGANISM: Zea mays

<400> SEQUENCE: 271

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Ile Phe Asn Val Leu
            20                  25                  30

Phe Phe Phe Ile Ala Ala Ile Asn Pro Gly Asn Gly Arg Phe Ile Ile
        35                  40                  45

Gly Glu Glu Glu Glu
        50

<210> SEQ ID NO 272
<211> LENGTH: 53
<212> TYPE: PRT
<213> ORGANISM: Zea mays

<400> SEQUENCE: 272

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Ile Phe Asn Val Leu
            20                  25                  30

Phe Phe Phe Ile Ala Ala Ile Asn Pro Gly Asn Gly Arg Phe Ile Ile
        35                  40                  45

Gly Glu Glu Glu Glu
    50

<210> SEQ ID NO 273
<211> LENGTH: 53
<212> TYPE: PRT
<213> ORGANISM: Nicotiana benthamiana

<400> SEQUENCE: 273

Glu Ile Ile Thr Gly Lys Gly Ala Leu Ala Gln Leu Asn Phe Glu Thr
1               5                   10                  15

Gly Val Pro Ile Asn Glu Ile Glu Pro Leu Leu Leu Phe Asn Ile Val
            20                  25                  30

Phe Phe Phe Val Ala Ala Ile Asn Pro Gly Thr Gly Lys Phe Val Thr
        35                  40                  45

Asp Glu Glu Glu Glu
    50

<210> SEQ ID NO 274
<211> LENGTH: 53
<212> TYPE: PRT
<213> ORGANISM: Nicotiana tabacum

<400> SEQUENCE: 274

Glu Ile Ile Thr Gly Lys Gly Ala Leu Ala Gln Leu Asn Phe Glu Thr
1               5                   10                  15

Gly Val Pro Ile Asn Glu Ile Glu Pro Leu Leu Leu Phe Asn Ile Val
            20                  25                  30

Phe Phe Phe Val Ala Ala Ile Asn Pro Gly Thr Gly Lys Phe Val Thr
        35                  40                  45

Asp Glu Glu Glu Glu
    50

<210> SEQ ID NO 275
<211> LENGTH: 53
<212> TYPE: PRT
<213> ORGANISM: Nicotiana tabacum

<400> SEQUENCE: 275

Glu Ile Ile Thr Gly Lys Gly Ala Leu Ala Gln Leu Asn Phe Glu Thr
1               5                   10                  15

Gly Val Pro Ile Asn Glu Ile Glu Pro Leu Leu Leu Phe Asn Ile Val
            20                  25                  30

Phe Phe Phe Ile Ala Ala Ile Asn Pro Gly Thr Gly Lys Phe Val Thr
        35                  40                  45

Asp Glu Glu Glu Glu
    50

<210> SEQ ID NO 276
<211> LENGTH: 53
<212> TYPE: PRT
<213> ORGANISM: Nicotiana benthamiana

```
<400> SEQUENCE: 276

Glu Ile Ile Thr Gly Lys Gly Ala Leu Ala Gln Leu Asn Phe Glu Thr
1               5                   10                  15

Gly Val Pro Ile Asn Glu Ile Glu Pro Leu Leu Leu Phe Asn Ile Val
                20                  25                  30

Phe Phe Phe Val Ala Ala Ile Asn Pro Gly Thr Gly Lys Phe Val Thr
            35                  40                  45

Asp Glu Glu Glu Glu
    50

<210> SEQ ID NO 277
<211> LENGTH: 54
<212> TYPE: PRT
<213> ORGANISM: Arabidopsis thaliana

<400> SEQUENCE: 277

Glu Ile Ile Thr Gly Lys Gly Ala Leu Ala Gln Leu Asn Ile Glu Thr
1               5                   10                  15

Gly Ile Pro Ile Gln Glu Ile Glu Pro Leu Val Leu Leu Asn Val Ala
                20                  25                  30

Phe Phe Phe Phe Ala Ala Ile Asn Pro Gly Asn Gly Lys Phe Ile Thr
            35                  40                  45

Asp Asp Gly Glu Glu Ser
    50

<210> SEQ ID NO 278
<211> LENGTH: 54
<212> TYPE: PRT
<213> ORGANISM: Hevea brasiliensis

<400> SEQUENCE: 278

Glu Ile Ile Thr Gly Lys Gly Ala Leu Ala Gln Leu Asn Ile Glu Thr
1               5                   10                  15

Gly Ile Pro Val Asn Glu Ile Glu Pro Leu Val Leu Phe Asn Val Ile
                20                  25                  30

Phe Phe Phe Ile Ala Ala Leu Asn Pro Gly Thr Gly Lys Phe Val Thr
            35                  40                  45

Asp Glu Asp Glu Asp Glu
    50

<210> SEQ ID NO 279
<211> LENGTH: 54
<212> TYPE: PRT
<213> ORGANISM: Manihot esculenta

<400> SEQUENCE: 279

Glu Ile Ile Thr Gly Lys Gly Ala Leu Ala Gln Leu Asn Ile Glu Thr
1               5                   10                  15

Gly Ile Pro Val Ser Glu Ile Glu Pro Leu Val Leu Phe Asn Val Leu
                20                  25                  30

Phe Phe Phe Val Ala Ala Leu Asn Pro Gly Thr Gly Lys Phe Val Thr
            35                  40                  45

Asp Glu Asp Glu Asp Glu
    50

<210> SEQ ID NO 280
<211> LENGTH: 54
<212> TYPE: PRT
<213> ORGANISM: Vigna unguiculata
```

<400> SEQUENCE: 280

Glu Ile Val Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Leu
                20                  25                  30

Phe Phe Phe Val Ala Ala Leu Asn Pro Gly Thr Gly Lys Phe Val Thr
            35                  40                  45

Asp Glu Gly Asp Asp Glu
        50

<210> SEQ ID NO 281
<211> LENGTH: 54
<212> TYPE: PRT
<213> ORGANISM: Glycine max

<400> SEQUENCE: 281

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Leu
                20                  25                  30

Phe Phe Phe Ile Ala Ala Leu Asn Pro Gly Thr Gly Lys Phe Val Thr
            35                  40                  45

Asp Glu Gly Glu Asp Asp
        50

<210> SEQ ID NO 282
<211> LENGTH: 54
<212> TYPE: PRT
<213> ORGANISM: Glycine max

<400> SEQUENCE: 282

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Leu
                20                  25                  30

Phe Phe Phe Ile Ala Ala Leu Asn Pro Gly Thr Gly Lys Phe Val Thr
            35                  40                  45

Asp Glu Gly Glu Asp Asp
        50

<210> SEQ ID NO 283
<211> LENGTH: 54
<212> TYPE: PRT
<213> ORGANISM: Glycine max

<400> SEQUENCE: 283

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Leu
                20                  25                  30

Phe Phe Phe Ile Ala Ala Leu Asn Pro Gly Thr Gly Lys Phe Val Thr
            35                  40                  45

Asp Asp Gly Glu Asp Asp
        50

<210> SEQ ID NO 284
<211> LENGTH: 54
<212> TYPE: PRT

```
<213> ORGANISM: Glycine max

<400> SEQUENCE: 284

Glu Ile Ile Thr Gly Lys Gly Ala Leu Ala Gln Leu Asn Ile Glu Thr
1               5                   10                  15

Gly Val Pro Ile Asn Glu Ile Glu Pro Leu Val Leu Phe Asn Val Leu
            20                  25                  30

Phe Phe Phe Ile Ala Ala Leu Asn Pro Gly Thr Gly Lys Phe Val Thr
            35                  40                  45

Gly Asp Gly Glu Asp Asp
    50
```

What is claimed is:

1. A method of cultivating a genetically altered plant with increased water use efficiency, comprising the steps of:
   a. providing the genetically altered plant, wherein the plant or a part thereof comprises a genetic alteration comprising a first nucleic acid encoding a Photosystem II Subunit S (PsbS) protein and the first nucleic acid is operably linked to a second nucleic acid comprising a heterologous promoter;
   b. selecting the genetically altered plant for increased water use efficiency compared to a wild type (WT) plant without the genetic alteration grown under the same conditions; and
   c. cultivating the genetically altered plant in a field under conditions wherein the genetic alteration increases activity of the PsbS protein as compared to a wild type (WT) plant without the genetic alteration, and wherein the increased activity of the PsbS protein increases water use efficiency and increases biomass as compared to the WT plant grown under the same conditions.

2. The method of claim 1, wherein the conditions are lower irrigation conditions than standard irrigation conditions for the WT plant, rain fed conditions, higher density growth conditions than standard growth density conditions for the WT plant, higher salinity conditions than standard salinity conditions for the WT plant, or conditions resulting in wet leaf surfaces.

3. The method of claim 2, wherein the increased activity of the PsbS protein provides the genetically altered plant with a higher yield, an increased growth rate, an increased tolerance of salinity, an increased ability to withstand salinity, an increased flow of nutrients to the roots, an increased availability of nutrients over time, an increased utilization of fertilizer, an increased utilization of nutrients, a decreased susceptibility to a plant disease requiring wet leaf surfaces for infection, a decreased susceptibility to infection by the plant disease, a reduced incidence of the plant disease, or a reduced incidence of infection by the plant disease, in each case as compared to the WT plant without the increased activity grown under the same conditions.

4. The method of claim 2, wherein the genetically altered plant does not comprise increased activity of zeaxanthin epoxidase (ZEP) protein, violaxanthin de-epoxidase (VDE) protein, or both, as compared to the WT plant, and wherein the genetically altered plant does not comprise reduced activity of K+ efflux antiporter 3 (KEA3) as compared to the WT plant.

5. The method of claim 2, wherein increased activity is increased expression.

6. The method of claim 5, wherein the increased expression is due to expression of a heterologous PsbS protein.

7. The method of claim 5, wherein the increased expression is due to overexpression of an endogenous PsbS protein.

8. The method of claim 1, wherein the plant is not a tobacco plant.

9. The method of claim 1, wherein the selecting for increased water use efficiency comprises measuring stomatal conductance.

* * * * *